(12) United States Patent
    Anand et al.

(10) Patent No.: US 10,766,864 B2
(45) Date of Patent: Sep. 8, 2020

(54) MORPHINAN DERIVATIVES FOR THE TREATMENT OF NEUROPATHIC PAIN

(71) Applicant: Nektar Therapeutics, San Francisco, CA (US)

(72) Inventors: Neel K. Anand, San Mateo, CA (US); Natalia Aurrecoechea, Oakland, CA (US); Lin Cheng, Sunnyvale, CA (US); Bo-Liang Deng, San Ramon, CA (US); Donogh John Roger O'Mahony, San Mateo, CA (US); YongQi Mu, Los Altos, CA (US); Erik Krogh-Jespersen, Greenbrae, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 15/569,726

(22) PCT Filed: May 5, 2016

(86) PCT No.: PCT/US2016/030933
§ 371 (c)(1),
(2) Date: Oct. 26, 2017

(87) PCT Pub. No.: WO2016/182840
PCT Pub. Date: Nov. 17, 2016

(65) Prior Publication Data
US 2018/0127375 A1    May 10, 2018

Related U.S. Application Data

(60) Provisional application No. 62/159,120, filed on May 8, 2015.

(51) Int. Cl.
| | | |
|---|---|---|
| *C07D 221/28* | (2006.01) | |
| *C07D 401/12* | (2006.01) | |
| *C07D 417/12* | (2006.01) | |
| *C07D 513/08* | (2006.01) | |
| *C07D 407/12* | (2006.01) | |
| *A61P 25/04* | (2006.01) | |
| *C07D 407/04* | (2006.01) | |
| *C07D 471/08* | (2006.01) | |

(52) U.S. Cl.
CPC ........... *C07D 221/28* (2013.01); *A61P 25/04* (2018.01); *C07D 401/12* (2013.01); *C07D 407/04* (2013.01); *C07D 407/12* (2013.01); *C07D 417/12* (2013.01); *C07D 471/08* (2013.01); *C07D 513/08* (2013.01)

(58) Field of Classification Search
CPC .................................................. C07D 221/28
See application file for complete search history.

(56) References Cited

U.S. PATENT DOCUMENTS

| | | |
|---|---|---|
| 3,654,280 A | 4/1972 | Sawa et al. |
| 3,793,329 A | 2/1974 | Merz et al. |
| 2005/0136031 A1 | 6/2005 | Bentley et al. |
| 2010/0048602 A1 | 2/2010 | Riggs-Sauthier et al. |

FOREIGN PATENT DOCUMENTS

| | | |
|---|---|---|
| GB | 1097167 | 12/1967 |
| WO | WO 02/098949 A1 | 12/2002 |
| WO | WO2004/045562 * | 6/2004 |
| WO | WO 2004/045562 A2 | 6/2004 |
| WO | WO 2006/071730 A1 | 7/2006 |

OTHER PUBLICATIONS

Zhang et al., J'nal of Med Chem, Am. Chem. Society, 47(1), 2004, pp. 165-174.*
Neumeyer et al., Bioorganic & Med. Chem. Letters. 11(20), 2001, pp. 2735-2740.*
Neunneyer et al., J'nal of Med. Chem. 43(1), 2000, pp. 114-122.*
Chen et al., "Synthesis and Properties of ABA Amphiphiles", J. Org Chem., vol. 64, pp. 6870-6873, (1999).
Decker et al., "Synthesis and Opioid Receptor Binding Affinities of 2-Substituted and 3-Aminomorphinans: Ligands for mu, kappa and delta Opioid Receptors", J. Med. Chem., vol. 53, No. 1, pp. 1-50, (Jan. 14, 2010).
Eddy et al., "Synthetic analgesics. Aralkyl substitution on nitrogen of morphinan", Bulletin on Narcotics, vol. 10, No. 4, pp. 23-41, (1958).
Ertl et al., "Fast Calculation of Molecular Polar Surface Area as a Sum of Fragment-Based Contributions and Its Applications to the Prediction of Drug Transport Properties", J. Med. Chem., vol. 43, pp. 3714-3717, (2000).
Foley, "Opioids and Chronic Neuropathic Pain", N. Engl. J. Med., vol. 348, No. 13, pp. 1279-1281, (Mar. 27, 2003).

(Continued)

*Primary Examiner* — Paul V Ward
(74) *Attorney, Agent, or Firm* — Jacqueline F. Mahoney

(57) ABSTRACT

The present invention relates to compounds and their use as ligands for mu opioid receptors. Also included are methods for preparing the compounds and pharmaceutical compositions containing the compounds. In one or more embodiments of the invention, a compound according to Formula I is provided: and pharmaceutically acceptable salts thereof, wherein $R^1$-$R^{11}$ are as described herein.

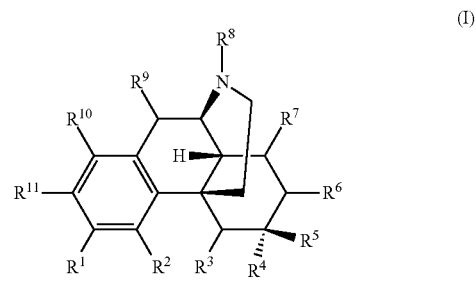

(I)

8 Claims, No Drawings

(56) References Cited

OTHER PUBLICATIONS

Herlihy et al., "Novel Opiates and Antagonists 5. 7-Carbethoxy-N-(cycloalkylmethyl)-3-hydroxymorphinan-6-ones and -isomorphinans-6-ones", J. Med. Chem., vol. 25, pp. 986-990, (1982).

Kelder et al., "Polar Molecular Surface as a Dominating Determinant for Oral Absorption and Brain Penetration of Drugs", Pharmaceutical Research, vol. 16, No. 10, pp. 1514-1519, (1999).

Neumeyer et al., "Mixed κ Agonists and μ Agonists/Antagonists as Potential Pharmacotherapeutics for Cocaine Abuse: Synthesis and Opioid Receptor Binding Affinity of N-Substituted Derivatives of Morphinan", Bioorganic & Medicinal Chemistry Letters, vol. 11, pp. 2735-2740, (2001).

Neumeyer et al., "Synthesis and Opioid Receptor Affinity of Morphinan and Benzomorphan Derivatives: Mixed κ Agonists and μ Agonists/Antagonists as Potential Pharmacotherapeutics for Cocaine Dependence", J. Med. Chem., vol. 43, pp. 114-122.

Neumeyer et al., "Synthesis, Binding Affinity, and Functional In Vitro Activity of 3-Benzylaminomorphinan and 3-Benzylaminomorphine Ligands at Opioid Receptors", J. Med. Chem., vol. 55, No. 8, pp. 3878-3890, (Apr. 26, 2012).

Prommer, "Levorphanol: the forgotten opioid", Support Care Cancer, vol. 15, pp. 259-264, (2007).

Rodriguez-Muñoz et al., "The Mu-Opioid Receptor and the NMDA Receptor Associate in PAG Neurons: Implications in Pain Control", Neuropsychopharmacology vol. 37, pp. 338-349, (2012).

Rowbotham et al., "Oral Opioid Therapy for Chronic Peripheral and Central Neuropathic Pain", The New England Journal of Medicine, vol. 348, pp. 1223-1232, (2003).

Rubin, "The Cell Biology of the Blood-Brain Barrier", Annu. Rev. Neurosci., vol. 22, pp. 11-28, (1999).

Summerfield et al., "Central Nervous System Drug Disposition: The Relationship between in Situ Brain Permeability and Brain Free Fraction", The Journal of Pharmacology and Experimental Therapeutics, vol. 322, No. 1, pp. 205-213, (2007).

Tsuji, "Small Molecular Drug Transfer across the Blood-Brain Barrier via Carrier-Mediated Transport Systems", NeuroRx: The Journal of the American Society for Experimental NeuroTherapeutics, vol. 2, pp. 54-62, (Jan. 2005).

Wager et al., "Defining Desirable Central Nervous System Drug Space through the Alignment of Molecular Properties, in Vitro ADME, and Safety Attributes", ACS Chem. Neurosci., vol. 1, pp. 420-434, (2010).

Zhang et al., "10-Ketomorphinan and 3-Substituted-3-desoxymorphinan Analogues as Mixed κ and μ Opioid Ligands: Synthesis and Biological Evaluation of Their Binding Affinity at Opioid Receptors", J. Med. Chem., vol. 47, pp. 165-174, (2004).

Zhang et al., "Synthesis and Pharmacological Evaluation of 6,7-Indolo/Thiazolo-Morphinans—Further SAR of Levorphanol", J. Med. Chem., vol. 50, pp. 2747-2751, (2007).

Zhang et al., "2-Aminothiazole-Derived Opioids. Bioisosteric Replacement of Phenols", J. Med. Chem., vol. 47, pp. 1886-1888, (2004).

PCT International Search Report and the Written Opinion in PCT Application No. PCT/US2016/030933 dated Aug. 29, 2016.

PCT International Preliminary Report on Patentability in PCT Application No. PCT/US2016/030933 dated Nov. 23, 2017.

Enzon Pharmaceuticals, Macromolecular Engineering Technologies, 16 pages, (2004).

Nektar™—Transforming Therapeutics, Nektar Molecule Engineering: Polyethylene Glycol and Derivatives for Advanced PEGylation, 24 pages, Catalog—2003, (Jul. 2003).

Nektar™—Transforming Therapeutics, Nektar Advanced PEGylation: Polyethylene Glycol and Derivatives for Advanced PEGylation, 27 pages, Catalog—2004, (Jul. 2004).

Nektar™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003-$1^{st}$, (Jan. 2003).

NOF Corporation, PEG Derivatives, Phospholipid and Drug Delivery Materials for Pharmaceuticals, 27 pages, Catalogue 2003-$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; BIOTINS, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™Technology, 31 pages, (Nov. 5, 2004).

Quanta Biodesign, Ltd., Leading innovator, producer and provider of monodisperse discrete PEG™(dPEG™) derivatives, (Product Catalog), 26 pages, (Updated: Jul. 18, 2005).

Quanta Biodesign, Ltd., Leading innovator, producer and provider of monodisperse discrete PEG™(dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

* cited by examiner

MORPHINAN DERIVATIVES FOR THE TREATMENT OF NEUROPATHIC PAIN

This application is a 35 U.S.C. § 371 application of International Application No. PCT/US2016/030933, filed May 5, 2016, designating the United States which claims the benefit of priority to U.S. provisional patent application No. 62/159,120 filed May 8, 2015, the disclosure of which are incorporated by reference in their entireties.

FIELD

The present disclosure relates to novel compounds and to their use as agonists of the mu opioid receptor. The disclosure also relates to methods for preparation of the compounds and to pharmaceutical compositions containing such compounds. The compounds described herein relate to and/or have application(s) in (among others) the fields of drug discovery, pharmacotherapy, physiology, organic chemistry and polymer chemistry.

BACKGROUND

Neuropathic pain is a form of chronic pain resulting from injury or disease to the peripheral or central nervous system that often persists long after initial injury has resolved. Multiple mechanisms are believed to play a role in the maintenance of the persistent pain state and therefore effective treatment of neuropathic pain often utilizes drugs that alternatives to prototypical and currently used mu opioid analgesics.

While mu opioid analgesics are commonly used to treat certain types of pain, their use for the treatment of neuropathic pain is limited due to concerns of addiction and tolerance that may develop following the chronic use of high doses of those compounds. Such effects can be amplified when mu opioid analgesics are used in treating patients suffering from neuropathic pain because the doses used are often increased over those used to treat nociceptive pain. Rodriguez-Munoz (2012) *Neuropsychophamacology* 37:338-349. Further, the NMDA receptor is believed to negatively regulate the ability of mu opioid agonists to alleviate neuropathic pain. It has been postulated that bifunctional drugs, e.g., those acting as both mu opioid agonists and NMDA receptor agonists could provide a new avenue for treating neuropathic pain.

Levorphanol is a synthetic opioid that is approved for the treatment of pain that has demonstrated some promise in the treatment of neuropathic pain. At a molecular level, levorphanol binds to the mu opioid receptor and also shows activity at inhibiting the serotonin transporter (SERT), norepinephrine transporter (NERT), and as an antagonist of the NMDA receptor. The multimodal mechanism of action at alleviating pain suggests that levorphanol could be potentially useful in the treatment of neuropathic pain. In this regard, levorphanol was shown to be effective in reducing neuropathic pain in a Phase II clinical study although its use was associated with severe dose-limiting side effects. Rowbotham et al. (2003) *N. Engl. J Med.* 348:13.

Although not bound by theory, it is believed that compounds designed to act as both mu opioid agonists and NMDA antagonists are candidates for treating patients suffering from neuropathic pain. In addition, because the dose-limiting opioid side effects are mediated centrally, it is hypothesized that reducing the entry of a compound across the blood-brain barrier may achieve two benefits. First, reducing entry of a compound across the blood-brain barrier would likely reduce or eliminate one or more central side effects. Second, reducing entry of a compound across the blood-brain barrier by peripheral restriction would allow for significantly higher doses to be used as a result of reduced or eliminated central side effects.

The incorporation of a poly(ethylene glycol) moiety into a small molecule scaffold has been utilized to modify the rate of CNS entry of several classes of molecules. U.S. Patent Application Publication No. 2005/0136031 and U.S. Patent Application Publication No. 2010/0048602. The sites of incorporation and further modifications to the molecules, however, have differing effects on the overall activity and pharmacological properties of the resulting molecule.

As such, there remains a need for drugs for the treatment of patients suffering from neuropathic pain, including those that act as mu opioid agonists with fewer or lessened side effects associated with mu opioid agonist-based therapy. Further, those compounds that effectively act as mu opioid agonists while antagonizing the NMDA receptor are of particular interest. The present invention seeks to address these and other needs.

SUMMARY

In one or more embodiments of the invention, a compound according to Formula I is provided:

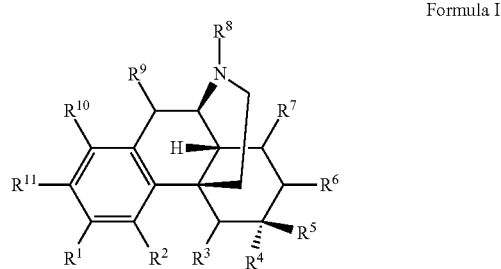

Formula I wherein:
$R^1$ is selected from hydroxyl, —O—($R^{12}$), —O—C(O)—N($R^{13}$)($R^{14}$), —NHC(O)—($R^{15}$), —NH—C(O)—NH($R^{16}$), —N($R^{17}$)($R^{18}$), —NHC(O)O—($R^{19}$), —NH—S(O)$_2$—($R^{20}$), —C(O)—N($R^{21}$)($R^{22}$), optionally substituted heteroaryl, and —X-POLY;

$R^2$ is selected from hydrogen, —O—($R^{25}$) and —X-POLY, or $R^1$ and $R^2$ are taken together with their intervening atoms to form a fused, optionally substituted heteroaryl or optionally substituted heterocyclyl;

$R^3$ is selected from hydrogen and X-POLY;

$R^4$ is selected from hydrogen, —O—($R^{26}$) and —X-POLY;

$R^5$ is selected from hydrogen, —O—($R^{27}$) and —X-POLY; or $R^4$ and $R^5$ are optionally taken together to form a carbonyl;

$R^6$ is selected from hydrogen, OH, and X-POLY; or $R^5$ and $R^6$ are taken together with their intervening atoms to form a fused, optionally substituted heteroaryl wherein $R^4$ is absent;

$R^7$ is selected from hydrogen, OH, and X-POLY;

$R^8$ is selected from hydrogen, optionally substituted alkyl, optionally substituted heterocyclyl, —C(O)—N($R^{23}$)($R^{24}$) and —X-POLY;

$R^{11}$ is hydrogen, or $R^1$ and $R^{11}$ are taken together with their intervening atoms to form a fused, optionally substituted heteroaryl or optionally substituted heterocyclyl, provided the heteroaryl is not thiazole substituted with —$NH_2$ when $R^8$ is methyl;

$R^9$ is selected from hydrogen and X-POLY;

$R^{10}$ is selected from hydrogen, OH, and X-POLY;

$R^{12}$ is selected from optionally substituted alkyl, aryl, and heteroaryl;

$R^{13}$ is selected from hydrogen and optionally substituted alkyl $R^{14}$ is selected from hydrogen and optionally substituted alkyl $R^{15}$ is selected from hydrogen, optionally substituted alkyl, optionally substituted aryl, X-POLY, and optionally substituted heteroaryl;

$R^{16}$ is selected from hydrogen, optionally substituted alkyl, optionally substituted aryl, and optionally substituted heteroaryl, provided that when $R^{16}$ is phenyl the phenyl is substituted with —X-POLY or if $R^{17}$ is benzyl the benzyl is substituted with —X-POLY;

$R^{17}$ is selected from hydrogen, optionally substituted alkyl, optionally substituted aryl, and optionally substituted heteroaryl, provided that when $R^{17}$ is phenyl the phenyl is substituted with —X-POLY or if $R^{17}$ is benzyl the benzyl is substituted with —X-POLY;

$R^{18}$ is selected from hydrogen, X-POLY, optionally substituted alkyl, optionally substituted aryl, and optionally substituted heteroaryl provided that when $R^{17}$ is phenyl the phenyl is substituted with —X-POLY;

$R^{19}$ is selected from hydrogen, optionally substituted alkyl, optionally substituted aryl, and optionally substituted heteroaryl;

$R^{20}$ is selected from hydrogen, optionally substituted alkyl, optionally substituted aryl, and optionally substituted heteroaryl;

$R^{21}$ is selected from hydrogen, optionally substituted alkyl, optionally substituted aryl, and optionally substituted heteroaryl;

$R^{22}$ is selected from hydrogen, optionally substituted alkyl, optionally substituted aryl, and optionally substituted heteroaryl;

$R^{23}$ is selected from hydrogen and optionally substituted alkyl;

$R^{24}$ is selected from hydrogen and optionally substituted alkyl;

$R^{25}$ is selected from hydrogen, optionally substituted alkyl, optionally substituted aryl, and optionally substituted heteroaryl;

$R^{26}$ is selected from hydrogen, optionally substituted alkyl, optionally substituted aryl, and optionally substituted heteroaryl;

$R^{27}$ is selected from hydrogen, optionally substituted alkyl, optionally substituted aryl, and optionally substituted heteroaryl; and pharmaceutically acceptable salts thereof, provided that when $R^1$ is $OCH_3$, $R^2$ is OH, $R^8$ is methyl and $R^4$ and $R^5$ form a carbonyl, $R^3$, $R^6$, $R^7$, and $R^{9-11}$ are not all hydrogen;

when $R^1$ is $OCH_3$, $R^8$ is methyl and $R^4$ and $R^5$ form a carbonyl, $R^2$, $R^3$, $R^6$, $R^7$, and $R^{9-11}$ are not all hydrogen;

when $R^1$ is $OCH_3$, $R^2$ is OH, and $R^8$ is methyl, $R^{3-7}$ and $R^{9-11}$ are not all hydrogen;

when $R^1$ is $OCH_3$ and $R^8$ is methyl, $R^2$-$R^7$ and $R^{9-11}$ are not all hydrogen;

when $R^1$ is OH, $R^8$ is methyl and $R^4$ and $R^5$ form a carbonyl, $R^2$, $R^3$, $R^6$, $R^7$, and $R^{9-11}$ are not all hydrogen;

when $R^1$ is $OCH_3$, $R^{2-11}$ are not all hydrogen;

when $R^1$ is OH and $R^8$ is methyl, $R^{2-7}$ and $R^{9-11}$ are not all hydrogen;

when $R^1$ is $OCH_2CH_2OCH_3$ and $R^8$ is methyl, $R^{2-7}$ and $R^{9-11}$ are not all hydrogen;

when $R^1$ is OH and $R^8$ is $CH_2CH_2OCH_3$, $R^{2-7}$ and $R^{9-11}$ are not all hydrogen;

when $R^1$ is $OCH_3$ and $R^8$ is $C(O)CH_3$ or $C(O)OCH_3$, $R^{2-7}$ and $R^{9-11}$ are not all hydrogen;

when $R^1$ is $NH_2$ and $R^8$ is methyl, $R^{2-7}$ and $R^{9-11}$ are not all hydrogen;

when $R^1$ is selected from $NHC(O)CH_3$, $C(O)NH_2$, and $C(O)OH$, and $R^8$ is methyl, $R^{2-7}$ and $R^{9-11}$ are not all hydrogen;

when $R^1$ is OH, $R^8$ is methyl and one of $R^4$ and $R^5$ are hydroxyl, $R^2$, $R^3$, $R^6$, $R^7$, and $R^{9-11}$ are not all hydrogen;

when $R^1$ is pyridinyl and $R^8$ is methyl, $R^{2-7}$ and $R^{9-11}$ are not all hydrogen; and when $R^8$ is $CH_3$ and $R^{2-7}$, $R^9$ and $R^{10}$ are hydrogen, $R^1$ and $R^{11}$ are not taken together to form thiazole substituted with $NH_2$.

In one or more embodiments of the invention, a composition is provided, the composition comprising (i) a compound as described herein, and, optionally, (ii) a pharmaceutically acceptable excipient.

In one or more embodiments of the invention, composition of matter is provided, the composition of matter comprising a compound as described herein, wherein the compound is present in a dosage form.

In one or more embodiments of the invention, a method is provided, the method comprising administering a compound as described herein to a patient in need thereof.

Additional embodiments of the present compounds, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

DETAILED DESCRIPTION

In describing and claiming the present invention, the following terminology will be used in accordance with the definitions described below.

Definitions

As used in this specification, the singular forms "a," "an," and "the" include plural referents unless the context clearly dictates otherwise.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like. As used herein, "lower alkyl" refers to an alkyl group having from 1 to 6 carbon atoms. Specific examples of lower alkyl include, but are not limited to, methyl, ethyl, n-propyl, iso-propyl, n-butyl, iso-butyl, t-butyl, n-hexyl, and the like.

The term "substituted alkyl" refers to an alkyl group having 1 to 5 substituents (in certain embodiments 1, 2, or 3) selected from alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxyl, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxy amino, alkoxy amino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2. "Substituted lower alkyl" refers to a lower alkyl group defined above, substituted as defined for alkyl.

The term "alkylene" refers to a diradical of a branched or unbranched saturated hydrocarbon chain, in certain embodiments, having from 1 to 20 carbon atoms (e.g., 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like. The term "lower alkylene" refers to a diradical of a branched or unbranched saturated hydrocarbon chain, in certain embodiments, having 1, 2, 3, 4, 5 or 6 carbon atoms.

The terms "substituted alkylene" and "substituted lower alkylene" refer to an alkylene group or lower alkylene group, respectively, as defined above having 1 to 5 substituents (in certain embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in certain embodiments, from 2 to 10 carbon atoms, e.g., 2 to 6 carbon atoms) and having from 1 to 6 carbon-carbon double bonds, e.g. 1, 2 or 3 carbon-carbon double bonds. In certain embodiments, alkenyl groups include ethenyl (or vinyl, i.e., —CH═CH$_2$), 1-propylene (or allyl, i.e., —CH$_2$CH═CH$_2$), isopropylene (—C(CH$_3$)═CH$_2$), and the like. The term "lower alkenyl" refers to alkenyl as defined above having from 2 to 6 carbon atoms.

The term "substituted alkenyl" refers to an alkenyl group as defined above having 1 to 5 substituents (in certain embodiments, 1, 2, or 3 substituents) as defined for substituted alkyl.

The term "substituted lower alkenyl" refers to a lower alkenyl group as defined above having 1 to 5 substituents (in certain embodiments, 1, 2, or 3 substituents) as defined for substituted alkyl.

The term "alkenylene" refers to a diradical of a branched or unbranched unsaturated hydrocarbon group having from 2 to 20 carbon atoms (in certain embodiments, from 2 to 10 carbon atoms, e.g., 2 to 6 carbon atoms) and having from 1 to 6 carbon-carbon double bonds, e.g., 1, 2, or 3 carbon-carbon double bonds.

The term "alkynyl" refers to a monoradical of an unsaturated hydrocarbon, in certain embodiments, having from 2 to 20 carbon atoms (in certain embodiments, from 2 to 10 carbon atoms, e.g., 2 to 6 carbon atoms) and having from 1 to 6 carbon-carbon triple bonds, e.g., 1, 2, or 3 carbon-carbon triple bonds. In certain embodiments, alkynyl groups include ethynyl (—C≡CH), propargyl (or propynyl, i.e., —C≡CCH$_3$), and the like.

The term "substituted alkynyl" refers to an alkynyl group as defined above having 1 to 5 substituents (in certain embodiments, 1, 2, or 3 substituents) as defined for substituted alkyl.

The term "alkynylene" refers to a diradical of an unsaturated hydrocarbon, in certain embodiments, having from 2 to 20 carbon atoms (in certain embodiments, from 2 to 10 carbon atoms, e.g., 2 to 6 carbon atoms) and having from 1 to 6 carbon-carbon triple bonds e.g., 1, 2, or 3 carbon-carbon triple bonds.

The terms "hydroxy" and "hydroxyl" refer to —OH.

The term "alkoxy" refers to the group R—O—, where R is alkyl or —Y—Z, in which Y is alkylene and Z is alkenyl or alkynyl, where alkyl, alkenyl and alkynyl are as defined herein. In certain embodiments, alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like. The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is optionally substituted alkylene and Z is substituted alkenyl or substituted alkynyl, where substituted alkyl, substituted alkenyl and substituted alkynyl are as defined herein.

The term "haloalkyl" refers to an alkyl group having from 1 to 3 carbon atoms covalently bonded to from 1 to 7, or from 1 to 6, or from 1 to 3, halogen(s), where alkyl and halogen are defined herein. In certain embodiments, C$_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, and 3-fluoropropyl.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in certain embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in certain embodiments, 1, 2 or 3 substituents), selected from alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxy amino, alkoxy amino, nitro, —S(O)-alkyl, —S(O)-cycloalkyl, —S(O)-heterocyclyl, —S(O)-aryl, —S(O)— heteroaryl, —S(O)$_2$-alkyl, —S(O)$_2$-cycloalkyl, —S(O)$_2$-heterocyclyl, —S(O)$_2$-aryl and —S(O)$_2$— heteroaryl.

The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

As used herein, "—X-POLY" refers to a water-soluble, nonpeptidic oligomer, POLY, attached through a linker, "X." In certain embodiments, POLY is made of one or more ethylene glycol sub-units.

"Water soluble oligomer" indicates a non-peptidic oligomer that is at least 35% (by weight) soluble, preferably greater than 70% (by weight), and more preferably greater than 95% (by weight) soluble, in water at room temperature. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. In certain embodiments, the oligomers used in connection with present the invention are homo-oligomers. The water-soluble oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 50 monomers, preferably from about 1 to about 30 monomers. In certain embodiments, an "oligomer" is a molecule possessing from about 2 to about 50 monomers, in certain embodiments from about 2 to about 30 monomers.

The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or any polyethylene glycol is one in which substantially all (preferably all) monomeric subunits are ethylene oxide subunits, though, the oligomer may contain distinct end capping moieties or functional groups, e.g., for providing a site of covalent modification or reaction with another compound. PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. For the PEG oligomers, the variable (n) ranges from about 1 to 50, and the terminal groups and architecture of the overall PEG can vary. When PEG further comprises a functional group, A, for linking to, e.g., a small molecule, the functional group when covalently attached to a PEG oligomer does not result in formation of an oxygen-oxygen bond (—O—O—, a peroxide linkage).

The terms "end-capped" or "terminally capped" are interchangeably used herein to refer to a terminal or endpoint of an oligomer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, alkyl, heteroaryl, cyclo, heterocyclo, and the like. Further examples include C$_{1-3}$ haloalkyl and carboxy. In addition, saturated, unsaturated, substituted and unsubstituted forms of each of the foregoing are envisioned. In certain embodiments, where the oligomer is an ethylene glycol of the formula (CH$_2$CH$_2$O)—R, R is a capping group selected from hydrogen, lower alkyl (e.g. CH$_3$), haloalkyl (e.g. CF$_3$), and carboxyl.

In the context of describing the consistency of oligomers in a given composition, "substantially" or "essentially" means nearly totally or completely, for instance, 95% or greater, in certain embodiments 97% or greater, in certain embodiments 98% or greater, in certain embodiments 99% or greater, and in certain embodiments 99.9% or greater.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially comprising molecules having a single and definable number of monomers rather than several different numbers of monomers (i.e., an oligomer composition having three or more different oligomer sizes). In certain embodiments, a monodisperse oligomer composition possesses a MW/Mn value of 1.0005 or less, and in certain embodiments, a MW/Mn value of 1.0000. By extension, a composition comprised of monodisperse compounds means that substantially all oligomers of all compounds in the composition have a single and definable number (as a whole number) of monomers rather than a distribution and would possess a MW/Mn value of 1.0005, and in certain embodiments, a MW/Mn value of 1.0000 if the oligomer were not attached to a compound of the present invention. A composition comprised of monodisperse compounds can include, however, one or more substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a distribution, and whose distribution of molecular weights, when plotted as a number fraction versus molecular weight, appears as two separate identifiable peaks. In certain embodiments, for a bimodal oligomer composition as described herein, each peak is generally symmetric about its mean, although the size of the two peaks may differ. Ideally, the polydispersity index of each peak in the bimodal distribution, Mw/Mn, is 1.01 or less, in certain embodiments 1.001 or less, in certain embodiments 1.0005 or less, and in certain embodiments a MW/Mn value of 1.0000. By extension, a composition comprised of bimodal compounds means that substantially all oligomers of all compounds in the composition have one of two definable and different numbers (as whole numbers) of monomers rather than a large distribution and would possess a MW/Mn value of 1.01 or less, in certain embodiments 1.001 or less, in certain embodiments 1.0005 or less, and in certain embodiments a MW/Mn value of 1.0000 if the oligomer were not attached to a compound of the present invention. A composition comprised of bimodal compounds can include, however, one or more substances such as solvents, reagents, excipients, and so forth.

"Branched", in reference to the geometry or overall structure of an oligomer, refers to an oligomer having two or more oligomers representing distinct "arms" that extend from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

As used herein "X" is a spacer moiety including a covalent bond or a group of 1-20 atoms. X may include, but is not limited to optionally substituted alkylene, optionally substituted alkenylene, optionally substituted alkynylene, optionally substituted alkoxy, hydroxyl, optionally substituted amino, optionally substituted awl, optionally substituted heterocyclyl, optionally substituted heteroaryl, optionally substituted ester, alkyl amine, dialkyl amine, keto, optionally substituted acyl, aminocarbonyl, carboxyalkyl, acyloxy, acylamino, alkoxycarbonylamino, aminocarbonylamino, and the like. It is understood that the spacer X will comprise diradicals of the respective groups. Exemplary spacer moieties include a covalent bond, —O—, —NH—, —S—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —CH$_2$CHOHCH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —NH—C(O)—CH$_2$—O—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$CHOHCH$_2$NH—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, a bivalent cycloalkyl group, amino, substituted amino. Additional spacers include, acylamino, acyl, aryloxy, alkylene, amino, substituted amino, piperidino, and pyrrolidino. For purposes of the present invention, however, a group of atoms is not considered a spacer when it is immediately adjacent to an oligomeric segment, and the group of atoms is the same as a monomer of the oligomer such that the group would represent a mere extension of the oligomer chain.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In certain embodiments, aryls include phenyl, fluorenyl, naphthyl, anthryl, and the like.

Unless otherwise constrained by the definition for the aryl substituent, such aryl groups can optionally be substituted with 1, 2, 3, 4, or 5 substituents (In certain embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In certain embodiments, the "heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in certain embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in certain embodiments, 1, 2, or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2, or 3 substituents chosen from alkyl; alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —NH$_2$. The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl or alkynyl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "alkyl amine" refers to —NHR in which R is optionally substituted alkyl.

The term "dialkyl amine" refers to —NRR in which each R is independently an optionally substituted alkyl.

The term "cyano" refers to the group —CN.

The term "azido" refers to a group N=N=N.

The term "keto" or "oxo" refers to a group =O.

The term "carboxy" or "carboxyl" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, cyano or —S(O)$_n$R$^a$, in which R$^a$ is alkyl, aryl or heteroaryl and n is 0, 1, or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "carboxyalkyl" refers to the groups —C(O)O-alkyl or —C(O)O— cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "aminocarbonyl" refers to the group —C(O) NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "alkoxycarbonylamino" refers to the group —N(R$^d$)C(O)OR in which R is alkyl and R$^d$ is hydrogen or alkyl. Unless otherwise constrained by the definition, each alkyl may optionally be further substituted by 1, 2, or 3 substituents selected from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "aminocarbonylamino" refers to the group —NR'C(O)NRR, wherein R$^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —S(O)$_2$R, in which R is alkyl, cycloalkyl, heterocyclyl, aryl or heteroaryl. "Substituted sulfone" refers to a group —S(O)$_2$R, in which R is substituted alkyl, substituted cycloalkyl, substituted heterocyclyl, substituted aryl or substituted heteroaryl, as defined herein.

The term "aminosulfonyl" refers to the group —S(O)$_2$NRR, wherein each R is independently hydrogen, alkyl, cycloalkyl, aryl, heteroaryl or heterocyclyl. Unless otherwise constrained by the definition, all substituents may optionally be further substituted by 1, 2, or 3 substituents selected from alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g., forming a branch), and also includes embodiments in which the substituent may be a diradical bridging group bound to two adjacent atoms of the substituted group, thereby forming a fused ring on the substituted group.

A "biological membrane" is any membrane, typically made from specialized cells or tissues, that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth. In certain contexts the term "biological membrane" does not include those membranes associated with the middle gastro-intestinal tract (e.g., stomach and small intestines). For example, in some instances it may be desirable for a compound of the invention to have a limited ability to cross the blood-brain barrier, yet be desirable that the same compound cross the middle gastro-intestinal tract.

A "biological membrane crossing rate," as used herein, provides a measure of a compound's ability to cross a biological membrane (such as the membrane associated with the blood-brain barrier). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known in the art, described herein and/or in the relevant literature, and/or can be determined by one of ordinary skill in the art.

"Pharmacologically effective amount," "physiologically effective amount," and "therapeutically effective amount" are used interchangeably herein to mean the amount of a compound of the present invention alone or present in a composition that is needed to provide a threshold level of the compound in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

The term "pharmaceutically acceptable salt" refers to non-toxic salts of the compounds of this invention. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Also included are salts with acidic amino acid such as aspartate and glutamate. Base addition salts include: alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with a basic amino acid such as lysine salt and arginine salt. The salts may be in some cases hydrates or solvates.

The term "solvate" refers to a complex formed by the combining of a compound of the present invention and a solvent.

The term "hydrate" refers to the complex formed by the combining of a compound of the present invention and water.

The term "patient," refers to a living organism suffering from or prone to a condition that can be prevented or treated by administration of a compound as described herein, and includes both humans and animals.

Compounds

In certain embodiments, provided herein is a compound of Formula I:

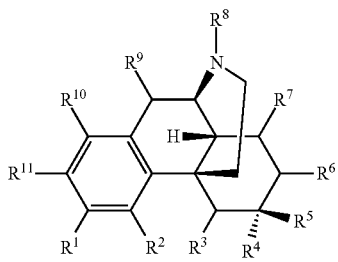

Formula I wherein:
$R^1$ is selected from hydroxyl, —O—($R^{12}$), —O—C(O)—N($R^{13}$)($R^{14}$), —NHC(O)—($R^{15}$), —NH—C(O)—NH($R^{16}$), —N($R^{17}$)($R^{18}$), —NHC(O)O—($R^{19}$), —NH—S(O)$_2$—($R^{20}$), —C(O)—N($R^{21}$)($R^{22}$), optionally substituted heteroaryl, and —X-POLY;

$R^2$ is selected from hydrogen, —O—($R^{25}$) and —X-POLY, or $R^1$ and $R^2$ are taken together with their intervening atoms to form a fused, optionally substituted heteroaryl or optionally substituted heterocyclyl;

$R^3$ is selected from hydrogen and X-POLY;

$R^4$ is selected from hydrogen, —O—($R^{26}$) and —X-POLY;

$R^5$ is selected from hydrogen, —O—($R^{27}$) and —X-POLY; or $R^4$ and $R^5$ are optionally taken together to form a carbonyl;

$R^6$ is selected from hydrogen, OH, and X-POLY; or $R^5$ and $R^6$ are taken together with their intervening atoms to form a fused, optionally substituted heteroaryl wherein $R^4$ is absent;

$R^7$ is selected from hydrogen, OH, and X-POLY;

$R^8$ is selected from hydrogen, optionally substituted alkyl, optionally substituted heterocyclyl, —C(O)—N($R^{23}$)($R^{24}$) and —X-POLY;

$R^{11}$ is hydrogen, or $R^1$ and $R^{11}$ are taken together with their intervening atoms to form a fused, optionally substituted heteroaryl or optionally substituted heterocyclyl, provided the heteroaryl is not thiazole substituted with —NH$_2$ when $R^8$ is methyl;

$R^9$ is selected from hydrogen and X-POLY;

$R^{10}$ is selected from hydrogen, OH, and X-POLY;

$R^{12}$ is selected from optionally substituted alkyl, aryl, and heteroaryl;

$R^{13}$ is selected from hydrogen and optionally substituted alkyl $R^{14}$ is selected from hydrogen and optionally substituted alkyl $R^{15}$ is selected from hydrogen, optionally substituted alkyl, optionally substituted aryl, X-POLY, and optionally substituted heteroaryl;

$R^{16}$ is selected from hydrogen, optionally substituted alkyl, optionally substituted aryl, and optionally substituted heteroaryl, provided that when $R^{16}$ is phenyl the phenyl is substituted with —X-POLY or if $R^{17}$ is benzyl the benzyl is substituted with —X-POLY;

$R^{17}$ is selected from hydrogen, optionally substituted alkyl, optionally substituted aryl, and optionally substituted heteroaryl, provided that when $R^{17}$ is phenyl the phenyl is substituted with —X-POLY or if $R^{17}$ is benzyl the benzyl is substituted with —X-POLY;

$R^{18}$ is selected from hydrogen, X-POLY, optionally substituted alkyl, optionally substituted aryl, and optionally substituted heteroaryl provided that when $R^{17}$ is phenyl the phenyl is substituted with —X-POLY;

$R^{19}$ is selected from hydrogen, optionally substituted alkyl, optionally substituted aryl, and optionally substituted heteroaryl;

$R^{20}$ is selected from hydrogen, optionally substituted alkyl, optionally substituted aryl, and optionally substituted heteroaryl;

$R^{21}$ is selected from hydrogen, optionally substituted alkyl, optionally substituted aryl, and optionally substituted heteroaryl;

$R^{22}$ is selected from hydrogen, optionally substituted alkyl, optionally substituted aryl, and optionally substituted heteroaryl;

$R^{23}$ is selected from hydrogen and optionally substituted alkyl;

$R^{24}$ is selected from hydrogen and optionally substituted alkyl;

$R^{25}$ is selected from hydrogen, optionally substituted alkyl, optionally substituted aryl, and optionally substituted heteroaryl;

$R^{26}$ is selected from hydrogen, optionally substituted alkyl, optionally substituted aryl, and optionally substituted heteroaryl;

$R^{27}$ is selected from hydrogen, optionally substituted alkyl, optionally substituted aryl, and optionally substituted heteroaryl; and pharmaceutically acceptable salts thereof, provided that
when $R^1$ is $OCH_3$, $R^2$ is OH, $R^8$ is methyl and $R^4$ and $R^5$ form a carbonyl,
$R^3$, $R^6$, $R^7$, and $R^{9-11}$ are not all hydrogen;
when $R^1$ is $OCH_3$, $R^8$ is methyl and $R^4$ and $R^5$ form a carbonyl,
$R^2$, $R^3$, $R^6$, $R^7$, and $R^{9-11}$ are not all hydrogen;
when $R^1$ is $OCH_3$, $R^2$ is OH, and $R^8$ is methyl,
$R^{3-7}$ and $R^{9-11}$ are not all hydrogen;
when $R^1$ is $OCH_3$ and $R^8$ is methyl,
$R^2$-$R^7$ and $R^{9-11}$ are not all hydrogen;
when $R^1$ is OH, $R^8$ is methyl and $R^4$ and $R^5$ form a carbonyl,
$R^2$, $R^3$, $R^6$, $R^7$, and $R^{9-11}$ are not all hydrogen;
when $R^1$ is $OCH_3$,
$R^{2-11}$ are not all hydrogen;
when $R^1$ is OH and $R^8$ is methyl,
$R^{2-7}$ and $R^{9-11}$ are not all hydrogen;
when $R^1$ is $OCH_2CH_2OCH_3$ and $R^8$ is methyl,
$R^{2-7}$ and $R^{9-11}$ are not all hydrogen;
when $R^1$ is OH and $R^8$ is $CH_2CH_2OCH_3$,
$R^{2-7}$ and $R^{9-11}$ are not all hydrogen;
when $R^1$ is $OCH_3$ and $R^8$ is $C(O)CH_3$ or $C(O)OCH_3$,
$R^{2-7}$ and $R^{9-11}$ are not all hydrogen;
when $R^1$ is $NH_2$ and $R^8$ is methyl,
$R^{2-7}$ and $R^{9-11}$ are not all hydrogen;
when $R^1$ is selected from $NHC(O)CH_3$, $C(O)NH_2$, and C(O)OH, and $R^8$ is methyl,
$R^{2-7}$ and $R^{9-11}$ are not all hydrogen;
when $R^1$ is OH, $R^8$ is methyl and one of $R^4$ and $R^5$ are hydroxyl,
$R^2$, $R^3$, $R^6$, $R^7$, and $R^{9-11}$ are not all hydrogen;
when $R^1$ is pyridinyl and $R^8$ is methyl,
$R^{2-7}$ and $R^{9-11}$ are not all hydrogen; and
when $R^8$ is $CH_3$ and $R^{2-7}$, $R^9$ and $R^{10}$ are hydrogen,
$R^1$ and $R^{11}$ are not taken together to form thiazole substituted with $NH_2$.

In certain embodiments, provided herein is a compound of Formula I, wherein $R^2$ is hydrogen.

In certain embodiments, provided herein is a compound of Formula I, wherein $R^3$ is hydrogen.

In certain embodiments, provided herein is a compound of Formula I, wherein $R^6$ is hydrogen.

In certain embodiments, provided herein is a compound of Formula I, wherein $R^7$ is hydrogen.

In certain embodiments, provided herein is a compound of Formula I, wherein $R^8$ is lower alkyl.

In certain embodiments, provided herein is a compound of Formula I, wherein $R^8$ is methyl.

In certain embodiments, provided herein is a compound of Formula I, wherein $R^9$ is hydrogen.

In certain embodiments, provided herein is a compound of Formula I, wherein $R^{10}$ is hydrogen.

In certain embodiments, provided herein is a compound of Formula I, wherein $R^4$ and $R^5$ are hydrogen. In certain embodiments, provided herein is a compound of Formula I, wherein $R^4$ and $R^5$ together from a carbonyl.

In certain embodiments, provided herein is a compound of Formula I, wherein $R^{11}$ is hydrogen.

In certain embodiments, provided herein is a compound of Formula I, wherein $R^1$ is selected from: —O—C(O)—N($R^{13}$)($R^{14}$), —NHC(O)—($R^{15}$), —NH—C(O)—NH($R^{16}$), —N($R^{17}$)($R^{18}$), —NHC(O)O—($R^{19}$), —NH—S(O)$_2$—($R^{20}$), —C(O)—N($R^{21}$)($R^{22}$), optionally substituted heterocyclyl, optionally substituted heteroaryl, and —X—(CH$_2$CH$_2$O)$_n$—R, where n is 1 to 30 and R is selected from hydrogen, lower alkyl; haloalkyl, and carboxyl.

In certain embodiments, provided herein is a compound of Formula I according to Formula II:

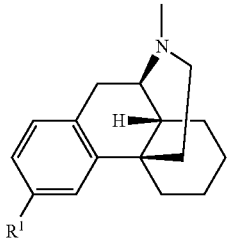

Formula II wherein:
$R^1$ is selected from —O—C(O)—N($R^{13}$)($R^{14}$), —NHC(O)—($R^{15}$), —NH—C(O)—NH($R^{11}$), —N($R^{17}$)($R^{18}$), —NHC(O)O—($R^{19}$), —NH—S(O)$_2$—($R^{20}$), —C(O)—N($R^{21}$)($R^{22}$), optionally substituted heterocyclyl, optionally substituted heteroaryl, and —X—(CH$_2$CH$_2$O)$_n$—R, where n is 1 to 30 and R is selected from hydrogen, lower alkyl, haloalkyl and carboxyl.

In certain embodiments, provided herein is a compound of Formula I or II, wherein $R^1$ is selected from:
—O—C(O)—N($R^{13}$)($R^{14}$) wherein $R^{13}$ is selected from hydrogen and optionally substituted lower alkyl and $R^{14}$ is selected from hydrogen and optionally substituted lower alkyl;

—NHC(O)—($R^{15}$) wherein $R^{15}$ is selected from hydrogen, optionally substituted phenyl, and optionally substituted lower alkyl;

—NH—C(O)—NH($R^{16}$) wherein $R^{16}$ is selected from hydrogen, optionally substituted lower alkyl, and phenyl substituted with —X—(CH$_2$CH$_2$O)$_n$—R;

—N($R^{17}$)($R^{18}$) wherein $R^{17}$ is selected from hydrogen and optionally substituted pyridinyl; and $R^{18}$ is selected from hydrogen, phenyl substituted with —X—(CH$_2$CH$_2$O)$_n$—R; optionally substituted pyridinyl, optionally substituted pyrimidinyl, optionally substituted pyrazinyl, optionally substituted pyridazinyl; optionally substituted imidazoyl, optionally substituted thiazolyl, optionally substituted pyrazolyl, optionally substituted furanyl, and optionally substituted heteroaryl;

—NHC(O)O—($R^{19}$) wherein $R^{19}$ is selected from hydrogen, optionally substituted alkyl, optionally substituted aryl, and optionally substituted heteroaryl;

—NH—S(O)$_2$—($R^{20}$) wherein $R^{20}$ is selected from hydrogen and optionally substituted lower alkyl;

—C(O)—N($R^{21}$)($R^{22}$) wherein $R^{21}$ is selected from hydrogen and optionally substituted heteroaryl and $R^{22}$ is selected from hydrogen, optionally substituted lower alkyl, and optionally substituted phenyl;

substituted pyridinyl, optionally substituted pyrazolyl, optionally substituted furanyl, and optionally substituted imidazolyl; and —X—(CH$_2$CH$_2$O)$_n$—R;

where in each instance, n is 1 to 30 and R is selected from hydrogen, lower alkyl, haloalkyl and carboxyl.

In certain embodiments, provided herein is a compound of Formula I or II, wherein R$^1$ is —O—C(O)—N(R$^{13}$)(R$^{14}$) wherein R$^{13}$ is selected from hydrogen and optionally substituted lower alkyl and R$^{19}$ is selected from hydrogen and optionally substituted lower alkyl.

In certain embodiments, provided herein is a compound of Formula I or II, wherein R$^1$ is —O—C(O)—N(R$^{13}$)(R$^{14}$) wherein R$^{11}$ is hydrogen and R$^{14}$ is selected from ethyl, ethyl substituted a group selected from hydroxyl and lower alkoxy.

In certain embodiments, provided herein is a compound of Formula I or II, wherein R$^1$ is —O—C(O)—N(R$^{13}$)(R$^{14}$) wherein R$^n$ is hydrogen and R$^{14}$ is 2-methoxyethyl.

In certain embodiments, provided herein is a compound of Formula I or II, wherein R$^1$ is —NHC(O)—(R$^{15}$), wherein R$^{15}$ is selected from hydrogen, phenyl; phenyl substituted with lower alkoxy, and lower alkyl substituted with X—(CH$_2$CH$_2$O)$_n$—R wherein n is an integer from 1 to 30, R is selected from hydrogen, CH$_3$, CF$_3$, and carboxyl, and X is selected from a covalent bond and —O—; and X—(CH$_2$CH$_2$O)$_n$—R wherein n is an integer from 1 to 30, R is selected from hydrogen, CH$_3$, CF$_3$, and carboxyl, and X is selected from a covalent bond and —O—.

In certain embodiments, provided herein is a compound of Formula I or II, wherein R$^1$ is —NHC(O)—(R$^{15}$), wherein R$^{15}$ is selected from phenyl, 2-methoxyphenyl, 3-methoxyphenyl, 4-methoxyphenyl, and methyl substituted with —X—(CH$_2$CH$_2$O)$_n$CH$_3$ wherein n is an integer from 1 to 10 and X is selected from a covalent bond and —O—.

In certain embodiments, provided herein is a compound of Formula I or II, wherein R$^1$ is —NH—C(O)—N(R$^{16}$) and wherein R$^{16}$ is selected from lower alkyl substituted with lower alkoxy.

In certain embodiments, provided herein is a compound of Formula I or II, wherein R$^{16}$ is 2-methoxyethyl.

In certain embodiments, provided herein is a compound of Formula I or II, wherein R$^1$ is —N(R$^{17}$)(R$^{18}$) wherein R$^{17}$ and R$^{18}$ are pyridinyl; or R$^{17}$ is hydrogen and R$^{18}$ is selected from pyrimidinyl, pyrazinyl, pyridazinyl, thiazolyl, pyridinyl, pyridinyl substituted with —X—(CH$_2$CH$_2$O)$_n$R wherein n is an integer from 1 to 30, R is selected from hydrogen, lower alkyl, haloalkyl, and carboxyl and X is selected from a covalent bond and —O—; and phenyl substituted with —X—(CH$_2$CH$_2$O)$_n$R wherein n is an integer from 1 to 30, R is selected from hydrogen, lower alkyl, haloalkyl, and carboxyl, and X is selected from a covalent bond and —O—.

In certain embodiments, provided herein is a compound of Formula I or II, wherein R$^1$ is —N(R$^{17}$)(R$^{18}$), wherein R$^{17}$ is hydrogen and R$^{18}$ is selected from pyrimidin-2-yl, pyrimidin-4-yl, pyrimidin-5-yl, pyrazin-2-yl, pyridazin-3-yl, pyridazin-4-yl, thiazol-2-yl, pyridin-2-yl, pyridin-3-yl, pyridin-4-yl, pyridin-3-yl substituted with —O—(CH$_2$CH$_2$O)$_n$CH$_3$ wherein n is an integer from 1 to 10, pyridin-4-yl substituted with —O—(CH$_2$CH$_2$O)$_n$CH$_3$ wherein n is an integer from 1 to 10, and phenyl substituted with —O—(CH$_2$CH$_2$O)$_n$CH$_3$ wherein n is an integer from 1 to 10.

In certain embodiments, provided herein is a compound of Formula I or II, wherein R$^1$ is —NH—S(O)$_2$—(R$^{20}$) and R$^{20}$ is lower alkyl.

In certain embodiments, provided herein is a compound of Formula I or II, wherein R$^1$ is —NH—S(O)$_2$—(R$^{20}$) and R$^{20}$ is methyl.

In certain embodiments, provided herein is a compound of Formula I or II, wherein R$^1$ is —C(O)—N(R$^{21}$)(R$^{22}$); wherein R$^{21}$ is hydrogen and R$^{22}$ is selected from phenyl, phenyl substituted with lower alkoxy, and lower alkyl substituted with —X—(CH$_2$CH$_2$O)$_n$R, wherein n is an integer from 1 to 30, R is selected from hydrogen, lower alkyl, haloalkyl, and carboxyl and X is a covalent bond or O.

In certain embodiments, provided herein is a compound of Formula I or II, wherein R$^1$ is —C(O)—N(R$^{21}$)(R$^{22}$), wherein R$^{21}$ is hydrogen and R$^{22}$ is selected from phenyl, 4-methoxyphenyl, and ethyl substituted with —O—(CH$_2$CH$_2$O)$_n$CH$_3$ wherein n is an integer from 1 to 10.

In certain embodiments, provided herein is a compound of Formula I or II, wherein R$^1$ is selected from pyrazolyl, furanyl, imidazolyl, and pyrazolyl substituted with lower alkyl substituted with —X—(CH$_2$CH$_2$O)$_n$R, wherein n is an integer from 1 to 30, R is selected from hydrogen, lower alkyl, haloalkyl, and carboxyl and X is a covalent bond or O.

In certain embodiments, provided herein is a compound of Formula I or II, wherein R$^1$ is selected from pyrazolyl, furanyl, imidazolyl, and pyrazolyl substituted with lower alkyl substituted with —O—(CH$_2$CH$_2$O)$_n$CH$_3$, wherein n is an integer from 1 to 10.

In certain embodiments, provided herein is a compound of Formula I or II, wherein R$^1$ is selected from pyridin-3-yl, 1H-pyrazol-4-yl, 1-(2-(2-methoxyethoxy)ethyl)-1H-pyrazol-4-yl, furan-3-yl, and 1H-imidazol-1-yl.

In certain embodiments, provided herein is a compound of Formula I or II, wherein R$^1$ is —X—(CH$_2$CH$_2$O)$_n$—R, where n is 1 to 30, R is selected from hydrogen, lower alkyl, haloalkyl and carboxyl, and X is a covalent bond or —O—.

In certain embodiments, provided herein is a compound of Formula I or II, wherein n is 1 to 10 and R is methyl.

In certain embodiments, provided herein is a compound of Formula I or II, wherein R$^1$ and R$^{11}$ are taken together with their intervening atoms to form a fused, optionally substituted heteroaryl, provided that the heteroaryl is not a thiazole substituted with an —NH$_2$.

In certain embodiments, provided herein is a compound of Formula I or II, wherein R$^1$ and R$^{11}$ are taken together with their intervening atoms to form an optionally substituted thiazole, optionally substituted imidazole, optionally substituted pyridine, optionally substituted pyrazine, and optionally substituted triazine.

In certain embodiments, provided herein is a compound of Formula I or II, wherein R$^1$ and R$^{11}$ are taken together with their intervening atoms to form a thiazole, imidazole, pyridine, pyrazine, or triazine.

In certain embodiments, provided herein is a compound of Formula I according to Formula III:

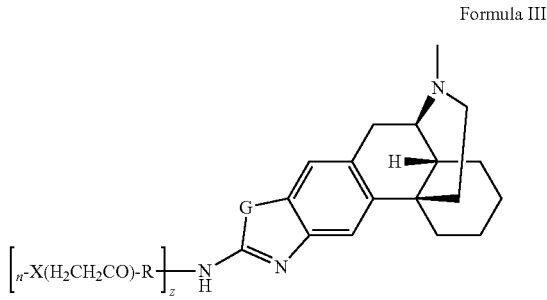

Formula III wherein:
z is 0 or 1;
G is selected from —S—, —NH—, —CH=CH—, —CH=N—, and —N=N—, provided that when G is S, z is not zero;
X is a linker;
n is 1 to 30; and
R is selected from hydrogen, lower alkyl, haloalkyl and carboxyl.

In certain embodiments, provided herein is a compound of Formula III, wherein X is selected from a covalent bond, —CH$_2$CH$_2$—, —CH$_2$C(O)—, —NH—C(=NH)—, —NHC(O)—, and

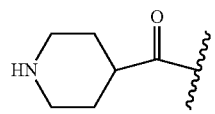

In certain embodiments, provided herein is a compound of Formula III, wherein G is S. In certain embodiments, provided herein is a compound of Formula III, wherein G is —NH—. In certain embodiments, provided herein is a compound of Formula III, wherein G is —CH=CH—. In certain embodiments, provided herein is a compound of Formula III, wherein G is —CH=N—. In certain embodiments, provided herein is a compound of Formula III, wherein G is —N=N—.

In certain embodiments, provided herein is a compound of Formula III, wherein z is 1.

In certain embodiments, provided herein is a compound of Formula III, wherein R is selected from hydrogen, CF$_3$, carboxy, and CH$_3$. In certain embodiments, provided herein is a compound of Formula III, wherein R is CH$_3$.

In certain embodiments, provided herein is a compound of Formula III, wherein n is 1 to 10.

In certain embodiments, provided herein is a compound of Formula I according to Formula IV:

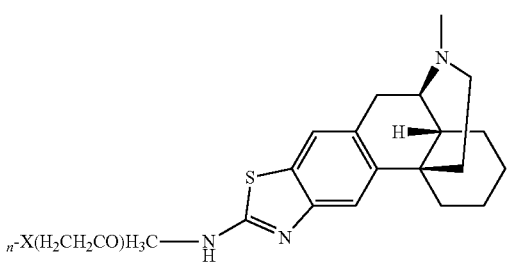

Formula IV wherein:
X is a linker; and
n is 1 to 30.

In certain embodiments, provided herein is a compound of Formula IV, wherein X is selected from a covalent bond, —CH$_2$CH$_2$—, —CH$_2$C(O)—, —NH—C(=NH)—, —NHC(O)—, and

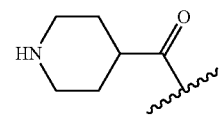

In certain embodiments, provided herein is a compound of Formula IV, wherein n is 1 to 10.

In certain embodiments, provided herein is a compound of Formula I according to Formula V:

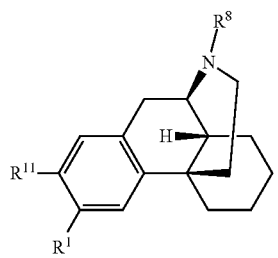

Formula V wherein:
$R^1$ is selected from hydroxyl, optionally substituted heteroaryl, —N($R^{17}$)($R^{18}$); and —O—($R^{12}$); and is hydrogen, or $R^{11}$ and are taken together with their intervening atoms to form a fused, optionally substituted heteroaryl;
$R^8$ is selected from —C(O)—N($R^{23}$)($R^{24}$), substituted alkyl, optionally substituted heterocyclyl, or X—(CH$_2$CH$_2$O)$_n$R, wherein X is a covalent bond or a lower alkyl group, n is 1 to 30, and R is selected from hydrogen, lower alkyl, haloalkyl and carboxyl, provided that when $R^1$ is hydroxyl and $R^8$ is X—(CH$_2$CH$_2$O)$_n$CH$_3$, n is 2 to 30;
$R^{12}$ is lower alkyl;
$R^{17}$ is selected from hydrogen, optionally substituted alkyl, optionally substituted awl, and optionally substituted heteroaryl;
$R^{18}$ is selected from hydrogen, optionally substituted alkyl, optionally substituted aryl, and optionally substituted heteroaryl;
$R^{23}$ is hydrogen; and
$R^{24}$ is lower alkyl.

In certain embodiments, provided herein is a compound of Formula V, wherein $R^8$ is —C(O)—N($R^{23}$)($R^{24}$), $R^{23}$ is hydrogen, and $R^{24}$ is ethyl.

In certain embodiments, provided herein is a compound of Formula V, wherein $R^8$ is optionally substituted heterocyclyl or lower alkyl substituted with optionally substituted heterocyclyl.

In certain embodiments, provided herein is a compound of Formula V, wherein $R^8$ is a 4 to 6 membered heterocyclyl having an oxygen within the heterocyclyl ring or $R^8$ is methyl substituted with a 4 to 6 membered heterocyclyl having an oxygen within the heterocyclyl ring.

In certain embodiments, provided herein is a compound of Formula V, wherein $R^8$ is oxetanyl or oxetanylmethyl.

In certain embodiments, provided herein is a compound of Formula V, wherein $R^8$ is $X-(CH_2CH_2O)_nR$, wherein X is a covalent bond, n is 1 to 30; and R is selected from hydrogen, $CH_3$, $CF_3$, and carboxyl, provided that when $R^1$ is hydroxyl and $R^8$ is $X-(CH_2CH_2O)_nCH_3$, n is 2 to 30.

In certain embodiments, provided herein is a compound of Formula V, wherein n is 1 to 10.

In certain embodiments, provided herein is a compound of Formula V, wherein $R^1$ is selected from hydroxyl, methoxy, ethoxy, optionally substituted pyrazolyl, and $-N(R^{17})(R^{18})$ where $R^{17}$ is hydrogen and $R^{18}$ is optionally substituted heteroaryl or hydrogen.

In certain embodiments, provided herein is a compound of Formula V, wherein $R^1$ is selected from hydroxyl, methoxy, ethoxy, pyrazol-4-yl, and $-N(R^{17})(R^{18})$ where $R^{17}$ is hydrogen and $R^{18}$ is selected from hydrogen, 5-fluoropyridin-3-yl, pyridin-4-yl, pyridin-3-yl, and pyridazin-4-yl.

In certain embodiments, provided herein is a compound of Formula V, wherein $R^1$ is methoxy and is hydrogen.

In certain embodiments, provided herein is a compound of Formula V, wherein $R^1$ is hydroxyl.

In certain embodiments, provided herein is a compound of Formula V, wherein $R^1$ and $R^{11}$ are taken together with their intervening atoms to form a fused, optionally substituted thiazole.

In certain embodiments, provided herein is a compound of Formula V, wherein $R^1$ and $R^{11}$ are taken together with their intervening atoms to form a fused thiazole substituted with $NH_2$ or $NH-X-(CH_2CH_2O)_n-R$, where X is a linker; n is 1 to 30; and R is selected from hydrogen, lower alkyl, haloalkyl and carboxyl.

In certain embodiments, provided herein is a compound of Formula V, wherein $R^1$ and are taken together with their intervening atoms to form a fused thiazole substituted with $NH_2$.

In certain embodiments, provided herein is a compound of Formula V, wherein X is selected from a covalent bond, $-CH_2CH_2-$, $-CH_2C(O)-$, $-NH-C(=NH)-$, $-NHC(O)-$, and

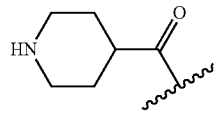

In certain embodiments, provided herein is a compound of Formula V, wherein R is $CH_3$.

In certain embodiments, provided herein is a compound of Formula V, wherein $R^1$ is hydroxyl.

In certain embodiments, provided herein is a compound of Formula I according to Formula VI:

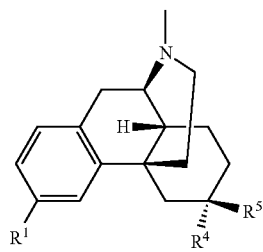

Formula VI wherein:
$R^1$ is selected from hydroxyl and $-O-(R^{12})$;
$R^4$ is selected from hydrogen and $-X-(CH_2CH_2O)_nR$,
$R^5$ is selected from hydrogen and $-X-(CH_2CH_2O)_nR$,
$R^{12}$ is a lower alkyl;
each X is selected from a covalent bond, $-O-$, and lower alkyl;
each n is 1 to 30; and
each R is selected from hydrogen, lower alkyl, haloalkyl, and carboxy;
provided that when $R^4$ is H, $R^5$ is $-X-(CH_2CH_2O)_nR$; and
provided that when $R^5$ is H, $R^4$ is $-X-(CH_2CH_2O)_nR$.

In certain embodiments, provided herein is a compound of Formula VI, wherein:
$R^1$ is selected from hydroxyl and $-O-CH_3$;
$R^4$ is selected from hydrogen and $-O-(CH_2CH_2O)_nCH_3$;
$R^5$ is selected from hydrogen and $-O-(CH_2CH_2O)_nCH_3$; and
each n is independently selected from 1 to 30.

In certain embodiments, provided herein is a compound of Formula VI, wherein each n is selected from 1 to 10.

In certain embodiments, provided herein is a compound of Formula I according for Formula VII:

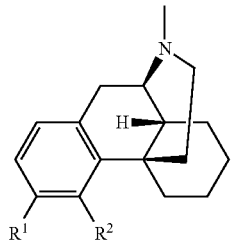

Formula VII wherein:
$R^1$ is selected from hydroxyl and $-O-(R^{12})$;
$R^2$ is selected from $-O-(R^{25})$ and $-X-(CH_2CH_2O)_n-R$; or $R^1$ and $R^2$ are taken together with their intervening atoms to form a fused, optionally substituted heteroaryl;
$R^{12}$ is a lower alkyl;
$R^{25}$ is a lower alkyl;
X is selected from a covalent bond, $-O-$, and lower alkyl;
n is 1 to 30; and
R is selected from hydrogen, lower alkyl, haloalkyl and carboxyl.

In certain embodiments, provided herein is a compound of Formula VII, wherein: $R^1$ is selected from hydroxyl and methoxy; and $R^2$ is selected from $-O(CH_2CH_2O)_nCH_3$, wherein n is 1 to 30.

In certain embodiments, provided herein is a compound of Formula VII, wherein n is 1 to 10.

In certain embodiments, provided herein is a compound of Formula VII, wherein $R^1$ and $R^{11}$ are taken together with their intervening atoms to form a fused, optionally substituted thiazole. In certain embodiments, provided herein is a compound of Formula VII, wherein $R^1$ and $R^{11}$ are taken together with their intervening atoms to form a fused thiazole substituted with $NH_2$ or $NH-X-(CH_2CH_2O)_n-R$, where X is a linker, n is 1 to 30; and R is selected from hydrogen, lower alkyl, haloalkyl and carboxyl. In certain embodiments, provided herein is a compound of Formula VII, wherein R¹ and R¹¹ are taken together with their intervening atoms to form a fused thiazole substituted with NH₂.

In certain embodiments, provided herein is a compound of Formula VII, wherein X is selected from a covalent bond, —CH₂CH₂—, —CH₂C(O)—, —NH—C(=NH)—, —NHC(O)—, and

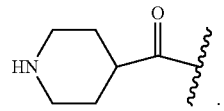

In certain embodiments, provided herein is a compound of Formula VII, wherein R is CH₃.

In certain embodiments, provided herein is a compound of Formula VII, wherein n is 1 to 10.

In certain embodiments, provided herein is a compound of Formula I according to Formula VIII:

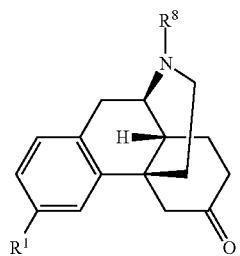

Formula VIII wherein:

R¹ is selected from hydroxyl, —O—(R¹²) and —X—(CH₂CH₂O)$_n$—R;

R⁸ is selected from optionally substituted alkyl and —X—(CH₂CH₂O)$_n$—R;

R¹² is a lower alkyl;

each X is selected from a covalent bond, —O—, or a lower alkyl group;

each n is 1 to 30; and each R is selected from hydrogen, lower alkyl, haloalkyl and carboxyl;

provided that when R¹² is CH₃, R⁸ is not CH₃.

In certain embodiments, provided herein is a compound according to Formula VIII, wherein R¹ is selected from hydroxyl, —O—(CH₂CH₂O)$_n$CH₃ where n is 1 to 10, and —O—(R¹²), where R¹² is lower alkyl.

In certain embodiments, provided herein is a compound according to Formula VIII, wherein R¹ is selected from hydroxyl, —O—(CH₂CH₂O)$_n$CH₃ where n is 1 to 10, and —O—CH₃.

In certain embodiments, provided herein is a compound according to Formula VIII, wherein R⁸ is methyl. In certain embodiments, provided herein is a compound according to Formula VIII, wherein R⁸ is —(CH₂CH₂O)$_n$CH₃ and n is 1 to 30.

In certain embodiments, provided herein is a compound according to Formula VIII, wherein n is 1 to 10.

In certain embodiments, provided herein is a compound of Formula I according to Formula IX:

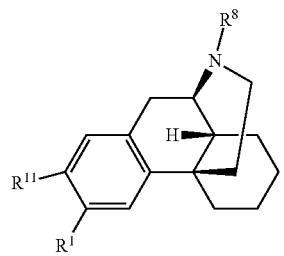

Formula IX and pharmaceutically acceptable salts thereof, wherein:

R¹ is —OH, —NH₂, or

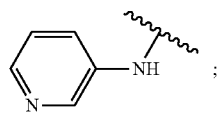

;

R¹¹ is hydrogen; or R¹ and R¹¹ together with their intervening atoms form

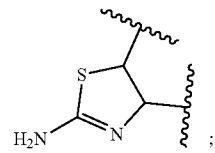

;

R⁸ is methyl or —(CH₂CH₂O)$_n$CH₃; and n is 1 or 2.

The compounds of the invention, if chiral, may be in a racemic mixture, or an optically active form, for example, a single optically active enantiomer, or any combination or ratio of enantiomers (i.e., scalemic mixture). In addition, the compound may possess one or more geometric isomers. With respect to geometric isomers, a composition can comprise a single geometric isomer or a mixture of two or more geometric isomers. A compound for use in the present invention can be in its customary active form, or may possess some degree of modification.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Selected substituents comprising the compounds of Formula I may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

In some instances, names of compounds of the present disclosure are provided using ACD/Name software for naming chemical compounds (Advanced Chemistry Development, Inc., Toronto, Canada). For example, a compound of the formula

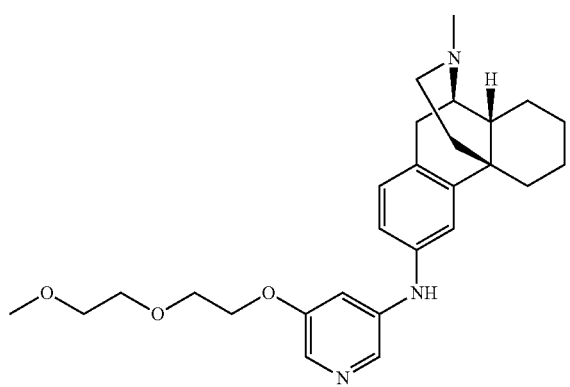 [SMILES: COCCOCCOc1cncc(Nc2ccc3c(c2)[C@@]24CCCC[C@H]2[C@@H](C3)N(C)CC4)c1]

is named N-{5-[2-(2-Methoxyethoxy)ethoxy]pyridin-3-yl}-17-methylmorphinan-3-amine.

Compound Preparation

The compounds of the present invention may be prepared using techniques known to one of skill in the art. As disclosed herein, certain compounds of Formula I comprise at least one —X-POLY group. The incorporation of the —X-POLY group into a compound of Formula I can be achieved by reacting a synthetic precursor/synthetic intermediate of a compound of Formula I with a -POLY group having a functional group that is capable of reacting with a functional group on the synthetic intermediate to compound of Formula I. The synthetic intermediate of a compound of Formula I may in certain embodiments possess a group suitable for covalent attachment of the oligomer. Such groups include, but are not limited to, a free hydroxyl, carboxyl, carbonyl, thio, amino group, or the like. Such groups can be incorporated into the synthetic intermediate to provide a point of attachment for the oligomer. As such, the oligomer can be incorporated at various stages of the synthesis, depending on the synthetic scheme. The introduction and conversion of functional groups in a synthetic intermediate are transformations that are generally known to those of skill in the art and can be found in the relevant texts. See e.g. M. Smith, *March's Advanced Organic Chemistry: Reactions, Mechanisms and Structure*, (7$^{th}$ ed. 2013); Carey and Sundberg, *Advanced Organic Chemistry*, (5$^{th}$ ed. 2007).

The group "X" adjacent to POLY in the compound of Formula I is often formed by reaction of a functional group on a terminus of the oligomer (or one or more monomers when it is desired to "grow" the oligomer onto the compound of the present invention) with a corresponding functional group within synthetic precursor/intermediate to a compound of Formula I. For example, an amino group on an oligomer may be reacted with a carboxylic acid or an activated carboxylic acid derivative on the intermediate, or vice versa, to produce an amide linkage. Alternatively, reaction of an amine on an oligomer with an activated carbonate (e.g., succinimidyl or benzotriazyl carbonate) on the intermediate, or vice versa, forms a carbamate linkage. Reaction of an amine on an oligomer with an isocyanate (R—N=C=O) on an intermediate, or vice versa, forms a urea linkage (R—NH—(C=O)—NH—R'). Further, reaction of an alcohol (alkoxide) group on an oligomer with an alkyl halide, or halide group within an intermediate, or vice versa, forms an ether linkage. In yet another approach, an intermediate having an aldehyde function is coupled to an oligomer amino group by reductive amination, resulting in formation of a secondary amine linkage between the oligomer and the compound (or intermediate thereof) of the present invention.

POLY Group

Accordingly, each "POLY" (oligomer) is composed of up to three different monomer types selected from the group consisting of: alkylene oxide, such as ethylene oxide or propylene oxide; olefinic alcohol, such as vinyl alcohol; 1-propenol or 2-propenol; vinyl pyrrolidone: hydroxyalkyl methacrylamide or hydroxyalkyl methacrylate, where in certain embodiments, alkyl is methyl; α-hydroxy acid, such as lactic acid or glycolic acid; phosphazene, oxazoline, amino acids, carbohydrates such as monosaccharides, saccharide or mannitol; and N-acryloylmorpholine. In certain embodiments, monomer types include alkylene oxide, olefinic alcohol, hydroxyalkyl methacrylamide or methacrylate, N-acryloylmorpholine, and α-hydroxy acid. In certain embodiments, each oligomer is, independently, a co-oligomer of two monomer types selected from this group, or, in certain embodiments, is a homo-oligomer of one monomer type selected from this group.

The two monomer types in a co-oligomer may be of the same monomer type, for example, two alkylene oxides, such as ethylene oxide and propylene oxide. In certain embodiments, the oligomer is a homo-oligomer of ethylene oxide. Usually, although not necessarily, the terminus (or termini) of the oligomer that is not covalently attached to a compound (or intermediate thereof) of the present invention is capped to render it unreactive. Alternatively, the terminus may include a reactive group. When the terminus is a reactive group, the reactive group is either selected such that it is unreactive under the conditions of formation of the final oligomer or during covalent attachment of the oligomer to a compound (or intermediate thereof) of the present invention, or it is protected as necessary. One common end-functional group is hydroxyl or —OH, particularly for oligoethylene oxides.

The water-soluble oligomer (e.g., "POLY" in the structures provided herein) can have any of a number of different geometries. For example, it can be linear, branched, or forked. Most typically, the water-soluble oligomer is linear or is branched, for example, having one branch point. Although much of the discussion herein is focused upon poly(ethylene oxide) as an illustrative oligomer, the discussion and structures presented herein can be readily extended to encompass any of the water-soluble oligomers described above.

The molecular weight of the water-soluble oligomer, excluding the linker portion, in certain embodiments is generally relatively low. For example, the molecular weight of the water-soluble oligomer is typically below about 2200 Daltons, and more typically at around 1500 Daltons or below. In certain other embodiments, the molecular weight of the water-soluble oligomer may be below 800 Daltons.

In certain embodiments, exemplary values of the molecular weight of the water-soluble oligomer include less than or equal to about 500 Daltons, or less than or equal to about 420 Daltons, or less than or equal to about 370 Daltons, or less than or equal to about 370 Daltons, or less than or equal to about 325 Daltons, less than or equal to about 280 Daltons, less than or equal to about 235 Daltons, or less than or equal to about 200 Daltons, less than or equal to about 175 Daltons, or less than or equal to about 150 Daltons, or less than or equal to about 135 Daltons, less than or equal to about 90 Daltons, or less than or equal to about 60 Daltons, or even less than or equal to about 45 Daltons.

In certain embodiments, exemplary values of the molecular weight of the water-soluble oligomer, excluding the linker portion, include: below about 1500 Daltons; below about 1450 Daltons; below about 1400 Daltons; below about 1350 Daltons; below about 1300 Daltons; below about 1250 Daltons; below about 1200 Daltons; below about 1150 Daltons; below about 1100 Daltons; below about 1050 Daltons; below about 1000 Daltons; below about 950 Daltons; below about 900 Daltons; below about 850 Daltons; below about 800 Daltons; below about 750 Daltons; below about 700 Daltons; below about 650 Daltons; below about 600 Daltons; below about 550 Daltons; below about 500 Daltons; below about 450 Daltons; below about 400 Daltons; and below about 350 Daltons; but in each case above about 250 Daltons.

In certain embodiments, the number of monomers in the water-soluble oligomer falls within one or more of the following inclusive ranges: between 1 and 30 (i.e., is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30); between 1 and 25 (i.e., is selected from 1, 2, 3, 4, 5, 6, 7, 8, 9, 10, 11, 12, 13, 14, 15, 16, 17, 18, 19, 20, 21, 22, 23, 24, and 25); between 1 and 20 (i.e., is selected from 1, 2, 3, 4, 5, 6, 7, 8, 9, 10, 11, 12, 13, 14, 15, 16, 17, 18, 19, and 20); between 1 and 15 (is selected from 1, 2, 3, 4, 5, 6, 7, 8, 9, 10, 11, 12, 13, 14, 15); between 1 and 10 (i.e., is selected from 1, 2, 3, 4, 5, 6, 7, 8, 9, and 10); between 10 and 25 (i.e., is selected from 10, 11, 12, 13, 14, 15, 16, 17, 18, 19, 20, 21, 22, 23, 24, and 25); and between 15 and 20 (i.e., is selected from 15, 16, 17, 18, 19, and 20). In certain instances, the number of monomers in series in the oligomer (and the corresponding compound) is one of 1, 2, 3, 4, 5, 6, 7, 8, 9, 10, 11, 12, 13, 14, 15, 16, 17, 18, 19, 20, 21, 22, 23, 24, or 25. Thus, for example, when the water-soluble oligomer includes $CH_3—(OCH_2CH_2)_n—$, "n" is an integer that can be 1, 2, 3, 4, 5, 6, 7, 8, 9, 10, 11, 12, 13, 14, 15, 16, 17, 18, 19, 20, 21, 22, 23, 24, or 25. In certain embodiments, the number of monomers in the water-soluble oligomer falls within one or more of the following inclusive ranges: between 1 and 5 (i.e., is selected from 1, 2, 3, 4, and 5); between 1 and 4 (i.e., can be 1, 2, 3, or 4); between 1 and 3 (i.e., selected from 1, 2, or 3); between 1 and 2 (i.e., can be 1 or 2); between 2 and 5 (i.e., can be selected from 2, 3, 4, and 5); between 2 and 4 (i.e., is selected from 2, 3, and 4); between 2 and 3 (i.e., is either 2 or 3); between 3 and 5 (i.e., is either 3, 4 or 5); between 3 and 4 (i.e., is 3 or 4); and between 4 and 5 (i.e., is 4 or 5). In a specific instance, the number of monomers in series in the oligomer (and the corresponding compound) is selected from 1, 2, 3, 4, or 5. Thus, for example, when the water-soluble oligomer includes $CH_3—(OCH_2CH_2)_n—$, "n" is an integer that can be 1, 2, 3, 4, or 5.

When a water-soluble oligomer is attached to the synthetic intermediate of a compound of Formula I (in contrast to the step-wise addition of one or more monomers to effectively "grow" the oligomer onto the compound of Formula I or synthetic intermediate thereof), the composition containing an activated form of the water-soluble oligomer may be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and in certain embodiments, is 1.001 or less, and in certain embodiments is 1.0005 or less. In certain embodiments, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

In certain embodiment, the water-soluble oligomer is obtained from a composition that is unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble oligomers can be prepared as described in Chen and Baker, *J. Org. Chem.* 6870-6873 (1999), WO 02/098949, and U.S. Patent Application Publication 2005/0136031.

Oligomer Functional Group

As stated above, the water-soluble oligomer includes at least one functional group prior to reaction with the synthetic intermediate of a compound of Formula I. The functional group typically comprises an electrophilic or nucleophilic group for covalent attachment to the intermediate, depending upon the reactive group contained within the intermediate. Examples of nucleophilic groups that may be present in either the oligomer or the intermediate include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most intermediates will possess a free hydroxyl, amino, thio, aldehyde, ketone, or carboxyl group for reaction with the functional group on the oligomer. In instances where no water-soluble oligomer is present on the compound of Formula I, similar functional groups can further be utilized to functionalize a synthetic intermediate of Formula I to arrive at a compound of Formula I.

Examples of electrophilic functional groups that may be present in either an oligomer, reactant, or the synthetic intermediate of a compound of Formula I include carboxylic acid, carboxylic ester; particularly imide esters, orthoester, carbonate, isocyanate, isothiocyanate, aldehyde, ketone, thione, alkenyl, acrylate; methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

It is possible, for example, to react a synthetic intermediate of a compound of Formula I bearing a carboxyl group by coupling it to an amino-terminated oligomeric ethylene glycol, to provide a synthetic intermediate for further modification or a compounds of Formula I wherein X comprises an amide. This can be performed, for example, by combining the carboxyl group-bearing intermediate with the amino-terminated oligomeric ethylene glycol in the presence of a coupling reagent, (such as dicyclohexylcarbodiimide or "DCC") in an anhydrous organic solvent. Similarly, the above reaction may take place between a synthetic intermediate of a compound of Formula I bearing an amino group and a carboxyl-terminated oligomeric ethylene glycol. The above reactions can also be used to form compounds of Formula I, where the reactant is not an oligomer, but contains an amine or carboxylic acid group for reacting with the synthetic intermediate of a compound of Formula I.

Further, it is possible to react a synthetic intermediate of a compound of Formula I bearing a hydroxyl group with an oligomeric ethylene glycol halide to result in a synthetic intermediate for further modification or a compound of Formula I wherein X comprises an ether (—O—). This can be performed, for example, by using sodium hydride to deprotonate the hydroxyl group followed by reaction with a halide-terminated oligomeric ethylene glycol. Similarly, the above reaction may take place between a synthetic intermediate of a compound of Formula I bearing a halo group and an oligomeric ethylene glycol bearing a hydroxyl group. The above reactions can also be used to form compounds of Formula I, where the reactant is not an oligomer, but contains a leaving group (e.g., halide) or hydroxyl for reacting with the synthetic intermediate of a compound of Formula I.

In another example, it is possible to convert a ketone of a synthetic intermediate of a compound of Formula I bearing a ketone group to a hydroxyl group by first reducing the ketone group to form the corresponding hydroxyl group. Thereafter, the synthetic intermediate may be reacted now bearing a hydroxyl group may be reacted as described herein.

In still another instance, it is possible to react a synthetic intermediate of a compound of Formula I bearing an amine group. In one approach, the amine group-bearing synthetic intermediate and a carbonyl-bearing oligomer are dissolved in a suitable buffer after which a suitable reducing agent (e.g., NaCNBH$_3$) is added. Following reduction, the result is an amine linkage formed between the amine group of the amine group-containing synthetic intermediate and the carbonyl carbon of the aldehyde-bearing oligomer. Similarly, the reaction may take place where the synthetic intermediate bears a carbonyl group and the oligomer bears and amine. In a similar matter, non oligomeric reactants bearing the above functional groups may be used to further functionalize the synthetic intermediates of a compound of Formula I.

In another approach for preparing a compound of the present invention, where the synthetic intermediate bears an amine group, a carboxylic acid-bearing oligomer (or other non-oligomeric reagent) and the amine group-bearing intermediate are combined, typically in the presence of a coupling reagent (e.g., DCC). The result is an amide linkage formed between the amine group of the amine group-containing synthetic intermediate and the carboxyl of the carboxylic acid-bearing reactant.

By means of further example, certain compounds of Formula I may be prepared according to the following scheme:

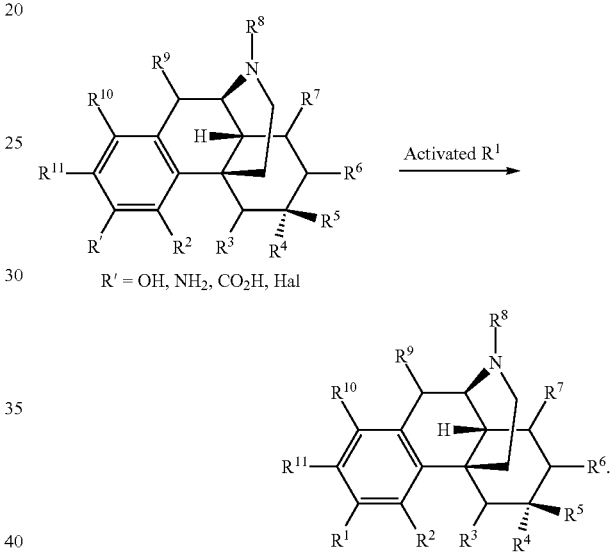

In the above reaction scheme, an "activated" $R^1$ represents a reactant that forms an $R^1$ group of Formula I after this initial reaction or through further modification. For example, when R' is $NH_2$, a compound of Formula I may be prepared by reacting an optionally substituted aryl halide or optionally substituted heteroaryl halide with R to form a compound of Formula I where $R^1$ is $NR^{16}R^{17}$ wherein $R^{16}$ is hydrogen and $R^{17}$ is an optionally substituted aryl or optionally substituted heteroaryl. Further, when R' is $NH_2$, a compound of Formula I may be prepared by reacting a carboxylic acid-bearing reactant to form a compound of Formula I where $R^1$ is —NHC(O)—$(R^{15})$. Further examples include where R' is OH and can be reacted with $R^1$-LG (LG is a leaving group), to form certain compounds of Formula I, where $R^1$ is, for example, —O—$(CH_2CH_2O)_n CH_3$ and $OR^{12}$. When $R^1$ is a halogen, a compound of Formula I where $R^1$ is optionally substituted aryl or optionally substituted heteroaryl may be formed by reacting a boronic acid derivative of the optionally substituted aryl or optionally substituted heteroaryl under conditions to result in coupling of the optionally substituted heteroaryl or optionally substituted aryl. Modifications at the $R^8$ position may performed by utilizing an unsubstituted precursor to a compound of Formula I, as depicted below:

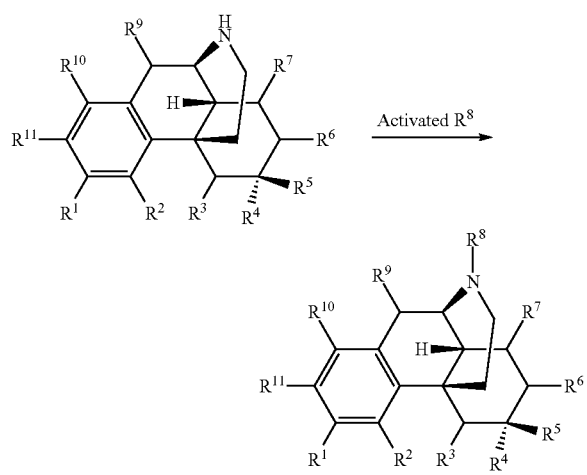

where "activated" R⁸ is a synthetic precursor to R⁸ that is capable of reacting with a free amine to form R⁸ of Formula I. Examples may include carboxylic acids, reactants containing a suitable leaving group (e.g. halogens, mesylates). The above general scheme may be used to prepare compounds of Formula I, such as where R⁸ is X—(CH₂CH₂O)$_n$—R, optionally substituted alkyl, optionally substituted heterocyclyl. The above schemes are meant to be exemplary and non-limiting. Compounds of the present invention may be made by means other than those disclosed herein or by modifying the general and/or specific examples provided herein.

Compound Activity

Certain compounds of the present invention are understood to have activity as agonists of at least one opioid receptor. In certain embodiments, the compounds are agonists of the mu opioid receptor. The ability of each compound disclosed herein to act as mu opioid agonists may be determined using methods known to those of skill in the art and as disclosed herein. For example, the activity of compounds as mu agonists can be assessed with in-vitro binding and functional assays in mu opioid receptor expressing cell lines/membranes and compared to known mu agonists.

Certain compounds of the present invention are understood to have activity as antagonists of the NMDA receptor. The ability of each compound disclosed herein to act as NMDA receptor antagonists may be determined using methods known to those of skill in the art and as disclosed herein. For example, the activity of compounds as mu agonists can be assessed with in-vitro binding and functional assays in NMDA receptor expressing cell lines/membranes and compared to known NMDA receptor antagonists.

In certain embodiments, the compounds of the present invention have measureable activities as both mu opioid agonists and NDMA receptor antagonists. In such a case, it is possible to characterize a compound by its ratio of mu opioid agonist activity to NMDA receptor antagonist activity. Exemplary ratios believed to be useful in the context of treating a patient suffering from neuropathic pain include a mu agonist activity:NMDA receptor antagonist activity ratio satisfying at least one of the following parameters: at least 0.01; at least 0.1; at least 1; at least 10; and at least 100.

In certain embodiments, the compounds of the present invention have oral analgesic activity in an automated formalin paw test. Briefly, in such an assay, the compound to be tested is administered 30-60 minutes prior to injection of 5% formalin in the hind-paw of rats and paw movements are measured using an automated system for 60 minutes post-formalin injection. In some instances, rats can be pre-treated 16-22 hours prior to injection of formalin with the cytochrome-P450 inhibitor, 1-aminobenzotriazole (ABT), which allows for the assessment of activity of the test compound in the absence of significant quantities of metabolites. ED$_{50}$ values can be calculated based on the cumulative number of flinches. Exemplary ED$_{50}$ values (based on the number of flinches 10-60 minutes versus the dose of the test compound) believed to be useful in the context of treating a patient suffering from neuropathic pain include those values satisfying at least one of the following parameters: less than 500 mg/kg; less than 250 mg/kg; less than 150 mg/kg; less than 100 mg/kg; less than 75 mg/kg; less than 60 mg/kg; less than 50 mg/kg; less than 40 mg/kg; less than 30 mg/kg; less than 20 mg/kg; less than 15 mg/kg; less than 10 mg/kg; and less than 5 mg/kg.

Preferably, a compound for use in the treatment of a patient suffering from neuropathic pain will satisfy at least one of: (a) a mu agonist activity:NMDA receptor antagonist activity ratio of at least 1; and (b) an ED$_{50}$ value based on an automatic formalin paw test (described in the preceding paragraph) of less than 250 mg/kg. More preferably, however, a compound for use in the treatment of neuropathic pain will satisfy both (a) and (b) in the preceding sentence.

CNS Properties

As recited above, in certain embodiments a compound Formula I includes at least one —X-POLY group. It is believed that the -POLY portion of the compound of Formula I acts to reduce the rate and/or extent to which the compound of Formula I crosses into the central nervous system. The propensity of a compound of the present invention to cross the blood-brain barrier may be measured by methods those described herein.

With respect to the blood-brain barrier ("BBB"), this barrier consists of a continuous layer of unique endothelial cells joined by tight junctions. The cerebral capillaries, which comprise more than 95% of the total surface area of the BBB, represent the principal route for the entry of most solutes and drugs into the central nervous system.

As will be understood by one of skill in the art, molecular size, lipophilicity, and P-glycoprotein ("PgP") interaction are among the primary parameters affecting the intrinsic BBB permeability properties of a given molecule. That is to say, these factors, when taken in combination, play a significant role in determining whether a given molecule passes through the BBB. Other factors (e.g., other active transport mechanisms) may also play a role in ultimately determining whether a given molecule will pass through the BBB.

With respect to molecular size, the molecular size plays a significant role in determining whether a given molecule will pass through the BBB. Relatively very large molecules, for example a molecule having a molecular weight of 5,000 Daltons, will not cross the BBB, whereas relatively small molecules are more likely to cross the BBB. Other factors, however, also play a role in BBB crossing. Antipyrine and atenolol are both small molecule drugs; antipyrine readily crosses the BBB, whereas passage of atenolol is very limited, or effectively non-existent. Antipyrine is an industry standard for a high BBB permeation; atenolol is an industry standard for low permeation of the BBB. See, e.g., Summerfield et al. (2007) *J Pharmacol Exp Ther* 322:205-213.

Lipophilicity is also a factor in BBB permeation. Lipophilicity may be expressed as log P (partition coefficient) or in some instances log D (distribution coefficient). The log P (or log D) for a given molecule can be readily assessed by one of ordinary skill in the art. The value for log P may be a negative number (indicating relatively greater hydrophilicity) or a positive number (indicating relatively greater hydrophobicity). As used herein when referring to log P, "more negative" means moving in the direction, on the log P scale, from positive to negative log P (e.g., a log P of 2.0 is "more negative" than a log P of 4.0, and a log P of −2.0 is "more negative" than a log P of −1.0). Molecules having a negative log P (hydrophilic molecules) generally do not permeate the BBB.

Permeability across the BBB is also dependent on the influence of transporters, such as P-glycoprotein, or PgP, an ATP-dependent efflux transporter highly expressed at the BBB. One of skill in the art can readily determine whether a compound is a substrate for PgP using in vitro methods. Compounds which are substrates for PgP in vitro likely will not permeate the BBB in vivo. Conversely, poor substrates for PgP, as assessed in vitro, are generally likely to display in vivo permeability of the BBB, provided the compound meets other criteria as discussed herein and as known to one of skill in the art. See, e.g., Tsuji (2005) *NeuroRx* 2:54-62 and Rubin et al. (1999) *Annu. Rev. Neurosci.* 22:11-28.

Even in the context of multiple variables (e.g., molecular size, lipophilicity, transporter influences, linkage type), it is possible to analyze a particular compound's ability to cross the BBB.

For any given compound whose degree of BBB crossing ability is not readily known, such BBB crossing ability can be determined using a suitable animal model such as an in situ rat brain perfusion ("RBP") model. Briefly, the RBP technique involves cannulation of the carotid artery followed by perfusion with a compound solution under controlled conditions, followed by a wash out phase to remove compound remaining in the vascular space. More specifically, in the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Wager et al. (2010) *ACS Chemical Neuroscience* 1(6): 420-434. Methods for determining a compound's PSA can be found, e.g., in, Ertl et al. (2000) *J. Med. Chem.* 43:3714-3717 and Kelder et al. (1999) *Pharm. Res.* 16:1514-1519.

Assays

The compounds of the present invention are expected to have varying degrees of activity against opioid receptors and/or NMDA receptors, as well as, varying degrees to which they cross the BBB. While the compounds of the present invention may have activity against the mu opioid receptor and/or NMDA receptors, they are believed to also have some degree of exclusion from the central nervous system based on, for example, the presence of a —X-POLY group in those compounds that have —X-POLY as a substituent.

Brain PK studies may also be conducted to measure the extent of brain entry in vivo drug concentrations that enter the CNS at various time post-dose. In brief, rodents are administered with the test article (oral, subcutaneous, or other). At various times post dose terminal blood is collected. Then the rodent is transcardially perfused with cold isotonic saline to remove most of the blood from the brain and tissues before the brain and tissues are extracted. Both plasma and brain are measured for drug content with LC/MS/MS.

The locomotor activity (LMA) model may be conducted to measure changes in activity following test article administration, which may be used to assess the CNS effects of the drug. In brief, at a predetermined time post-dose, rats are placed into observation chambers which are equipped with infrared photocells that can sense motion in the x, y, and z planes. Activity is measured as the number of photobeam breaks in a given plane (horizontal or vertical) or total distance traveled.

Compositions

In further embodiments, the invention provides for compositions comprising the compounds disclosed herein (e.g., a compound of any of Formulas I-IX) and a pharmaceutically acceptable excipient or carrier. Generally, the compound itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Non-limiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the compound or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the compound in the composition will vary depending on a number of factors, but will optimally be a therapeutically effective dose when the composition is stored in a unit dose container. A therapeutically effective dose can be determined experimentally by repeated administration of increasing amounts of the compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, in certain embodiments from about 5%-98% by weight, in certain embodiments from about 15-95% by weight of the excipient, and in certain embodiments concentrations less than 30% by weight.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

Dosage Forms

The pharmaceutical compositions can take any number of forms and the invention is not limited in this regard. In certain embodiments, preparations are in a form suitable for oral administration such as a tablet, caplet, capsule, gel cap, troche, dispersion, suspension, solution, elixir, syrup, lozenge, transdermal patch, spray, suppository, and powder. Oral dosage forms are preferred for those compounds that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the compounds described herein. In addition to the compound, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or cross-linked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the compound-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of non-aqueous solutions, suspensions, or emulsions, each typically being sterile. Examples of non-aqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compound can also be administered through the skin using conventional transdermal patch or other transdermal delivery system, wherein the compound is contained within a laminated structure that serves as a drug delivery device to be affixed to the skin. In such a structure, the compound is contained in a layer, or "reservoir," underlying an upper backing layer. The laminated structure can contain a single reservoir, or it can contain multiple reservoirs.

The compound can also be formulated into a suppository for rectal administration. With respect to suppositories, the compound is mixed with a suppository base material which is (e.g., an excipient that remains solid at room temperature but softens, melts or dissolves at body temperature) such as coca butter (*theobroma* oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

As such, provided herein is a compound described herein (e.g., a compound of any of Formulas I-IX) in a dosage form.

Methods of Use

The invention also provides a method for administering a compound provided herein to a patient suffering from a condition that is responsive to treatment with the compound such as pain, in certain embodiments, neuropathic pain. The method comprises administering, generally orally, a therapeutically effective amount of the compound (in certain embodiments provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In certain embodiments, provided herein is a method for treating an individual in need to treatment for neuropathic pain, the method comprising the step of administering to the individual a compound described herein (e.g., a compound of any of Formulas I-IX). In certain embodiments, provided herein is a method for treating an individual in need to treatment for neuropathic pain, the method comprising the step of administering to the individual a compound having the following Formula I:

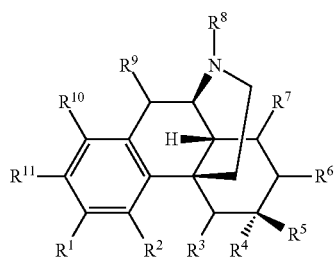

Formula I wherein:

$R^1$ is selected from hydroxyl, —O—($R^{12}$), —O—C(O)—N($R^{13}$)($R^{14}$), —NHC(O)—($R^{15}$), —NH—C(O)—NH($R^{16}$), —N($R^{17}$)($R^{18}$), —NHC(O)O—($R^{19}$), —NH—S(O)$_2$-(e), —C(O)—N($R^{21}$)($R^{22}$), optionally substituted heteroaryl, and —X-POLY;

$R^2$ is selected from hydrogen, —O—($R^{25}$) and —X-POLY;

$R^3$ is selected from hydrogen and X-POLY;

$R^4$ is selected from hydrogen, —O—($R^{26}$) and —X-POLY;

$R^5$ is selected from hydrogen, —O—($R^{27}$) and —X-POLY; or $R^4$ and $R^5$ are optionally taken together to form a carbonyl;

$R^6$ is selected from hydrogen, OH, and X-POLY; or $R^5$ and $R^6$ are taken together with their intervening atoms to form a fused, optionally substituted heteroaryl wherein $R^4$ is absent;

$R^7$ is selected from hydrogen, OH, and X-POLY;

$R^8$ is selected from hydrogen, optionally substituted alkyl, optionally substituted heterocyclyl, —C(O)—N($R^{23}$)($R^{24}$) and —X-POLY;

$R^{11}$ is hydrogen; or $R^1$ and $R^{11}$ are taken together with their intervening atoms to form a fused, optionally substituted heteroaryl or optionally substituted heterocyclyl, provided the heteroaryl is not thiazole substituted with —NH$_2$ when $R^8$ is methyl;

$R^9$ is selected from hydrogen and X-POLY;

$R^{10}$ is selected from hydrogen, OH, and X-POLY;

$R^{12}$ is selected from optionally substituted alkyl, aryl, and heteroaryl;

$R^{13}$ is selected from hydrogen and optionally substituted alkyl $R^{14}$ is selected from hydrogen and optionally substituted alkyl $R^{15}$ is selected from hydrogen, optionally substituted alkyl, optionally substituted aryl, X-POLY, and optionally substituted heteroaryl;

$R^{16}$ is selected from hydrogen, optionally substituted alkyl, optionally substituted aryl, and optionally substituted heteroaryl, provided that when $R^{16}$ is phenyl the phenyl is substituted with —X-POLY or if $R^{17}$ is benzyl the benzyl is substituted with —X-POLY;

$R^{17}$ is selected from hydrogen, optionally substituted alkyl, optionally substituted aryl, and optionally substituted heteroaryl, provided that when $R^{17}$ is phenyl the phenyl is substituted with —X-POLY or if $R^{17}$ is benzyl the benzyl is substituted with —X-POLY;

$R^{18}$ is selected from hydrogen, X-POLY, optionally substituted alkyl, optionally substituted aryl, and optionally substituted heteroaryl provided that when $R^{17}$ is phenyl the phenyl is substituted with —X-POLY;

$R^{19}$ is selected from hydrogen, optionally substituted alkyl, optionally substituted aryl, and optionally substituted heteroaryl;

$R^{20}$ is selected from hydrogen, optionally substituted alkyl, optionally substituted aryl, and optionally substituted heteroaryl;

$R^{21}$ is selected from hydrogen, optionally substituted alkyl, optionally substituted aryl, and optionally substituted heteroaryl;

$R^{22}$ is selected from hydrogen, optionally substituted alkyl, optionally substituted aryl, and optionally substituted heteroaryl;

$R^{23}$ is selected from hydrogen and optionally substituted alkyl;

$R^{24}$ is selected from hydrogen and optionally substituted alkyl;

$R^{25}$ is selected from hydrogen, optionally substituted alkyl, optionally substituted aryl, and optionally substituted heteroaryl;

R²⁶ is selected from hydrogen, optionally substituted alkyl, optionally substituted aryl, and optionally substituted heteroaryl;

R²⁷ is selected from hydrogen, optionally substituted alkyl, optionally substituted aryl, and optionally substituted heteroaryl; and pharmaceutically acceptable salts thereof.

In certain embodiments, provided herein is a method for treating an individual in need to treatment for neuropathic pain, the method comprising the step of administering to the individual a compound selected from the group consisting of: 17-[2-(2-methoxyethoxy)ethyl]-N-(pyridin-3-yl)morphinan-3-amine; 3-hydroxy-17-(2-methoxyethyl)morphinan; 3-amino-17-morphinan; (4aR,5R,11bR)-14-methyl-2,3,4,4a,5,6-hexahydro-1H-5,11b-(epiminoethano)phenanthro[3,2-d]thiazol-9-amine; and pharmaceutically acceptable salts of each of the foregoing.

The method of administering may be used to treat any condition that can be remedied or prevented by administration of a mu opioid agonist and/or a NMDA antagonist. Most commonly, the compounds provided herein are administered for the management of pain, including neuropathic pain. Those of ordinary skill in the art appreciate which conditions a specific compound can effectively treat. The actual dose to be administered will vary depending upon the age, weight, and general condition of the subject as well as the severity of the condition being treated, the judgment of the health care professional, and compound being administered. Therapeutically effective amounts are known to those skilled in the art and/or are described in the pertinent reference texts and literature. Generally, a therapeutically effective amount will range from about 0.001 mg to 1000 mg, in certain embodiments in doses from 0.01 mg/day to 750 mg/day, and in certain embodiments in doses from 0.10 mg/day to 500 mg/day.

The unit dosage of any given compound (in certain embodiments, provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are hereby incorporated by reference in their entireties.

It is to be understood that while the invention has been described in conjunction with certain and specific embodiments, the foregoing description as well as the examples that follow are intended to illustrate and not limit the scope of the invention. Other aspects, advantages and modifications within the scope of the invention will be apparent to those skilled in the art to which the invention pertains.

EXAMPLES

All chemical reagents referred to in the appended examples are commercially available unless otherwise indicated. The preparation of PEG-mers is described in, for example, U.S. Patent Application Publication No. 2005/0136031.

In the examples that follow, a compound that is provided in salt form (e.g., a compound provided as a hydrochloride salt) is understood to be in the salt form produced by the conditions recited for the compound. Thus, for example, a reference to a compound provided as the "hydrochloride salt," shall mean the hydrochloride salt form (e.g., the monohydrochloride salt, the dihydrochloride salt, the trihydrochloride salt, and so forth), which is dependent upon the number of basic sites in the compound, the pKa of those basic sites, the conditions used to form the salt, and so forth. Using conventional techniques, one of ordinary skill in the art can determine the specific salt form in view of the information provided in the example.

Example 1

Preparation of (6α)-3-methoxy-6-{2-[2-(2-methoxyethoxy)ethoxy]ethoxy}-17-methylmorphinan (1), hydrochloride salt (1)

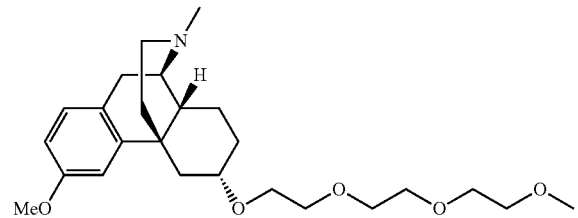

Step 1: Preparation of (6α)-3-methoxy-17-methylmorphinan-6-ol

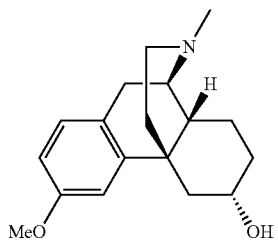 [SMILES: COc1ccc2c(c1)[C@]13CCN(C)[C@H](C2)[C@@H]1CC[C@H](O)C3]

3-Methoxy-17-methyl-morphinan-6-one (2.00 g, 7.01 mmol) was dissolved in tetrahydrofuran (20 mL) and the mixture cooled to −20° C. in a dry ice/acetone bath. A 1 M solution of K-Selectride in tetrahydrofuran (16.8 mL) was then added dropwise for fifteen minutes, and the mixture was allowed to warm up to room temperature over a two hour period. The reaction was quenched with 1M hydrochloric acid, diluted to 100 mL with water and extracted with 2×25 mL of diethyl ether. The aqueous phase was then adjusted to pH 9-10 with ammonium hydroxide and extracted with 3×25 mL of chloroform. The combined organic fractions were dried over magnesium sulfate and concentrated under vacuum to get 1.7 g of (6α)-3-Methoxy-17-methylmorphinan-6-ol (84%). ¹H NMR (250 MHz, Chloroform-d): δ 12.4 (s, 1H), 7.1 (d, J=7.5 Hz, 1H), 7.0 (d, J=2.5 Hz, 1H), 6.8 (dd, J=7.5, 2.5 Hz, 1H), 4.2 (m, 1H), 3.8 (s, 3H), 3.5 (s, 1H), 3.3-3.0 (m, 3H), 2.9 (m, 1H), 2.8-2.2 (m, 6H), 2.0 (m, 1H), 1.9-1.7 (m, 2H), 1.6 (s, 2H), 1.5-1.4 (m, 2H). MS (EI) for $C_{18}H_{25}NO_2$: 288 (MH⁺).

Step 2: Preparation of (6α)-3-methoxy-6-{2-[2-(2-methoxyethoxy)ethoxy]ethoxy}-17-methylmorphinan, hydrochloride salt (6α)-3-Methoxy-17-methylmorphinan-6-ol (500 mg, 1.74 mmol) was dissolved in tetrahydrofuran (10 mL) and the resulting mixture was chilled in an ice water bath. Sodium hydride (60% in mineral oil) (174 mg, 4.35 mmol) was then added, followed by 2-(2-(2-methoxyethoxy)ethoxy)ethyl methanesulfonate (0.84 g, 3.48 mmol). The mixture was heated at 80° C. overnight in a heat block. The material was purified by reversed phase HPLC to afford (6α)-3-methoxy-6-{2-[2-(2-methoxyethoxy)ethoxy]ethoxy}-17-methylmorphinan (1) trifluoroacetic acid salt (695 mg, 72%). $^1$H NMR (250 MHz, Chloroform-d): δ 12.2 (s, 1H), 7.0 (d, J=8.5 Hz, 1H). 6.9 (d, J=2.3 Hz, 1H), 6.7 (dd, J=8.5, 2.3 Hz, 1H), 3.8 (s, 3H), 3.7-3.5 (m, 8H), 3.4-3.0 (m, 9H), 2.9-2.0 (m, 8H), 1.9-1.3 (m, 8H). MS (EI) for $C_{25}H_{39}NO_5$: 434 (MH$^+$). Using conventional techniques, the resulting trifluoroacetic acid salt was prepared as its corresponding hydrochloride salt.

Example 2

Preparation of (6α)-3-methoxy-17-methyl-6-(2,5,8,11,14-pentaoxahexadecan-16-yloxy)morphinan (2), hydrochloride salt

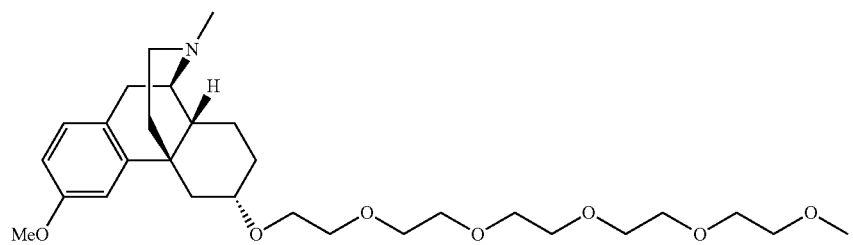

(2)

(6α)-3-Methoxy-17-methylmorphinan-6-ol (500 mg, 1.74 mmol) was dissolved in 10 mL of tetrahydrofuran and the resulting mixture was chilled in an ice water bath. Sodium hydride (60% in mineral oil) (174 mg, 4.35 mmol) was then added, followed by 2,5,8,11,14-pentaoxahexadecan-16-yl methanesulfonate (1.15 g, 3.48 mmol). The mixture was heated at 80° C. overnight in a heat block and purified by reversed phase HPLC to afford (6α)-3-methoxy-17-methyl-6-(2,5,8,11,14-pentaoxahexadecan-16-yloxy)morphinan (2) trifluoroacetic acid salt (850 mg, 77%). $^1$H NMR (250 MHz, Chloroform-d): δ 12.2 (s, 1H), 6.9 (d, J=7.5, 1H), 6.8 (d, J=2.5, 1H), 6.6 (dd, J=7.5, 2.5, 1H), 3.8 (s, 3H), 3.7-3.4 (m, 18H), 3.3-3.0 (m, 10H), 2.9-2.6 (m, 4H), 2.5-2.2 (m, 2H), 2.1-1.8 (m, 2H), 1.6-1.3 (m, 5H). MS (EI) for $C_{29}H_{47}NO_7$: 522.7 (MH$^+$). Using conventional techniques of salt preparation, the resulting trifluoroacetic acid salt was converted to the corresponding hydrochloride salt.

Example 3

Preparation of 3-hydroxy-17-(2-methoxyethyl)morphinan-6-one (3), hydrochloride salt

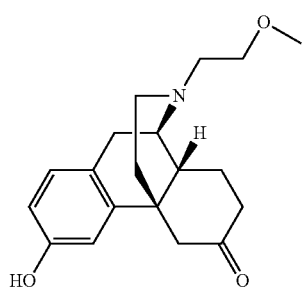

(3)

Step 1: Preparation of 3-Methoxy-17-(2-methoxyethyl)morphinan-6-one trifluoroacetic acid salt

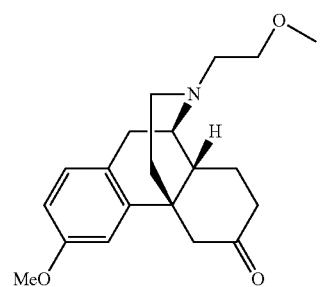 [SMILES: COCCN1CC[C@]23CC(=O)CC[C@H]2[C@H]1Cc1ccc(OC)cc13]

3-Methoxymorphinan-6-one [Zhang et al. (2007) J. Med. Chem. 50(11):2747-2751] (310 mg, 1.14 mmol), 2-methoxyethyl 4-methylbenzenesulfonate (262 mg, 1.14 mmol) and diisopropylethylamine (177 mg, 1.37 mmol) were dissolved in acetonitrile (2 mL) and allowed to react for 16 hours at 60° C. The solvent was evaporated in vacuo and the residue was purified by reversed phase HPLC to afford 3-methoxy-17-(2-methoxyethyl)morphinan-6-one trifluoroacetic acid salt (174 mg, 46.4%). MS (EI) for $C_{20}H_{27}NO_3$: 330.5 (MH$^+$).

Step 2: Preparation of 3-Hydroxy-17-(2-methoxyethyl)morphinan-6-one hydrochloride salt 3-Methoxy-17-(2-methoxyethyl)morphinan-6-one (90 mg, 0.27 mmol) was dissolved in dimethylformamide (500 uL) and potassium carbonate (74 mg, 0.54 mmol) and thiophenol (30 mg, 0.27 mmol) were added. The reaction mixture was heated at 150° C. for 16 hours. Water (3 mL) and ethyl acetate (3 mL) were added. The aqueous layer was made acidic with 0.1N citric acid, then basified with 5% sodium bicarbonate, and finally extracted with ethyl acetate (3×30 mL). The combined organic layer was concentrated in vacuo and the residue was purified by reverse phase HPLC to afford 3-hydroxy-17-(2-methoxyethyl)morphinan-6-one (3) trifluoroacetic acid salt. (34 mg, 39.9%). $^1$H NMR (250 MHz, Chloroform-d): δ 12.04 (bs, 1H), 6.99-6.81 (m, 3H), 4.11-3.85 (m, 3H), 3.39-2.95 (m, 11H), 2.7-1.4 (m, 8H). MS (EI) for $C_{19}H_{25}NO_3$: 316.4 (MH$^+$). Using conventional techniques of salt preparation, the resulting trifluoroacetic acid salt was converted to the corresponding hydrochloride salt.

Example 4

Preparation of 3-methoxy-17-{2-[2-(2-methoxyethoxy)ethoxy]ethyl}morphinan-6-one (4), hydrochloride salt

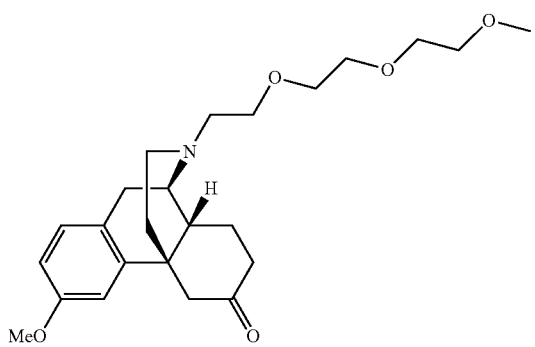

(4)

3-Methoxy-17-{2-[2-(2-methoxyethoxy)ethoxy]ethyl}morphinan-6-one (4) trifluoroacetic acid salt was prepared via the same procedure as Example 3, except in Step 1 2-(2-(2-methoxyethoxy)ethoxy)ethyl methanesulfonate was substituted for 2-methoxyethyl 4-methylbenzenesulfonate. $^1$H NMR (250 MHz, Chloroform-d): δ 12.51 (bs, 1H), 7.06 (d, J=8.5 Hz, 1H), 6.80 (m, 2H), 4.3-4.0 (m, 3H), 3.8 (s, 3H), 3.7-3.5 (m, 8H), 3.3-3.0 (m, 9H), 2.7-2.2 (m, 3H), 2.0-1.9 (m, 5H), 1.7-1.4 (m, 2H). MS (EI) for $C_{24}H_{35}NO_5$: 418.4 (MH$^+$). Using conventional techniques of salt preparation, the resulting trifluoroacetic acid salt was converted to the corresponding hydrochloride salt.

Example 5

Preparation of 3-methoxy-17-[2-(2-methoxyethoxy)ethyl]morphinan-6-one (5), hydrochloride salt

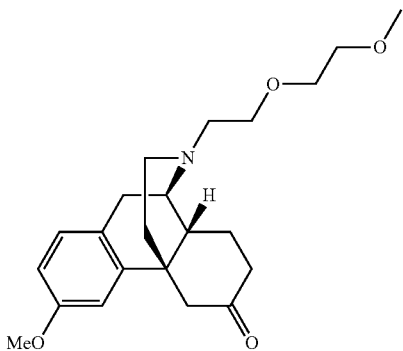

(5)

3-Methoxy-17-[2-(2-methoxyethoxy)ethyl]morphinan-6-one (5), trifluoroacetic acid salt was prepared via the same procedure as Example 3, except in Step 1 2-(2-methoxyethoxy)ethyl methanesulfonate was substituted for 2-methoxyethyl 4-methylbenzenesulfonate. $^1$H NMR (250 MHz, Chloroform-d): δ 12.51 (bs, 1H), 7.06 (d, J=8.5 Hz, 1H), 6.80 (m, 2H), 4.3-4.0 (m, 3H), 3.8 (s, 3H), 3.7-3.5 (m, 8H), 3.3-3.0 (m, 9H), 2.7-2.2 (m, 3H), 2.0-1.4 (m, 2H). MS (EI) for $C_{22}H_{31}NO_4$: 374.3 (MH$^+$). Using conventional techniques of salt preparation, the resulting trifluoroacetic acid salt was converted to the corresponding hydrochloride salt.

Example 6

Preparation of 3-hydroxy-17-{2-[2-(2-methoxyethoxy)ethoxy]ethyl}morphinan-6-one (6), hydrochloride salt

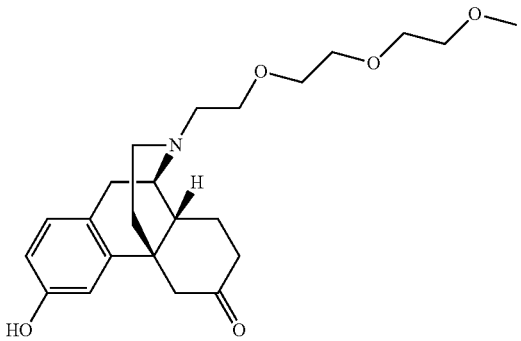

(6)

3-Hydroxy-17-{2-[2-(2-methoxyethoxy)ethoxy]ethyl}morphinan-6-one (6), trifluoroacetic acid salt was prepared by converting the compound of Example 4 as described in Example 3, step 2. $^1$H NMR (250 MHz, Chloroform-d): δ 12.13 (bs, 1H), 6.95 (bm, 1H), 6.80 (m, 2H), 4.3-3.9 (m, 3H), 3.7-2.9 (m, 20H), 2.7-0.8 (m, 7H). MS (EI) for $C_{23}H_{33}NO_5$: 404.4 (MH$^+$). Using conventional techniques of salt preparation, the resulting trifluoroacetic acid salt was converted to the corresponding hydrochloride salt.

Example 7

Preparation of 3-(2-methoxyethoxy)-17-methylmorphinan-6-one (7), hydrochloride salt

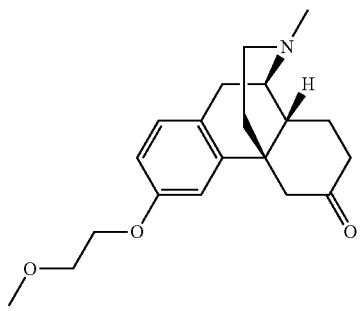

(7)

Step 1: Preparation of 3-Hydroxy-17-methylmorphinan-6-one

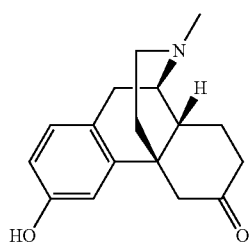 [SMILES: CN1CC[C@]23CC(=O)CC[C@H]2[C@H]1Cc1ccc(O)cc13]

A solution of sodium ethanethiolate (4.6 g, 54.68 mmol) in dimethylformamide (30 mL) was added into a solution of 3-methoxy-17-methylmorphinan-6-one (2.0 g, 7.0 mmol) in dimethylformamide (5 mL) and the resulting mixture was heated at 150° C. for 20 hours. The crude was diluted with water, acidified with 4 N hydrochloric acid (350 mL) to pH~7 and extracted with a 1:1 mixture of diethyl ether and ethyl acetate. The organic layer was dried over anhydrous magnesium sulfate and the solvent was removed under reduced pressure to yield 3-hydroxy-17-methylmorphinan-6-one (1.38 g, 73%) as a light brown solid that was used without further purification. $^1$H NMR (250 MHz, Chloroform-d): δ 11.0 (s, 1H), 7.0 (d, J=8.3 Hz, 1H), 6.7 (m, 2H), 3.8 (bs, 1H), 3.3-1.2 (m, 13H), 2.8 (m, 3H). MS (EI) for $C_{17}H_{21}NO_2$: 272 (MH$^+$).

Step 2: Preparation of 3-(2-methoxyethoxy)-17-methylmorphinan-6-one, hydrochloride salt 3-Hydroxy-17-methylmorphinan-6-one (200 mg, 0.737 mmol) was added to an 8 mL vial. 2-methoxyethyl 4-methylbenzenesulfonate (170 mg, 0.737 mmol), sodium hydride 60% in mineral oil, (88 mg, 4.977 mmol) and tetrahydrofuran (4 mL) were then added. The resulting solution was heated at 55° C. for 2 days. The solution was then acidified to pH 3 with 1 N hydrochloric acid and then washed with hexanes. The aqueous solution was then purified by reverse phase HPLC to afford 3-(2-methoxyethoxy)-17-methylmorphinan-6-one (7) trifluoroacetic acid salt. $^1$H NMR (250 MHz, Chloroform-d): δ 12.5 (s, 1H), 7.0 (d, J=8.5 Hz, 1H), 6.9 (d, J=2.5 Hz, 1H), 6.8 (dd, J=8.7, 2.3 Hz, 1H), 4.1 (t, J=4.5 Hz, 2H), 3.7 (t, J=5.5 Hz, 5H), 3.5 (s, 3H), 3.3-1.2 (m, 14H). MS (EI) for $C_{20}H_{27}NO_3$: 330.2 (MH$^+$).

The resulting trifluoroacetic acid salt was treated with sodium bicarbonate and extracted with chloroform. The freebase was solved in acetonitrile and 2.0 M hydrochloric acid in diethyl ether was added. This solution was then lyophilized to give the corresponding hydrochloride salt as a pale yellow oil (90 mg, 42.4%).

Example 8

Preparation of 17-methyl-3-(2,5,8,11,14-pentaoxahexadecan-16-yloxy)morphinan-6-one (8), hydrochloride salt

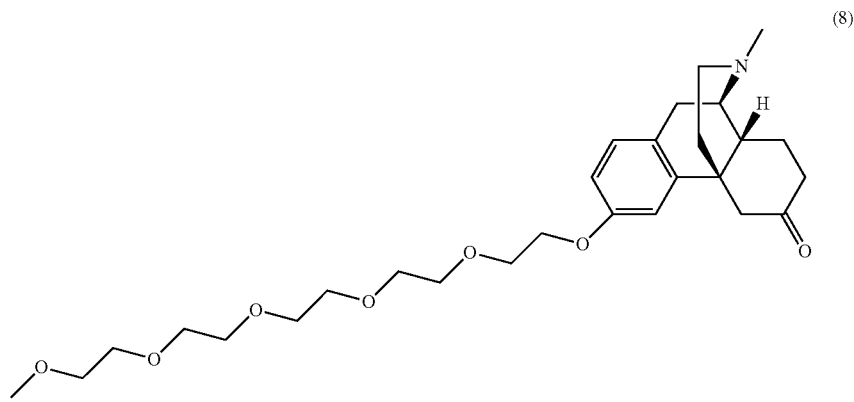 [SMILES: COCCOCCOCCOCCOCCOc1ccc2c(c1)[C@]13CCN(C)[C@H](C2)[C@@H]1CCC(=O)C3]

(8)

3-Hydroxy-17-methylmorphinan-6-one (110 mg, 0.400 mmol) was added to an 8 mL vial with a stirring bar. 2,5,8,11,14-pentaoxahexadecan-16-yl methanesulfonate (132 mg, 0.040 mmol), potassium carbonate (102 mg, 0.738 mmol) and acetonitrile (2 mL) were then added. The resulting solution was heated at 50° C. for 2.5 hours, then at 55°

C. for 16 hours and finally at 60° C. for 2 days. The solution was decanted off of the potassium carbonate and was concentrated. The resulting solution was then purified by reverse phase HPLC to afford 17-methyl-3-(2,5,8,11,14-pentaoxahexadecan-16-yloxy)morphinan-6-one (8) trifluoroacetic acid salt. $^1$H NMR (250 MHz, Chloroform-d): δ 12.5 (s, 1H), 7.0 (d, J=7.3 Hz, 1H), 6.8 (s, 1H), 6.7 (d, J=5.8 Hz, 1H), 4.1 (t, J=4.5 Hz, 2H), 3.8 (t, J=4.3 Hz, 2H), 3.7-3.5 (m, 18H), 3.5 (m, 2H), 3.4-3.3 (s, 3H), 3.3 (m, 4H), 3.2-3.0 (m, 2H), 2.9-2.8 (bs, 1H), 2.6-2.5 (m, 2H), 2.3-2.2 (m, 1H), 2.0 (s, 1H), 1.7-1.4 (m, 2H). MS (EI) for $C_{28}H_{43}NO_7$: 506.4 (MH$^+$).

The resulting trifluoroacetic acid salt was treated with sodium bicarbonate and extracted with chloroform. The freebase was solved in acetonitrile and 2.0 M hydrochloric acid in diethyl ether was added. This solution was then lyophilized to give the corresponding hydrochloride salt as a pale yellow oil (76 mg, 37.6%).

Example 9

Preparation of (6α)-6-{2-[2-(2-methoxyethoxy)ethoxy]ethoxy}-17-methylmorphinan-3-ol (9), hydrochloride salt (9)

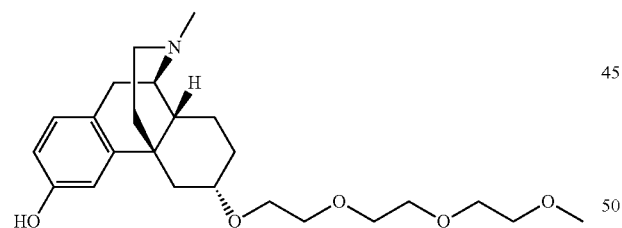

(6α)-3-Methoxy-6-{2-[2-(2-methoxyethoxy)ethoxy]ethoxy}-17-methylmorphinan (474 mg, 0.866 mmol, preparation described in Example 1) was dissolved in 4.0 mL of dimethylformamide, along with sodium ethanethiolate (364 mg, 4.33 mmol). LC/MS showed the completion of the reaction after seven days at 150° C. The mixture was purified by reverse phase HPLC to afford (6α)-6-{2-[2-(2-methoxyethoxy)ethoxy]ethoxy}-17-methylmorphinan-3-ol (9) trifluoroacetic acid salt (120 mg, 33%). $^1$H NMR (250 MHz, Chloroform-d): δ 12.2 (s, 1H), 6.9 (m, 2H), 6.6 (dd, J=7.5, 2.5, 1H), 3.8-3.5 (m, 8H), 3.4-3.3 (m, 9H), 3.2-1.8 (m, 12H), 1.6-1.3 (m, 5H). MS (EI) for $C_{24}H_{37}NO_5$: 420.5 (MH$^+$). Using conventional techniques of salt preparation, the resulting trifluoroacetic acid salt was converted to the corresponding hydrochloride salt.

Example 10

Preparation of (6α)-17-methyl-6-(2,5,8,11,14-pentaoxahexadecan-16-yloxy)morphinan-3-ol (10), hydrochloride salt (10)

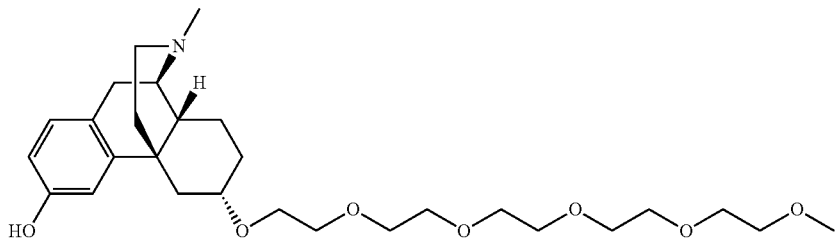

(6α)-3-Methoxy-17-methyl-6-(2,5,8,11,14-pentaoxahexadecan-16-yloxy)morphinan (681 mg, 1.03 mmol, preparation described in Example 2) was dissolved in 4.0 mL of dimethylformamide, along with sodium ethanethiolate (433 mg, 5.15 mmol). LC/MS showed the completion of the reaction after 18 hours at 150° C. The mixture was purified by reversed phase HPLC to afford (6α)-17-methyl-6-(2,5,8,11,14-pentaoxahexadecan-16-yloxy)morphinan-3-ol (10) trifluoroacetic acid salt (320 mg, 61%). $^1$H NMR (250 MHz, Chloroform-d): δ 12.2 (s, 1H), 6.9 (m, 2H), 6.6 (dd, J=7.5, 2.5, 1H), 3.8-3.3 (m, 25H), 3.2-3.0 (m, 3H), 2.9-2.7 (m, 4H), 2.6-2.4 (m, 2H), 2.3-1.9 (m, 2H), 1.6-1.3 (m, 5H). MS (EI) for $C_{28}H_{45}NO_7$: 508.8 (MH$^+$). Using conventional techniques of salt preparation, the resulting trifluoroacetic acid salt was converted to the corresponding hydrochloride salt.

Example 11

Preparation of 3-methoxy-17-(2-methoxyethyl)-morphinan (11), hydrochloride salt (11)

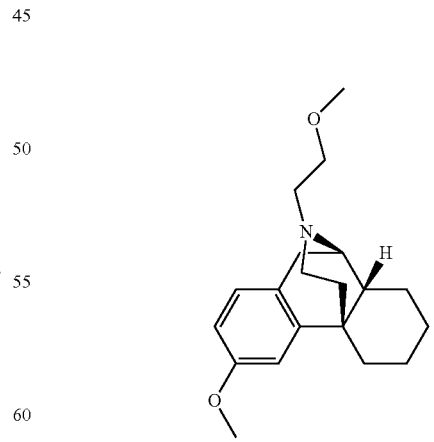

3-Methoxy-morphinan (250 mg, 0.97 mmol) was dissolved in acetonitrile and diisopropylethylamine (150 mg, 1.16 mmol) and 2-methoxyethyl 4-methylbenzenesulfonate (223 mg, 0.97 mmol) was added. The reaction was heated at 50° C. and stirred at this temperature until the reaction was complete (ca. 90 minutes). The reaction mixture was allowed to cool at room temperature, the solvent was removed and the mixture was purified by HPLC to afford 3-methoxy-17-(2-methoxyethyl)morphinan (11), trifluoroacetic acid salt (36 mg, 11.75% yield). $^1$H NMR (250 MHz, Chloroform-d): δ 12.16 (bs, 1H), 7.06 (d, J=8.5 Hz, 1H), 6.80 (m, 2H), 4.2-3.0 (complex multiple includes Ar—OMe at 3.8 and PEG-OMe at 3.36, 13H), 2.7-2.3 (complex multiplet, 3H), 1.9-1.0 (very complex multiplet, 10H). MS (EI) for $C_{20}H_{29}NO_2$: 316 (MH$^+$). Using conventional techniques of salt preparation, the resulting trifluoroacetic acid salt was converted to the corresponding hydrochloride salt.

Example 12

Preparation of 3-methoxy-17-[2-(2-methoxyethoxy)ethyl]-morphinan (12), hydrochloride salt

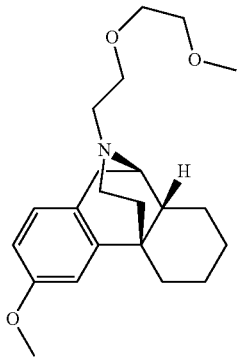

(12)

Using the approach described in Example 11 [except 2-(methoxyethoxy)ethyl methanesulfonate was used in place of 2-(methoxy)ethyl methanesulfonate], 3-methoxy-17-[2-(2-methoxyethoxy)ethyl]-morphinan (12), trifluoroacetic acid salt (26 mg, 7.5% yield) was prepared. $^1$H NMR (250 MHz, Chloroform-d): δ 12.16 (bs, 1H), 7.06 (d, J=8.5 Hz, 1H), 6.80 (m, 2H), 4.0-3.0 (complex multiple includes Ar—OMe at 3.8 and PEG-OMe at 3.36, 17H), 2.7-2.0 (complex multiplet, 3H), 1.9-1.0 (10H, very complex multiplet). MS (EI) for $C_{22}H_{33}NO_3$: 360 (MH$^+$). Using conventional techniques of salt preparation, the resulting trifluoroacetic acid salt was converted to the corresponding hydrochloride salt.

Example 13

Preparation of 3-methoxy-17-{2-[2-(2-methoxyethoxy)ethoxy]ethyl}-morphinan (13), hydrochloride salt

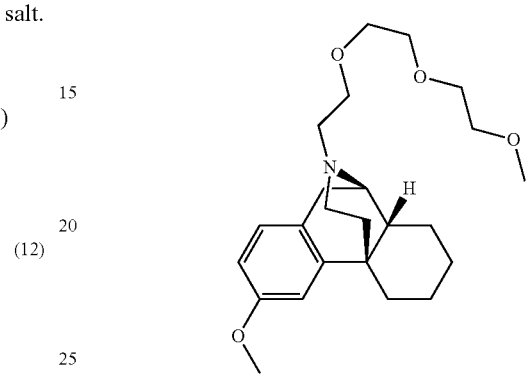

Using the approach described in Example 11 [except 2-(2-methoxyethoxy)ethoxy)ethyl methanesulfonate was used in place of 2-(methoxy)ethyl methanesulfonate], 3-methoxy-17-{2-[2-(2-methoxyethoxy)ethoxy]ethyl}-morphinan (13), trifluoroacetic acid salt (59 mg, 15% yield) was prepared. $^1$H NMR (250 MHz, Chloroform-d): δ 12.10 (bs, 1H), 7.06 (d, J=8.5 Hz, 1H), 6.80 (m, 2H), 4.2-3.0 (complex multiple includes Ar—OMe at 3.8 and PEG-OMe at 3.36, 21H), 2.7-2.0 (complex multiplet, 3H), 1.9-1.0 (very complex multiplet, 10H). MS (EI) for $C_{24}H_{37}NO_4$: 404 (MH$^+$). Using conventional techniques of salt preparation, the resulting trifluoroacetic acid salt was converted to the corresponding hydrochloride salt.

Example 14

Preparation of 17-methyl-3-(2,5,8,11,14-pentaoxahexadecan-16-yloxy)morphinan (14), hydrochloride salt

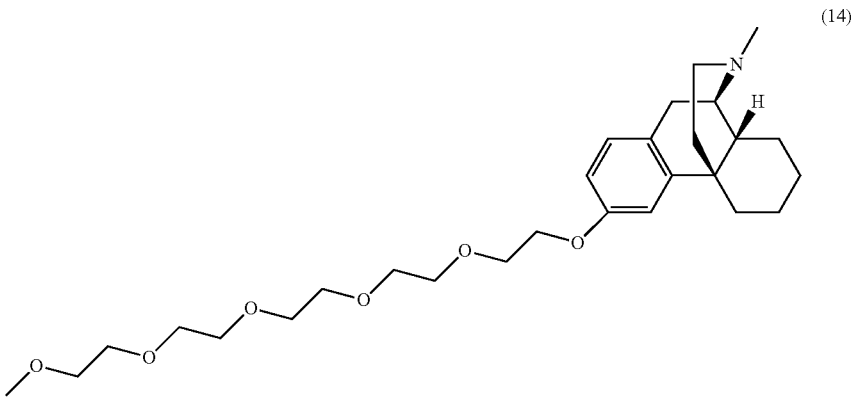 [SMILES: COCCOCCOCCOCCOCCOc1ccc2c(c1)[C@@]13CCCC[C@H]1[C@@H](C2)N(C)CC3]

(14)

17-Methylmorphinan-3-ol (also known as levorphanol) (80 mg, 0.35 mmol) was added to an 8 mL vial with a stir bar. 2,5,8,11,14-Pentaoxahexadecan-16-yl methanesulfonate (128 mg, 0.39 mmol), potassium carbonate (97 mg, 0.70 mmol) and acetonitrile (2 mL) were then added. The resulting mixture was heated at 60° C. for two days. Potassium carbonate was filtered and the resulting solution was then purified by reverse phase HPLC to afford 17-methyl-3-(2,5,8,11,14-pentaoxahexadecan-16-yloxy)morphinan (14) trifluoroacetic acid salt. $^1$H NMR (250 MHz, Chloroform-d): δ 12.0 (bs, 1H), 7.0 (d, J=9.0 Hz, 1H), 6.9-6.7 (m, 2H), 4.1 (m, 2H), 3.9 (m, 2H), 3.8-3.4 (m, 18H), 3.3 (s, 3H), 3.3-2.2 (m, 8H), 1.7-0.8 (m, 10H). MS (EI) for $C_{28}H_{45}NO_6$: 492.4 (MH$^+$).

The resulting trifluoroacetic acid salt was treated with sodium bicarbonate and extracted with chloroform. The freebase was solved in acetonitrile and 2.0 M hydrochloric acid in diethyl ether was added. This solution was then lyophilized to give the corresponding hydrochloride salt as a pale yellow oil (14 mg, 8.1%).

Example 15

Preparation of 17-[2-(2-methoxyethoxy)ethyl]morphinan-3-ol (15), hydrochloride salt

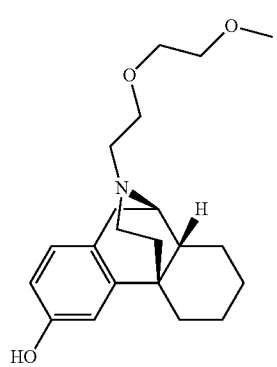

(15)

In an 8 mL vial, 3-methoxy-17-[2-(2-methoxyethoxy)ethyl]morphinan (12) (0.210 g, 0.56 mmol) was dissolved in anhydrous dimethylformamide (2 mL) and thiophenol (0.062 g, 0.56 mmol) and potassium carbonate (0.100 g, 0.73 mmol) were added. The reaction was heated at 150° C. until completion (about two hours). Upon cooling, the reaction mixture was partitioned between ethyl ether and 5% sodium hydroxide solution. The basic aqueous layer was acidified to pH 5 with citric acid and the pH adjusted to 8-9 with a saturated sodium bicarbonate solution. The aqueous solution was then extracted with chloroform and evaporated to dryness. The crude residue was purified by HPLC to afford 17-[2-(2-methoxyethoxy)ethyl]morphinan-3-ol (15) trifluoroacetic acid salt (70 mg, 34.7% yield). $^1$H NMR (250 MHz, Chloroform-d): δ 11.77 (bs, 1H), 6.98 (bm, 1H), 6.82 (m, 2H), 6.49 (bs, 1H), 4.2-4.0 (bm, 2H), 3.8-2.9 (m, 13H), 2.7-2.2 (m, 3H), 1.8-1.0 (very complex multiplet, 8H). MS (EI) for $C_{21}H_{31}NO_3$: 346 (MH$^+$). Using conventional techniques of salt preparation, the resulting trifluoroacetic acid salt was converted to the corresponding hydrochloride salt.

Example 16

Preparation of 17-{2-{2-(2-methoxyethoxy)ethoxy]ethyl}-morphinan-3-ol (16), hydrochloride salt

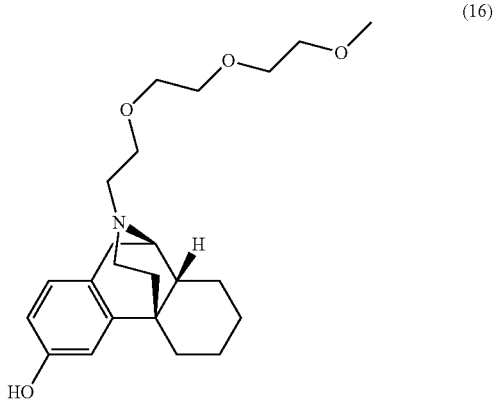 [SMILES: COCCOCCOCCN1CC[C@]23CCCC[C@H]2[C@H]1Cc1ccc(O)cc13]

(16)

The title compound was prepared following the same method as for Compound 15, but using 3-methoxy-17-{2-[2-(2-methoxyethoxy)ethoxy)ethyl}-morphinan (13) as a starting material to afford 17-{2-[2-(2-methoxyethoxy)ethoxy)ethyl}-morphinan-3-ol (16) trifluoroacetic acid salt (8 mg, 16.6%). $^1$H NMR (250 MHz, Chloroform-d): δ 11.72 (bs, 1H), 6.95 (bm, 1H), 6.81 (m, 2H). 4.10 (m, 2H), 3.8-2.95 (complex m, 18H), 2.7-2.2 (m, 4H) 1.7-0.8 (very complex multiplet, 8H). MS (EI) for $C_{23}H_{35}NO_4$: 390 (MH$^+$). Using conventional techniques of salt preparation, the resulting trifluoroacetic acid salt was converted to the corresponding hydrochloride salt.

Example 17

Preparation of N-ethyl-3-methoxymorphinan-17-carboxamide (17)

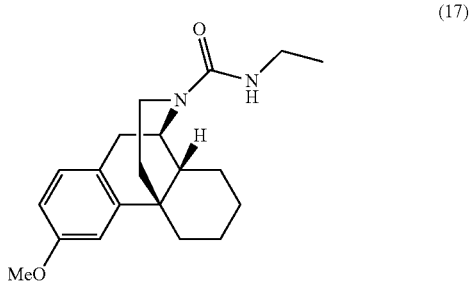 [SMILES: CCNC(=O)N1CC[C@]23CCCC[C@H]2[C@H]1Cc1ccc(OC)cc13]

(17)

3-Methoxy-morphinan (available commercially from, for example, Sigma-Aldrich, St. Louis Mo.) (150 mg, 0.58 mmol) was dissolved in dichloromethane and ethyl isocyanate (52 uL, 0.67 mmol) and diisopropylethylamine (130 uL, 0.75 mmol) were added. The reaction was allowed to stir for one hour. When complete, the dichloromethane layer was concentrated in vacuo and the residue submitted directly for HPLC purification to afford N-ethyl-3-methoxymorphinan-17-carboxamide (17) (31 mg, 16.3%). $^1$H NMR (250 MHz, Chloroform-d): δ 7.0 (d, J=8.5 Hz, 1H), 8.8 (d, J=2.8 Hz, 1H), 6.7 (dd, J=8.5, 2.8 Hz, 1H), 4.4-4.3 (m, 2H), 3.8 (s, 3H), 3.5-3.2 (m, 3H), 3.2-3.0 (dd, J=18.0, 5.3 Hz, 1H), 2.8-2.5 (m, 2H), 2.4-2.3 (m, 1H), 1.9-1.0 (m, 13H). MS (EI) for $C_{20}H_{28}N_2O_2$: 329.3 (MH$^+$).

Example 18

Preparation of 17-methylmorphinan-3-yl (2-methoxyethyl)carbamate (18), hydrochloride salt 17-Methylmorphinan-3-ol (167 mg, 0.65 mmol) was added to a 20 mL vial with a stirring bar. Chloroform (6 mL) was then added, followed by addition of 4-nitrophenyl chloroformate (144 mg, 0.838 mmol) and diisopropylethylamine (0.30 mL, 1.72 mmol). The resulting solution was stirred at 40-45° C. for four hours. 2-Methoxyethanamine (150 mg, 2.00 mmol) was dissolved in 5 mL of dimethylformamide and added to the reaction, which was then allowed to stir overnight at room temperature. The chloroform was removed in vacuo and the crude was diluted with 30 mL of water and extracted with ethyl acetate. The combined organic layers were dried over anhydrous magnesium sulfate and concentrated. The residue was then purified by reverse phase HPLC to afford 17-methylmorphinan-3-yl (2-methoxyethyl)carbamate (18) trifluoroacetic acid salt. $^1$H NMR (250 MHz, Chloroform-d): δ 12.2 (bs, 1H), 7.1 (m, 1H), 7.0 (m, 2H), 5.4 (m, 1H), 3.6-3.4 (m, 8H), 3.2-3.1 (m, 2H), 3.0-2.9 (m, 1H), 2.8 (d, 3H), 2.6-2.5 (m, 2H), 2.4-2.2 (m, 2H), 1.8-1.0 (m, 8H). MS (EI) for $C_{21}H_{30}N_2O_3$: 359.3 (MH$^+$).

The resulting trifluoroacetic acid salt was treated with sodium bicarbonate and extracted with chloroform. The freebase was solved in acetonitrile and 2.0 M hydrochloric acid in diethyl ether was added. This solution was then lyophilized to give the corresponding hydrochloride salt over two steps (81 mg, 34.8%).

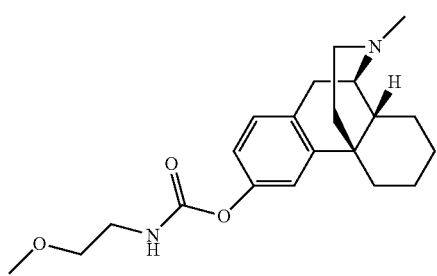

(18)

Example 19

Preparation of (6α)-6-(2, 5, 8, 11, 14, 17-hexaoxanonadecan-19-yloxy)-17-methylmorphinan-3-ol (19), hydrochloride salt

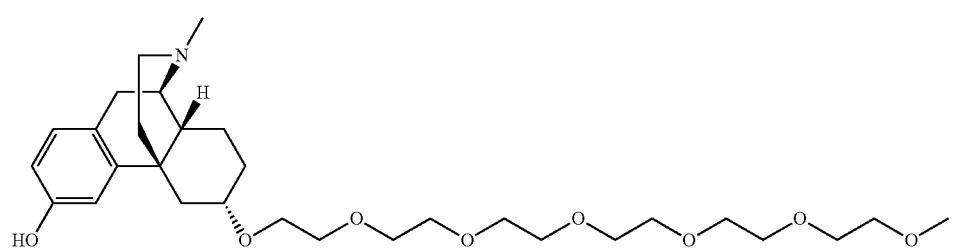

(19)

The title compound was prepared following the same method as for Example 10, but using 2,5,8,11,14,17-hexaoxanonadecan-19-yl 4-methylbenzenesulfonate instead. From 200 mg of (6α)-3-methoxy-17-methylmorphinan-6-ol, 203 mg of (6α)-6-(2, 5, 8, 11, 14, 17-hexaoxanonadecan-19-yloxy)-17-methylmorphinan-3-ol (19) trifluoroacetic acid salt was obtained (53%). $^1$H NMR (250 MHz, Chloroform-d): δ 12.23 (bs, 1H), 6.96-6.86 (m, 2H), 6.67 (dd, J=8.4, 2.3 Hz, 1H), 4.94 (bs, 1H), 3.73-2.81 (m, 33H), 2.75 (d, J=4.8 Hz, 3H), 2.59-2.43 (m, 2H), 2.33-2.14 (m, 1H), 1.96-1.81 (m, 1H), 1.62-1.18 (m, 5H). MS (EI) for $C_{30}H_{49}NO_8$: 552.6 (MH$^+$). Using conventional techniques of salt preparation, the resulting trifluoroacetic acid salt was converted to the corresponding hydrochloride salt.

Example 20

Preparation of (6α)-6-(2,5,8,11,14,17,20-heptaoxadocosan-22-yloxy)-17-methylmorphinan-3-ol (20), hydrochloride salt

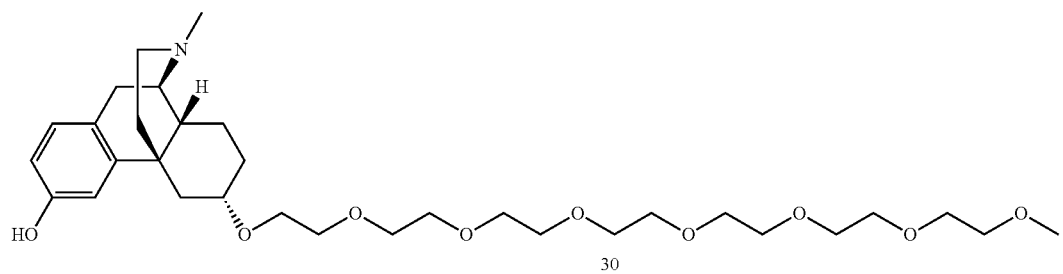

(20)

The title compound was prepared following the same method as for Example 10, but using 2,5,8,11,14,17,20-heptaoxadocosan-22-yl 4-methylbenzenesulfonate instead. From 200 mg of (6α)-3-methoxy-17-methylmorphinan-6-ol, 174 mg of (6α)-6-(2,5,8,11,14,17,20-heptaoxadocosan-22-yloxy)-17-methylmorphinan-3-01 (20) trifluoroacetic acid salt was obtained (42%). $^1$H NMR (250 MHz, Chloroform-d): δ 12.25 (bs, 1H), 6.97-6.86 (m, 2H), 6.66 (dd, J=8.4, 2.5 Hz, 1H), 4.88 (bs, 1H), 3.82-2.80 (m, 37H), 2.75 (d, J=4.8 Hz, 3H), 2.60-2.44 (m, 2H), 2.34-2.15 (m, 1H), 1.98-1.81 (m, 1H), 1.61-1.19 (m, 5H). MS (EI) for $C_{32}H_{53}NO_9$: 596.6 (MH$^+$). Using conventional techniques of salt preparation, the resulting trifluoroacetic acid salt was converted to the corresponding hydrochloride salt.

Example 21

Preparation of 3-methoxy-4-(2-methoxyethoxy)-17-methylmorphinan (21), hydrochloride salt

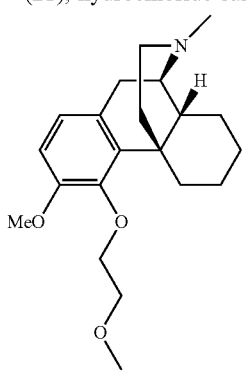

(21)

To a stirring solution of 3-methoxy-17-methylmorphinan-4-ol (CAS #: 3327-79-5) (0.84 g, 2.9 mmol) in 29 mL of tetrahydrofuran was slowly added a 60% dispersion of sodium hydride in mineral oil (0.21 g, 5.3 mmol). The sodium hydride was allowed to react for five minutes, then 1-bromo-2-methoxyethane (0.38 mL, 4.1 mmol) was syringed into the reaction and the mixture was heated at 80° C. for 16 hours. The tetrahydrofuran was removed in vacuo, and the resulting residue was treated with 20 mL of a 30% sodium hydroxide solution and extracted with ethyl acetate (30 mL×2). The combined organic layer was concentrated in vacuo and the crude mixture purified by reverse phase HPLC to afford 3-methoxy-4-(2-methoxyethoxy)-17-methylmorphinan (21) trifluoroacetic acid salt (0.65 g, 65%) as a yellow oil. $^1$H NMR (250 MHz, Chloroform-d): δ 12.06 (bs, 1H), 6.89-6.80 (m, 2H), 4.21-4.00 (m, 2H), 3.83 (s, 3H), 3.80-3.65 (m, 2H), 3.41 (s, 3H), 3.44-3.10 (m, 4H), 2.98-2.85 (m, 1H), 2.74 (d, J=5.0 Hz, 3H), 2.60-2.35 (m, 2H), 2.04 (m, 1H), 1.70-1.01 (m, 8H). MS (EI) for $C_{21}H_{31}NO_3$: 346.3 (MH$^+$). Using conventional techniques of salt preparation, the resulting trifluoroacetic acid salt was converted to the corresponding hydrochloride salt.

Example 22

Preparation of 4-(2-methoxyethoxy)-17-methylmorphinan-3-ol (22), hydrochloride salt

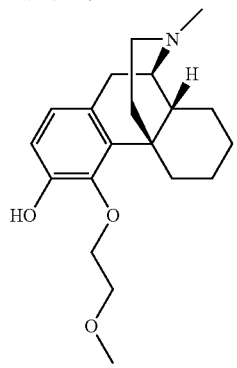

(22)

A crude mixture of 3-methoxy-4-(2-methoxyethoxy)-17-methylmorphinan (21) (0.35 g, 1.0 mmol) was dissolved in 1.0 mL of N-methylpyrrolidone. Sodium ethanethiolate (0.51 g, 6.1 mmol) was added and the mixture stirred at 150° C. for 17 hours. To this solution was then added 10 mL of dichloromethane, which was washed with water (2×10 mL). The dichloromethane was removed in vacuo, and the residue was taken up in 10 mL of ethyl acetate. The ethyl acetate solution was washed with an aqueous solution of 1 M hydrochloric acid (2×10 mL). The crude mixture was then concentrated in vacuo and purified by reverse phase HPLC to afford 4-(2-methoxyethoxy)-17-methylmorphinan-3-ol (22) trifluoroacetic acid salt (0.24 g, 72% yield). $^1$H NMR (250 MHz, Chloroform-d): δ 12.24 (bs, 1H), 8.23 (bs, 1H), 6.88-6.79 (m, 2H), 4.11-3.62 (m, 4H), 3.55 (s, 3H), 3.44-2.82 (m, 4H), 2.75 (d, J=4.5 Hz, 3H), 2.65-2.21 (m, 2H), 1.70-1.01 (m, 9H). MS (EI) for $C_{20}H_{29}NO_3$: 332.3 (MH$^+$). Using conventional techniques of salt preparation, the resulting trifluoroacetic acid salt was converted to the corresponding hydrochloride salt.

Example 23

Preparation of 1-(2-methoxyethyl)-3-(17-methylmorphinan-3-yl)urea (23), hydrochloride salt

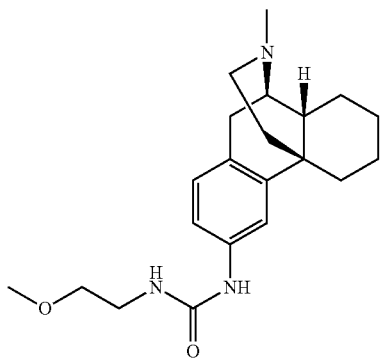

(23)

17-Methylmorphinan-3-amine [preparation described in Decker et al. (2010) *J Med Chem* 53(41-50] (51.8 mg, 0.202 mmol) was dissolved in dichloromethane (2 mL). To the solution was added triethylamine (0.056 mL, 0.404 mmol), followed by 1-isocyanato-2-methoxyethane (26.6 mg, 0.263 mmol). The reaction was stirred at room temperature for two hours. Solvent was removed under reduced pressure. The residue was purified on reverse phase C18 column to give the desired product (23) as a free base (25.9 mg) in 36% yield. MS (EI) for $C_2H_{32}N_3O_2$: 358.2 (MH$^+$). $^1$H NMR (500 MHz, DMSO-$d_6$) δ 8.41 (s, 1H), 7.24 (d, J=2.2 Hz, 1H), 7.11 (dd, J=8.2, 2.2 Hz, 1H), 6.95 (d, J=8.3 Hz, 1H), 6.11 (t, J=5.6 Hz, 1H), 3.35 (t, J=5.5 Hz, 2H), 3.29-3.17 (m, 5H), 2.88 (d, J=18.1 Hz, 1H), 2.67 (dd, J=5.5, 3.1 Hz, 1H), 2.50-2.41 (m, 1H), 2.32-2.19 (m, 5H), 1.93 (td, J=12.1, 3.2 Hz, 1H), 1.69 (dt, J=13.1, 3.1 Hz, 1H), 1.59 (td, J=12.4, 4.8 Hz, 2H), 1.46 (d, J=12.7 Hz, 1H), 1.38-1.09 (m, 6H), 1.07-0.94 (m, 1H).

The free base (19.7 mg) was dissolved in 1 mL of acetonitrile. To the solution was added 0.5 mL of 1N hydrochloride. The mixture was lyophilized to afford 21.2 mg of product as hydrochloride salt.

Example 24

Preparation of 4-methoxy-N-((4bR,8aR,9R)-11-methyl-6,7,8,8a,9,10-hexahydro-5H-9,4b-(epiminoethano)phenanthren-3-yl)benzamide (24), hydrochloride salt

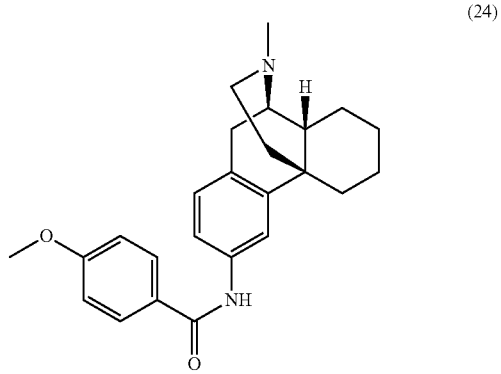 [SMILES: COc1ccc(C(=O)Nc2ccc3c(c2)[C@@]24CCCC[C@H]2[C@@H](C3)N(C)CC4)cc1]

(24)

To a solution of 4-methoxybenzoic acid (49.1 mg, 0.323 mmol), EDC (61.9 mg, 0.323 mmol) and DIPEA (0.075 mL, 0.431 mmol) in 3 mL of dichloromethane were added to 17-methylmorphinan-3-amine (55.2 mg, 0.215 mmol). The reaction was stirred at room temperature overnight. The reaction was then taken up in 10 mL of dichloromethane and washed with 10 mL of brine/1N HCl (1:1), 1N NaOH 10 mL and brine 10 mL. The organic layer was dried over sodium sulfate and was concentrated. The residue was purified on flash silica gel column to give the title compound (24) as a free base (42.6 mg, 50.7%). MS (EI) for $C_{25}H_{30}N_2O_2$: 391.2 (MH+). $^1$H NMR (500 MHz, DMSO-$d_6$) δ 9.96 (s, 1H), 7.99-7.92 (m, 2H), 7.65-7.56 (m, 2H), 7.11-7.02 (m, 3H), 3.84 (s, 3H), 2.96 (d, J=18.4 Hz, 1H), 2.73 (s, 1H), 2.30 (d, J=18.9 Hz, 5H), 2.02-1.92 (m, 1H), 1.74 (dt, J=13.3, 3.1 Hz, 1H), 1.70-1.58 (m, 2H), 1.50 (d, J=12.2 Hz, 1H), 1.42-1.15 (m, 5H), 1.03 (qd, J=13.0, 4.2 Hz, 1H).

The free base (20.9 mg) was dissolved in 1 mL of acetonitrile. To the solution was added 0.5 mL of 1N hydrochloride. The mixture was lyophilized to afford 23 mg of product as hydrochloride salt.

Example 25

Preparation of 3-methoxy-N-((4bR,8aR,9R)-11-methyl-6,7,8,8a,9,10-hexahydro-5H-9,4b-(epiminoethano)phenanthren-3-yl)benzamide (25), hydrochloride salt

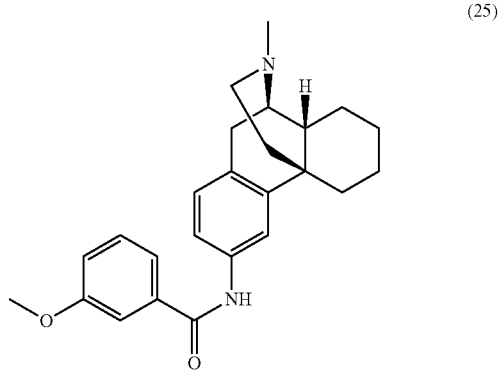 [SMILES: COc1cccc(C(=O)Nc2ccc3c(c2)[C@@]24CCCC[C@H]2[C@@H](C3)N(C)CC4)c1]

(25)

To a solution of 3-methoxybenzoic acid (48.2 mg, 0.317 mmol), EDC (60.7 mg, 0.317 mmol) and DIPEA (54.5 mg, 0.422 mmol) in 3 mL of dichloromethane were added to 17-methylmorphinan-3-amine (54.2, 0.211 mmol). The reaction was stirred at room temperature overnight. The reaction was then taken up in 10 mL of dichloromethane and washed with 10 mL of brine/1N HCl (1:1), 1N NaOH 10 mL and brine 10 mL. The organic layer was dried over sodium sulfate, was filtered and was concentrated. The residue was purified on flash silica gel column to give desired product (25) as a free base (47.1 mg, 57.2%). MS (EI) for $C_{25}H_{30}N_2O_2$: 391.2 (MH+). $^1$H NMR (500 MHz, DMSO-$d_6$) δ 10.09 (s, 1H), 7.65 (d, J=2.2 Hz, 1H), 7.62-7.53 (m, 2H), 7.49 (dd, J=2.7, 1.6 Hz, 1H), 7.44 (t, J=7.9 Hz, 1H), 7.15 (ddd, J=8.2, 2.7, 1.0 Hz, 1H), 7.10 (d, J=8.3 Hz, 1H), 7.06-7.03 (m, OH), 3.84 (s, 3H), 2.96 (d, J=18.5 Hz, 1H), 2.75-2.70 (m, 1H), 2.37-2.30 (m, 2H), 2.28 (s, 3H), 2.11 (s, 1H), 1.98-1.93 (m, 1H), 1.74 (dt, J=12.9, 3.2 Hz, 1H), 1.64 (qd, J=13.8, 13.1, 3.7 Hz, 2H), 1.53-1.47 (m, 1H), 1.42-1.26 (m, 3H), 1.22 (dt, J=12.3, 2.9 Hz, 2H), 1.04 (td, J=12.7, 4.0 Hz, 1H).

The free base (23 mg) was dissolved in 1 mL of acetonitrile. To the solution was added 0.5 mL of 1N hydrochloride. The mixture was lyophilized to afford 23.7 mg of product as hydrochloride salt.

Example 26

Preparation of 2-methoxy-N-((4bR,8aR,9R)-11-methyl-6,7,8,8a,9,10-hexahydro-5H-9,4b-(epiminoethano)phenanthren-3-yl)benzamide (26), hydrochloride salt

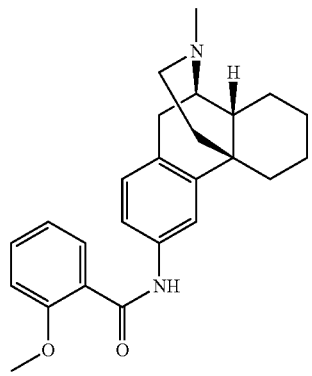

(26)

To a solution of 2-methoxybenzoic acid (41.7 mg, 0.274 mmol), EDC (52.5 mg, 0.274 mmol) and DIPEA (47.2 mg, 0.365 mmol) in 3 mL of dichloromethane were added to 17-methylmorphinan-3-amine (46.8, 0.183 mmol). The reaction was stirred at room temperature overnight. The reaction was then taken up in 10 mL of dichloromethane and washed with 10 mL of brine/1N HCl (1:1), 1N NaOH 10 mL and brine 10 mL. The organic layer was dried over sodium sulfate, was filtered and was concentrated. The residue was purified on flash silica gel column to give desired product (26) as free base (30.3 mg, 42.5%). MS (EI) for $C_{25}H_{30}H_2O_2$: 391.2 (MH+). $^1$H NMR (500 MHz, DMSO-d6) δ 9.99 (s, 1H), 7.70-7.58 (m, 2H), 7.56-7.43 (m, 2H), 7.17 (dd, J=8.4, 0.9 Hz, 1H), 7.12-7.01 (m, 2H), 3.89 (s, 3H), 2.96 (d, J=18.3 Hz, 1H), 2.72 (dd, J=5.7, 3.1 Hz, 1H), 2.33 (dd, J=6.6, 4.6 Hz, 1H), 2.27 (s, 3H), 1.95 (td, J=12.1, 3.2 Hz, 1H), 1.78-1.72 (m, 1H). 1.69-1.55 (m, 2H), 1.50 (d, J=12.9 Hz, 1H), 1.43-1.17 (m, 6H), 1.08-0.98 (m, 1H).

The free base (16.9 mg) was dissolved in 1 mL of acetonitrile. To the solution was added 0.5 mL of 1N hydrochloride. The mixture was lyophilized to afford 18.3 mg of product as hydrochloride salt.

Example 27

Preparation of 1-(4-methoxyphenyl)-3-(17-methylmorphinan-3-yl)urea (27), hydrochloride salt

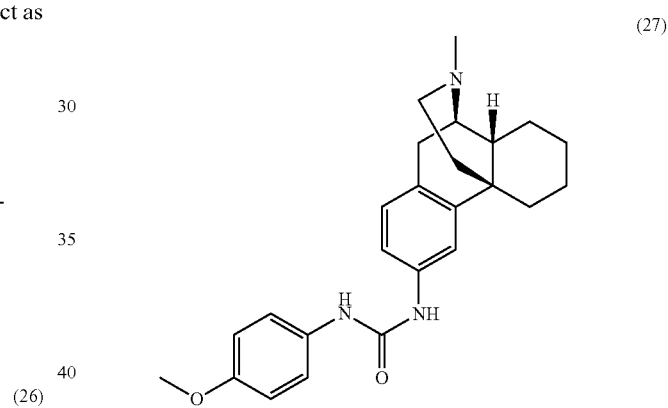

(27)

17-Methylmorphinan-3-amine (68 mg, 0.265 mmol) was dissolved in dichloromethane (2 mL). To the solution was added 1-isocyanato-4-methoxybenzene (0.041 mL, 0.318 mmol). The reaction was stirred at room temperature overnight. The reaction was taken up in 10 mL of dichloromethane and washed with brine 10 mL. The organic layer was dried over magnesium sulfate, was filtered and was concentrated. The residue was purified on flash silica gel column to give the desired product (27) as free base (40.4 mg, 37.6%). MS (EI) for $C_{25}H_{31}N_3O_2$: 406.2 (MH+). $^1$H NMR (500 MHz, DMSO-$d_6$) δ 8.48 (s, 1H), 8.40 (s, 1H), 7.39-7.28 (m, 3H), 7.19 (dd, J=8.2, 2.1 Hz, 1H), 7.01 (d, J=8.3 Hz, 1H), 6.91-6.83 (m, 2H), 3.72 (s, 3H), 2.92 (d, J=18.2 Hz, 1H), 2.70 (dd, J=5.8, 3.1 Hz, 1H), 2.34-2.22 (m, 5H), 1.95 (td, J=12.0, 3.1 Hz, 1H), 1.72 (dt, J=13.1, 3.1 Hz, 1H), 1.62 (ddt, J=12.6, 9.4, 4.7 Hz, 2H), 1.49 (d, J=12.6 Hz, 1H), 1.43-1.14 (m, 6H), 1.02 (qd, J=12.6, 3.7 Hz, 1H).

The free base (36 mg) was dissolved in 2 mL of acetonitrile. To the solution was added 0.5 mL of 1N hydrochloride. The mixture was lyophilized to afford 37.6 mg of product as hydrochloride salt.

Example 28

Preparation of
N-(4-methoxyphenyl)-17-methylmorphinan-3-amine
(28), hydrochloride salt (28)

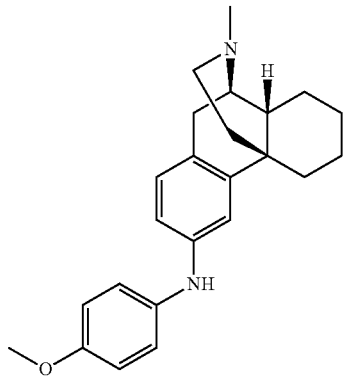

A solution of 17-methylmorphinan-3-amine (119.8 mg, 0.467 mmol) and 1-bromo-4-methoxybenzene (131 mg, 0.701 mmol) in anhydrous dioxane (5 mL) was purged with nitrogen. The catalyst tris(dibenzylideneacetone)dipalladium(0):BINAP:sodium tert-butoxide (0.05:0.15:2) (117.3 mg) was added to the solution. The mixture was stirred at 100° C. for 22 hours. The mixture was cooled to room temperature, was filtered and the solvent was removed. The residue was mixed with water and was extracted with dichloromethane (3×25 mL). The combined organic solution was washed with brine, dried over anhydrous sodium sulfate, was filtered and was concentrated. The residue was purified with flash column chromatography on silica gel to result in 34.7 mg of the product (28) as a free base in 20.5% yield. MS (EI) for $C_{24}H_{30}N_2O$: 363.2 (MH+). 1H NMR (500 MHz, DMSO-d6) δ 7.67 (s, 1H), 7.01-6.96 (m, 2H), 6.94 (d, J=8.2 Hz, 1H), 6.88-6.81 (m, 3H), 6.74 (dd, J=8.1, 2.3 Hz, 1H), 3.70 (s, 3H), 2.90 (d, J=18.1 Hz, 1H), 2.77-2.71 (m, 1H), 2.39-2.18 (m, 6H), 2.03 (t, J=12.1 Hz, 1H), 1.77-1.69 (m, 1H), 1.62 (ddd, J=12.3, 8.1, 4.1 Hz, 3H), 1.54-1.44 (m, 2H), 1.44-1.18 (m, 6H), 1.14-0.97 (m, 1H).

The free base (31.5 mg) was dissolved in 2 mL of acetonitrile. To the solution was added 0.5 mL of 1N hydrochloride. The mixture was lyophilized to afford 35.3 mg of the product as hydrochloride salt.

Example 29

Preparation of
N-(3-methoxyphenyl)-17-methylmorphinan-3-amine
(29), hydrochloride salt (29)

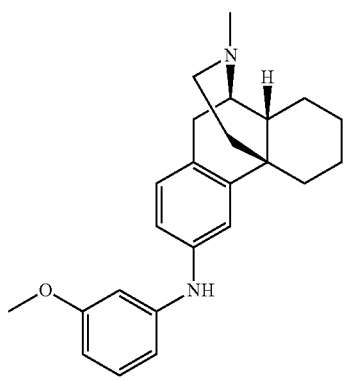

A solution of 17-methylmorphinan-3-amine (112.5 mg, 0.439 mmol) and 1-bromo-3-methoxybenzene (123 mg, 0.658 mmol) in anhydrous dioxane (5 mL) was purged with nitrogen. The catalyst tris(dibenzylideneacetone)dipalladium(0):BINAP:sodium tert-butoxide (0.05:0.15:2) (117.3 mg) was added to the solution. The mixture was stirred at 100° C. for 22 hours. The mixture was cooled to room temperature, was filtered and the solvent was removed. The residue was mixed with water and was and extracted with dichloromethane (3×25 mL). The combined organic solution was washed with brine, dried over anhydrous sodium sulfate, was filtered and was concentrated. The residue was purified with flash column chromatography on silica gel to result in 102.7 mg of the product (29) as free base in 64.6% yield. MS (EI) for $C_{24}H_{30}N_2O$: 363.2 (MH+). 1H NMR (500 MHz, DMSO-d6) δ 8.01 (s, 1H), 7.10-7.06 (m, 1H), 7.03-6.98 (m, 2H), 6.86 (dd, J=8.1, 2.2 Hz, 1H), 6.56 (dd, J=6.9, 1.3 Hz, 2H), 6.35-6.30 (m, 1H), 3.69 (s, 3H), 2.92 (d, J=18.1 Hz, 1H), 2.70 (dd, J=5.5, 3.1 Hz, 1H), 2.39-2.21 (m, 6H), 1.99 (td, J=12.1, 3.2 Hz, 1H), 1.71 (dt, J=13.3, 3.2 Hz, 1H), 1.62 (ddt, J=12.2, 8.5, 4.9 Hz, 2H), 1.49 (d, J=10.5 Hz, 1H), 1.44-1.17 (m, 7H), 1.13-1.01 (m, 1H).

The free base (30.6 mg) was dissolved in 2 mL of acetonitrile. To the solution was added 0.5 mL of 1N hydrochloride. The mixture was lyophilized to afford 31 mg of product as hydrochloride salt.

Example 30

Preparation of
N-(2-methoxyphenyl)-17-methylmorphinan-3-amine
(30), hydrochloride salt (30)

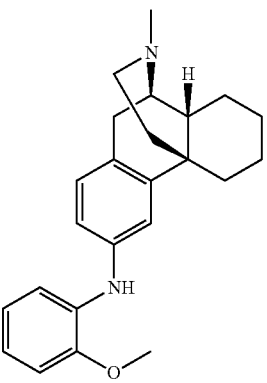

A solution of 17-methylmorphinan-3-amine (72.9 mg, 0.284 mmol) and 1-bromo-2-methoxybenzene (80 mg, 0.427 mmol) in anhydrous dioxane (5 mL) was purged with nitrogen. The catalyst tris(dibenzylideneacetone)dipalladium(0):BINAP:sodium tert-butoxide (0.05:0.15:2) (97.5 mg) was added to the solution. The mixture was stirred at 100° C. for 22 hours. The mixture was cooled to room temperature, was filtered and the solvent was removed. The residue was mixed with water and was extracted with dichloromethane (3×25 mL). The combined organic solution was washed with brine, dried over anhydrous sodium sulfate, was filtered and was concentrated. The residue was purified with flash column chromatography on silica gel to result in 50.1 mg of the product (30) as a free base in 48.6% yield. MS (EI) for $C_{24}H_{30}N_2O$: 363.2 (MH+). 1H NMR (500

MHz, DMSO-d6) δ 7.15-7.09 (m, 2H), 7.01 (d, J=2.4 Hz, 1H), 6.96 (t, J=4.7 Hz, 2H), 6.87 (dd, J=8.1, 2.2 Hz, 1H), 6.80 (dd, J=6.6, 4.4 Hz, 1H), 3.82 (s, 3H), 2.91 (d, J=18.1 Hz, 1H), 2.70 (dd, J=6.0, 3.1 Hz, 1H), 2.36-2.22 (m, 6H), 1.99 (td, J=12.1, 3.2 Hz, 1H), 1.70 (dt, J=13.0, 3.3 Hz, 1H), 1.60 (td, J=12.5, 4.9 Hz, 2H), 1.48 (d, J=8.9 Hz, 1H), 1.42-1.17 (m, 7H), 1.07 (qd, J=12.5, 3.7 Hz, 1H).

The free base (23 mg) was dissolved in 1 mL of acetonitrile. To the solution was added 0.5 mL of 1N hydrochloride. The mixture was lyophilized to afford 20.5 mg of product as hydrochloride salt.

Example 31

Preparation of (6β)-6-(2-methoxyethoxy)-17-methylmorphinan-3-ol (31), hydrochloride salt

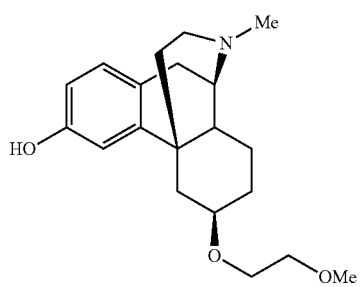

(31)

Step 1: Preparation of (6β)-3-methoxy-6-(2-methoxyethoxy)-17-methylmorphinan

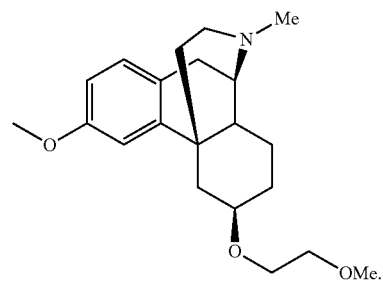 [SMILES: COCCO[C@@H]1CCC2[C@H]3Cc4ccc(OC)cc4[C@@]2(CCN3C)C1]

A solution of (6β)-3-methoxy-17-methylmorphinan-6-ol [FR1361070(A) to Shionogi, published 1964 May 29] (144 mg, 0.50 mmol) in dry N,N-dimethylformamide (5 mL) was added via cannula to a nitrogen purged 25 mL flask containing sodium hydride (81 mg, 2.0 mmol) (degreased with hexane), and the suspension was stirred at room temperature for 15 minutes, before 1-bromo-2-methoxyethane (57 µL, 0.61 mmol) was added. The mixture was placed in an oil bath at 60° C. THF (2 mL) and additional 1-bromo-2-methoxyethane (57 µL, 0.61 mmol) was added after 23.5 hours. After 28 hours, the mixture was concentrated, and the residue was purified by chromatography on silica (1:10:900 to 1:10:90 ammonium hydroxide:methanol:dichloromethane) to afford (6β)-3-methoxy-6-(2-methoxyethoxy)-17-methylmorphinan as a pale brown oil/gum (43 mg, 25%). MS (EI) for $C_{21}H_{31}NO_3$: 346.2 (MH$^+$). The material was carried forward to the next step without further characterization.

Step 2: Preparation of (6β)-6-(2-methoxyethoxy)-17-methylmorphinan-3-ol

A 0.5-2 mL microwave vial charged with sodium ethanethiolate (52 mg, 0.62 mmol) and a solution of (6β)-3-methoxy-6-(2-methoxyethoxy)-17-methylmorphinan (43 mg, 0.12 mmol) in dry N-methyl-2-pyrrolidinone (0.5 mL) was heated in a microwave at 150° C. for 3.5 hours, and then partitioned between ethyl acetate (15 mL) and brine (15 mL) buffered with saturated aqueous ammonia/ammonium chloride (0.5 mL). The aqueous layer was back extracted with ethyl acetate (10 mL), and the combined organic layer was washed with additional brine (2×5 mL), was dried (sodium sulfate), was filtered and was concentrated. Chromatography on silica (3:2 hexane:dichloromethane to dichloromethane, then dichloromethane to 1:10:90 ammonium hydroxide: methanol:dichloromethane) afforded (6β)-6-(2-methoxyethoxy)-17-methylmorphinan-3-ol (31) as a pale brown viscous oil (33 mg, 80%), which solidified on standing. $^1$H NMR (500 MHz, Chloroform-d) δ 6.98 (d, J=8.2 Hz, 1H), 6.84 (d, J=2.6 Hz, 1H), 6.64 (dd, J=8.2, 2.6 Hz, 1H), 5.25 (br s, 1H), 3.66 (dt, J=9.7, 4.7 Hz, 1H), 3.62 (dt, J=9.7, 4.7 Hz, 1H), 3.55 (t, J=4.7 Hz, 2H), 3.41 (s, 3H), 3.30 (tt, J=11.1, 4.0 Hz, 1H), 2.98 (d, J=18.1 Hz, 1H), 2.90 (dd, J=5.6, 3.2 Hz, 1H), 2.70 (dt, J=13.2, 2.5 Hz, 1H), 2.57 (dd, J=18.1, 5.8 Hz, 1H), 2.44 (app dt, J=12.2, 3.0 Hz, 1H), 2.42 (s, 3H), 2.12-2.02 (m, 2H), 1.85-1.75 (m, 2H), 1.56 (app dq, J=12.9, 3.4 Hz, 1H), 1.44-1.32 (m, 3H), 0.1.21 (qd, J=13.1, 3.6 Hz, 1H); MS (ESI) for $C_{20}H_{29}NO_3$: 332.2 (MH$^+$).

The material was converted to the HCl salt in methanol/water (1/5; 3 mL), and lyophilized overnight to afford the HCl salt as a pale tan glass.

Example 32

Preparation of 17-methyl-N-(pyrimidin-2-yl)morphinan-3-amine (32), hydrochloride salt

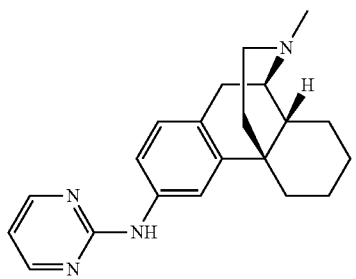

(32)

2-Bromopyrimidine (35.3 mg, 0.22 mmol) was added to a solution of 17-methylmorphinan-3-amine [Zhang et al. (2004) J Med Chem 47(1):165-174] (57 mg, 0.22 mmol) in dimethylsulfoxide (0.25 mL). The solution was heated in a microwave oven at 150° C. for 20 minutes. The crude product was purified by reverse phase chromatography (0-30% water/acetonitrile/0.01% hydrochloric acid) and the combined fractions were treated with 1 N hydrochloric acid to afford 17-methyl-N-(pyrimidin-2-yl)morphinan-3-amine (32) hydrochloride salt (12 mg, 13.2%) as a dark yellow solid. $^1$H NMR (500 MHz, Methanol-d$_4$): δ 8.65 (d, J=5.0 Hz, 2H), 7.56 (s, 1H), 7.48 (d, J=8.1 Hz, 1H), 7.39 (d, J=8.1 Hz, 1H), 7.13 (t, J=5.2 Hz, 1H), 3.72 (d, J=4.8 Hz, 1H), 3.50-3.20 (m, 3H), 2.96 (s, 3H), 2.76 (dd, J=14.5, 11.4 Hz, 1H), 2.55 (d, J=14.1 Hz, 1H), 2.15 (d, J=12.4 Hz, 1H), 2.00 (td, J=13.8, 4.3 Hz, 1H), 1.78-1.67 (m, 2H), 1.66-1.59 (m, 2H), 1.58-1.43 (m, 2H), 1.35 (q, J=13.6 Hz, 1H), 1.16 (qd, J=15.3, 5.5 Hz, 1H). MS (EI) for $C_{21}H_{26}N_4$: 335 (MH+).

Example 33

Preparation of 2-[2-(2-methoxyethoxy)ethoxy]-N-(17-methylmorphinan-3-yl)acetamide (33), hydrochloride salt (33)

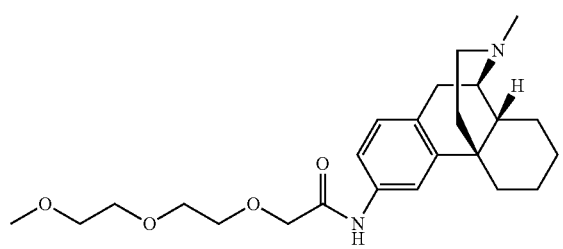

To a solution of 2-(2-(2-methoxyethoxy)ethoxy)acetic acid (0.083 mL, 0.543 mmol), EDC (104 mg, 0.543 mmol) and DIPEA (0.126 mL, 0.724 mmol) in 3 mL of dichloromethane were added 17-methylmorphinan-3-amine (92.8, 0.362 mmol). The reaction was stirred at room temperature for two hours. The reaction was then taken up in 10 mL of dichloromethane and sequentially washed with 10 mL of brine/1N HCl (1:1), saturated sodium bicarbonate 10 mL and brine 10 mL. The organic layer was dried over sodium sulfate, was filtered and was concentrated. The residue was purified on flash silica gel column to give desired product (33) as free base (89.2 mg, 59.2%). MS (EI) for $C_{24}H_{36}N_2O_4$: 417.2 (MH+). $^1$H NMR (500 MHz, DMSO-$d_6$) δ 9.42 (s, 1H), 7.49-7.39 (m, 2H), 7.04 (d, J=8.3 Hz, 1H), 4.02 (s, 2H), 3.67-3.50 (m, 6H), 3.47-3.39 (m, 2H), 3.22 (s, 3H), 2.92 (d, J=18.4 Hz, 1H), 2.69 (dd, J=5.6, 3.1 Hz, 1H), 2.49 (dd, J=18.6, 5.5 Hz, 1H), 2.33-2.22 (m, 5H), 1.90 (td, J=12.1, 3.2 Hz, 1H), 1.71 (dt, J=13.0, 3.2 Hz, 1H), 1.66-1.54 (m, 2H), 1.52-1.43 (m, 1H), 1.39-1.09 (m, 6H), 0.98 (qd, J=12.8, 4.0 Hz, 1H).

The free base (82.4 mg) was dissolved in 2 mL of acetonitrile. To the solution was added 0.5 mL of 1N hydrochloride. The mixture was lyophilized to afford 88.8 mg of product as hydrochloride salt.

Example 34

Preparation of N-{3-[2-(2-methoxyethoxy)ethoxy]phenyl}-17-methylmorphinan-3-amine (34), hydrochloride salt (34)

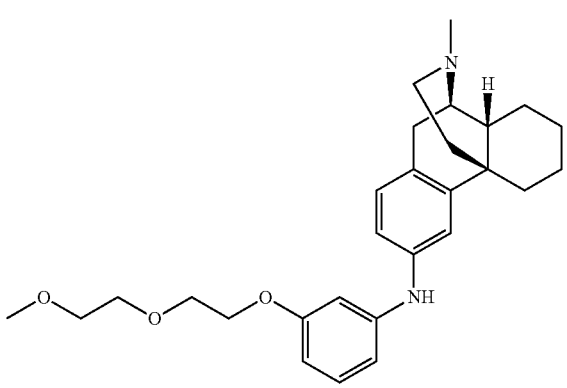

Step 1. Synthesis of 1-bromo-3-(2-(2-methoxyethoxy)ethoxy)benzene

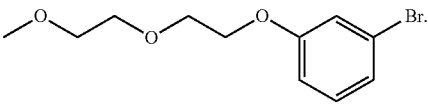

A mixture of 3-bromophenol (0.3271 g, 1.891 mmol), 1-bromo-2-(2-methoxyethoxy)ethane (0.28 mL, 2.080 mmol), and potassium carbonate (0.784 g, 5.67 mmol) in dimethyl formamide (5 mL) was stirred at 60° C. overnight. The reaction mixture was poured into 20 mL of 5% LiCl solution and extracted with ethyl acetate 3×30 mL. The organic layers were combined, washed with brine, dried over sodium sulfate and concentrated. After drying under high vacuum, the pure product was obtained as colorless oil in quantitative yield. 1H NMR (400 MHz, CDCl3): δ 7.12 (d, 1H), 7.08 (d, 2H), 6.84 (tt, 1H), 4.11 (t, 2H), 3.85 (t, 2H), 3.71 (t, 2H), 3.57 (t, 2H), 3.39 (s, 3H). MS (EI) for $C_{11}H_{15}BrO_3$: 292 (MNH4+).

Step 2. Synthesis of N-{3-[2-(2-methoxyethoxy)ethoxy]phenyl}-17-methylmorphinan-3-amine A solution of 17-methylmorphinan-3-amine (46.3 mg, 0.181 mmol) and 1-bromo-3-(2-(2-methoxyethoxy)ethoxy)benzene (64.6 mg, 0.235 mmol) in toluene (2 mL) was degassed under nitrogen for five minutes before the catalyst tris(dibenzylideneacetone)dipalladium(0):BINAP:sodium tert-butoxide (0.05:0.15:2) (57.5 mg) was added to the solution. The mixture was degassed and irradiated in microwave at 100° C. for four hours. The catalyst was removed by filtration. The filtrate was concentrated. The residue was first purified by flash column chromatography on silica gel and further purified on C18 column using 0.01% HCl in water and acetonitrile. The product (34) was obtained as the hydrochloride salt. MS (EI) for $C_{28}H_{38}N_2O_3$: 451.2 (MH+). 1H NMR (400 MHz, DMSO-d6) δ 10.82 (s, 1H), 7.15-7.00 (m, 3H), 6.98 (dd, J=8.2, 2.2 Hz, 1H), 6.66-6.52 (m, 2H), 6.41-6.33 (m, 1H), 4.00 (dd, J=5.7, 3.7 Hz, 2H), 3.76-3.67 (m, 2H), 3.61-3.54 (m, 2H), 3.49-3.42 (m, 2H), 3.24 (s, 3H), 3.15-3.04 (m, 1H), 2.96 (dd, J=17.7, 5.4 Hz, 1H), 2.75 (d, J=4.7 Hz, 2H), 2.31 (d, J=13.3 Hz, 1H), 2.23-2.10 (m, 1H), 1.90 (td, J=13.6, 4.5 Hz, 1H), 1.70-1.60 (m, 1H), 1.53 (d, J=11.5 Hz, 1H), 1.46 (d, J=13.6 Hz, 2H), 1.40-1.16 (m, 3H), 1.02 (td, J=12.8, 12.3, 9.0 Hz, 1H).

Example 35

Preparation of N-{2-[2-(2-methoxyethoxy)ethoxy]phenyl}-17-methylmorphinan-3-amine (35), hydrochloride salt (35)

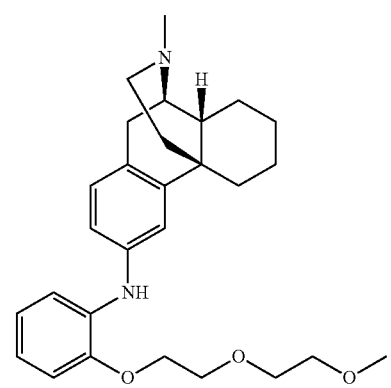

Step 1. Synthesis of 1-bromo-2-(2-(2-methoxyethoxy)ethoxy)benzene

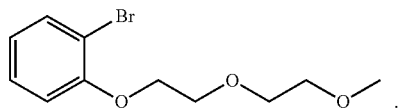

A mixture of 2-bromophenol (0.448 g, 2.59 mmol), 1-bromo-2-(2-methoxyethoxy)ethane (0.383 mL, 2.85 mmol), and potassium carbonate (1.073 g, 7.76 mmol) in dimethyl formamide (5 mL) was stirred at 60° C. overnight. The reaction mixture was poured into 20 mL of 5% LiCl solution and extracted with ethyl acetate 3×30 mL. The organic layer was washed with brine, was dried over sodium sulfate, was filtered and was concentrated. After drying under high vacuum, the pure product was obtained as colorless oil (656.7 mg) in 92% yield. $^1$H NMR (400 MHz, CDCl-3): δ 7.54 (d, 1H), 7.24 (t, 1H), 6.92 (d, 1H), 6.83 (t, 1H), 4.40 (t, 2H), 3.92 (t, 2H), 3.80 (t, 2H), 3.58 (t, 2H), 3.39 (s, 3H). MS (EI) for $C_{11}H_{15}BrO_3$: 292 (MNH4+).

Step 2. Synthesis of N-{2-[2-(2-Methoxyethoxy)ethoxy]phenyl}-17-methylmorphinan-3-amine A solution of 17-methylmorphinan-3-amine (81.4 mg, 0.317 mmol) and 1-bromo-2-(2-(2-methoxyethoxy)ethoxy) benzene (131 mg, 0.476 mmol) in toluene (3 mL) was degassed under nitrogen for five minutes before the catalyst tris(dibenzylideneacetone)dipalladium(0):BINAP:sodium tert-butoxide (0.05:0.15:2) (71.8 mg) was added to the solution. The mixture was degassed and irradiated in microwave at 100° C. for four hours. The catalyst was removed by filtration. The filtrate was concentrated. The residue was purified by flash column chromatography on silica gel to afford the product (35) as the free base (17.6 mg, 12.3%). MS (EI) for $C_{28}H_{38}H_2O_3$: 451.2 (MH+). 1H NMR (500 MHz, DMSO-d6) δ 7.11 (dd, J=7.9, 1.6 Hz, 1H), 7.03-6.93 (m, 3H), 6.94-6.70 (m, 5H), 4.15-4.09 (m, 2H), 3.80-3.74 (m, 2H), 3.63-3.56 (m, 2H), 3.48-3.42 (m, 2H), 3.23 (s, 3H), 2.93 (d, J=18.2 Hz, 1H), 2.74 (s, 1H), 2.35 (d, J=11.2 Hz, 1H), 2.32-2.24 (m, 4H), 2.02 (t, J=11.6 Hz, 1H), 1.73 (dt, J=12.8, 3.1 Hz, 1H), 1.62 (td, J=12.3, 4.8 Hz, 2H), 1.54-1.46 (m, 1H), 1.42-1.18 (m, 6H), 1.07 (qd, J=12.6, 3.8 Hz, 1H).

The free base (12.3 mg) was dissolved in 1 mL of acetonitrile. To the solution was added 0.2 mL of 1N hydrochloride. The mixture was lyophilized to afford 12.8 mg of the product as hydrochloride salt.

Example 36

Synthesis of N-{4-[2-(2-methoxyethoxy)ethoxy]phenyl}-17-methylmorphinan-3-amine (36), hydrochloride salt

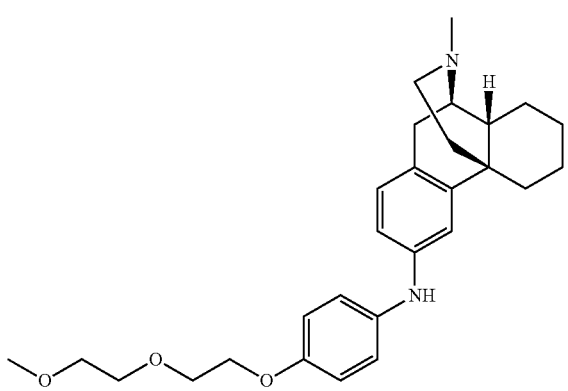

(36)

Step 1: Potassium carbonate (839 mg, 6.07 mmol) was suspended in DMF (5 mL). 4-Bromophenol (350 mg, 2.023 mmol) and 1-bromo-2-(2-methoxyethoxy)ethane (407 mg, 2.225 mmol) were added to the suspension. The mixture was stirred at 60° C. overnight. The reaction mixture was poured into 20 mL of 5% LiCl solution and extracted with ethyl acetate (3×30 mL). The organic layer was washed with brine, was dried over sodium sulfate, was filtered and was concentrated. After drying under high vacuum, 1-bromo-4-(2-(2-methoxyethoxy)ethoxy)benzene was obtained as colorless oil (537.9 mg) in 97% yield. $^1$H NMR (500 MHz, Chloroform-d) δ 7.36-7.31 (m, 2H), 6.80-6.74 (m, 2H), 4.10-4.07 (m, 2H), 3.84-3.82 (m, 2H), 3.70-3.68 (m, 2H), 3.56-3.55 (m, 2H), 3.37 (s, 3H).

Step 2: A flask was charged with 17-methylmorphinan-3-amine (132.3 mg, 0.516 mmol) [Neumeyer et al. (2012) *J Med Chem* 55(8):3878-3890 and Zhang et al. (2004) *J Med Chem* 47(1):165-174] and 1-bromo-4-(2-(2-methoxyethoxy)ethoxy)benzene (151.1 mg, 0,549 mmol). Then, anhydrous toluene (12 mL) was added. Thereafter, a pre-mixed catalyst mixture of tris(dibenzylideneacetone)dipalladium(0):BINAP:sodium tert-butoxide (0.05:0.15:2) (124.3 mg) was added. The mixture was purged with nitrogen. The mixture was stirred at 95° C. for 19 hours. The mixture was cooled to room temperature, filtered and the solvent was removed. The residue was mixed with water, and then extracted with dichloromethane (3×25 mL). The combined organic solution was washed with brine, was dried over sodium sulfate, was filtered and was concentrated. The residue was purified by flash column chromatography on silica gel to result in 78.8 mg of product (36) as the free base in 29% yield. $^1$H NMR (500 MHz, Chloroform-d) δ 6.97-6.93 (m, 3H), 6.84-6.82 (m, 3H), 6.73 (dd, J=8.2, 2.1 Hz, 1H), 5.38 (s, 1H), 4.10 (t, J=4.9 Hz, 2H), 3.83 (t, J=5.0 Hz, 2H), 3.71 (dd, J=5.5, 3.7 Hz, 2H), 3.57-3.56 (m, 2H), 3.38 (s, 3H), 2.94 (d, J=18.1 Hz, 1H), 2.77 (br, 1H), 2.59-2.46 (m, 2H), 2.42-2.40 (m, 1H), 2.38 (s, 3H), 2.24 (d, J=11.4 Hz, 1H), 2.13-2.08 (m, 1H), 1.78 (d, J=12.5 Hz, 1H), 1.68 (m, 2H), 1.51-1.42 (m, 1H), 1.43-1.10 (m, 4H), 1.01 (m, 1H). MS for $C_{28}H_{38}N_2O_3$: 451 (MH$^+$). The free base was then dissolved in 1.5 mL of acetonitrile, followed by the addition of 3 mL of 1M hydrochloride to form the HCl salt.

Example 37

Preparation of N-(17-methylmorphinan-3-yl)methanesulfonamide (37), hydrochloride salt

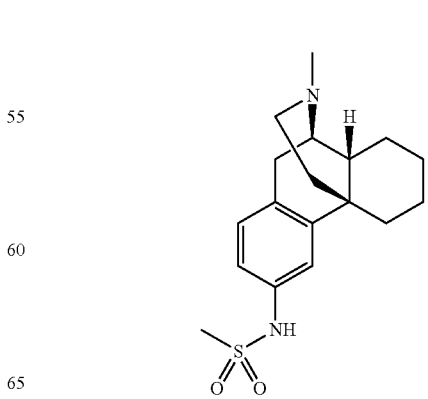

(37)

A solution of 17-methylmorphinan-3-amine (50.1 mg, 0.195 mmol) and triethylamine (0.054 mL, 0.391 mmol) in dichloromethane (2 mL) was cooled to 0° C. Methanesulfonyl chloride (0.018 mL, 0.234 mmol) was added to the above solution. The reaction was then stirred at room temperature for two hours. The reaction was taken up in 10 mL of dichloromethane, was sequentially washed with saturated sodium bicarbonate (10 mL) and brine (10 mL), and was dried over magnesium sulfate. After filtration, the solvent was removed and the residue was purified by flash column chromatography on silica gel to afford 17.2 mg of the product (37) as free base in 26.3% yield. 1H NMR (500 MHz, DMSO-d6) δ 9.53 (s, 1H), 7.13 (dd, J=5.4, 3.0 Hz, 2H), 7.02 (dd, J=8.2, 2.1 Hz, 1H), 3.07 (d, J=18.8 Hz, 1H), 2.92 (s, 3H), 2.83 (t, J=23.5 Hz, 1H), 2.30 (s, 9H), 1.82 (d, J=65.9 Hz, 1H), 1.65-1.25 (m. 6H), 1.18-0.86 (m, 2H). MS (EI) for $C_{18}H_{26}N_2O_2S$: 335.2 (MH+). 1H NMR (500 MHz, DMSO-d6) δ 9.53 (s, 1H), 7.13 (dd, J=5.4, 3.0 Hz, 2H), 7.02 (dd, J=8.2, 2.1 Hz, 1H), 4.07 (d, J=5.2 Hz, 0H), 3.07 (d, J=18.8 Hz, 1H), 2.92 (s, 3H), 2.83 (t, J=23.5 Hz, 1H), 2.72-2.57 (m, 0H), 2.30 (s, 9H), 1.82 (d, J=65.9 Hz, 1H), 1.65-1.25 (m, 6H), 1.18-0.86 (m, 2H).

The free base (10.5 mg) was dissolved in 1 mL of acetonitrile. To the solution was added 0.2 mL of 1N hydrochloride. The mixture was lyophilized to afford 9.5 mg of the product as the hydrochloride salt.

Example 38

Preparation of N-(4-methoxyphenyl)-17-methylmorphinan-3-carboxamide (38), hydrochloride salt

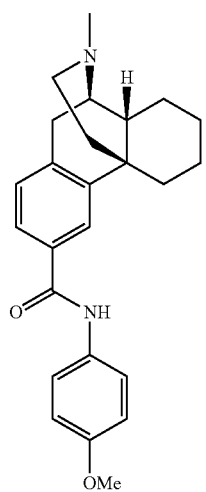

(38)

To a solution of 17-methylmorphinan-3-carboxylic acid [Zhang et al. (2004) *J Med Chem* 47(4165-174] (49.5 mg, 0.173 mmol), EDC (49.9 mg, 0.260 mmol) and triethylamine (0.048 mL, 0.347 mmol) in 3 mL of dichloromethane, 4-methoxyaniline (32 mg, 0.26 mmol) was added. The reaction was stirred at room temperature for two hours. The reaction was then taken up in 10 mL of dichloromethane and washed with 10 mL of brine/1N HCl (1:1), saturated sodium bicarbonate (10 mL) and brine (10 mL). The organic layer was dried over sodium sulfate and concentrated. The residue was purified on flash silica gel column to give the desired product (38) as the free base (28.1 mg, 41.5%). MS (EI) for $C_{25}H_{30}N_2O_2$: 391.2 (MH+). 1H NMR (500 MHz, DMSO-d6) δ 9.98 (s, 1H), 7.83 (d, J=1.9 Hz, 1H), 7.71 (dd, J=7.9, 1.8 Hz, 1H), 7.68-7.61 (m, 2H), 7.27 (d, J=8.0 Hz, 1H), 6.97-6.89 (m, 2H), 3.75 (s, 3H), 3.05 (d, J=18.8 Hz, 1H), 2.76 (dd, J=5.7, 3.1 Hz, 1H), 2.67-2.58 (m, 1H), 2.35 (ddd, J=12.0, 4.8, 1.9 Hz, 1H), 2.28 (s, 3H), 1.89 (td, J=12.1, 3.2 Hz, 1H), 1.78 (dt, J=13.1, 3.3 Hz, 1H), 1.68 (td, J=12.5, 4.7 Hz, 1H), 1.60 (d, J=13.1 Hz, 1H), 1.51 (d, J=13.4 Hz, 1H), 1.44-1.22 (m, 5H), 1.14 (dddd, J=17.2, 13.8, 8.6, 3.7 Hz, 1H), 0.98 (qd, J=12.6, 3.7 Hz, 1H).

The free base (23.8 mg) was dissolved in 2 mL of acetonitrile. To the solution was added 0.5 mL of 1N hydrochloric acid. The mixture was lyophilized to afford 25.9 mg of the product as the hydrochloride salt.

Example 39

Preparation of N-[2-(2-methoxyethoxy)ethyl]-17-methylmorphinan-3-carboxamide (39), hydrochloride salt

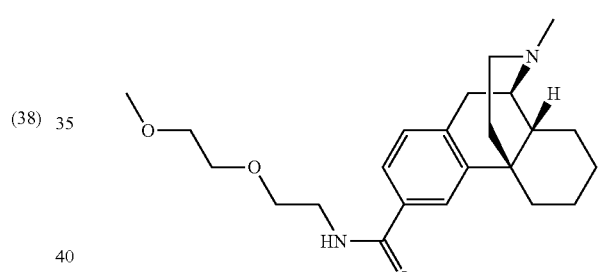

(39)

To a solution of 17-methylmorphinan-3-carboxylic acid (50.4 mg, 0.177 mmol), EDC (50.8 mg, 0.265 mmol) and triethylamine (0.049 mL, 0.353 mmol) in 3 mL of dichloromethane was added 2-(2-methoxyethoxy)ethanamine (31.6 mg, 0.265 mmol). The reaction was stirred at room temperature for two hours. The reaction was then taken up in 10 mL of dichloromethane and was sequentially washed with 10 mL of brine/1N HCl (1:1), saturated sodium bicarbonate (10 mL) and brine (10 mL). The organic layer was dried over sodium sulfate, was filtered and was concentrated. The residue was purified on flash silica gel column to give the desired product (39) as the free base (33.4 mg, 48.9%). MS (EI) for $C_{23}H_{34}N_2O_3$: 387.2 (MH+). 1H NMR (500 MHz, DMSO-d6) δ 8.43 (t, J=5.7 Hz, 1H), 7.75 (d, J=1.8 Hz, 1H), 7.59 (dd, J=7.9, 1.8 Hz, 1H), 7.20 (d, J=8.0 Hz, 1H), 3.57-3.47 (m, 4H), 3.47-3.35 (m, 4H), 3.23 (s, 3H), 3.02 (d, J=18.8 Hz, 1H), 2.74 (dd, J=5.7, 3.1 Hz, 1H), 2.64-2.53 (m, 1H), 2.48 (q, J=2.7, 1.7 Hz, 1H), 2.27 (s, 4H), 1.86 (td, J=12.2, 3.1 Hz, 1H), 1.76 (dt, J=13.1, 3.2 Hz, 1H), 1.71-1.55 (m, 2H), 1.54-1.46 (m, 1H), 1.42-1.20 (m, 5H), 1.10 (ddt, J=16.9, 13.5, 6.7 Hz, 1H), 0.96 (qd, J=12.9, 4.0 Hz, 1H).

The free base (26.8 mg) was dissolved in 2 mL of acetonitrile. To the solution was added 0.5 mL of 1N hydrochloric acid. The mixture was lyophilized to afford 33.7 mg of the product as the hydrochloride salt.

Example 40

Preparation of tert-butyl (17-methylmorphinan-3-yl)carbamate (40)

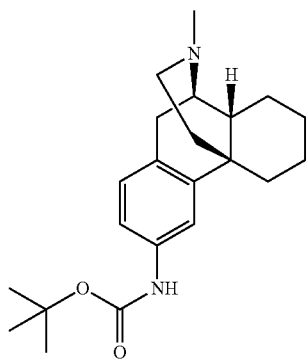

(40)

17-Methylmorphinan-3-amine (133.3 mg, 0.52 mmol) was dissolved in dichloromethane. To the solution were added imidazole (42.5 mg, 0.624 mmol), followed by Boc anhydride (136 mg, 0.624 mmol). The reaction was stirred at room temperature overnight. The reaction was taken up by dichloromethane (50 mL) and washed with brine. The organic layer was dried over sodium sulfate. After filtration and removal of solvent, the crude product was purified on a flash silica gel column to give the desired product (40) (100 mg, 54%) as a foaming solid. MS (EI) for $C_{22}H_{32}N_2O_2$: 357.2 (MH+). 1H NMR (400 MHz, DMSO-d6) δ 9.13-9.05 (m, 1H), 7.33 (d, J=2.1 Hz, 1H), 7.19 (d, J=8.2 Hz, 1H), 6.98 (d, J=8.3 Hz, 1H), 2.89 (d, J=18.3 Hz, 1H), 2.69 (dd, J=5.4, 3.0 Hz, 1H), 2.36-2.20 (m, 5H), 1.91 (td, J=12.1, 3.1 Hz, 1H), 1.70 (dt, J=13.3, 3.2 Hz, 1H), 1.60 (td, J=12.6, 5.1 Hz, 2H), 1.45 (s, 9H), 1.41-1.11 (m, 6H), 1.07-0.93 (m, 1H).

Example 41

Preparation of N-{2-[2-(2-methoxyethoxy)ethoxy]ethyl}-17-methylmorphinan-3-carboxamide (41), hydrochloride salt

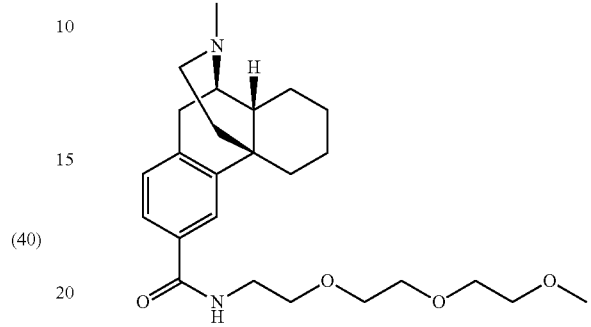

(41)

To a solution of 17-methylmorphinan-3-carboxylic acid (45 mg, 0.158 mmol), EDC (45.3 mg, 0.237 mmol) and triethylamine (0.044 mL, 0.315 mmol) in 3 mL of dichloromethane was added 2-(2-(2-methoxyethoxy)ethoxy)ethanamine (38.6 mg, 0.237 mmol). The reaction was stirred at room temperature for two hours. The reaction was then taken up in 10 mL of dichloromethane and was sequentially washed with 10 mL of brine/1N HCl (1:1), saturated sodium bicarbonate (10 mL) and brine 10 mL. The organic layer was dried over sodium sulfate, was filtered and was concentrated. The residue was purified on flash silica gel column to give the desired product (41) as the free base (40.2 mg, 59.2%). MS (EI) for $C_{25}H_{38}N_2O_4$: 431.2 (MH+). 1H NMR (400 MHz, DMSO-d6) δ 10.98 (s, 1H), 8.53 (t, J=5.6 Hz, 1H), 7.82 (d, J=2.1 Hz, 1H), 7.70 (dd, J=8.0, 1.7 Hz, 1H), 7.27 (d, J=8.1 Hz, 1H), 3.59-3.33 (m, 12H), 3.21 (s, 3H), 3.07 (s, 2H), 2.72 (s, 3H), 2.60-2.50 (m, 1H), 1.94 (s, 1H), 1.57 (dd, J=32.2, 13.0 Hz, 2H), 1.44 (d, J=13.0 Hz, 2H), 1.33 (d, J=12.7 Hz, 2H), 1.26-1.15 (m, 1H), 1.15-1.00 (m, 1H), 0.99-0.83 (m, 1H).

The free base (33.6 mg) was dissolved in 2 mL of acetonitrile. To the solution was added 0.5 mL of 1N hydrochloric acid. The mixture was lyophilized to afford 35 mg of the product as the hydrochloride salt.

Example 42

Preparation of N-(17-methylmorphinan-3-yl)-2,5,8,11,14,17-hexaoxanonadecan-19-amide (42), hydrochloride salt

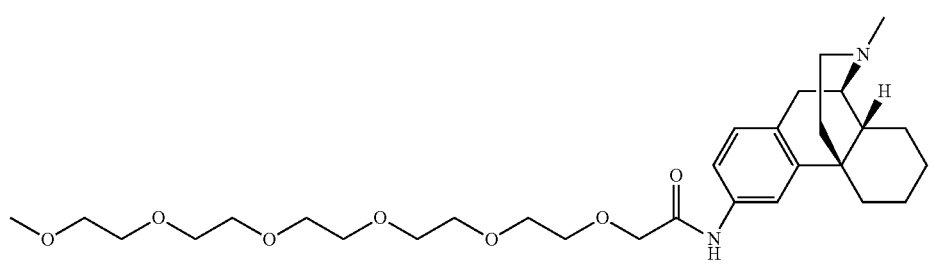

(42)

To a solution of 2,5,8,11,14,17-hexaoxanonadecan-19-oic acid (105 mg, 0.338 mmol), EDC (64.7 mg, 0.338 mmol) and triethylamine (0.094 mL, 0.675 mmol) in 3 mL of dichloromethane was added 17-methylmorphinan-3-amine (57.7, 0.225 mmol). The reaction was stirred at room temperature for two hours. The reaction was then taken up in 10 mL of dichloromethane and was sequentially washed with 10 mL of brine/1N HCl (1:1), saturated sodium bicarbonate (10 mL and brine (10 mL). The organic layer was dried over sodium sulfate, was filtered and was concentrated. The residue was purified on flash silica gel column to give the desired product (42) as the free base (69.8 mg, 56.5%). MS (EI) for $C_{30}H_{48}N_2O_7$: 594.4 (MH+). 1H NMR (400 MHz, DMSO-d6) δ 9.47 (s, 1H), 7.49 (d, J=2.2 Hz, 1H), 7.45 (dd, J=8.3, 2.1 Hz, 1H), 7.06 (d, J=8.3 Hz, 1H), 4.04 (s, 1H), 3.71-3.58 (m, 3H), 3.58-3.46 (m, 14H), 3.44-3.38 (m, 2H), 3.23 (d, J=4.3 Hz, 3H), 3.01-2.92 (m, 1H), 2.81 (s, 1H), 2.41-2.12 (m, 6H), 1.99 (t, J=11.8 Hz, 1H), 1.76 (d, J=12.5 Hz, 1H), 1.70-1.56 (m, 2H), 1.50 (dd, J=15.6, 9.6 Hz, 1H), 1.43-1.13 (m, 6H), 1.10-0.92 (m, 2H).

The free base (65.7 mg) was dissolved in 3 mL of acetonitrile. To the solution was added 1 mL of 1N hydrochloric acid. The mixture was lyophilized to afford 71.4 mg of the product as the hydrochloride salt.

Example 43

Preparation of 17-methyl-N-(pyridin-3-yl)morphinan-3-amine (43), hydrochloride salt (43)

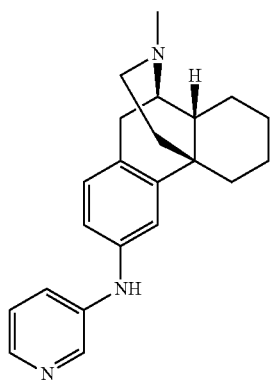

A solution of 17-methylmorphinan-3-amine (52.6 mg, 0.205 mmol) and 3-bromopyridine (42.1 mg, 0.26 mmol) in toluene (2 mL) was degassed under nitrogen for five minutes before the catalyst tris(dibenzylideneacetone)dipalladium (0):BINAP:sodium tert-butoxide (0.05:0.15:2) (31.8 mg) was added to the solution. The mixture was degassed and irradiated in microwave at 100° C. for four hours. The catalyst was removed by filtration. After removal of the solvent, the crude product was purified on an Aktar C18 column, using 0.01% HCl in acetonitrile and water. Pure fractions were combined and lyophilized to afford the product (43) as the hydrochloride salt (4.0 mg, 4.8%). MS (EI) for $C_{22}H_{27}N_3$: 334.2 (MH+). 1H NMR (500 MHz, Methanol-d4) δ 8.30-8.16 (m, 1H), 8.01 (d, J=5.5 Hz, 1H), 7.92 (ddt, J=8.8, 2.5, 1.3 Hz, 1H), 7.70 (ddd, J=8.2, 6.1, 2.1 Hz, 1H), 7.29-7.08 (m, 3H), 3.55 (ddd, J=28.9, 6.0, 3.1 Hz, 1H), 3.26-2.97 (m, 5H), 2.83 (t, J=1.5 Hz, 2H), 2.63 (td, J=13.2, 3.4 Hz, 1H), 2.40 (d, J=14.1 Hz, 1H), 2.10-1.95 (m, 1H), 1.86 (td, J=13.6, 4.3 Hz, 1H), 1.64 (d, J=13.0 Hz, 1H), 1.61-1.14 (m, 7H), 1.12-0.98 (m, 1H).

Example 44

Preparation of 17-methyl-3-(1H-pyrazol-4-yl)morphinan (44), hydrochloride salt (44)

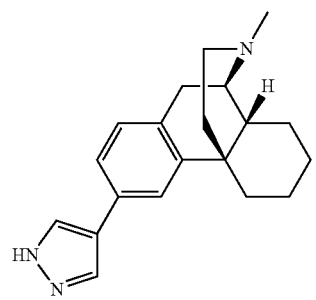

17-Methylmorphinan-3-yl trifluoromethanesulfonate [Neumeyer et al. (2012) *J Med Chem* 55(8):3878-3890 and Zhang et al. (2004) *J Med Chem* 47(1):165-174] (108.9 mg, 0.28 mmol), (1H-pyrazol-4-yl)boronic acid (46.9 mg, 0.419 mmol) and sodium carbonate (89 mg, 0.839 mmol) were placed in a microwave reaction tube (2-5 mL). Dioxane (2 mL) and water (1 mL) were added to the tube and the mixture was degassed for five minutes before tetrakis(triphenylphosphine)palladium(0) (64.6 mg, 0.056 mmol) was added. The mixture was degassed and was irradiated in a microwave for two hours at 100° C. The mixture was cooled to room temperature, and was partitioned between dichloromethane (50 mL) and water (10 mL). Brine (30 mL) was added. The organic solution was separated and the aqueous solution was extracted with dichloromethane (25 mL). The combined organic solution was dried over anhydrous sodium sulfate, was filtered and was concentrated. The residue was purified on flash column chromatography on silica gel to afford the product (44) (35.7 mg) as free base in 41.5% yield. MS (EI) for $C_{20}H_{25}N_3$: 308.2 (MH+). 1H NMR (500 MHz, Methanol-d4) δ 7.79 (s, 2H), 7.36 (s, 1H), 7.24 (d, J=7.9 Hz, 1H), 7.03 (d, J=8.1 Hz, 1H), 2.99 (d, J=19.0 Hz, 1H), 2.90 (s, 1H), 2.76-2.67 (m, 1H), 2.48 (t, J=12.0 Hz, 2H), 2.39 (s, 3H), 2.21-2.12 (m, 1H), 1.77 (d, J=12.7 Hz, 1H), 1.67 (td, J=13.0, 4.6 Hz, 1H), 1.61-1.54 (m, 1H), 1.46 (d, J=12.9 Hz, 1H), 1.40-1.14 (m, 6H), 1.08 (dd, J=14.6, 11.0 Hz, 1H).

The free base (35.7 mg) was dissolved in 2 mL of acetonitrile. To the solution was added 0.5 mL of 1N hydrochloric acid. The mixture was lyophilized to afford 39.2 mg of the product as the hydrochloride salt.

Example 45

Preparation of 17-methyl-3-(pyridin-4-yl)morphinan (45), hydrochloride salt (45)

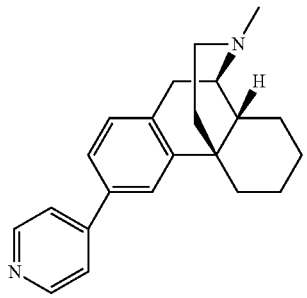

17-Methylmorphinan-3-yl trifluoromethanesulfonate [Neumeyer et al. (2012) *J Med Chem* 55(8):3878-3890 and Zhang et al. (2004) *J Med Chem* 47(1):165-174] (105.5 mg, 0.27 mmol), pyridin-4-ylboronic acid (49.9 mg, 0.406 mmol), sodium carbonate (86 mg, 0.813 mmol) were placed in a microwave reaction tube (2-5 mL). Dioxane (2 mL) and water (1 mL) were added to the tube and the mixture was degassed for five minutes before tetrakis(triphenylphosphine)palladium(0) (62.6 mg, 0.054 mmol) was added. The mixture was degassed and was irradiated in a microwave for two hours at 100° C. The mixture was cooled to room temperature, and was partitioned between dichloromethane (50 mL) and water (10 mL). Brine (30 mL) was added. The organic solution was separated and the aqueous solution was extracted with dichloromethane (25 mL). The combined organic solution was dried over anhydrous sodium sulfate, was filtered and was concentrated. The residue was purified on flash column chromatography on silica gel to afford the product (45) (57.4 mg) as the free base in 66.6% yield. MS (EI) for $C_{22}H_{26}N_2$: 319.2 (MH+). 1H NMR (500 MHz, Methanol-d4) δ 8.46-8.41 (m, 2H), 7.60-7.39 (m, 4H), 7.23 (d, J=7.9 Hz, 1H), 3.14-3.06 (m, 2H), 2.88 (dd, J=19.6, 6.1 Hz, 1H), 2.69-2.61 (m, 1H), 2.51 (s, 4H), 2.30-2.21 (m, 1H), 1.89-1.82 (m, 1H), 1.75 (td, J=13.8, 13.2, 4.6 Hz, 1H), 1.59 (d, J=13.0 Hz, 1H), 1.49 (d, J=13.3 Hz, 1H), 1.45-1.12 (m, 6H), 1.04 (tt, J=14.0, 7.1 Hz, 1H).

The free base (57.4 mg) was dissolved in 3 mL of acetonitrile. To the solution was added 1 mL of 1N hydrochloric acid. The mixture was lyophilized to afford 65.3 mg of the product as the hydrochloride salt.

Example 46

Preparation of 17-methyl-N-(1,3-thiazol-2-yl)morphinan-3-amine (46), hydrochloride salt (46)

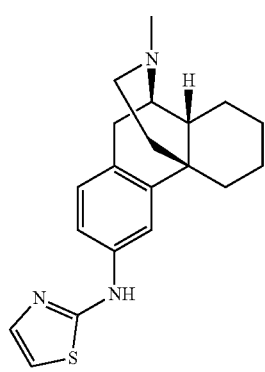

A solution of 17-methyl-morphinan-3-amine (48.6 g, 0.19 mmol), 2-bromothiazole (62.2 mg, 0.379 mmol) and hydrochloric acid (37%, 0.031 mL, 0.379 mmol) in ethanol (1.8 mL) and water (0.2 mL) was irradiated in a microwave for two hours at 100° C. The reaction was cooled to room temperature and mixed with dichloromethane (30 mL) and saturated sodium bicarbonate (30 mL). The organic layer was washed with brine (30 mL), dried over anhydrous sodium sulfate, was filtered and was concentrated. The residue was purified by flash column chromatography on silica gel to afford the product (46) (20.6 mg) as the free base in 32% yield. MS (EI) for $C_{20}H_{25}N_3S$: 340.2 (MH+). 1H NMR (500 MHz, Methanol-d4) δ 7.25 (d, J=2.3 Hz, 1H), 7.11 (dd, J=8.3, 2.2 Hz, 1H), 7.03 (dd, J=3.7, 1.2 Hz, 1H), 6.93 (d, J=8.2 Hz, 1H), 6.56 (d, J=3.7 Hz, 1H), 2.89 (d, J=18.5 Hz, 1H), 2.70 (dd, J=5.8, 3.1 Hz, 1H), 2.54 (dd, J=18.5, 5.8 Hz, 1H), 2.35-2.22 (m, 5H), 2.00 (td, J=12.5, 3.3 Hz, 1H), 1.69 (dt, J=12.9, 3.2 Hz, 1H), 1.64-1.49 (m, 2H), 1.43-1.34 (m, 1H), 1.34-1.11 (m, 6H), 1.02 (qd, J=13.6, 12.9, 4.2 Hz, 1H).

The free base (20.6 mg) was dissolved in 2 mL of acetonitrile. To the solution was added 0.5 mL of 1N hydrochloric acid. The mixture was lyophilized to afford 22.6 mg of the product as the hydrochloride salt.

Example 47

Preparation of (6β)-6-{2-[2-(2-methoxyethoxy)ethoxy]ethoxy}-17-methylmorphinan-3-ol (47), hydrochloride salt (47)

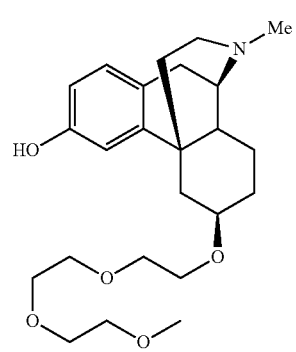

Step 1: Preparation of 3-methoxy-9-(2-(2-(2-methoxy(ethoxy(ethoxy(ethoxy)))-17-methylmorphinan

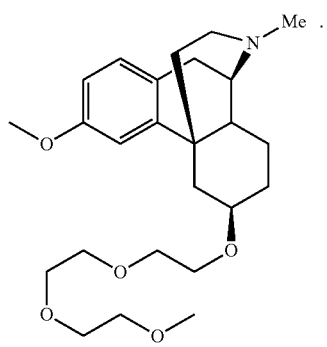 [SMILES: COCCOCCOCCO[C@@H]1CCC2[C@H]3Cc4ccc(OC)cc4[C@@]2(CCN3C)C1]

A dried, nitrogen-flushed 13×100 mm test tube was charged with sodium hydride (61 mg, 1.51 mmol, 60% disp.), then degreased under nitrogen with dry ether (2 mL). Solid (6β)-3-methoxy-17-methylmorphinan-6-ol (87 mg, 0.30 mmol) and dry N,N-dimethylformamide (1 mL) were added, and after 20 minutes neat 2-(2-(2-methoxyethoxy)ethoxy)ethyl methanesulfonate (HO mg, 0.45 mmol) was added, and the mixture was placed in an oil bath heated at 80° C. After four hours, the mixture was partitioned between ethyl acetate (50 mL) and brine (20 mL). The organic layer was washed with brine (3×20 mL), water (20 mL), dried (sodium sulfate), filtered and concentrated. Chromatography on silica (1:10:900 to 1:10:90 ammonium hydroxide:methanol:dichloromethane) afforded (6β)-3-methoxy {2-[2-(2-methoxyethoxy)ethoxy]ethoxy}-17-methylmorphinan as an almost colorless oil (63 mg, 48%). 1H NMR (500 MHz, Chloroform-d) δ 7.04 (d, J=8.3 Hz, 1H), 6.89 (d, J=2.6 Hz, 1H), 6.72 (dd, J=8.4, 2.6 Hz, 1H), 3.81 (s, 3H), 3.73-3.58 (m, 11H), 3.60-3.54 (m, 2H), 3.40 (s, 3H), 3.28 (tt, J=11.2, 3.9 Hz, 1H), 3.00 (d, J=18.1 Hz, 1H), 2.90 (t, J=5.5, 3.2 Hz, 1H), 2.78-2.70 (m, 1H), 2.57 (dd, J=18.1, 6.0 Hz, 1H), 2.47-2.42 (m, 1H), 2.42 (s, 3H), 2.12-1.99 (m, 2H), 1.85-1.75 (m, 2H), 1.56 (dq, J=13.1, 3.5 Hz, 1H), 1.41 (ddd, J=12.9, 3.3, 1.9 Hz, 1H), 1.39-1.29 (m, 2H), 1.20 (qd, J=13.1, 3.6 Hz, 4H); MS (ESI) for $C_{25}H_{39}NO_5$: 434.2 (MH+).

Step 2: Preparation of (6β)-6-{2-[2-(2-Methoxyethoxy)ethoxy]ethoxy}-17-methylmorphinan-3-ol A 0.5-2 mL microwave vial charged with sodium ethanethiolate (83 mg, 0.99 mmol) and a solution of 6β-3-methoxy-6-{2-[2-(2-methoxyethoxy)ethoxy]ethoxy}-17-methylmorphinan (61 mg, 0.14 mmol) in dry N-methyl-2-pyrrolidinone (0.5 mL) was heated in a microwave at 150° C. for three hours, then partitioned between ethyl acetate (25 mL) and brine (25 mL) buffered with saturated aqueous ammonia:ammonium chloride (0.5 mL each). The aqueous layer was diluted with brine (25 mL), and back extracted with ethyl acetate (25 mL). The combined organic layers were washed with additional brine (3×25 mL), dried (sodium sulfate), filtered and concentrated. Chromatography on silica (1:10:450 to 1:10:150 ammonium hydroxide:methanol:dichloromethane) afforded (6β)-6-{2-[2-(2-methoxyethoxy)ethoxy]ethoxy}-17-methylmorphinan-3-ol (47) as a light yellow wax (56 mg, 95%). 1H NMR (500 MHz, Chloroform-d) δ 6.97 (d, J=8.2 Hz, 1H), 6.92 (d, J=2.5 Hz, 1H), 6.81 (s, 1H), 6.66 (dd, J=8.2, 2.6 Hz, 1H), 3.80-3.66 (m, 7H), 3.66-3.54 (m, 5H), 3.41 (s, 3H), 3.38 (tt, J=11.0, 4.0 Hz, 1H), 2.98 (d, J=18.1 Hz, 1H), 2.91-2.85 (m, 1H), 2.72 (dt, J=13.1, 2.8 Hz, 1H), 2.54 (dd, J=18.1, 5.8 Hz, 1H), 2.44 (ddd, J=12.0, 5.0, 2.0 Hz, 1H), 2.41 (s, 3H), 2.12 (td, J=12.3, 3.3 Hz, 1H), 2.06-1.97 (m, 1H), 1.84-1.75 (m, 2H), 1.55 (dq, J=13.0, 3.2 Hz, 1H), 1.41 (ddd, J=12.6, 3.2, 1.8 Hz, 1H), 1.38-1.25 (m, 2H), 1.20 (qd, J=12.8, 3.4 Hz, 1H); MS (ESI) for $C_{24}H_{37}NO_5$: 420.2 (MH+). The material was converted to the HCl salt by dissolution in acetonitrile (5 mL), water (0.5 mL) and 2 M HCl (200 uL), and concentrated in vacuo to yield the HCl salt as a light yellow wax.

Example 48

Preparation of N-{5-[2-(2-methoxyethoxy)ethoxy]pyridin-3-yl}-17-methylmorphinan-3-amine (48), hydrochloride salt

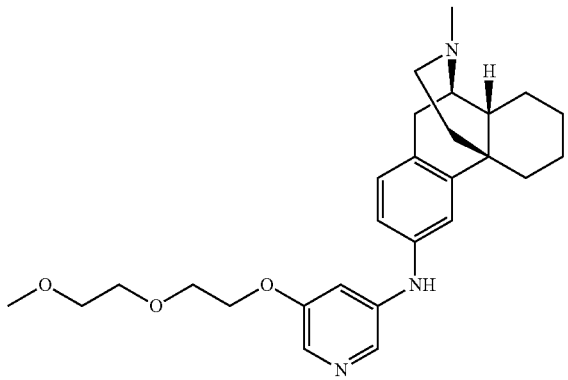

(48)

Step 1. Synthesis of 3-bromo-5-(2-(2-methoxyethoxy)ethoxy)pyridine

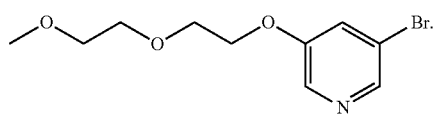

A mixture of 5-bromopyridin-3-ol (100 mg, 0.575 mmol), 1-bromo-2-(2-methoxyethoxy)ethane (105 mg, 0.575 mmol) and $K_2CO_3$ (159 mg, 1.149 mmol) in DMF (3 mL) was irradiated in a microwave at 80° C. for two hours. The reaction mixture was cooled to room temperature and poured into 15 mL of ethyl acetate and 1N NaOH (20 mL). The organic layer was washed with brine (20 mL), dried over anhydrous sodium sulfate, was filtered and was concentrated. The crude product was purified by flash column chromatography on silica gel to afford 3-bromo-5-(2-(2-methoxyethoxy)ethoxy)pyridine (82.7 mg, 52.1%). MS (EI) for $C_{10}H_{14}BrNO_3$: 277.8 (MH+).

Step 2. Synthesis of N—{5-[2-(2-methoxyethoxy)ethoxy]pyridin-3-yl}-17-methylmorphinan-3-amine A solution of 17-methylmorphinan-3-amine (53.9 mg, 0.21 mmol) and 3-bromo-5-(2-(2-methoxyethoxy)ethoxy)pyridine (75 mg, 0.273 mmol) in toluene (3 mL) was degassed under nitrogen for five minutes before the catalyst tris(dibenzylideneacetone)dipalladium(0):BINAP:sodium tert-butoxide (0.05:0.15:2) (52.3 mg) was added to the solution. The mixture was degassed and irradiated in a microwave at 100° C. for two hours. The catalyst was removed by filtration. The filtrate was concentrated. The residue was purified by flash column chromatography on silica gel to afford the product (48) as the free base (50.9 mg, 53.7%). MS (EI) for $C_{27}H_{37}N_3O_3$: 452.2 (MH+). 1H NMR (500 MHz, Methanol-d4) δ 7.89 (d, J=2.2 Hz, 1H), 7.72 (d, J=2.4 Hz, 1H), 7.25-7.15 (m, 2H), 7.12-7.05 (m, 2H), 4.20-4.12 (m, 2H), 3.88-3.79 (m, 2H), 3.73-3.63 (m, 3H), 3.62-3.52 (m, 2H), 3.38 (s, 3H), 3.20 (d, J=20.5 Hz, 3H), 2.97 (s, 3H), 2.82 (s, 1H), 2.48 (d, J=13.2 Hz, 1H), 2.07 (d, J=12.2 Hz, 1H), 1.96 (dt, J=15.3, 7.8 Hz, 1H), 1.83-1.75 (m, 1H), 1.69-1.57 (m, 3H), 1.56-1.17 (m, 4H).

The free base (48 mg) was dissolved in 2 mL of acetonitrile. To the solution was added 1 mL of 1N hydrochloric acid. The mixture was lyophilized to afford 46 mg of the product as the hydrochloride salt.

Example 49

Preparation of 17-methyl-N-(pyridin-4-yl)morphinan-3-amine (49), hydrochloride salt

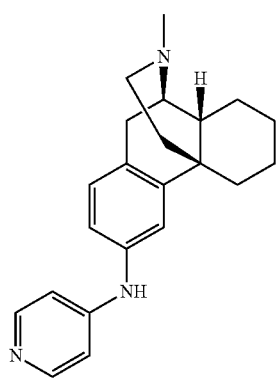

(49)

17-Methyl-morphinan-3-amine (38.9 mg, 0.152 mmol) and 4-chloropyridine (HCl salt, 29.6 mg, 0.197 mmol) were dissolved in 2-propanol (1 mL). The solution was irradiated in a microwave at 85° C. for four hours. The solvent was removed and the residue was purified on a C-18 column to afford the desired product (49) as a hydrochloride salt (3.6 mg, 5.8%). MS (EI) for $C_{22}H_{27}N_3$: 334.2 (MH$^+$). 1H NMR (500 MHz, Methanol-d4) δ 8.27-8.16 (m, 4H), 7.43 (dd, J=12.7, 8.2 Hz, 2H), 7.35 (d, J=2.2 Hz, 2H), 7.33-7.26 (m, 2H), 7.15-7.09 (m, 4H), 4.94-4.82 (m, 1H), 3.74 (dd, J=5.9, 3.1 Hz, 2H), 3.53-3.37 (m, 1H), 3.34-3.22 (m, 4H), 3.14 (s, 1H), 3.07 (dd, J=12.6, 3.9 Hz, 1H), 2.97 (s, 5H), 2.75 (td, J=13.3, 3.6 Hz, 2H), 2.54 (d, J=14.3 Hz, 2H), 2.13 (d, J=12.5 Hz, 2H), 2.06-1.95 (m, 2H), 1.81-1.59 (m, 9H), 1.61-1.43 (m, 4H), 1.38-1.25 (m, 2H), 1.18 (qd, J=12.9, 3.9 Hz, 2H).

Example 50

Preparation of 17-methyl-N-(pyrimidin-4-yl)morphinan-3-amine (50), hydrochloride salt

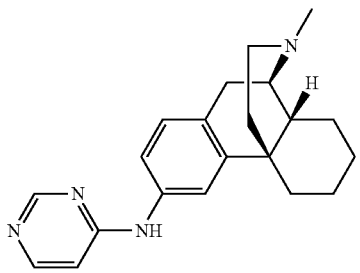

(50)

4-Chloropyrimidine hydrochloride (18.4 mg, 0.12 mmol) was added to a solution of 17-methylmorphinan-3-amine [Zhang et al. (2004) *J Med Chem* 47(1):165-174] (30 mg, 0.11 mmol) in ethanol (0.2 mL). The solution was heated in a microwave oven at 140° C. for 20 minutes. Additional 4-chloropyrimidine hydrochloride was added (5 mg, 0.03 mmol) and the mixture was heated in the microwave at the same temperature for 15 additional minutes. The solvent was removed under reduced pressure and the crude product was purified by reverse phase chromatography (0-20% water/acetonitrile/0.01% hydrochloric acid). The combined fractions were treated with 1 N hydrochloric acid to afford 17-methyl-N-(pyrimidin-4-yl)morphinan-3-amine (50), hydrochloride salt (18.4 mg, 38.5%) as a light yellow solid. $^1$H NMR (500 MHz, Methanol-d$_4$): δ 8.83 (s, 1H), 8.28 (d, J=7.0 Hz, 1H), 7.75 (bs, 1H), 7.68 (bs, 1H), 7.38 (bs, 1H), 7.07 (bs, 1H), 3.73 (dd, J=6.1, 3.1 Hz, 1H), 3.39-3.31 (m, 1H), 3.30-3.22 (m, 2H), 2.96 (s, 3H), 2.73 (td, J=13.2, 3.5 Hz, 1H), 2.55 (dd, J=13.7, 2.9 Hz, 1H), 2.16 (dt, J=12.5, 3.2 Hz, 1H), 2.02 (td, J=13.9, 4.7 Hz, 1H), 1.80-1.72 (m, 1H), 1.72-1.60 (m, 3H), 1.60-1.43 (m, 2H), 1.35 (q, J=13.6 Hz, 1H), 1.16 (qd, J=12.8, 3.9 Hz, 1H). MS (EI) for $C_{21}H_{26}N_4$: 335 (MR$^+$).

Example 51

Preparation of 3-(3-furyl)-17-methylmorphinan (51), hydrochloride salt

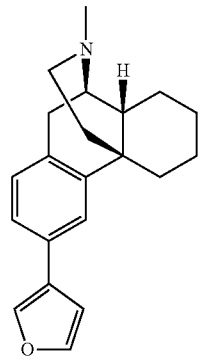

(51)

17-Methylmorphinan-3-yl trifluoromethanesulfonate [Neumeyer et al. (2012) *J Med Chem* 55(8):3878-3890 and Zhang et al. (2004) *J Med Chem* 47(4165-174] (145 mg, 0.372 mmol), 3-furanboronic acid pinacol ester (117.7 mg, 0.594 mmol), and sodium carbonate (126 mg, 1,189 mmol) were placed in a microwave reaction tube. Dioxane (2 mL) and water (1 mL) were added to the tube and the mixture was degassed for five minutes before tetrakis(triphenylphosphine)palladium(0) (83.5 mg, 0.072 mmol) was added. The mixture was degassed and was irradiated in a microwave for one hour at 100° C. The mixture was cooled to room temperature, and partitioned between with dichloromethane (50 mL) and water (10 mL). Brine (30 mL) was added. The organic solution was separated and the aqueous solution was extracted with dichloromethane (25 mL). The combined organic solution was dried over anhydrous sodium sulfate, was filtered and was concentrated. The residue was purified by flash column chromatography on silica gel to afford the product (51) (75.5 mg) as the free base in 66% yield. $^1$H NMR (500 MHz, Chloroform-d) δ 7.69-7.65 (m, 1H), 7.44 (t, J=1.7 Hz, 1H), 7.33 (d, J=1.8 Hz, 1H), 7.22 (dd, J=7.9, 1.8 Hz, 1H), 7.09 (d, J=7.9 Hz, 1H), 6.66 (dd, J=1.8, 0.9 Hz, 1H), 3.02 (d, J=18.5 Hz, 1H), 2.84-2.79 (m, 1H), 2.63 (dd, J=18.5, 5.8 Hz, 1H), 2.45-2.42 (m, 2H), 2.39 (s, 3H), 2.08 (td, J=12.4, 3.3 Hz, 1H), 1.88-1.82 (m, 1H), 1.78-1.70 (m, 1H), 1.56-1.48 (m, 1H), 1.45-1.21 (m, 6H), 1.12 (qd, J=12.6, 3.9 Hz, 1H). MS for $C_{21}H_{25}NO$, 308 (MH$^+$).

The free base was dissolved in 3 mL of acetonitrile, and 3 mL of 1M hydrochloric acid was added. The mixture was lyophilized to afford 80.8 mg of the product as the hydrochloride salt.

Example 52

Preparation of 5-(17-methylmorphinan-3-yl)pyrimidin-2-amine (52), hydrochloride salt

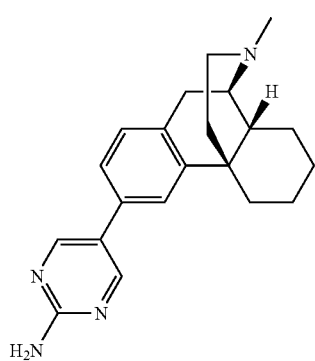

(52)

A microwave vial was charged with potassium carbonate (50.6 mg, 0.366 mmol), (2-aminopyrimidin-5-yl)boronic acid (33.9 mg, 0.244 mmol) and tetrakis(triphenylphosphine)palladium(0) (28.2 mg, 0.024 mmol). The mixture was purged under nitrogen, followed by the addition of a degassed mixture of 17-methylmorphinan-3-yl trifluoromethanesulfonate [Zhang et al. (2004) *J Med Chem* 47(1):165-174] (47.5 mg, 0.122 mmol) in dimethylformamide (0.5 mL) and water (50 μL). The vial was then irradiated in a microwave oven at 130° C. for thirty minutes. The mixture was diluted with water (25 mL) and was extracted with ethyl acetate (3×25 mL). The combined organic layer was dried over anhydrous magnesium sulfate, was filtered and was concentrated. The residue was first purified by flash chromatography (99:1:0.1 to 90:10:1 dichloromethane/methanol/aqueous ammonia) and then by reverse phase chromatography (0-20% water/acetonitrile/0.01% hydrochloric acid). The combined fractions were treated with 1 N hydrochloric acid to afford 5-(17-methylmorphinan-3-yl)pyrimidin-2-amine (52) hydrochloride salt (5.6 mg, 13.7%) as a yellow solid. $^1$H NMR (500 MHz, Methanol-d$_4$): δ 8.92 (s, 2H), 7.69 (s, 1H), 7.57 (d, J=8.0, Hz, 1H), 7.45 (d, J=8.0 Hz, 1H), 3.73 (dd, J=6.1, 3.0 Hz, 1H), 3.41-3.22 (m, 3H), 2.96 (s, 3H), 2.76-2.69 (m, 2H), 2.15 (dt, J=12.8, 3.1 Hz, 1H), 2.01 (td, J=13.9, 4.5 Hz, 1H), 1.78-1.71 (m, 2H), 1.68-1.60 (m, 2H), 1.60-1.43 (m, 2H), 1.31 (qt. J=12.8, 3.1 Hz, 1H), 1.15 (qd, J=13.2, 4.4 Hz, 1H). MS (EI) for $C_{21}H_{26}N_4$: 335 (MH$^+$).

Example 53

Preparation of 17-methyl-N-(pyrimidin-5-yl)morphinan-3-amine (53)

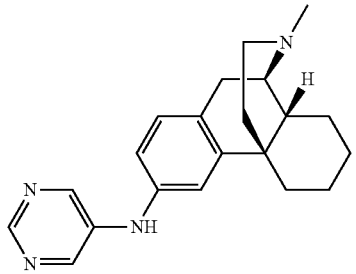

(53)

A microwave vial was charged with 5-bromopyrimidine (62 mg, 0.390 mmol), 2,2'-bis(diphenylphosphino)-1,1'-binaphthalene (24.2 mg, 0.039 mmol), sodium tert-butoxide (56.2 mg, 0.585 mmol), 17-methylmorphinan-3-amine [Zhang et al. (2004) *J Med Chem* 47(1):165-174] (50 mg, 0.195 mmol) and tris(dibenzylideneacetone)dipalladium(0) (17.8 mg, 0.02 mmol). The mixture was purged under nitrogen, followed by the addition of degassed toluene (1 mL). The vial was then irradiated in a microwave oven at 130° C. for 30 minutes. The solids were filtered and washed with tetrahydrofuran and the filtrate was concentrated. The residue was purified by flash chromatography (99:1:0.1 to 93:7:0.7 dichloromethane/methanol/aqueous ammonia) to afford 17-methyl-N-(pyrimidin-5-yl)morphinan-3-amine (53) (14.7 mg, 22.5%) as a light yellow oil. $^1$H NMR (500 MHz, Chloroform-d): δ 8.73 (s, 1H), 8.46 (s, 2H), 7.11 (d, J=8.1 Hz, 1H), 7.04 (d, J=2.3 Hz, 1H), 6.94 (dd, J=8.2, 2.3 Hz, 1H), 5.74 (dd, J=6.6, 3.1 Hz, 1H), 3.04 (d, J=18.4 Hz, 1H), 2.86 (dd, J=5.7, 3.0 Hz, 1H), 2.65 (dd, J=18.4, 5.8 Hz, 1H), 2.50 (dd, J=12.1, 4.6 Hz, 1H), 2.44 (s, 3H), 2.30 (dq, J=13.7, 2.2 Hz, 1H), 2.13 (td, J=12.2, 3.0 Hz, 1H), 1.88 (dd, J=12.8, 3.4 Hz, 1H), 1.84-1.74 (m, 1H), 1.73-1.65 (m, 1H), 1.59-1.52 (m, 1H), 1.51-1.43 (m, 1H), 1.43-1.22 (m, 4H), 1.16 (qd, J=12.6, 3.8 Hz, 1H). MS (EI) for $C_{21}H_{26}N_4$: 335 (MH$^+$).

Example 54

Preparation of (4bR,8aR,9R)—N-(5-(2,5,8,11,14-pentaoxahexadecan-16-yloxy)pyridin-3-yl)-11-methyl-6,7,8,8a,9,10-hexahydro-5H-9,4b-(epiminoethano)phenanthren-3-amine (54), hydrochloride salt

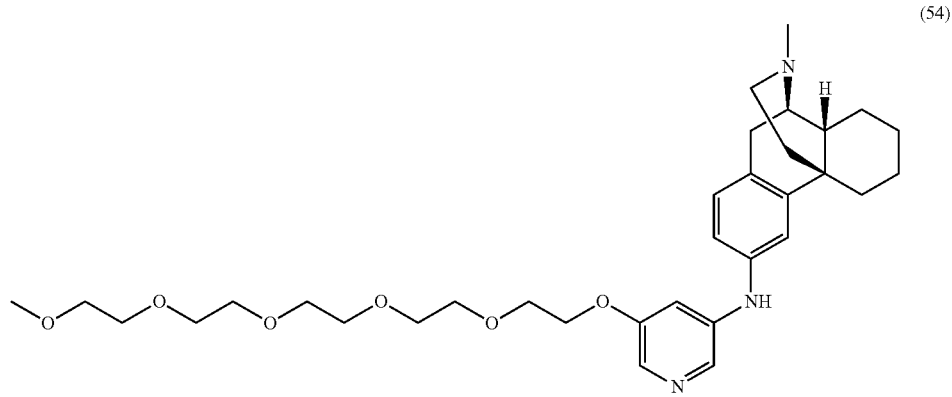 [SMILES: COCCOCCOCCOCCOCCOc1cncc(Nc2ccc3c(c2)[C@@]24CCCC[C@H]2[C@@H](C3)N(C)CC4)c1]

(54)

Step 1. Synthesis of 3-(2,5,8,11,14-pentaoxahexadecan-16-yloxy)-5-bromopyridine

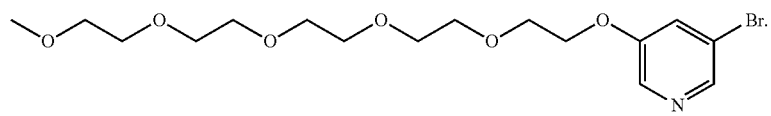 [SMILES: COCCOCCOCCOCCOCCOc1cncc(Br)c1]

A mixture of 16-bromo-2,5,8,11,14-pentaoxahexadecane (336 mg, 1.066 mmol), 5-bromopyridin-3-ol (185 mg, 1.066 mmol) and potassium carbonate (295 mg, 2.132 mmol) in DMF was irradiated in microwave at 80° C. for two hours. The reaction mixture was cooled to room temperature and was added to ethyl acetate (15 mL) and saturated sodium bicarbonate (15 mL). The organic layer was then washed with brine, was dried over anhydrous sodium sulfate, was filtered and was concentrated. The crude product was purified by flash column chromatography on silica gel to afford pure product (264 mg) in 60.7% yield. MS (EI) for $C_{16}H_{26}BrNO_6$: 408.0 (MH+).

Step 2. Synthesis of (4bR,8aR,9R)—N-(5-(2,5,8,11,14-pentaoxahexadecan-16-yloxy)pyridin-3-yl)-11-methyl-6,7,8,8a,9,10-hexahydro-5H-9,4b-(epiminoethano)phenanthren-3-amine A solution of 17-methylmorphinan-3-amine (41.4 mg, 0.16 mmol) and 3-(2,5,8,11,14-pentaoxahexadecan-16-yloxy)-5-bromopyridine (86 mg, 0.21 mmol) in toluene (3 mL) was degassed under nitrogen for five minutes before the catalyst tris(dibenzylideneacetone)dipalladium(0):BINAP:sodium tert-butoxide (0.05:0.15:2) (41.3 mg) was added to the solution. The mixture was degassed and irradiated in a microwave at 100° C. for two hours. The catalyst was removed by filtration. The filtrate was concentrated. The residue was purified on flash column chromatography on silica gel to afford the product (54) as the free base (41 mg, 43.4%). MS (EI) for $C_{33}H_{49}N_3O_6$: 584.2 (MH+). 1H NMR (500 MHz, Methanol-d4) δ 7.85 (d, J=2.2 Hz, 1H), 7.67 (d, J=2.5 Hz, 1H), 7.15-7.09 (m, 2H), 7.06 (t, J=2.4 Hz, 1H), 6.98 (dd, J=8.2, 2.3 Hz, 1H), 4.88 (d, J=13.2 Hz, 2H), 4.66 (s, 1H), 4.16 (dd, J=5.6, 3.6 Hz, 2H), 3.89-3.80 (m, 2H), 3.74-3.50 (m, 15H), 3.35 (s, 3H), 3.08 (d, J=18.6 Hz, 1H), 2.90 (t, J=4.3 Hz, 1H), 2.74 (dd, J=18.5, 5.8 Hz, 1H), 2.52 (dd, J=12.4, 4.3 Hz, 1H), 2.44 (s, 4H), 2.21 (ddd, J=15.2, 12.0, 3.2 Hz, 1H), 1.87 (dt, J=12.9, 3.1 Hz, 1H), 1.82-1.70 (m, 2H), 1.62-1.54 (m, 1H), 1.54-1.33 (m, 5H), 1.33-1.16 (m, 1H).

The free base (39.5 mg) was dissolved in 2 mL of acetonitrile. To the solution was added 1 mL of 1N hydrochloric acid. The mixture was lyophilized to afford 44.7 mg of the product as the hydrochloride salt.

Example 55

Preparation of 17-methyl-N-(pyrazin-2-yl)morphinan-3-amine (55), hydrochloride salt

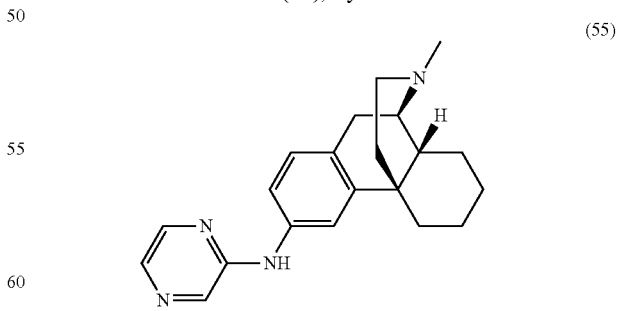

(55)

A microwave vial was charged with 2,2'-bis(diphenylphosphino)-1,1'-binaphthalene (28.6 mg, 0.046 mmol), sodium tert-butoxide (29.5 mg, 0.307 mmol), 17-methylmorphinan-3-amine [Zhang et al. (2004) *J Med Chem* 47(1): 165-174] (39.3 mg, 0.153 mmol) and tris(dibenzylideneacetone)dipalladium(0) (21.05 mg, 0.023 mmol). The mixture was purged under nitrogen, followed by the addition of a degassed mixture of 2-chloropyrazine (18 μL, 0.199 mmol) in toluene (0.9 mL). The vial was then irradiated in a microwave oven at 130° C. for 30 minutes. The solids were filtered and washed with tetrahydrofuran and the filtrate was concentrated. The residue was first purified by flash chromatography (99:1:0.1 to 93:7:0.7 dichloromethane/methanol/aqueous ammonia) and then by reverse phase chromatography (0-30% water/acetonitrile/0.01% hydrochloric acid). The combined fractions were treated with 1N hydrochloric acid to afford 17-methyl-N-(pyrazin-2-yl)morphinan-3-amine (55) hydrochloride salt (3.9 mg, 6.2%) as a bright yellow solid. $^1$H NMR (500 MHz, Methanol-d$_4$): δ 8.44 (s, 1H), 8.32 (bs, 1H), 7.98 (bs, 1H), 7.71 (s, 1H), 7.61 (d, J=7.7 Hz, 1H), 7.33 (d, J=8.1 Hz, 1H), 3.70 (d, J=4.5 Hz, 2H), 3.32-3.18 (m, 3H), 2.96 (s, 3H), 2.76 (t, J=12.8 Hz, 1H), 2.56 (d, J=13.9 Hz, 1H), 2.12 (d, J=12.2 Hz, 1H), 2.04-1.94 (m, 1H), 1.79-1.67 (m, 2H), 1.67-1.59 (m, 2H), 1.57-1.44 (m, 2H), 1.37 (q, J=13.0 Hz, 1H), 1.25-1.11 (m, 1H). MS (EI) for $C_{21}H_{26}N_4$: 335 (MH$^+$).

Example 56

Preparation of 17-methyl-N-(pyridazin-4-yl)morphinan-3-amine (56), hydrochloride salt

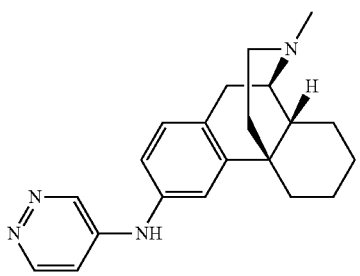

(56)

A microwave vial was charged with dicyclohexyl(2',4',6'-triisopropyl-[1,1'-biphenyl]-2-yl)phosphine (27.5 mg, 0.058 mmol), cesium carbonate (84 mg, 0.257 mmol), pyridazin-4-amine (15.8 mg, 0.167 mmol) and tris(dibenzylideneacetone)dipalladium(0) (17.6 mg, 0.019 mmol). The mixture was purged under nitrogen, followed by the addition of a degassed mixture of 17-methylmorphinan-3-yl trifluoromethanesulfonate [Zhang et al. (2004) *J Med Chem* 47(1): 165-174] (0.128 mmol) in dioxane (1.5 mL). The vial was then irradiated in a microwave oven at 150° C. for 30 minutes. The solids were filtered and washed with tetrahydrofuran and the filtrate was concentrated. The residue was first purified by flash chromatography (99:1:0.1 to 93:7:0.7 dichloromethane/methanol/aqueous ammonia) and then by reverse phase chromatography (0-30% water/acetonitrile/ 0.01% hydrochloric acid). The combined fractions were treated with 1 N hydrochloric acid to afford 17-methyl-N-(pyridazin-4-yl)morphinan-3-amine (56) hydrochloride salt (14.3 mg, 27.3%) as a light yellow solid. $^1$H NMR (500 MHz, Methanol-d$_4$): δ 8.77-8.71 (m, 2H), 7.47 (d, J=8.1 Hz, 1H), 7.43 (d, J=2.3 Hz, 1H), 7.35 (d, J=7.1 Hz, 2H), 3.74 (dd, J=6.0, 2.9 Hz, 1H), 3.36-3.22 (m, 3H), 2.97 (s, 3H), 2.80-2.70 (m, 1H), 2.55 (d, J=14.2 Hz, 1H), 2.18 (dt, J=12.7, 3.0 Hz, 1H), 2.04 (td, J=13.6, 4.3 Hz, 1H), 1.80-1.69 (m, 2H), 1.69-1.60 (m, 2H), 1.60-1.43 (m, 2H), 1.30 (ddd, J=16.4, 13.2, 10.1 Hz, 1H), 1.16 (qd, J=12.9, 4.0 Hz, 1H). MS (EI) for $C_{21}H_{26}N_4$: 335 (MH$^+$).

Example 57

Preparation of 17-methyl-N,N-di(pyridin-2-yl)morphinan-3-amine (57), hydrochloride salt

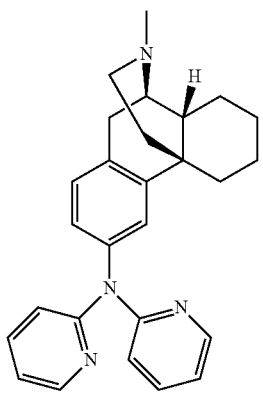

(57)

A toluene solution of 17-methylmorphinan-3-amine (0.110 g, 0.43 mmol), 2-bromopyridine (0.149 g, 0.94 mmol) and tris(dibenzylideneacetone)dipalladium(0): BINAP:sodium tert-butoxide (0.05:0.15:2, 0.285 g, 0.043 mmol palladium) was heated to 100° C. in an oil bath for two hours. HPLC indicated that the reaction was complete. After all solvents were removed, a black residue was obtained, which was dissolved in 0.1 N hydrochloric acid solution and washed with dichloromethane four times. Potassium carbonate was then added into acidic water phase to adjust the pH to 8-9 and the basic water phase was extracted with dichloromethane twice. A light-yellow solid was obtained after the solvent removal. The crude product was dissolved in dichloromethane and loaded on a 10 g silica gel column and purified by Biotage with dichloromethane/methanol. 17-Methyl-N, N-di(pyridin-2-yl)morphinan-3-amine (57) (0.050 g, 28% yield) was obtained as a colorless solid. $^1$H NMR (500 MHz, d$_4$-methanol): δ 8.42 (d, 2H), 7.90 (t, 2H), 7.55 (d, 1H), 7.48 (s, 1H), 7.29 (m, 3H), 6.66 (d, 2H), 3.67 (m, 1H), 3.35 (d, 1H), 3.24 (m, 1H), 2.88 (s, 3H), 2.76 (m, 1H), 2.34 (d, 1H), 2.04 (d, 1H), 1.89 (m, 1H), 1.60 (d, 1H), 1.56 (t, 2H), 1.34-1.46 (m, 3H), 1.11 (m, 2H); MS (EI) for $C_{27}H_{30}N_4$: 411.0 (MH$^+$).

The free base (0.050 g, 0.12 mmol) was dissolved in 1:1 acetonitrile/methanol and 2 N hydrochloric acid ether solution (0.61 mL, 1.2 mmol) was added. The mixture was then lyophilized to give 17-methyl-N,N-di(pyridin-2-yl)morphinan-3-amine hydrochloride salt as a colorless solid (0.061 g, 0.11 mmol, 90% yield).

Example 58

Preparation of N-{6-[2-(2-methoxyethoxy)ethoxy]pyridin-3-yl}-17-methylmorphinan-3-amine (58), hydrochloride salt

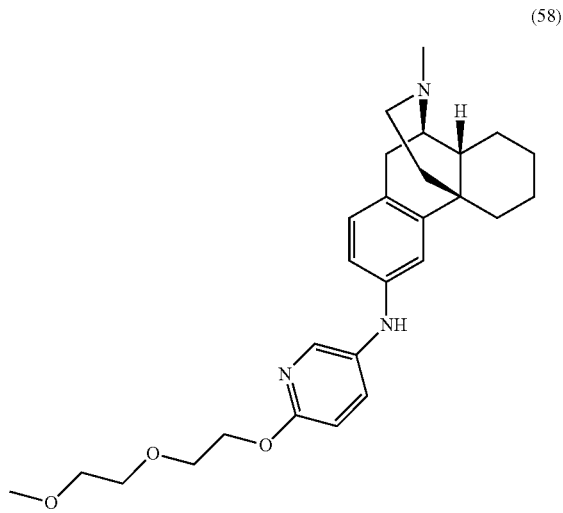 [SMILES: COCCOCCOc1ccc(Nc2ccc3c(c2)[C@@]24CCCC[C@H]2[C@@H](C3)N(C)CC4)cn1]
(58)

Step 1: Preparation of 5-bromo-2-[2-(2-methoxyethoxy)ethoxy]pyridine

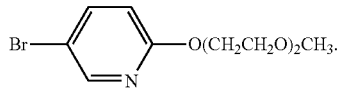

To a N, N-dimethylformamide solution of 2-(2-methoxyethoxy)ethanol (0.51 g, 4.22 mmol) was added sodium hydride (60% in mineral oil, 0.15 g, 3.80 mmol). The reaction mixture was stirred at room temperature for ten minutes. Thereafter, 2,5-dibromopyridine (0.50 g, 2.11 mmol) was added and the reaction solution was heated at 80° C. for eighteen hours. HPLC showed that the reaction was complete. Ethyl acetate was added and the organic phase was washed with a potassium carbonate/sodium chloride aqueous solution three times. After the organic phase was concentrated, a light-yellow liquid was obtained. The crude product was purified by Biotage silica gel chromatography with ethyl acetate/hexane eluents and pure 5-bromo-2-[2-(2-methoxyethoxy)ethoxy]pyridine was obtained as a colorless liquid (0.39 g, 67% yield). $^1$H NMR (500 MHz, Chloroform-d): δ 8.16 (s, 1H), 7.63 (m, 1H), 6.70 (d, 1H), 4.45 (m, 2H), 3.84 (m, 2H), 3.70 (m, 2H), 3.58 (m, 2H), 3.39 (s, 3H).

Step 2: Preparation of N-{6-[2-(2-methoxyethoxy)ethoxy]pyridin-3-yl}-17-methylmorphinan-3-amine hydrochloride salt To a toluene solution of 17-methylmorphinan-3-amine (0.074 g, 0.29 mmol), 5-bromo-2-[2-(2-methoxyethoxy)ethoxy]pyridine (0.096 g, 0.35 mmol) and tris(dibenzylideneacetone)dipalladium(0):BINAP:sodium tert-butoxide (0.05:0.15:2, 0.191 g, 0.029 mmol palladium) was heated to 100° C. in an oil bath for eighteen hours. HPLC indicated that the reaction was complete. After all solvent was removed, a black residue was obtained. The crude product was dissolved in dichloromethane and loaded on a 10 g silica gel column and purified by Biotage with dichloromethane/methanol. A light-yellow solid was obtained. HPLC, LC-MS and proton NMR confirmed that it was pure N-{6-[2-(2-methoxyethoxy)ethoxy]pyridin-3-yl}-17-methylmorphinan-3-amine (58) (0.022 g, 17% yield). $^1$H NMR (500 MHz, d$_4$-methanol): δ 7.82 (d, 1H), 7.75 (s, 1H), 7.19 (d, 1H), 7.09 (d, 1H), 6.97 (s, 1H), 6.91 (d, 1H), 4.38 (m, 2H), 3.76 (m, 2H), 3.55 (m, 2H), 3.43 (m, 2H), 3.23 (s, 3H), 3.10 (m, 3H), 2.81 (s, 3H), 2.64 (t, 1H), 2.34 (d, 1H), 1.92 (d, 1H), 1.82 (t, 1H), 1.62 (d, 1H), 1.52 (m, 3H), 1.23-1.39 (m, 3H), 1.11 (m, 1H); MS (EI) for C$_{27}$H$_{37}$N$_3$O$_3$: 452.0 (MH$^+$).

The free base (0.022 g, 0.049 mmol) was dissolved in 1:1 acetonitrile/methanol and a 2 N hydrochloric acid ether solution (0.24 mL, 0.49 mmol) was added. The mixture was lyophilized to give N-{6-[2-(2-methoxyethoxy)ethoxy]pyridin-3-yl}-17-methylmorphinan-3-amine hydrochloride salt as a white solid (0.024 g. 0.042 mmol, 80% yield).

Example 59

Preparation of N-(2-methoxyethyl)-17-methylmorphinan-3-amine (59), hydrochloride salt

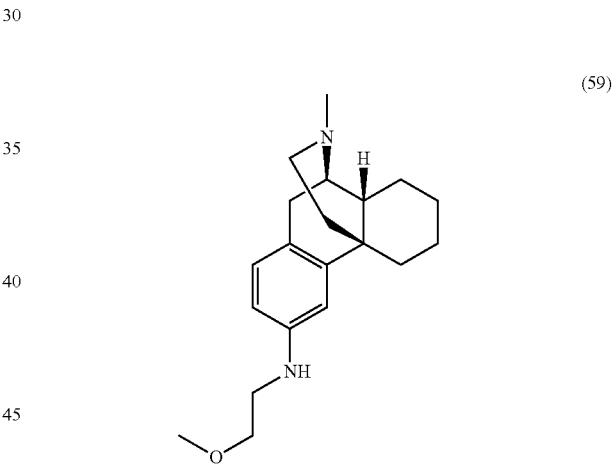
(59)

A flask was charged with 17-methylmorphinan-3-yl trifluoromethanesulfonate (135.6 mg, 0.348 mmol) and 2-methoxyethanamine (61.7 mg, 0.813 mmol). Thereafter, anhydrous toluene (10 mL) was added. Cesium carbonate (325.8 mg, 1.0 mmol), 2-(di-tert-butylphosphino)-2',4',6'-triisopropyl-3,6-dimethoxy-1,1'-biphenyl (34.9 mg, 0.070 mmol), and palladium acetate (8.2 mg, 0.036 mmol) were then added. The starting material was purged with nitrogen. The mixture was stirred at 90° C. for 24 hours. The mixture was concentrated to remove the solvent. The residue was mixed with water. A small amount of brine was added. The mixture was extracted with dichloromethane (3×30 mL). The combined organic solution was dried over anhydrous sodium sulfate, was filtered and was concentrated. The residue was purified on silica gel to afford 99.2 mg of product (59) as the free base in 91% yield. $^1$H NMR (500 MHz, Chloroform-d) δ 6.90 (d, J=8.2 Hz, 1H), 6.53 (d, J=2.4 Hz, 1H), 6.45 (dd, J=8.2, 2.4 Hz, 1H), 3.86 (br, 1H), 3.59 (t, J=5.0 Hz, 2H), 3.37 (s, 3H), 3.25 (t, J=5.0 Hz, 2H), 2.91 (d, J=17.9 Hz, 1H), 2.79-2.73 (m, 1H), 2.53 (ddd, J=18.1, 5.9, 1.0 Hz, 1H), 2.40 (ddd, J=11.9, 4.8, 1.8 Hz, 1H), 2.37 (s, 3H), 2.30 (dd, J=10.7, 3.1 Hz, 1H), 2.09 (td, J=12.3, 3.3 Hz, 1H), 1.81-1.56 (m. 4H), 1.51-1.42 (m, 1H), 1.42-1.21 (m, 4H), 1.22-1.09 (m, 1H). MS for $C_{20}H_{30}N_2O$: 315 (MH$^+$).

The free base was dissolved in 3 mL of acetonitrile, followed by the addition of 2.5 mL of 1 M hydrochloric acid. The mixture was lyophilized to afford 100.9 mg of the product as the hydrochloride salt.

Example 60

Synthesis of 17-methyl-3-(2,5,8,11,14-pentaoxa-hexadecan-16-yloxy)morphinan (60), hydrochloride salt (60)

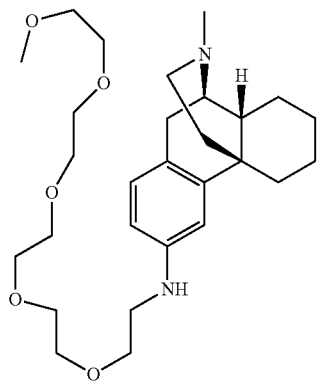

A flask was charged with 17-methylmorphinan-3-yl trifluoromethanesulfonate (171.6 mg, 0.441 mmol) and 2,5,8,11,14-pentaoxahexadecan-16-amine (361.5 mg, 1.438 mmol). Anhydrous toluene (10 mL) was added, followed by the addition of cesium carbonate (566.2 mg, 1.738 mmol) and 2-(di-tert-butylphosphino)-2',4',6'-triisopropyl-3,6-dimethoxy-1,1'-biphenyl (44.1 mg, 0.088 mmol), palladium acetate (11.3 mg, 0.049 mmol). The starting material was purged with nitrogen. The mixture was stirred at 90° C. for 17 hours. The mixture was concentrated. The residue was mixed with water. A small amount of brine was added. The mixture was then extracted with dichloromethane (3×30 mL). The combined organic solution was dried over anhydrous sodium sulfate, was filtered and was concentrated. The residue was purified with flash column chromatography on silica gel to afford 133.9 mg of product the (60) as the free base in 62% yield. $^1$H NMR (500 MHz, Chloroform-d) δ 6.89 (d, J=8.1 Hz, 1H), 6.52 (d, J=2.4 Hz, 1H), 6.44 (dd, J=8.2, 2.4 Hz, 1H), 3.96 (s, 1H), 3.68 (t, J=5.0 Hz, 2H), 3.67-3.61 (m, 14H), 3.53-3.52 (m, 2H), 3.35 (s, 3H), 3.25 (t, J=5.2 Hz, 2H), 2.91 (d, J=18.0 Hz, 1H), 2.78 (br, 1H), 2.54 (dd, J=17.9, 5.8 Hz, 1H), 2.43-2.41 (m, 1H), 2.38 (s, 3H), 2.30 (d, J=10.6 Hz, 1H), 2.11 (t, J=11.8 Hz, 1H), 1.79 (d, J=12.5 Hz, 1H), 1.75-1.67 (m, 3H), 1.48 (m, 1H), 1.41-1.09 (m, 5H). MS for $C_{28}H_{46}N_2O_5$: 491 (MH$^+$). The free base was dissolved in 3 mL of acetonitrile, followed by the addition of 1 mL of 1 M hydrochloric acid. The mixture was lyophilized to afford 166.1 mg of the product as hydrochloride salt.

Example 61

Preparation of 17-methyl-N-(pyridazin-3-yl)morphinan-3-amine (61), hydrochloride salt (61)

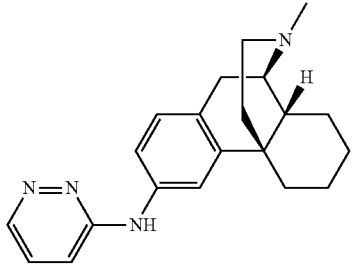

A microwave vial was charged with dicyclohexyl(2',4',6'-triisopropyl-[1,1'-biphenyl]-2-yl)phosphine (28.6 mg, 0.06 mmol), cesium carbonate (87 mg, 0.267 mmol), pyridazin-3-amine (16.5 mg, 0.174 mmol) and tris(dibenzylideneacetone)dipalladium(0) (18.3 mg, 0.02 mmol). The mixture was purged under nitrogen, followed by the addition of a degassed mixture of 17-methylmorphinan-3-yl trifluoromethanesulfonate [Zhang et al. (2004) *J Med Chem* 47(1): 165-174] (52 mg, 0.134 mmol) in dioxane (1.5 mL). The vial was then irradiated in a microwave oven at 150° C. for 30 minutes. The solids were filtered and washed with tetrahydrofuran and the filtrate was concentrated. The residue was purified by flash chromatography (99:1:0.1 to 93:7:0.7 dichloromethane/methanol/aqueous ammonia) to afford 17-methyl-N-(pyridazin-3-yl)morphinan-3-amine (61) (10 mg, 29.9%) as a colorless solid. $^1$H NMR (500 MHz, Chloroform-d): δ 8.65 (dd, J=4.6, 1.4 Hz, 1H), 7.46 (s, 1H), 7.23 (dd, J=9.1, 4.5 Hz, 1H), 7.20 (s, 1H), 7.14 (d, J=1.7 Hz, 2H), 7.08 (dd, J=9.1, 1.4 Hz, 1H), 3.05 (d, J=18.3 Hz, 1H), 2.87 (dd, J=5.8, 3.1 Hz, 1H), 2.66 (dd, J=18.4, 5.8 Hz, 1H), 2.50 (ddd, J=12.1, 4.8, 1.8 Hz, 1H), 2.44 (s, 3H), 2.36 (dq, J=13.5, 2.4 Hz, 1H), 2.13 (td, J=12.3, 3.3 Hz, 1H), 1.88 (dt, J=12.9, 3.2 Hz, 1H), 1.80 (td, J=12.7, 4.8 Hz, 1H), 1.68 (ddt, J=12.8, 5.3, 2.3 Hz. 1H), 1.60-1.52 (m, 1H), 1.46 (ddd, J=13.5, 5.2, 3.1 Hz, 1H), 1.43-1.22 (m, 4H), 1.16 (qd, J=12.2, 3.5 Hz, 1H). MS (EI) for $C_{21}H_{26}N_4$: 335 (MH$^+$).

The free base was solved in acetonitrile and water and treated with 1 N hydrochloric acid. The solvents were removed in the lyophilizer to generate the hydrochloride salt of the title compound as a bright yellow solid.

Example 62

Preparation of 3-(1H-imidazol-1-yl)-17-methylmorphinan (62), hydrochloride salt (62)

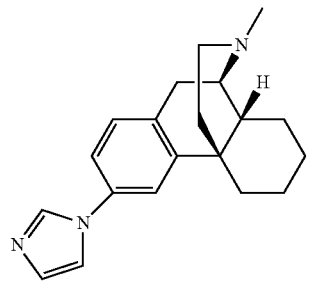

17-Methylmorphinan-3-yl trifluoromethanesulfonate (54.7 mg, 0.140 mmol) and 1H-imidazole (14.4 mg, 0.211 mmol) were dissolved in tert-butanol (2 mL). Potassium phosphate (59.6 mg, 0.281 mmol) was added to the solution. The mixture was degassed under nitrogen for five minutes.

Tris(dibenzylideneacetone)dipalladium(0) (6.4 mg, 0.007 mmol), and di-tert-butyl(2',4',6'-triisopropyl-3,4,5,6-tetramethyl-[1,1'-biphenyl]-2-yl)phosphine (13.5 mg, 0.028 mmol) were added. The mixture was degassed for ten minutes under nitrogen and irradiated in microwave at 120° C. for two hours. The solvent was removed. The residue was dissolved in dichloromethane (15 mL) and washed with brine (15 mL). The organic solution was dried over anhydrous sodium sulfate, was filtered and was concentrated. The residue was purified by flash column chromatography on silica gel to afford the product (62) as the free base (12.2 mg, 28.3%). MS (EI) for $C_{20}H_{25}N_3$: 308.2 (MH+). 1H NMR (500 MHz, Methanol-d4) δ 8.10 (t, J=1.2 Hz, 3H), 7.78-7.62 (m, 1H), 7.54 (t, J=1.4 Hz, 3H), 7.48-7.10 (m, 15H), 3.16 (d, J=18.8 Hz, 3H), 2.91 (dd, J=5.9, 3.1 Hz, 3H), 2.79 (dd, J=18.8, 5.8 Hz, 3H), 2.59-2.32 (m, 17H), 2.12 (td, J=12.5, 3.3 Hz, 3H), 1.91 (dt, J=12.7, 3.1 Hz, 3H), 1.86-1.65 (m, 7H), 1.66-1.21 (m, 24H), 1.16 (qd, J=12.9, 4.3 Hz, 4H), 0.98-0.84 (m, 1H).

The free base (12.2 mg) was dissolved in 1 mL of acetonitrile. To the solution was added 0.5 mL of 1 N hydrochloric acid. The mixture was lyophilized to afford 14.5 mg of the product as the hydrochloride salt.

Example 63

Preparation of 17-methyl-N-(pyridin-2-yl)morphinan-3-amine (63), hydrochloride salt

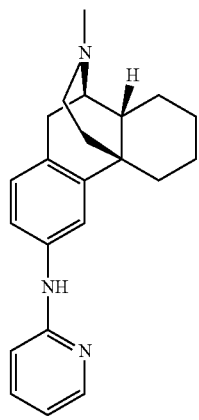

(63)

A toluene solution of 17-methylmorphinan-3-amine (0.070 g, 0.27 mmol), 2-bromopyridine (0.035 g, 0.22 mmol) and tris(dibenzylideneacetone)dipalladium(0): BINAP:sodium tert-butoxide (0.05:0.15:2, 0.090 g, 0.014 mmol palladium) was heated to 80° C. in an oil bath for 3.5 hours. HPLC indicated that the reaction was complete. After all solvents were removed, a black residue was obtained, which was dissolved in 0.1 N hydrochloric acid aqueous solution and was washed with dichloromethane three times. Potassium carbonate was then added into the acidic water phase to adjust the pH to 8-9. The basic water phase was extracted with dichloromethane twice. A light-yellow solid was obtained after solvent removal. The crude product was dissolved in dichloromethane and loaded on a 10 g silica gel column and purified by Biotage with dichloromethane/methanol. 17-Methyl-N-(pyridin-2-yl)morphinan-3-amine (63) (0.026 g, 29% yield) was obtained as a colorless solid. $^1$H NMR (500 MHz, $d_4$-methanol): δ 8.05 (m, 1H), 7.92 (d, 1H), 7.46 (d, 1H), 7.41 (d, 1H), 7.34 (m. 1H), 7.22 (d, 1H), 7.05 (t, 1H), 3.73 (m, 1H), 3.37 (d, 1H), 3.26 (m, 2H), 2.98 (s, 3H), 2.79 (m, 1H), 2.55 (d, 1H), 2.15 (d, 1H), 2.00 (m, 1H), 1.46-1.78 (m, 6H), 1.33 (m, 1H), 1.17 (m, 1H); MS (EI) for $C_{22}H_{27}N_3$: 334 (MH$^+$).

The free base (0.026 g, 0.078 mmol) was dissolved in 1:1 acetonitrile/methanol, followed by the addition of a 2 N hydrochloric acid ether solution (0.039 mL, 0.78 mmol). The mixture was lyophilized to give 17-methyl-N-(pyridin-2-yl)morphinan-3-amine, hydrochloride salt as a colorless solid (0.034 g, 0.076 mmol, 98% yield).

Example 64

Preparation of 17-methyl-N-[6-(2,5,8,11,14-pentaoxahexadecan-16-yloxy)pyridin-3-yl]morphinan-3-amine (64), hydrochloride salt

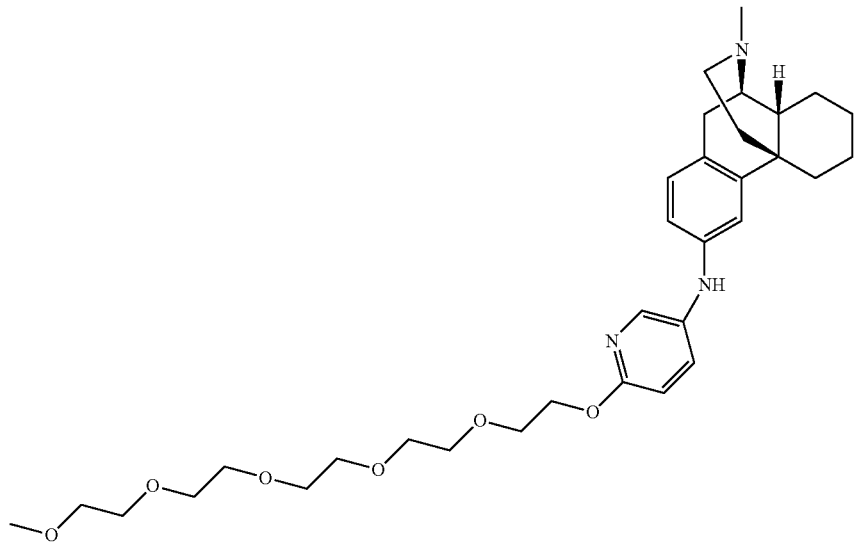

(64)

Step 1: Preparation of 5-bromo-2-(2,5,8,11,14-pentaoxahexadecan-16-yloxy)pyridine

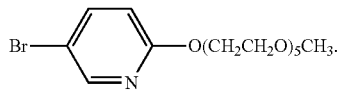

To a N,N-dimethylformamide solution of 2,5,8,11,14-pentaoxahexadecan-16-ol (1.07 g, 4.22 mmol) was added sodium hydride (60% in mineral oil, 0.15 g, 3.80 mmol). The reaction mixture was stirred at room temperature for ten minutes. 2,5-Dibromopyridine (0.50 g, 2.11 mmol) was added and the reaction solution was heated at 80° C. for 18 hours. HPLC showed that the reaction was complete. Ethyl acetate was added and the ethyl acetate phase was washed with a potassium carbonate/sodium chloride aqueous solution three times. After solvent removal, a light-yellow liquid was obtained. The crude product was purified by silica gel chromatography using a Biotage with ethyl acetate/hexane as eluents and pure 5-bromo-2-(2,5,8,11,14-pentaoxahexadecan-16-yloxy)pyridine was obtained as a colorless liquid (0.67 g, 78% yield). $^1$H NMR (500 MHz, Chloroform-d): δ 8.16 (s, 1H), 7.63 (m, 1H), 6.71 (d, 1H), 4.43 (m, 2H), 3.83 (m, 2H), 3.69 (m, 14H), 3.55 (m, 2H), 3.38 (s, 3H).

Step 2: Preparation of 17-methyl-N-[6-(2,5,8,11,14-pentaoxahexadecan-16-yloxy)pyridin-3-yl]morphinan-3-amine hydrochloride salt The toluene solution of 17-methylmorphinan-3-amine (0.070 g, 0.27 mmol), 5-bromo-2-(2,5,8,11,14-pentaoxahexadecan-16-yloxy)pyridine (0.111 g, 0.27 mmol) and tris(dibenzylideneacetone)dipalladium(0):BINAP:Sodium tert-butoxide (0.05:0.15:2, 0.090 g, 0.014 mmol palladium) was heated to 100° C. in an oil bath for three hours. HPLC indicated that the reaction was complete. After all solvents were removed, a black residue was obtained, which was dissolved in 0.1 N hydrochloric acid solution and washed with dichloromethane three times. Potassium carbonate was then added and the acidic water phase was adjusted to a pH of 8-9, followed by the extraction of the basic water phase via two rounds of dichloromethane treatment. A sticky solid was obtained after the solvent removal. The crude product was dissolved in dichloromethane and loaded on a 10 g silica gel column and purified by Biotage with dichloromethane/methanol. 17-Methyl-N-[6-(2,5,8,11,14-pentaoxahexadecan-16-yloxy)pyridin-3-yl]morphinan-3-amine (64) (0.050 g, 31% yield) was obtained as a colorless liquid. MS (EI) for $C_{33}H_{49}N_3O_6$: 584.0 (MH$^+$).

The free base (0.041 g, 0.070 mmol) was dissolved in 1:1 acetonitrile/methanol and a 2 N hydrochloric acid ether solution (0.35 mL, 0.70 mmol) was thereafter added. The mixture was lyophilized to give 17-methyl-N-[6-(2,5,8,11,14-pentaoxahexadecan-16-yloxy)pyridin-3-yl]morphinan-3-amine hydrochloride salt as a light-yellow solid (0.009 g, 0.013 mmol, 19% yield). $^1$H NMR (500 MHz, d$_4$-methanol): δ 7.89 (m, 2H), 7.19 (m, 2H), 7.07 (d, 1H), 7.01 (m, 1H), 4.50 (m, 2H), 3.89 (m, 2H), 3.70 (m, 2H), 3.64 (m, 12H), 3.53 (m, 2H), 3.35 (s, 3H), 3.05-3.25 (m, 3H), 2.94 (s, 3H), 2.76 (t, 1H), 2.49 (d, 1H), 2.05 (m, 1H), 1.92 (m, 1H), 1.75 (m, 1H), 1.61 (m, 3H), 1.32-1.52 (m, 3H), 1.23 (m, 1H).

Example 65

Preparation of 3-{1-[2-(2-methoxyethoxy)ethyl]-1H-pyrazol-4-yl}-17-methylmorphinan (65), hydrochloride salt

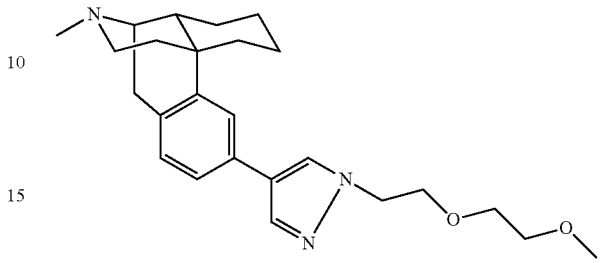

To an acetonitrile solution of 17-methyl-3-(1H-pyrazol-4-yl)morphinan (0.015 g, 0.050 mmol) and mPEG$_2$-Ms (0.015 g, 0.076 mmol) was added sodium hydride (10 mg, 0.25 mmol), the reaction mixture was heated at 80° C. for three hours. HPLC indicated that the reaction was complete. The reaction mixture was loaded on a 10 g silica gel column and purified by Biotage with dichloromethane/methanol. 3-{1-[2-(2-Methoxyethoxy)ethyl]-1H-pyrazol-4-yl}-17-methylmorphinan (65) was obtained as a colorless solid (0.015 g, 73% yield). $^1$H NMR (500 MHz, d$_4$-methanol): δ 8.06 (s, 1H), 7.85 (s, 1H), 7.54 (d, 1H), 7.45 (m, 1H), 7.25 (d, 1H), 4.35 (t, 2H), 3.88 (t, 2H), 3.60 (m, 2H), 3.52 (m, 2H), 3.33 (s, 3H), 3.22 (s, 1H), 3.19 (d, 1H), 3.08 (m, 1H), 2.88 (s, 3H), 2.66 (m, 2H), 2.05 (m, 1H), 1.94 (m, 1H) 1.74 (m 1H), 1.66 (d, 2H), 1.59 (d, 1H), 1.44 (m, 2H), 1.35 (m, 1H), 1.20 (m, 1H); MS (EI) for $C_{25}H_{35}N_3O_2$: 410.0 (MH$^+$).

The free base (0.015 g, 0.037 mmol) was dissolved in 1:1 acetonitrile/methanol, followed by the addition of a 2 N hydrochloric acid ether solution (0.055 mL, 0.11 mmol). The mixture was lyophilized to give 3-{1-[2-(2-methoxyethoxy)ethyl]-1H-pyrazol-4-yl}-17-methylmorphinan, hydrochloride salt as a colorless solid (0.018 g, 0.037 mmol, 100% yield).

Example 66

Preparation of (4bR,8aR,9R)—N-(3-(2-(2-methoxyethoxy)ethoxy)pyridin-4-yl)-11-methyl-6,7,8,8a,9,10-hexahydro-5H-9,4b-(epiminoethano)phenanthren-3-amine (6α), hydrochloride salt

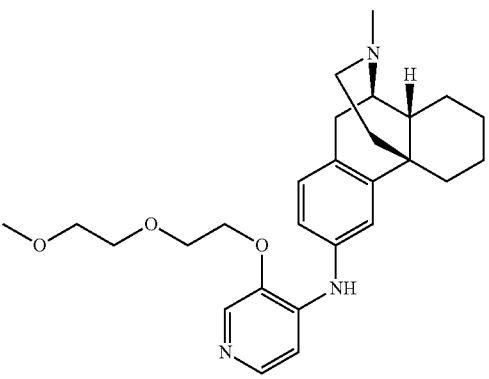

Step 1. Synthesis of 4-chloro-3-(2-(2-methoxyethoxy)ethoxy)pyridine

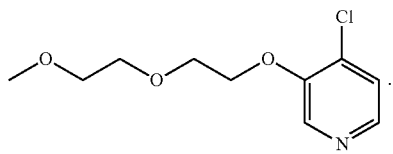

A mixture of 4-chloropyridin-3-ol (100 mg, 0.772 mmol), 1-bromo-2-(2-methoxyethoxy)ethane (141 mg, 0.772 mmol) and $Cs_2CO_3$ (503 mg, 1.544 mmol) in dimethylacetamide (5 mL) was irradiated in a microwave at 120° C. for two hours. The reaction mixture was cooled to room temperature and poured into 20 mL of water. The aqueous solution was extracted with ethyl acetate 3×20 mL. The organic layer was combined, was washed with brine (50 mL), was dried over anhydrous sodium sulfate, was filtered and was concentrated. The crude product was purified via flash column chromatography on silica gel to afford 4-chloro-3-(2-(2-methoxyethoxy)ethoxy)pyridine (87.4 mg, 48.9%). MS (EI) for $C_{10}H_{14}ClNO_3$: 232.0 (MH+).

Step 2. Synthesis of (4bR,8aR,9R)—N-(3-(2-(2-methoxyethoxy)ethoxy)pyridin-4-yl)-11-methyl-6,7,8,8a,9,10-hexahydro-5H-9,4b-(epiminoethano)phenanthren-3-amine A solution of 17-methylmorphinan-3-amine (49.9 mg, 0.195 mmol) and 4-chloro-3-(2-(2-methoxyethoxy)ethoxy)pyridine (67.6 mg, 0.292 mmol) in toluene (3 mL) was degassed under nitrogen for five minutes before catalyst the tris(dibenzylideneacetone)dipalladium(0):BINAP:sodium tert-butoxide (0.05:0.15:2) (67.4 mg) was added to the solution. The mixture was degassed and irradiated in microwave at 120° C. for two hours. The catalyst was removed by filtration. The filtrate was concentrated. The residue was purified two times by flash column chromatography on silica gel to afford the product (66) as the free base (18 mg, 20.5%). MS (EI) for $C_{27}H_{37}N_3O_3$: 452.2 (MH+). 1H NMR (500 MHz, Methanol-d4) δ 7.99 (d, J=2.3 Hz, 1H), 7.87-7.81 (m, 1H), 7.22-7.16 (m, 2H), 7.10 (d, J=8.1 Hz, 1H), 6.98-6.92 (m, 1H), 4.28 (dt, J=5.3, 3.0 Hz, 2H), 3.93 (dt, J=5.6, 2.9 Hz, 2H), 3.75 (dt, J=4.7, 2.7 Hz, 2H), 3.59 (dt, J=5.6, 3.0 Hz, 2H), 3.33 (d, J=2.3 Hz, 2H), 3.11 (d, J=18.6 Hz, 1H), 2.89 (dd, J=4.6, 2.4 Hz, 1H), 2.80-2.71 (m, 1H), 2.51 (dd, J=12.5, 3.9 Hz, 1H), 2.45-2.39 (m, 4H), 2.18 (t, J=12.5 Hz, 1H), 1.88 (dd, J=12.9, 3.5 Hz, 1H), 1.83-1.69 (m, 2H), 1.59 (d, J=11.2 Hz, 1H), 1.53-1.28 (m, 6H), 1.21 (qt, J=12.6, 3.4 Hz, 1H).

The free base (18 mg) was dissolved in methanol. To the clear solution was added 5 eq. of 4 N hydrochloric acid in methanol solution. The solution was concentrated and dried under high vacuum to afford the hydrochloride salt (22 mg) as a colorless solid.

Example 67

Preparation of N-{2-[2-(2-methoxyethoxy)ethoxy]pyridin-4-yl}-17-methylmorphinan-3-amine (67), hydrochloride salt

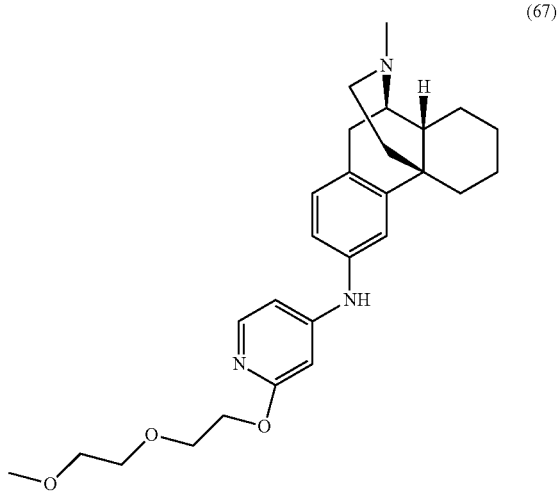 [SMILES: COCCOCCOc1cc(Nc2ccc3c(c2)[C@@]24CCCC[C@H]2[C@@H](C3)N(C)CC4)ccn1]

(67)

Step 1: Preparation of 4-chloro-2-[2-(2-methoxyethoxy)ethoxy]pyridine

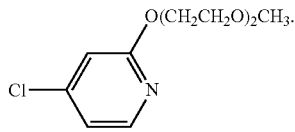

To an acetonitrile solution of 2-(2-methoxyethoxy)ethanol (0.56 g, 4.68 mmol) was added sodium hydride (60% in mineral oil, 0.14 g, 3.43 mmol). The reaction mixture was stirred at room temperature for ten minutes. 2-Bromo-4-chloropyridine (0.60 g, 3.11 mmol) was added and the reaction solution was stirred at room temperature for 21 hours. HPLC showed that product was formed with 73% conversion. Ethyl acetate was added and the ethyl acetate phase was washed with a potassium carbonate/sodium chloride aqueous solution three times. After the solvent was removed, a light-yellow liquid was obtained. The crude product was purified by Biotage silica gel chromatography using dichloromethane/methanol as eluent and pure 4-chloro-2-[2-(2-methoxyethoxy)ethoxy]pyridine (0.13 g, 18% yield) was obtained as a colorless liquid. 1H NMR (500 MHz, Chloroform-d): δ 8.16 (s, 1H), 7.03 (s, 1H), 6.80 (m, 1H). 4.18 (m, 2H), 3.86 (m, 2H), 3.70 (m, 2H), 3.57 (m, 2H), 3.39 (s, 3H).

Step 2: Preparation of N-{2-[2-(2-methoxyethoxy)ethoxy]pyridin-4-yl}-17-methylmorphinan-3-amine, hydrochloride salt A toluene solution of 17-methylmorphinan-3-amine (0.066 g, 0.26 mmol), 4-chloro-2-[2-(2-methoxyethoxy)ethoxy]pyridine (0.060 g, 0.26 mmol) and tris(dibenzylideneacetone)dipalladium(0):BINAP:sodium tert-butoxide (0.05:0.15:2, 0.086 g, 0.013 mmol palladium) was heated to 100° C. in an oil bath for three hours. HPLC indicated that the reaction was complete. After all solvent was removed, a sticky solid was obtained. The crude product was dissolved in dichloromethane and loaded on a 10 g silica gel column and purified repeatedly using a Biotage chromatography instrument using dichloromethane/methanol as eluent pure N-{2-[2-(2-methoxyethoxy)ethoxy]pyridin-4-yl}-17-methylmorphinan-3-amine (67) (0.020 g, 17% yield) was obtained. $^1$H NMR (500 MHz, d$_4$-methanol): δ 7.85 (d, 1H), 7.25 (d, 1H), 7.21 (m, 1H), 7.08 (d, 1H), 6.37 (m, 1H), 6.32 (d, 1H), 4.12 (m, 2H), 3.82 (m, 2H), 3.67 (m, 2H), 3.55 (m, 2H), 3.35 (s, 3H), 3.04 (d, 1H), 2.87 (m, 1H), 2.72 (m, 1H), 2.49 (m, 1H), 2.41 (s, 3H), 2.19 (m, 1H), 1.84 (m, 1H), 1.70 (m, 2H), 1.54 (m, 1H), 1.33-1.49 (m, 5H), 1.20 (m, 1H); MS (EI) for $C_{27}H_{37}N_3O_3$: 452.0 (MH$^+$).

The free base (0.020 g, 0.044 mmol) was dissolved in 1:1 acetonitrile/methanol, followed by the addition of a 2 N hydrochloric acid ether solution (0.22 mL, 0.44 mmol). The mixture was lyophilized to give N-{2-[2-(2-methoxyethoxy)ethoxy]pyridin-4-yl}-17-methylmorphinan-3-amine hydrochloride salt as a colorless solid (0.020 g, 0.035 mmol, 78% yield).

Example 68

Preparation of 2-[2-(2-methoxyethoxy)ethoxy]-N—[(4aR,5R,11bR)-14-methyl-2,3,4,4a,5,6-hexahydro-1H-5,11b-(epiminoethano)phenanthro[3,2-d][1,3]thiazol-9-yl]acetamide (68), hydrochloride salt To a solution of 2-(2-(2-methoxyethoxy)ethoxy)acetic acid (39.1 mg, 0.220 mmol), O-(7-azabenzotriazol-1-yl)-n,n,n',n'-tetramethyluronium hexafluorophosphate (104 mg, 0.543 mmol) and triethylamine (0.034 mL 0.439 mmol) in 3 mL of dichloromethane, (4aR,5R,11bR)-14-methyl-2,3,4,4a,5,6-hexahydro-1H-5,11b-(epiminoethano)phenanthro[3,2-d][1,3]thiazol-9-amine [Zhang et al. (2004) *J. Med. Chem.* 47(8):1886-1888] (45.9 mg, 0.146 mmol) was added. The reaction was stirred at room temperature overnight. The reaction was then taken up in 10 mL of dichloromethane and was sequentially washed with saturated sodium bicarbonate (10 mL) and brine (10 mL). The organic layer was dried over sodium sulfate, was filtered and was concentrated. The residue was purified on flash silica gel column to give desired product (68) as the free base (19.4 mg, 28%). MS (EI) for $C_{25}H_{35}N_3O_4S$: 474.2 (MH+). 1H NMR (500 MHz, Methanol-d4) δ 7.79 (d, J=7.1 Hz, 2H), 4.34 (s, 2H), 3.82 (dd, J=5.6, 2.9 Hz, 2H), 3.80-3.60 (m, 7H), 3.46-3.29 (m, 5H), 3.15-3.07 (m, 1H), 2.93 (s, 3H), 2.74-2.61 (m, 2H), 2.13 (dt, J=12.5, 3.2 Hz, 1H), 2.01 (td, J=13.8, 4.6 Hz, 1H), 1.75 (dt, J=12.9, 3.4 Hz, 1H), 1.69-1.43 (m, 5H), 1.43-1.26 (m, 2H), 1.19 (qd, J=12.8, 3.9 Hz, 1H).

The free base (17.4 mg) was dissolved in 2 mL of acetonitrile. To the solution was added 0.5 mL of 1 N hydrochloride. The mixture was lyophilized to afford 16.4 mg of the product as the hydrochloride salt.

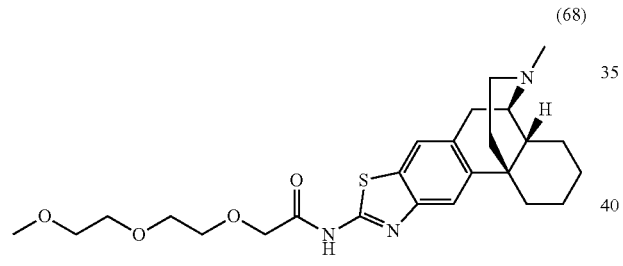

(68)

Example 69

Preparation of 2-[2-(2-methoxyethoxy)ethoxy]-N—[(4aR,5R,11bR)-14-methyl-2,3,4,4a,5,6-hexahydro-1H-5,11b-(epiminoethano)phenanthro[3,2-d][1,3]thiazol-9-yl]-2,5,8,11,14,17-hexaoxanonadecan-19-amide (69), hydrochloride salt

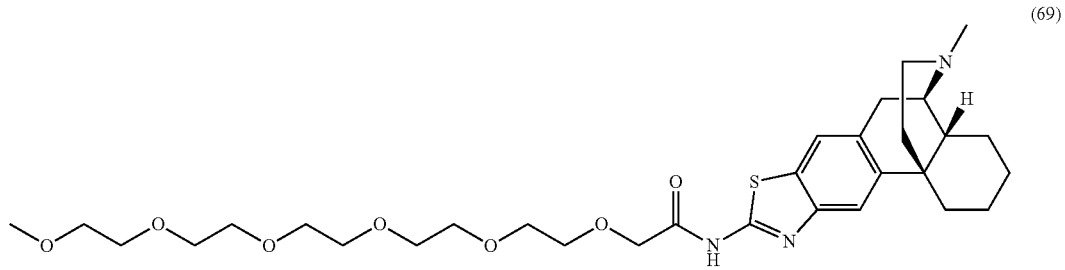 [SMILES: COCCOCCOCCOCCOCCOCC(=O)Nc1nc2cc3c(cc2s1)C[C@@H]1[C@@H]2CCCC[C@]32CCN1C]

(69)

To a solution of 2,5,8,11,14,17-hexaoxanonadecan-19-oic acid (109 mg, 0.351 mmol), O-(7-azabenzotriazol-1-yl)-n,n,n',n'-tetramethyluronium hexafluorophosphate (123 mg, 0.383 mmol) and triethylamine (0.133 mL, 0.957 mmol) in 3 mL of dichloromethane, (4aR,5R,11bR)-14-methyl-2,3,4,4a,5,6-hexahydro-1H-5,11b-(epiminoethano)phenanthro[3,2-d][1,3]thiazol-9-amine (100 mg, 0.319 mmol) was added. The reaction was stirred at room temperature overnight. The reaction was then taken up in 10 mL of dichloromethane and was sequentially washed with saturated sodium bicarbonate (10 mL) and brine (10 mL). The organic layer was dried over sodium sulfate, was filtered and was concentrated. The residue was purified on a flash silica gel column to give the desired product (69) as the free base (83.2 mg, 43.1%). MS (EI) for $C_{31}H_{47}N_3O_7S$: 607.4 (MH+). 1H NMR (500 MHz, Methanol-d4) δ 7.73 (d, J=18.0 Hz, 2H), 4.35 (s, 2H), 3.86-3.70 (m, 8H), 3.71-3.56 (m, 10H), 3.56-3.49 (m, 2H), 3.21 (dd, J=5.9, 3.2 Hz, 1H), 3.12-3.03 (m, 1H), 2.78-2.70 (m, 1H), 2.64 (s, 4H), 2.36 (td, J=12.8, 3.3 Hz, 1H), 2.00 (dt, J=12.7, 3.2 Hz, 1H), 1.89 (td, J=13.3, 4.7 Hz, 1H), 1.72 (dt, J=12.8, 3.4 Hz, 1H), 1.66-1.41 (m, 6H), 1.40-1.27 (m, 2H), 1.19 (qd, J=12.6, 3.8 Hz, 1H).

The free base (83.2 mg) was dissolved in 3 mL of methanol. To the solution was added 3 equivalents of 4 N hydrochloric acid in methanol. The mixture was concentrated and dried under high vacuum to afford 87.6 mg of the product as the hydrochloride salt.

Example 70

Preparation of (4aR,5R,11bR)-14-methyl-N-(2,5,8,11,14,17-hexaoxanonadecan-19-yl)-2,3,4,4a,5,6-hexahydro-1H-5,11b-(epiminoethano)phenanthro[3,2-d][1,3]thiazol-9-amine (70)

To a suspension of LiAlH4 (17.3 mg, 0.46 mmol) in THF (4 mL) was added dropwise a solution of 2-[2-(2-methoxyethoxy)ethoxy]-N-[(4aR,5R,11bR)-14-methyl-2,3,4,4a,5,6-hexahydro-1H-5,11b-(epiminoethano)phenanthro[3,2-d][1,3]thiazol-9-yl]-2,5,8,11,14,17-hexaoxanonadecan-19-amide (from Example 69) starting material (230 mg, 0.380 mmol) in THF (1 mL+1 mL rinsing). The reaction was stirred at 50° C. under nitrogen for four hours. LCMS showed the completion of the reaction. The reaction was quenched with sodium sulfate×H2O, followed by addition of 1 N NaOH (1 mL). The solid was filtered off, the filtrate was concentrated, and the residue was purified on a Biotage KP-NH column twice. The product (70) was obtained as clear oil (107.4 mg, 48%). MS (EI) for $C_{31}H_{49}N_3O_6S$: 593.2 (MH+). 1H NMR (500 MHz, Methanol-d4) δ 7.38 (d, J=10.4 Hz, 2H), 3.73 (t, J=5.3 Hz, 2H), 3.70-3.58 (m, 18H), 3.56-3.50 (m, 2H), 3.36 (s, 3H), 3.15 (d, J=18.5 Hz, 1H), 2.89 (t, J=4.3 Hz, 1H), 2.81 (dd, J=18.4, 5.8 Hz, 1H), 2.54-2.45 (m, 2H), 2.43 (s, 3H), 2.17 (td, J=12.4, 12.0, 3.2 Hz, 1H), 1.88 (dt, J=13.2, 3.0 Hz, 1H), 1.79 (td, J=12.8, 4.7 Hz, 1H), 1.73-1.66 (m, 1H), 1.61-1.54 (m, 1H), 1.52-1.29 (m, 5H), 1.20 (tt, J=13.4, 7.0 Hz, 1H).

Example 71

Preparation of (4aR,5R,11bR)—N-(2-(2-(2-methoxyethoxy)ethoxy)ethyl)-14-methyl-2,3,4,4a,5,6-hexahydro-1H-5,11b-(epiminoethano)phenanthro[3,2-d]thiazol-9-amine (71)

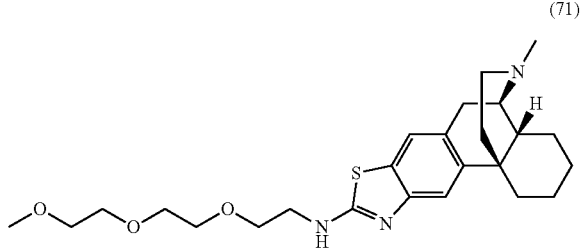 [SMILES: COCCOCCOCCNc1nc2cc3c(cc2s1)C[C@@H]1[C@@H]2CCCC[C@]32CCN1C]

(71)

Following the procedure described for Example 70 {except the starting material for this example was 2-[2-(2-methoxyethoxy)ethyl]-N-[(4aR,5R,11bR)-14-methyl-2,3,4,4a,5,6-hexahydro-1H-5,11b-(epiminoethano)phenanthro[3,2-d][1,3]thiazol-9-yl]acetamide, from Example 681, (4aR,5R,11bR)—N-(2-(2-(2-methoxyethoxy)ethoxy)ethyl)-14-methyl-2,3,4,4a,5,6-hexahydro-1H-5,11b-(epiminoethano)phenanthro[3,2-d]thiazol-9-amine (71) was obtained as a clear oil in 35.3% yield.

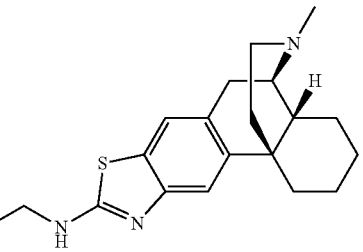

(70)

Example 72

Preparation of 1-(2-methoxyethyl)-3-((4aR,5R,11bR)-14-methyl-2,3,4,4a,5,6-hexahydro-1H-5,11b-(epiminoethano)phenanthro[3,2-d]thiazol-9-yl)urea (72), hydrochloride salt

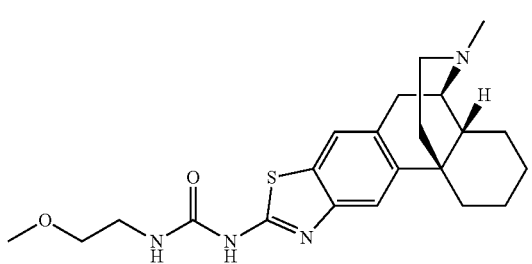

(72)

To a mixture of (4aR,5R,11bR)-14-methyl-2,3,4,4a,5,6-hexahydro-1H-5,11b-(epiminoethano)phenanthro[3,2-d][1,3]thiazol-9-amine (80.8 mg, 0.258 mmol) in dichloromethane was added triethylamine (0.108 mL, 0.773 mmol), followed by the addition of 1-isocyanato-2-methoxyethane (52.1 mg, 0.516 mmol). The reaction was stirred at room temperature overnight. The reaction was taken up in dichloromethane (30 mL), sequentially washed with saturated sodium bicarbonate (30 mL) and brine (30 mL), was dried over sodium sulfate, was filtered and was concentrated. The crude product was purified on a flash silica gel column to give the title product (72) as the free base (46.3 mg, 43.3%). MS (EI) for $C_{22}H_{30}H_4O_2S$: 415.2 (MH+). 1H NMR (500 MHz, Methanol-d4) δ 7.61-7.54 (m, 2H), 3.54 (dt, J=6.6, 3.6 Hz, 2H), 3.47 (dd, J=5.3, 3.0 Hz, 2H), 3.35-3.26 (m, 4H), 3.22 (d, J=18.6 Hz, 1H), 2.94-2.82 (m, 2H), 2.57-2.41 (m, 4H), 2.14 (td, J=12.4, 3.3 Hz, 1H), 1.90 (dd, J=13.0, 3.4 Hz, 1H), 1.81 (tt, J=12.7, 3.6 Hz, 1H), 1.72-1.65 (m, 1H), 1.62-1.54 (m, 1H), 1.53-1.26 (m, 5H), 1.17 (q, J=12.9, 12.3 Hz, 1H).

The free base (31.9 mg) was dissolved in 2 mL of acetonitrile. To the solution was added 0.5 mL of 1 N hydrochloric acid. The mixture was lyophilized to afford 37.5 mg of colorless solid as the hydrochloride salt.

Example 73

Preparation of 2-(2-methoxyethoxy)-17-methylmorphinan-3-ol (73), hydrochloride salt

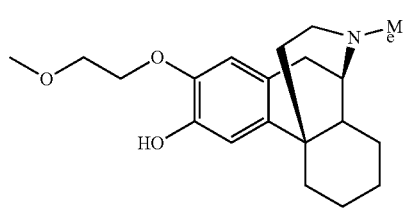

Step Preparation of 2-iodo-17-methylmorphinan-3-ol,

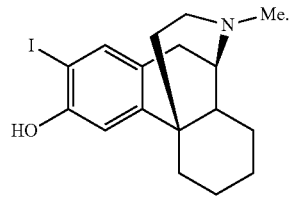 [SMILES: CN1CC[C@]23CCCCC2[C@H]1Cc1cc(I)c(O)cc13]

A solution of potassium tri-iodide was prepared by stirring potassium iodide (351 mg, 2.11 mmol) and iodine (357 mg, 1.408 mmol) in water (12 mL). The iodine did not completely dissolve. A portion (7 mL) of the resultant solution of potassium triiodide was added dropwise over five minutes to a solution of 17-methylmorphinan-3-ol tartrate dihydrate (312 mg, 0.70 mmol) and sodium hydroxide (MO mg, 3.52 mmol) in water (12 mL), until the color of the potassium triiodide solution no longer dissipated rapidly. Additional portions (0.6 mL and 0.3 mL) were added after 1.16 hours and 4.7 hours respectively. After five hours, dry ice and 0.5 M sodium bisulfite (1 mL) were added to quench the reaction. The mixture was diluted with 30% aqueous ammonia (7 mL) and dichloromethane (30 mL), affording a clear biphasic mixture on vigorous stirring. The aqueous layer was extracted with dichloromethane (3×30 mL), and the combined organic layer was dried (sodium sulfate), filtered and concentrated. Chromatography on silica (1:10:800 to 1:10:100 ammonium hydroxide:methanol:dichloromethane) afforded 2-iodo-17-methylmorphinan-3-ol as a cream-colored crystalline solid (261 mg, 97%). $^1$H NMR (500 MHz, Chloroform-d) δ 7.41 (d, J=1.0 Hz, 1H), 6.88 (s, 1H), 5.30 (s, 1H), 2.98-2.90 (m, 1H), 2.79 (dd, J=5.7, 3.2 Hz, 1H), 2.60-2.50 (m, 1H), 2.45 (ddd, J=12.2, 5.1, 1.9 Hz, 1H), 2.39 (s, 3H), 2.32-2.23 (m, 1H), 2.07 (td, J=12.4, 3.3 Hz, 1H), 1.82 (dt, J=12.7, 3.2 Hz, 1H), 1.74 (dt, J=4.8, 12.7 Hz, 1H), 1.65 (dt with fine str, J=11.2, 3.5 Hz, 1H), 1.55-1.47 (m, 1H), 1.46-1.18 (m, 5H), 1.09 (qd, J=12.2, 3.5 Hz, 1H). MS (ESI) for $C_{17}H_{22}INO$: 384.0 (MH$^+$). A 10 mg sample was converted to the HCl salt in methanol:acetonitrile:water (1:1:4, 3 mL), and lyophilized overnight to afford a colorless solid.

Step 2: Preparation of 2-(2-methoxyethoxy)-17-methylmorphinan-3-ol

A 16×100 mm test tube was charged with 2-iodo-17-methylmorphinan-3-ol (60 mg, 0.157 mmol), sodium tert-butoxide (195 mg, 2.03 mmol), copper(I) iodide (45 mg, 0.24 mmol), and a magnetic stir bar, fitted with a serrated 14/20 septum and purged with nitrogen. Dry N,N-dimethylformamide (1 mL) and 2-methoxyethanol (0.16 mL, 2.04 mmol) were added via syringe, and the resulting light brown suspension was placed in an oil bath heated at 80° C. for 15.5 hours, then at 120° C. for three hours. The mixture was quenched with acetic acid (0.125 mL, 2.20 mmol), diluted with methanol (10 mL), filtered and concentrated to remove N,N-dimethylformamide. The residue was partitioned between dichloromethane (15 mL) and 0.5 M sodium bicarbonate (10 mL), and the organic phase was dried (sodium sulfate), was filtered and was concentrated to afford a brown oil. Automated reverse phase flash chromatography (C18 cartridge, 10-80% acetonitrile in 0.1% formic acid/water) afforded impure phenol as a brown oil. A second chromatography on silica (dichloromethane to 20% isopropanol/dichloromethane, then dichloromethane to 1/10/90 ammonium hydroxide(aq.)/methanol/dichloromethane) followed by recrystallization from water/methanol (10/1) afforded 2-(2-methoxyethoxy)-17-methylmorphinan-3-ol (73) as an off-white crystalline solid (plates) (11 mg, 21%). 1H NMR (500 MHz, Chloroform-d) δ 6.84 (s, 1H), 6.66 (s, 1H), 6.33 (br s, 1H), 4.19 (dt, J=10.7, 3.8 Hz, 1H), 4.16 (dt, J=10.7, 3.8 Hz, 1H), 3.74 (t, J=4.6 Hz, 2H), 3.49 (s, 3H), 2.93 (d, J=18.0 Hz, 1H), 2.79 (dd, J=5.2, 3.3 Hz, 1H), 2.56 (dd, J=18.0, 5.8 Hz, 1H), 2.44 (dt, J=12.0, 4.6, 1.5 Hz, 1H), 2.41 (s, 3H), 2.32 (dd, J=10.5, 2.9 Hz, 1H), 2.10 (td, J=12.3, 3.3 Hz, 1H), 1.80 (dt, J=12.9, 2.9 Hz, 1H), 1.71 (td, J=12.7, 4.9 Hz, 1H), 1.67-1.64 (m, 1H), 1.54-1.49 (m, 1H), 1.45-1.26 (m, 5H), 1.16 (qd, J=12.1, 3.6 Hz, 1H); MS (EI) for $C_{20}H_{29}NO_3$: 332.2 (MH$^+$). The sample was converted to the HCl salt by dissolution in methanol/acetonitrile/water (1/1/4, 3 mL) and 2 M HCl (200 uL), and lyophilized overnight to afford a pale yellow film.

Example 74

Preparation of 1-(2-methoxyethoxy)-17-methylmorphinan-3-ol (74), hydrochloride salt

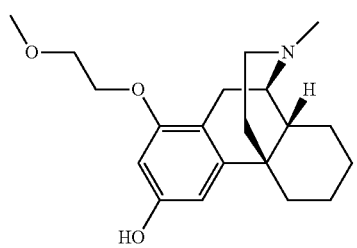
(74)

Step 1: Preparation of 1-iodo-3-methoxy-17-methylmorphinan-4-ol

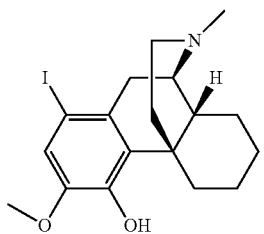 [SMILES: COc1cc(I)c2c(c1O)[C@@]13CCCC[C@H]1[C@@H](C2)N(C)CC3]

A solution of potassium tri-iodide was prepared by stirring potassium iodide (1.02 g, 6.0 mmol) and iodine (1.02 g, 4.0 mmol) in water (35 mL). A portion (7 mL) of the resultant solution of potassium triiodide was added dropwise over five minutes to a solution of 3-methoxy-17-methylmorphinan-4-ol [Zhang et al. (2007) *J. Med. Chem.* 50(11): 2747-2751] (202 mg, 0.70 mmol) and sodium hydroxide (420 mg, 10.5 mmol) in methanol (25 mL), tetrahydrofuran (15 mL) and water (12 mL) until the color of the potassium triiodide solution no longer dissipated rapidly. Aqueous 0.5 M sodium bisulfate (1 mL) was added to quench the reaction after twenty minutes, followed by the addition of powdered dry ice. The mixture was diluted with 30% aqueous ammonia (10 mL) and brine (75 mL), and was extracted with dichloromethane (60 mL, 3×30 mL). The combined organic layer was dried (sodium sulfate), filtered and concentrated to afford a tan oil/solid, which was purified by chromatography on silica (dichloromethane to 1:10:180 ammonium hydroxide:methanol:dichloromethane) to afford 1-iodo-3-methoxy-17-methylmorphinan-4-ol as a pale tan crystalline solid (97 mg, 33%). 1H NMR (500 MHz, Chloroform-d) δ 8.52 (s, 1H), 7.27 (s, 1H), 3.89 (s, 3H), 3.40 (d, J=13.4 Hz, 2H), 3.13 (d, J=12.5 Hz, 1H), 2.90-2.76 (m, 2H), 2.70 (s, 3H), 2.35 (q, J=11.3, 4.5 Hz, 1H), 2.11 (dt, J=12.5, 3.3 Hz, 1H), 1.97-1.84 (m, 2H), 1.67-1.54 (m, 3H), 1.54-1.48 (m, 1H), 1.42 (qt, J=13.1, 4.2 Hz, 1H), 1.22 (td, J=13.4, 2.7 Hz, 1H), 1.12 (qd, J=12.9, 4.1 Hz, 1H); MS (EI) for $C_{18}H_{24}INO_2$: 384.0 (MH+).

Step 2: Preparation of 3-methoxy-1-(2-methoxyethoxy)-17-methylmorphinan-4-yl trifluoromethanesulfonate

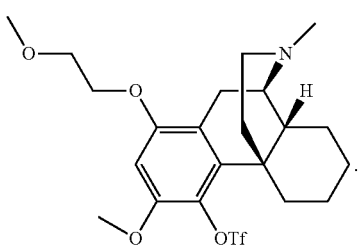 [SMILES: COCCOc1cc(OC)c(OS(=O)(=O)C(F)(F)F)c2c1C[C@@H]1[C@@H]3CCCC[C@]23CCN1C]

A 25 mL flask was charged with 1-iodo-3-methoxy-17-methylmorphinan-4-ol (289 mg, 0.70 mmol), copper(I) iodide (200 mg, 1.05 mmol), sodium tert-butoxide (336 mg, 3.49 mmol), and a magnetic stir bar, fitted with a septum and purged with nitrogen. Dry nitrogen-sparged N,N-dimethylformamide (4 mL) and 2-methoxyethanol (0.165 mL, 2.10 mmol) were added via syringe, and the resulting dark purple-brown suspension was stirred at room temperature for five minutes, before being placed in an oil bath preheated to 80° C. for 17 hours. A solution of 1,1,1-trifluoro-N-phenyl-N-((trifluoromethyl)sulfonyl)methanesulfonamide (1.123 g, 3.14 mmol) in dry tetrahydrofuran (4 mL) was added to the cooled mixture. The mixture was placed in an oil bath at 50° C. After six hours, additional 1,1,1-trifluoro-N-phenyl-N-((trifluoromethyl)sulfonyl)methanesulfonamide (0.53 g, 1.48 mmol, 2 equiv.) in tetrahydrofuran (2 mL) was added. Two portions of 1 M sodium hexamethyldisilazide in tetrahydrofuran (0.7 mL, 0.70 mmol) were added at 6.7 hours and 7.2 hours respectively and after 7.7 hours, the cooled reaction was quenched with acetic acid dropwise (0.8 mL, 14.0 mmol). The mixture was partitioned between ethyl acetate (60 mL) and brine (40 mL). The aqueous phase (pH~4) was brought to pH 7-8 with saturated aqueous ammonia (0.5 mL), then was diluted with brine (40 mL) and back extracted with ethyl acetate (25 mL). The combined organic layer was sequentially washed with brine (3×25 mL), saturated sodium bicarbonate (25 mL), and water (25 mL), was dried (sodium sulfate), was filtered and was concentrated to afford a brown oil. Chromatography on silica (dichloromethane to 1:10:180 ammonium hydroxide:methanol:dichloromethane) yielded 3-methoxy-1-(2-methoxyethoxy)-17-methylmorphinan-4-yl trifluoromethanesulfonate as a yellow-orange oil (87 mg, 25%). 1H NMR (400 MHz, Chloroform-d) δ 6.47 (s, 1H), 4.23-4.08 (m, 2H), 3.83 (s, 3H), 3.87-3.75 (m, 2H), 3.48 (s, 3H), 3.31 (d, J=7.0 Hz, 1H), 3.06 (d, J=14.0 Hz, 1H), 2.86 (d, J=18.7 Hz, 1H), 2.82 (d, J=3.2 Hz, 1H), 2.55-2.46 (m, 1H), 2.39 (dd, J=18.7, 6.4 Hz, 1H), 2.38 (s, 3H), 2.12 (td, J=12.4, 3.4 Hz, 1H), 1.88-1.67 (m, 3H), 1.65-1.52 (m, 1H), 1.42-1.35 (m, 2H), 1.23 (td, J=13.9, 13.5, 2.5 Hz, 1H), 1.16-1.00 (m, 2H); MS (EI) for $C_{22}H_{30}F_3NO_6S$: 494.2 (MH+).

Step 3: Preparation of 3-methoxy-1-(2-methoxyethoxy)-17-methylmorphinan

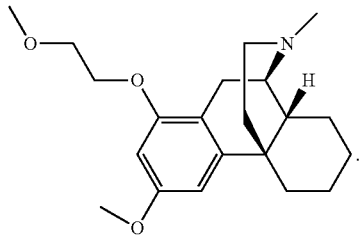 [SMILES: COCCOc1cc(OC)cc2c1C[C@@H]1[C@@H]3CCCC[C@]23CCN1C]

A 10 mL flask was charged with 3-methoxy-1-(2-methoxyethoxy)-17-methylmorphinan-4-yl trifluoromethanesulfonate (97 mg, 0.197 mmol), palladium(II) acetate (17 mg, 0.076 mmol) and 1,3-bis(diphenylphosphino)propane (42 mg, 0.102 mmol), capped with a septum, and purged with nitrogen. Dry nitrogen-sparged N,N-dimethylformamide (1 mL) was added, followed by triethylsilane (0.069 mL, 0.43 mmol) and the resultant brown solution was stirred at room temperature for five minutes, becoming deep red-brown, then placed in an oil bath heated at 80° C. for four hours. The mixture was cooled to room temperature, was diluted with ethyl acetate (20 mL), was washed with brine (3×10 mL) and was extracted with 1 M aqueous phosphoric acid (2×10 mL, 2×5 mL). The combined acid layer was basified to pH>12 with 2 M sodium hydroxide, was extracted with chloroform (2×50 mL) and the combined chloroform layer was dried (sodium sulfate), was filtered and was concentrated. Chromatography on silica (dichloromethane to 1:10:90 ammonium hydroxide:methanol:dichloromethane) afforded 3-methoxy-1-(2-methoxyethoxy)-17-methylmorphinan as a cloudy pale brown oil (36 mg, 53%). 1H NMR (500 MHz, Chloroform-d) δ 6.45 (d, J=3.0 Hz, 1H), 6.31 (d, J=3.2 Hz, 1H), 4.13 (t, J=4.9 Hz, 2H), 3.85-3.74 (m, 2H), 3.79 (s, 3H), 3.49 (s, 3H), 2.94 (d, J=18.8 Hz, 1H), 2.84 (dd, J=6.2, 3.1 Hz, 1H), 2.43 (dd, J=12.3, 4.4 Hz, 1H), 2.39 (t, J=1.2 Hz, 3H), 2.36-2.27 (m, 2H), 2.10 (td, J=12.3, 3.0 Hz, 1H), 1.81 (dt, J=13.0, 3.2 Hz, 1H), 1.73 (td, J=12.6, 4.9 Hz, 1H), 1.66-1.59 (m, 1H), 1.55-1.47 (m, 1H), 1.47-1.19 (m, 5H), 1.14 (qd, J=12.7, 12.3, 3.7 Hz, 1H); MS (EI) for $C_{21}H_{31}NO_3$: 346.2 (MH$^+$).

Step 4: Preparation of 1-(2-methoxyethoxy)-17-methylmorphinan-3-ol

A 0.5-2 mL microwave vial charged with sodium ethanethiolate (88 mg, 1.04 mmol) and a solution of 3-methoxy-1-(2-methoxyethoxy)-17-methylmorphinan (36 mg, 0.10 mmol) in dry N-methyl-2-pyrrolidinone (0.4 mL) was heated in a microwave at 150° C. for 3.5 hours, then partitioned between ethyl acetate (15 mL) and brine (15 mL) buffered with saturated ammonia/ammonium chloride (1/1, 0.5 mL). The aqueous layer was back extracted with ethyl acetate (10 mL), and the combined organic layer was washed with additional brine (3×5 mL), was dried (sodium sulfate), was filtered and was concentrated. Chromatography on silica (3:2 hexane:dichloromethane to dichloromethane, then dichloromethane to 1:10:90 ammonium hydroxide: methanol:dichloromethane) followed by reverse phase chromatography (C18 cartridge, 2-90% acetonitrile in 10 mM aqueous ammonium formate) afforded the phenol admixed with ammonium formate after evaporation of solvent. The residue was partitioned between ethyl acetate (10 mL) and 1 M citric acid (2×10 mL), and the combined aqueous layer was basified to pH~8 with 1 M aqueous tripotassium phosphate (~50 mL), followed by extraction with dichloromethane (2×20 mL). The combined dichloromethane layer was dried (sodium sulfate), was filtered and was concentrated to afford 1-(2-methoxyethoxy)-17-methylmorphinan-3-ol (74) as a cream-colored solid foam (27 mg, 78%). $^1$H NMR (500 MHz, Chloroform-d) δ 6.36 (d, J=2.3 Hz, 1H), 6.26 (d, J=2.3 Hz, 1H), 4.11 (t, J=4.8 Hz, 2H), 3.86-3.75 (m, 2H), 3.49 (s, 3H), 2.95 (d, J=18.9 Hz, 1H), 2.92-2.87 (m, 1H), 2.48 (t, J=12.3, 3.2 Hz, 1H), 2.42 (s, 3H), 2.35 (dd, J=18.9, 6.0 Hz, 1H), 2.26 (d, J=11.7 Hz, 1H), 2.16 (td, J=12.3, 3.3 Hz, 1H), 1.86 (d, J=12.5 Hz, 1H), 1.75 (td, J=12.8, 4.9 Hz, 1H), 1.63 (d, J=11.5 Hz, 1H), 1.53-1.45 (m, 1H), 1.43-1.21 (m, 6H), 1.16 (qd, J=12.6, 4.2 Hz, 1H); MS (EI) for $C_{20}H_{29}NO_3$: 332.2 (MH$^+$). The sample was converted to the HCl salt by dissolution in methanol (2 mL), dilution with 2 M HCl (0.20 mL), and concentration to dryness to afford a pale brown solid.

Example 75

Preparation of (5α)-5-{2-[2-(2-methoxyethoxy)ethoxy]ethoxy}-17-methylmorphinan-3-ol (75), hydrochloride salt (75)

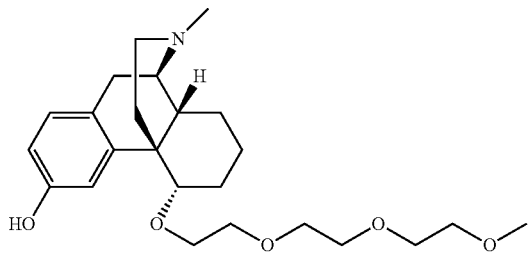

Step 1: Preparation of (5α)-3-methoxy-5-{2-[2-(2-methoxyethoxy)ethoxy]ethoxy}-17-methylmorphinan

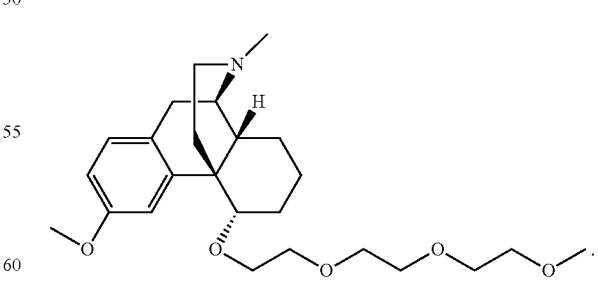

A dried nitrogen-flushed 13×100 mm test tube was charged with sodium hydride, (61 mg, 1.51 mmol, 60% disp.), then degreased under nitrogen with dry ether (2 mL). Solid (5α)-3-methoxy-17-methylmorphinan-5-ol (87 mg, 0.303 mmol) and dry N,N-dimethylformamide (1 mL) were added, and after ten minutes neat 2-(2-(2-methoxyethoxy)ethoxy)ethyl methanesulfonate (110 mg, 0.45 mmol) was added to the grey suspension, and the pale tan mixture was placed in an oil bath heated at 80° C. After four hours, the mixture was partitioned between ethyl acetate (50 mL) and brine (20 mL). The organic layer was washed with brine (3×20 mL) and water (20 mL), was dried (sodium sulfate), was filtered and was concentrated. Chromatography on silica (1:10:900 to 1:10:90 ammonium hydroxide:methanol:dichloromethane) afforded (5α)-3-methoxy-5-{2-[2-(2-methoxyethoxy)ethoxy]ethoxy}-17-methylmorphinan as an almost colorless oil (98 mg, 75%).

$^1$H NMR (500 MHz, Chloroform-d) δ 7.80 (d, J=2.8 Hz, 1H), 7.00 (d, J=8.4 Hz, 1H), 6.70 (dd, J=8.4, 2.8 Hz, 1H), 3.89 (dt, J=10.3, 5.3 Hz, 1H), 3.77 (s, 3H), 3.76-3.71 (m, 4H), 3.67 (dd, J=6.3, 3.4 Hz, 4H), 3.60-3.56 (m, 1H), 3.56 (dd, J=5.7, 3.6 Hz, 2H), 3.39 (s, 2H), 3.29 (dd, J=11.8, 3.4 Hz, 1H), 2.97 (d, J=18.2 Hz, 1H), 2.85 (dd, J=6.0, 3.2 Hz, 1H), 2.55 (dd, J=18.2, 6.0 Hz, 1H), 2.49 (ddd, J=12.0, 5.0, 1.9 Hz, 1H), 2.41 (s, 3H), 2.10 (td, J=12.3, 3.3 Hz, 1H), 2.04 (dt, J=13.0, 2.5 Hz, 1H), 1.91 (dt, J=11.4, 3.4 Hz, 1H), 1.76 (dt, J=12.5, 3.2 Hz, 1H), 1.70 (ddd, J=12.7, 8.6, 4.2 Hz, 1H), 1.54 (qd, J=12.4, 3.7 Hz, 1H), 1.42 (qt, J=12.9, 3.9 Hz, 1H), 1.37-1.31 (m, 1H), 1.13 (qd, J=12.9, 4.2 Hz, 1H); MS (EI) for $C_{25}H_{39}NO_5$: 434.2 (MH$^+$).

Step 2: Preparation of (5α)-5-{2-[2-(2-methoxyethoxy)ethoxy]ethoxy}-17-methylmorphinan-3-ol A 0.5-2 mL microwave vial charged with sodium ethanethiolate (83 mg, 0.99 mmol) and a solution of (5α)-3-methoxy-5-{2-[2-(2-methoxyethoxy)ethoxy]ethoxy}-17-methylmorphinan (86 mg, 0.20 mmol) in dry N-methyl-2-pyrrolidinone (0.5 mL) was heated in a microwave at 150° C. for 2.6 hours, then was partitioned between ethyl acetate (25 mL) and brine (25 mL) buffered with saturated aqueous ammonia/ammonium chloride (0.5 mL each). The aqueous layer was diluted with brine (25 mL), and was back extracted with ethyl acetate (25 mL). The combined organic layer was washed with additional brine (3×25 mL), was dried (sodium sulfate), was filtered and was concentrated. Chromatography on silica (1:10:450 to 1:10:150 ammonium hydroxide:methanol:dichloromethane) afforded (5α)-5-{2-[2-(2-methoxyethoxy)ethoxy]ethoxy}-17-methylmorphinan-3-ol (75) as a light yellow wax (75 mg, 90%). $^1$H NMR (500 MHz, Chloroform-d) δ 7.75 (d, J=2.7 Hz, 1H), 7.51 (br s, 1H, OH), 6.95 (d, J=8.3 Hz, 1H), 6.66 (dd, J=8.3, 2.7 Hz, 1H), 3.94 (ddd, J=10.5, 8.0, 2.6 Hz, 1H), 3.85-3.64 (m, 7H), 3.63-3.53 (m, 2H), 3.49-3.41 (m, 1H), 3.39 (s, 3H), 3.26 (dd, J=11.9, 3.5 Hz, 1H), 2.95 (d, J=18.2 Hz, 1H), 2.85 (dd, J=5.9, 3.2 Hz, 1H), 2.54 (dd, J=18.2, 5.9 Hz, 1H), 2.53-2.48 (m, 1H), 2.41 (s, 3H), 2.14 (td, J=12.3, 3.3 Hz, 1H), 2.04 (dt, J=12.8, 2.7 Hz, 1H), 1.93-1.86 (m, 1H), 1.79-1.64 (m, 4H), 1.58 (qd, J=12.5, 3.8 Hz, 1H), 1.41 (qt, J=13.0, 4.0 Hz, 1H), 1.36-1.29 (m, 1H), 1.16 (qd, J=12.9, 4.1 Hz, 1H); MS (EI) for $C_{24}H_{37}NO_5$: 420.2 (MH$^+$). The sample was converted to the HCl salt by dissolution in acetonitrile (1 mL) and 2 M HCl (200 uL), diluted with water (2 mL), frozen and lyophilized to yield the HCl salt as a dark yellow oil.

Example 76

Preparation of N-(2-methoxyethyl)-17-methyl-2-nitromorphinan-3-amine (76), hydrochloride salt

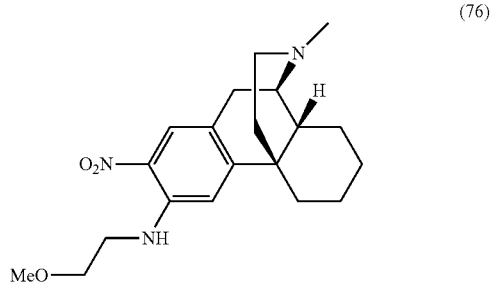 [SMILES: COCCNc1cc2c(cc1[N+](=O)[O-])C[C@@H]1[C@@H]3CCCC[C@]23CCN1C]

(76)

Step 1: Preparation of 17-methyl-2-nitromorphinan-3-yl trifluoromethanesulfonate

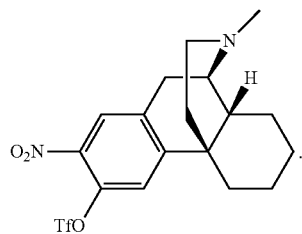 [SMILES: CN1CC[C@]23CCCC[C@H]2[C@H]1Cc1cc([N+](=O)[O-])c(OS(=O)(=O)C(F)(F)F)cc13]

A solution of 500 mg (1.28 mmol) of 17-methylmorphinan-3-yl trifluoromethanesulfonate [Zhang et al. (2004) *J Med Chem* 47(1):165-174] in 2.5 mL of sulfuric acid was cooled to 0° C. A mixture of concentrated nitric acid (0.13 mL) and sulfuric acid (0.32 mL) was added dropwise and the reaction mixture was stirred at room temperature for 20 hours. The crude was cooled to 0° C. and basified with 4 M sodium hydroxide to pH 7, extracted with dichloromethane (100 mL) and dried over anhydrous magnesium sulfate. The solution was filtered and the filtrate was concentrated under reduced pressure to yield 17-methyl-2-nitromorphinan-3-yl trifluoromethanesulfonate (0.44 g, 79%) as a light brown oil that was used without further purification. $^1$H NMR (500 MHz, Chloroform-d): δ 7.98 (s, 1H), 7.29 (s, 1H), 3.16 (d, J=19.0 Hz, 1H), 3.01-2.93 (m, 1H), 2.75 (dd, J=19.0, 5.9 Hz, 1H), 2.61-2.53 (m, 1H), 2.45 (s, 3H), 2.31 (dd, J=14.4, 3.5 Hz, 1H), 2.05-1.95 (m, 2H), 1.91 (td, J=12.8, 4.6 Hz, 1H), 1.71 (dt, J=13.4, 3.5 Hz, 1H), 1.65 (q, J=6.0, 4.8 Hz, 1H), 1.56-1.30 (m, 4H), 1.14 (qt, J=13.4, 3.4 Hz, 1H), 0.99 (qd, J=13.0, 3.9 Hz, 1H). MS (EI) for $C_{18}H_{21}F_3N_2O_5S$: 435 (MH$^+$).

Step 2: Preparation of N-(2-methoxyethyl)-17-methyl-2-nitromorphinan-3-amine

2-Methoxyethanamine (0.115 mL, 1.322 mmol) was added to a solution of 17-methyl-2-nitromorphinan-3-yl trifluoromethanesulfonate (0.383 g, 0.882 mmol) in dioxane (2.5 mL). The resulting mixture was heated in a microwave oven at 160° C. for ninety minutes. The solvent was removed under reduced pressure and the residue was solved in dichloromethane (100 mL) and washed with 1M sodium hydroxide. The organic layer was dried over anhydrous magnesium sulfate, was filtered and was concentrated. The crude product was purified by silica gel flash chromatography (99:1:0.1 to 95:5:0.5 dichloromethane:methanol:aqueous ammonia) to afford N-(2-methoxyethyl)-17-methyl-2-nitromorphinan-3-amine (76) (75.8 mg, 19.9%) as an orange oil. $^1$H NMR (500 MHz, Chloroform-d): δ 8.02 (t, J=5.1 Hz, 1H), 7.95 (s, 1H), 6.78 (s, 1H), 3.70 (t, J=5.1 Hz, 2H), 3.49 (qd, J=5.3, 2.0 Hz, 2H), 3.45 (s, 3H), 3.03 (d, J=18.1 Hz, 1H), 2.87 (dd, J=6.2, 3.1 Hz, 1H), 2.61 (dd, J=18.2, 5.9 Hz, 1H), 2.50 (dd, J=12.4, 4.9 Hz, 1H), 2.43 (s, 3H), 2.41-2.32 (m, 1H), 2.13 (td, J=12.5, 3.2 Hz, 1H), 1.93-1.79 (m, 2H), 1.74-1.65 (m, 1H), 1.58 (dd, J=10.3, 6.5 Hz, 1H), 1.51-1.23 (m, 5H), 1.10 (qd, J=12.7, 3.9 Hz, 1H). MS (EI) for $C_{20}H_{29}N_3O_3$: 360 (MH$^+$).

The free base (5 mg) was solved in acetonitrile and water and treated with 1 N hydrochloric acid. The solvents were removed in the lyophilizer to generate the hydrochloride salt of the title compound as a bright orange solid.

Example 77

Preparation of (7R,7aR,11aR)—N-(2,5,8,11,14-pentaoxahexadecan-16-yl)-14-methyl-7,7a,8,9,10,11-hexahydro-6H-7,11a-(epiminoethano)phenanthro[3,4-d]thiazol-2-amine (77), hydrochloride salt

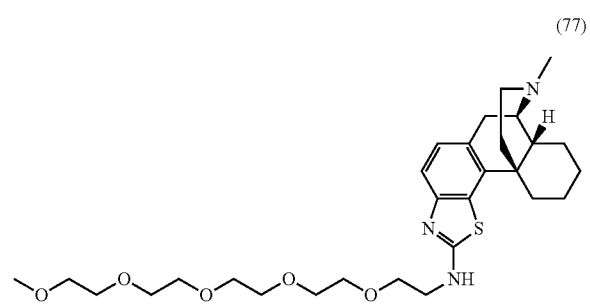 [SMILES: COCCOCCOCCOCCOCCNc1nc2ccc3c(c2s1)[C@@]12CCCC[C@H]1[C@@H](C3)N(C)CC2]

(77)

Step 1: Synthesis of (4bR,8aR,9R)-3-isothiocyanato-11-methyl-6,7,8,8a,9,10-hexahydro-5H-9,4b-(epiminoethano)phenanthrene

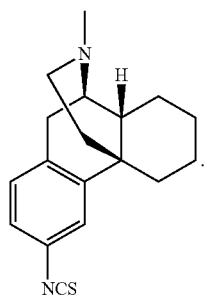

17-Methyl-morphinan-3-amine (100.7 mg, 0.393 mmol) was dissolved in dichloromethane (4 mL). To the solution was added 0,0-di(pyridin-2-yl) carbonothioate (91 mg, 0.393 mmol). The reaction was stirred at room temperature for thirty minutes. LCMS indicated the complete formation of (4bR,8aR,9R)-3-isothiocyanato-11-methyl-6,7,8,8a,9,10-hexahydro-5H-9,4b-(epiminoethano)phenanthrene. MS (EI) for $C_{18}H_{22}N_2S$: 299.2 (MH+).

Step 2: Synthesis of 1-(2,5,8,11,14-pentaoxahexadecan-16-yl)-3-((4bR,8aR,9R)-11-methyl-6,7,8,8a,9,10-hexahydro-5H-9,4b-(epiminoethano)phenanthren-3-yl)thiourea

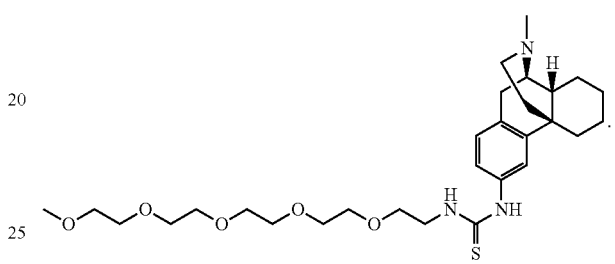

To the reaction mixture produced in Step 1 of this example was added 2,5,8,11,14-pentaoxahexadecan-16-amine (99 mg, 0.393 mmol). The reaction was stirred at room temperature for two hours. The reaction was diluted with dichloromethane (25 mL), and washed with saturated sodium bicarbonate (30 mL). The organic layer was dried over sodium sulfate, was filtered and was concentrated. The crude product was used directly in the next reaction. MS (EI) for $C_{29}H_{47}N_3O_5S$: 550.2 (MH+).

Step 3: Synthesis of (7R,7aR,11aR)—N-(2,5,8,11,14-pentaoxahexadecan-16-yl)-14-methyl-7,7a,8,9,10,11-hexahydro-6H-7,11a-(epiminoethano)phenanthro[3,4-d]thiazol-2-amine The above product from step 2 was dissolved in dichloromethane (4 mL). To the solution was added benzyltrimethyl ammonium tribromide (153 mg, 0.393 mmol). The reaction was stirred at room temperature overnight. The reaction was diluted with dichloromethane (20 mL) and was washed sequentially with saturated sodium bicarbonate (30 mL) and brine (30 mL). The organic layer was dried over sodium sulfate, was filtered and was concentrated. The residue was purified on a flash silica gel column to give the desired product (77) as the free base (43 mg, 20% for 3 steps). MS (EI) for $C_{29}H_{45}N_3O_5S$: 548.2 (MH+). 1H NMR (500 MHz, Methanol-d4) δ 7.31 (d, J=8.2 Hz, 1H), 7.12 (d, J=8.0 Hz, 1H), 3.76-3.59 (m, 17H), 3.53 (dd, J=6.0, 3.3 Hz, 2H), 3.35 (s, 2H), 3.12 (dd, J=17.6, 3.7 Hz, 1H), 2.92-2.79 (m, 3H), 2.52-2.38 (m, 4H), 2.11 (td, J=12.6, 12.2, 4.8 Hz, 1H), 1.92-1.85 (m, 1H), 1.73-1.57 (m, 4H), 1.56-1.25 (m, 4H), 1.19-1.07 (m, 1H).

The free base (12.1 mg) was dissolved in 1 mL of methanol. To the solution was added 3 equivalents of 2 N hydrochloric acid in diethyl ether. The mixture was concentrated and dried under high vacuum to afford 12.49 mg of the hydrochloride salt.

Example 78

Preparation of (7R,7aR,11aR)—N-(2-(2-(2-methoxyethoxy)ethoxy)ethyl)-14-methyl-7,7a,8,9,10,11-hexahydro-6H-7,11a-(epiminoethano)phenanthro[3,4-d]thiazol-2-amine (78), hydrochloride salt

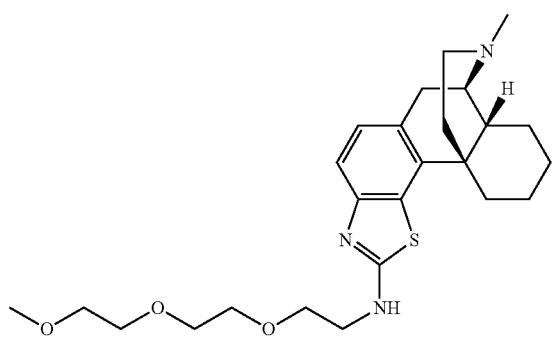
(78)

Step 1: Synthesis of 1-(2-(2-(2-methoxyethoxy)ethoxy)ethyl)-3-44bR,8aR,9R)-11-methyl-6,7,8,8a,9,10-hexahydro-5H-9,4b-(epiminoethano)phenanthren-3-yl)thiourea

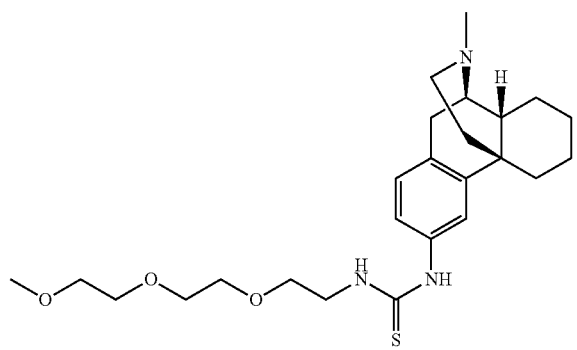

17-Methyl-morphinan-3-amine (114.2 mg, 0.445 mmol) was dissolved in dichloromethane (4 mL). To the solution was added O,O-di(pyridin-2-yl) carbonothioate (103 mg, 0.445 mmol). The reaction was stirred at room temperature for 30 min before 2-(2-(2-methoxyethoxy)ethoxy)ethanamine (72.7 mg, 0.445 mmol) was added. Stirring was continued for one hour. LCMS indicated the completion of the reaction. MS (EI) for $C_{18}H_{22}N_2S$: 462.2 (MH+).

Step 2: Synthesis of (7R,7aR,11aR)—N-(2-(2-(2-methoxyethoxy)ethoxy)ethyl)-14-methyl-7,7a,8,9,10,11-hexahydro-6H-7,11a-(epiminoethano)phenanthro[3,4-d]thiazol-2-amine To the reaction mixture produced in Step 1 of this example was added benzyltrimethyl ammonium tribromide (0.174 g, 0.445 mmol). The reaction was stirred at room temperature overnight. The reaction was diluted with dichloromethane (20 mL) and was washed sequentially with saturated sodium bicarbonate (30 mL) and brine (30 mL). The organic layer was dried over sodium sulfate, was filtered and was concentrated. The residue was purified on a flash silica gel column to give the desired product (78) as the free base (45.1 mg, 22% for three steps). MS (EI) for $C_{25}H_{37}N_3O_3S$: 460.2 (MH+). The free base (9.2 mg) was dissolved in 1 mL of methanol. To the solution was added 3 equivalents of 2 N hydrochloric acid in diethyl ether. The mixture was concentrated and dried under high vacuum to afford 9.5 mg of the product as the hydrochloride salt.

Example 79

3-(2-methoxyethoxy)-N-((4bR,8aR,9R)-11-methyl-6,7,8,8a,9,10-hexahydro-5H-9,4b-(epiminoethano)phenanthren-3-yl)propanamide (79)

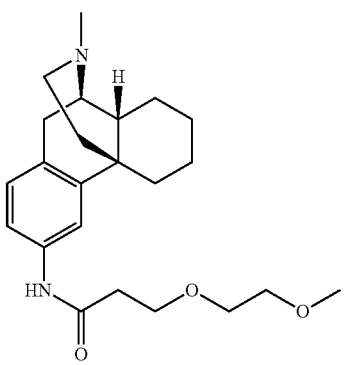
(79)

3-Amino-17-methyl-morphinan (55.44 mg, 0.216 mmol) was dissolved in dichloromethane (2.5 mL). To the solution were added EDC (62.2 mg, 0.324 mmol), 3-(2-methoxyethoxy)propanoic acid (32.0 mg, 0.216 mmol) and triethylamine (0.090 mL, 0.649 mmol). The reaction was stirred at room temperature overnight. The reaction was taken up in 10 mL of dichloromethane and was sequentially washed with saturated sodium bicarbonate and brine. The organic layer was dried over sodium sulfate, was filtered and was concentrated. After purification by silica gel chromatography using Biotage, 3-(2-methoxyethoxy)-N-((4bR,8aR,9R)-11-methyl-6,7,8,8a,9,10-hexahydro-5H-9,4b-(epiminoethano)phenanthren-3-yl)propanamide (79) (43.2 mg, 0.112 mmol, 51.7% yield) was obtained as clear oil. MS (EI) for $C_{23}H_{34}N_2O_3$: 387.2 (MH+). 1H NMR (500 MHz, Methanol-d4) δ 7.51 (d, J=2.1 Hz, 1H), 7.37 (dd, J=8.3, 2.1 Hz, 1H), 7.09 (d, J=8.3 Hz, 1H), 3.82 (t, J=6.1 Hz, 2H), 3.68-3.60 (m, 2H), 3.59-3.52 (m, 2H), 3.36 (s, 3H), 3.07 (d, J=18.6 Hz, 1H), 2.86 (dd, J=5.8, 3.1 Hz, 1H), 2.70 (dd, J=18.6, 5.9 Hz, 1H), 2.62 (t, J=6.1 Hz, 2H), 2.51-2.38 (m, 5H), 2.12 (td, J=12.5, 3.3 Hz, 1H), 1.85 (dt, J=12.7, 3.1 Hz, 1H), 1.80-1.64 (m, 2H), 1.59-1.51 (m, 1H), 1.51-1.27 (m, 5H), 1.23-1.10 (m, 1H).

Example 80

Preparation of N-[(4aR,5R,11bR)-14-methyl-2,3,4,4a,5,6-hexahydro-1H-5,11b-(epiminoethano)phenanthro[3,2-d][1,3]thiazol-9-yl]-2,5,8,11,14-pentaoxaoctadecan-18-amide (80), hydrochloride salt

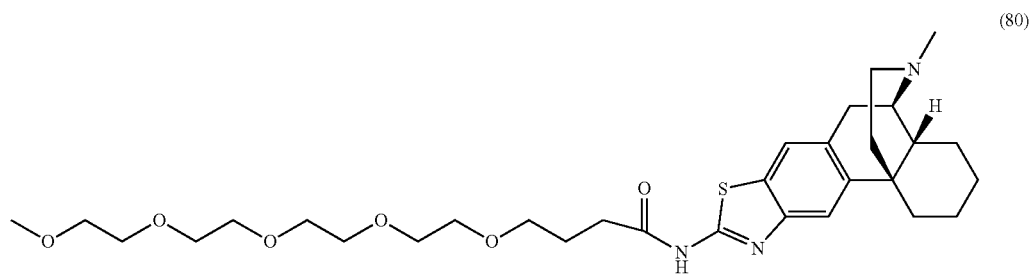 [SMILES: COCCOCCOCCOCCOCCCC(=O)Nc1nc2cc3c(cc2s1)C[C@@H]1[C@@H]2CCCC[C@]32CCN1C]

Step 1: Preparation of 2,5,8,11-tetraoxapentadecan-15-oic acid

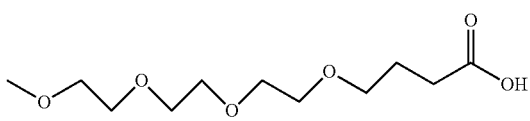 [SMILES: COCCOCCOCCOCCCC(=O)O]

To an acetonitrile solution of 2,5,8,11-tetraoxatridecan-13-ol (5.0 g, 24.0 mmol) and 1-(3-bromopropyl)-4-methyl-2,6,7-trioxabicyclo[2.2.2]octane (12.1 g, 48.0 mmol) was slowly added sodium hydride (0.86 g, 36 mmol). The reaction mixture was heated at 70° C. for 22 hours. After all solvent was removed, the residue was loaded on a 50 g silica gel column and purified by Biotage with dichloromethane/methanol. The crude 4-methyl-1-(2,5,8,11-tetraoxatetradecan-14-yl)-2,6,7-trioxabicyclo[2.2.2]octane (4.0 g, 12.0 mmol) was dissolved in water, followed by the addition of phosphoric acid to bring the solution to pH 1. Thereafter, the solution was stirred at room temperature for one hour, and potassium hydroxide was added to adjust to pH 12, followed by stirring at room temperature for 18 hours. The pH was adjusted back to 3 by addition of phosphoric acid and the water phase was extracted with dichloromethane three times. Thereafter, once all dichloromethane extracts were combined and all solvent was removed, a colorless liquid was obtained. The crude product was loaded onto a 25 g silica gel column and purified by Biotage with dichloromethane/methanol, and a colorless semi-solid was obtained (1.8 g, 7.2 mmol, 30% yield). Proton NMR confirmed that it was pure 2,5,8,11-tetraoxapentadecan-15-oic acid. $^1$H NMR (500 MHz, Chloroform-d): δ 3.65 (m, 12H), 3.60 (m, 2H), 3.55 (m, 4H), 3.39 (s, 3H), 2.46 (t, 2H), 1.92 (m, 2H).

Step 2: Preparation of N-[(4aR,5R,11bR)-14-methyl-2,3,4,4a,5,6-hexahydro-1H-5,11b-(epiminoethano)phenanthro[3,2-d][1,3]thiazol-9-yl]-2,5,8,11,14-pentaoxaoctadecan-18-amide hydrochloride salt A dichloromethane solution of (4aR,5R,11bR)-14-methyl-2,3,4,4a,5,6-hexahydro-1H-5,11b-(epiminoethano) phenanthro[3,2-d][1,3]thiazol-9-amine 2'-amino-thiazolo[5,4-b]-17-methyl-morphinan (0.060 g, 0.19 mmol), 2,5,8,11-tetraoxapentadecan-15-oic acid (0.056 g, 0.19 mmol), O-(benzotriazol-1-yl)-N,N,N',N'-tetramethyluronium tetrafluoroborate (0.074 g, 0.23 mmol) and triethyl amine (0.058 g, 57 mmol) was stirred at room temperature for 18 hours. HPLC showed that the reaction was complete. Hydrochloric acid (0.1N) solution was added to the reaction mixture and the aqueous phase was washed with dichloromethane twice. Potassium carbonate was added to achieve pH 8-9, followed by extraction with dichloromethane twice. After the solvent was removed, the crude product was purified by chromatography on silica gel using Biotage with dichloromethane/methanol as eluent. N-[(4aR,5R,11bR)-14-methyl-2,3,4,4a,5,6-hexahydro-1H-5,11b-(epiminoethano)phenanthro[3,2-d][1,3]thiazol-9-yl]-2,5,8,11,14-pentaoxaoctadecan-18-amide (80) was obtained as a colorless solid (0.050 g, 44% yield). $^1$H NMR (500 MHz, d$_4$-methanol): δ 7.74 (s, 2H), 3.66 (m, 1H), 3.55 (m, 16H), 3.49 (m, 2H), 3.37 (m, 1H), 3.33 (s, 3H), 2.71 (m, 1H), 2.63 (t, 3H), 2.15 (m, 1H), 1.97 (m, 3H), 1.45-1.74 (m, 6H), 1.31 (m, 1H), 1.15 (m, 1H); MS (EI) for $C_{31}H_{47}N_3O_6S$: 591.0 (MH$^+$).

The free base (0.050 g, 0.085 mmol) was dissolved in 1:1 acetonitrile/methanol followed by the addition of a 2 N hydrochloric acid ether solution (0.25 mL, 0.25 mmol). The mixture was lyophilized to give N—[(4aR,5R,11bR)-14-methyl-2,3,4,4a,5,6-hexahydro-1H-5,11b-(epiminoethano) phenanthro[3,2-d][1,3]thiazol-9-yl]-2,5,8,11,14-pentaoxaoctadecan-18-amide hydrochloride salt as a colorless solid (0.053 g, 0.084 mmol, 99% yield).

Example 81

Preparation of (4aR,5R,11bR)-14-methyl-1,2,3,4,4a,5,6,10-octahydro-5,11b-(epiminoethano)phenanthro[2,3-d]imidazole (81), hydrochloride salt

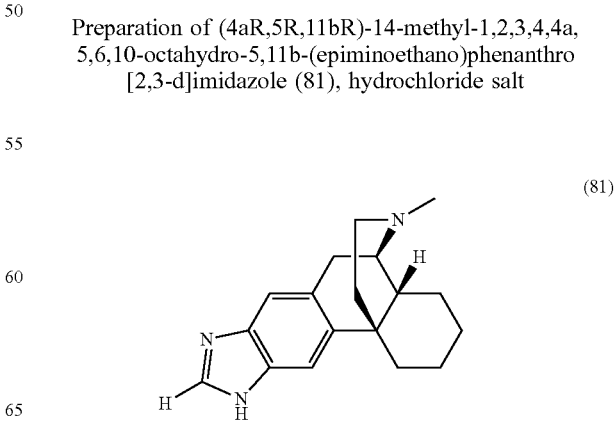

Step 1: Preparation of
N-(17-methyl-morphinan-3-yl)acetamide

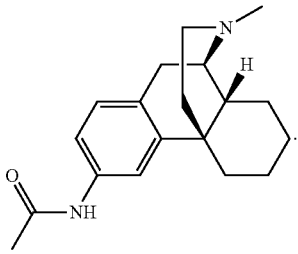 [SMILES: CC(=O)Nc1ccc2c(c1)[C@@]13CCCC[C@H]1[C@@H](C2)N(C)CC3]

A solution of 17-methylmorphinan-3-amine (352 mg, 1.37 mmol) in dichloromethane (20 mL) was cooled to 0° C., whereupon a solution of acetic anhydride (0.194 mL, 2.06 mmol) in dichloromethane (1 mL) was added dropwise over one minute. The mixture was then warmed to room temperature. After thirty minutes, the mixture was concentrated in vacuo, and the thick yellow oily residue (614 mg) was carried forward to the next step without further purification. MS (EI) for $C_{19}H_{26}NO$: 299.2 ($MH^+$).

Step 2: Preparation of
N-(17-methyl-2-nitromorphinan-3-yl)acetamide

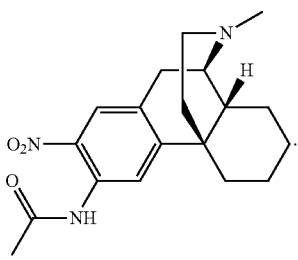 [SMILES: CC(=O)Nc1cc2c(cc1[N+](=O)[O-])C[C@@H]1[C@@H]3CCCC[C@]23CCN1C]

A solution of N-(17-methyl-morphinan-3-yl)acetamide (614 mg, assumed 1.37 mmol) in sulfuric acid (10 mL, 188 mmol) was cooled to 0° C., whereupon 70% nitric acid (0.44 mL, 6.9 mmol) was added dropwise over two minutes. After two hours, the mixture was poured onto ice (100 g), basified to pH>12 with 50% aqueous sodium hydroxide (21 mL, 0.40 mol), and was extracted with dichloromethane (2×75 mL). The combined dichloromethane layer was dried (sodium sulfate), was filtered and was concentrated to afford crude N-(17-methyl-2-nitromorphinan-3-yl)acetamide as a viscous orange oil (538 mg), which was carried forward to the next step without further purification. MS (EI) for $C_{19}H_{26}N_3O_3$: 344.2 ($MH^+$).

Step 3: Preparation of
17-methyl-2-nitromorphinan-3-amine

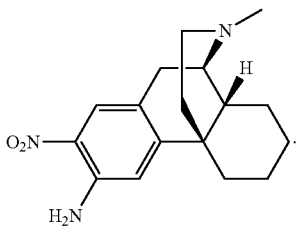 [SMILES: CN1CC[C@]23CCCC[C@H]2[C@H]1Cc1cc([N+](=O)[O-])c(N)cc13]

A solution of N-(17-methyl-2-nitromorphinan-3-yl)acetamide (538 mg, assumed 1.37 mmol) in methanol (10 mL) was treated with 4 M aqueous sodium hydroxide (2.0 mL, 8.0 mmol), and the resultant red solution was heated in an oil bath at 60° C. After seven hours, the mixture was partitioned between dichloromethane (50 mL) and half-saturated brine (50 mL), and the aqueous layer was extracted with dichloromethane (50 mL). The combined organic layer was dried (sodium sulfate), was filtered and was concentrated. Automated flash chromatography on silica (1:10:45 to 1:10:180 ammonium hydroxide:methanol:dichloromethane) afforded 17-methyl-2-nitromorphinan-3-amine as a semi-solid orange foam (382 mg; 95% over 3 steps). $^1H$ NMR (500 MHz, $CDCl_3$) δ 7.89 (s, 1H), 6.72 (s, 1H), 5.91 (s, 2H), 3.03 (d, J=18.1 Hz, 1H), 2.84 (dd, J=5.9, 3.2 Hz, 1H), 2.59 (ddd, J=18.2, 5.9, 1.2 Hz, 1H), 2.47 (ddd, J=12.2, 4.9, 1.9 Hz, 1H), 2.41 (s, 3H), 2.30 (dt, J=14.0, 3.0 Hz, 1H), 2.11 (td, J=12.5, 3.2 Hz, 1H), 1.85 (dt, J=13.4, 3.7 Hz, 1H), 1.79 (dd, J=12.8, 4.9 Hz, 1H), 1.73-1.65 (m, 1H), 1.57 (dt, J=13.2, 3.0 Hz, 1H), 1.48 (ddd, J=13.1, 2.9, 0.8 Hz, 1H), 1.46-1.32 (m, 3H), 1.26 (qt, J=13.2, 3.2 Hz, 1H), 1.09 (qd, J=12.8, 3.9 Hz, 1H); $^{13}C$ NMR (126 MHz, $CDCl_3$) δ 151.22, 143.17, 130.62, 127.23, 124.10, 115.12, 77.32, 77.06, 76.81, 57.45, 47.04, 45.12, 42.76, 42.29, 37.88, 36.64, 27.02, 26.38, 22.89, 22.24; MS (EI) for $C_{17}H_{23}N_3O_2$: 302.2 ($MH^+$).

Step 4: Preparation of
17-methylmorphinan-2,3-diamine

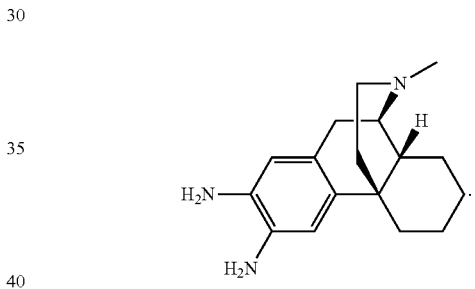

A solution of 17-methyl-2-nitromorphinan-3-amine (151 mg, 0.50 mmol) in ethanol (10 mL) was treated with 10% palladium on carbon (20 mg), and the mixture was hydrogenated at room temperature. After 64 hours, the mixture was filtered through celite, and the filtrate was concentrated in vacuo to afford 17-methylmorphinan-2,3-diamine as a pale yellow film (136 mg, quant). The sample was carried forward to the next step without further purification. $^1H$ NMR (500 MHz, $CDCl_3$) δ 6.56 (s, 1H), 6.45 (s, 1H), 3.33 (s, 5H), 2.86 (d, J=18.0 Hz, 1H), 2.75 (dd, J=5.7, 3.1 Hz, 1H), 2.51 (dd, J=18.1, 5.8 Hz, 1H), 2.40 (ddd, J=11.5, 4.8, 1.9 Hz, 1H), 2.36 (s, 3H), 2.28-2.20 (m, 1H), 2.12 (td, J=12.3, 3.4 Hz, 1H), 1.76 (dt, J=12.8, 3.2 Hz, 1H), 1.67 (td, J=12.6, 4.8 Hz, 1H), 1.50-1.44 (m, 1H), 1.40-1.09 (m, 7H). MS (EI) for $C_{17}H_{25}N_3$: 272.2 ($MH^+$).

Step 5: Preparation of (4aR,5R,11bR)-14-methyl-1,
2,3,4,4a,5,6,10-octahydro-5,11b-(epiminoethano)
phenanthro[2,3-d]imidazole A solution of 17-methylmorphinan-2,3-diamine (68 mg, 0.25 mmol) in formic acid (2 mL) was heated in a microwave at 100° C. for one hour. The mixture was concentrated in vacuo, and the pink residue was partitioned between dichloromethane (15 mL) and 1 M sodium bicarbonate (10 mL). The aqueous layer was extracted with dichloromethane (10 mL), and 3:1 chloroform:isopropanol (3×20 mL). The combined organic layer was dried (sodium sulfate), filtered and concentrated. Automated flash chromatography on silica (1:10:450 to 1:10:90 ammonium hydroxide:methanol:dichloromethane) afforded (4aR,5R,11bR)-14-methyl-1,2,3,4,4a,5,6,10-octahydro-5,11b-(epiminoethano)phenanthro[2,3-d]imidazole (81) as a yellow oil (18.3 mg, 26%). $^1$H NMR (500 MHz, CDCl$_3$) δ 8.02 (s, 1H), 7.61 (br s, 2H), 7.43 (br s, 1H), 3.26 (d, J=17.2 Hz, 1H), 2.96-2.82 (m, 2H), 2.52-2.48 (m, 1H), 2.47 (s, 3H), 2.15 (td, J=12.4, 3.2 Hz, 1H), 1.93 (dt, J=13.0, 3.2 Hz, 1H), 1.84 (td, J=12.7, 4.8 Hz, 1H), 1.71-1.61 (m, 1H), 1.55 (dt, J=10.9, 2.9 Hz, 1H), 1.51-1.25 (m, 6H), 1.20 (qd, J=12.1, 3.6 Hz, 1H); MS (EI) for C$_{18}$H$_{23}$N$_3$: 282.2 (MH$^+$). The sample was converted to the HCl salt by dissolution in acetonitrile (1 mL) and 2 M hydrochloric acid (0.10 mL), dilution with water (2 mL), and concentration in vacuo to afford the HCl salt as a very pale pink solid.

Example 82

Preparation of (4aR,5R,11bR)-14-methyl-1,2,3,4,4a,5,6,10-octahydro-5,11b-(epiminoethano)phenanthro[2,3-d]imidazol-9-amine (82), hydrochloride salt

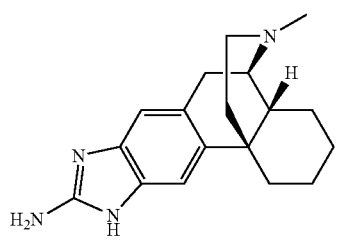

(82)

Cyanogen bromide (33 mg, 0.31 mmol) was added to a solution of 17-methylmorphinan-2,3-diamine (68 mg, 0.25 mmol) and acetic acid (0.019 ml, 0.33 mmol) in methanol (3 mL), and the mixture was stirred at room temperature. Additional cyanogen bromide (21 mg, 0.20 mmol) was added after 1.75 hours. After twenty hours, the mixture was treated with aqueous 4 M sodium hydroxide (1 mL) for one hour, then was poured into saturated brine (30 mL) and extracted with 3:1 chloroform:isopropanol (4×25 mL). The combined organic layer was dried (sodium sulfate), was filtered and was concentrated. Purification via automated flash chromatography on silica (1:10:490 to 1:10:57 ammonium hydroxide:methanol:dichloromethane), followed by chromatography on amine-silica (dichloromethane to 10% methanol/dichloromethane) afforded (4aR,5R,11bR)-14-methyl-1,2,3,4,4a,5,6,10-octahydro-5,11b-(epiminoethano)phenanthro[2,3-d]imidazol-9-amine (82) (28 mg, 38%) as a very pale brown glass. $^1$H NMR (500 MHz, DMSO-d6) δ 10.37 (s, 1H), 6.94 (s, 1H), 6.82 (s, 1H), 5.98 (s, 2H), 3.00 (d, J=17.7 Hz, 1H), 2.67 (dd, J=5.5, 3.0 Hz, 1H), 2.59 (dd, J=17.7, 5.8 Hz, 1H), 2.42-2.33 (m, 1H), 2.27 (s, 3H), 2.30-2.23 (m, 1H), 1.96 (td, J=12.1, 3.0 Hz, 1H), 1.69 (dt, J=13.1, 3.0 Hz, 1H), 1.64-1.54 (m, 2H), 1.46 (d, J=10.9 Hz, 1H), 1.38-1.15 (m, 5H), 1.09 (qd, J=13.4, 13.0, 12.3, 3.4 Hz, 1H); MS (EI) for C$_{18}$H$_{24}$N$_4$: 297.2 (MH$^+$). The sample was converted into the HCl salt by dissolution in methanol (1 mL), followed by the addition of 2 M hydrochloric acid (0.1 mL) and dilution with water (1 mL). The mixture was concentrated in vacuo to afford the HCl salt as a cream colored solid.

Example 83

Preparation of 17-[2-(2-methoxyethoxy)ethyl]-N-(pyridin-3-yl)morphinan-3-amine (83), hydrochloride salt

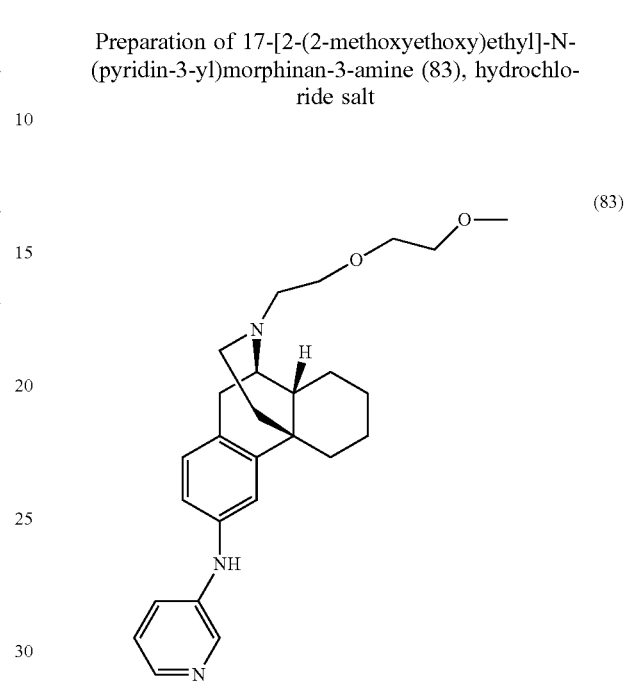

(83)

Step 1: Preparation of 17-[2-(2-methoxyethoxy)ethyl]morphinan-3-yl trifluoromethanesulfonate

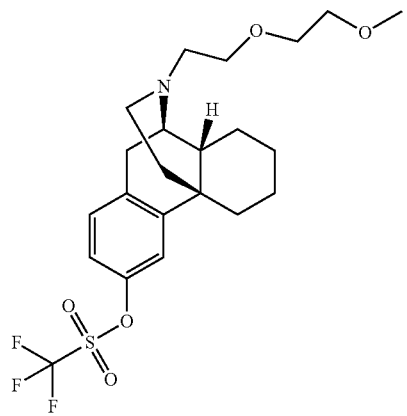 [SMILES: COCCOCCN1CC[C@]23CCCC[C@H]2[C@H]1Cc1ccc(OS(=O)(=O)C(F)(F)F)cc13]

The acetonitrile solution of morphinan-3-yl trifluoromethanesulfonate (2.7 g, 7.19 mmol), 1-bromo-2-(2-methoxyethoxy)ethane (2.6 g, 14.4 mmol) and cesium carbonate (2.6 g, 43.2 mmol) was heated at 50° C. for 18 hours. After cooling the mixture to room temperature, all solvent was removed and the reaction mixture was extracted with dichloromethane twice. The solvent was evaporated and the residue was purified by silica gel chromatography using Biotage with dichloromethane/methanol eluents. 17-[2-(2-Methoxyethoxy)ethyl]morphinan-3-yl trifluoromethanesulfonate was obtained as a light-yellow liquid (2.5 g, 73% yield), MS (EI) for C$_{22}$H$_{30}$F$_3$NO$_5$S: 478.2 (MH$^+$).

Step 2: Preparation of 17-[2-(2-methoxyethoxy)ethyl]-N-(pyridin-3-yl)morphinan-3-amine A dioxane solution of 17-[2-(2-methoxyethoxy)ethyl]morphinan-3-yl trifluoromethanesulfonate (1.8 g, 3.77 mmol), tris(dibenzylideneacetone)dipalladium(0) (0.17 g, 0.19 mmol), dicyclohexyl(2',4',6'-triisopropyl-[1,1'-biphenyl]-2-yl)phosphine (0.22 g, 0.45 mmol), pyridin-3-amine (0.53 g, 5.65 mmol) and cesium carbonate (2.5 g, 7.7 mmol) was heated at 80° C. for 3.5 hours. HPLC indicated that the reaction was complete. After all solvent was removed, a brown solid was obtained. The crude product was dissolved in ethyl acetate and was washed with water three times. All solvent was removed again and the residue was loaded on a 25 g silica gel column and purified by Biotage with dichloromethane/methanol. Pure 17-{2-(2-methoxyethoxy)ethyl}-N-(pyridin-3-yl)morphinan-3-amine (83) was obtained as a light-yellow solid (1.2 g, 76% yield). $^1$H NMR (500 MHz, Chloroform-d) δ 8.32 (d, 1H), 8.10 (dt, 1H), 7.34-7.24 (m, 1H), 7.13 (dd, 1H), 7.07-6.97 (m, 2H), 6.89 (dd, 1H), 5.65 (s, 1H), 3.67-3.52 (m, 6H), 3.41-3.36 (m, 3H), 3.00-2.88 (m, 1H), 2.82 (dt, 1H), 2.68 (ddd, 2H), 2.60-2.54 (m, 1H), 2.31-2.24 (m, 1H), 2.21-2.12 (m, 1H), 1.85 (d, 1H), 1.75 (td, 1H), 1.66 (d, 1H), 1.53 (d, 1H), 1.45-1.26 (m, 5H), 1.20-1.10 (m, 1H). MS (EI) for $C_{26}H_{35}N_3O_2$: 422.2 (MH$^+$).

The free base (1.0 g, 2.37 mmol) was dissolved in methanol and a 2 N hydrochloric acid ether solution (11.9 mL, 23.7 mmol) was added. The resulting mixture was lyophilized to give 17-[2-(2-methoxyethoxy)ethyl]-N-(pyridin-3-yl)morphinan-3-amine hydrochloride salt as a light-yellow solid (1.2 g, 2.26 mmol, 95% yield).

Example 84

Preparation of 1-((4aR,5R,11bR)-14-methyl-2,3,4,4a,5,6-hexahydro-1H-5,11b-(epiminoethano)phenanthro[3,2-d]thiazol-9-yl)guanidine (84)

(84)

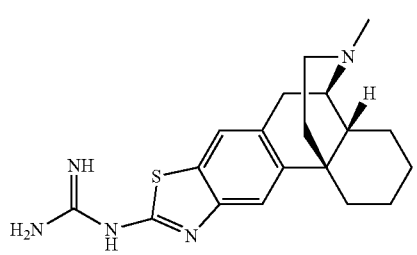

(4aR,5R,11bR)-14-methyl-2,3,4,4a,5,6-hexahydro-1H-5,11b-(epiminoethano)phenanthro[3,2-d]thiazol-9-amine (247.6 mg, 0.632 mmol) and di(1H-imidazol-1-yl)methanimine (204 mg, 1.264 mmol) were dissolved in tetrahydrofuran (3 ml). The solution was irradiated in a microwave at 110° C. for one hour. Ammonia (7 M in methanol) (0.271 ml, 1.896 mmol) was added to the reaction. The mixture was irradiated in a microwave at 110° C. for an additional two hours. The solvent was removed via rotovap. The residue was dissolved in dichloromethane and washed with brine. The organic layer was dried over sodium sulfate, was filtered and was concentrated. After purification by chromatography on silica gel using Biotage, 1-44aR,5R,11bR)-14-methyl-2,3,4,4a,5,6-hexahydro-1H-5,11b-(epiminoethano)phenanthro[3,2-d]thiazol-9-yl)guanidine (84) (42 mg, 0.118 mmol, 18.70% yield) was obtained as a colorless solid. MS (EI) for $C_{19}H_{25}N_5S$: 356.2 (MH+). 1H NMR (500 MHz, Methanol-d4) δ 7.49 (s, 1H), 7.41 (s, 1H), 3.37 (s, 1H), 3.18 (d, J=18.3 Hz, 1H), 2.93-2.79 (m, 2H), 2.57-2.39 (m, 5H), 2.18 (tt, J=12.3, 2.8 Hz, 1H), 1.92-1.72 (m, 2H), 1.74-1.67 (m, 1H), 1.57 (d, J=12.1 Hz, 1H), 1.53-1.29 (m, 6H), 1.21 (qd, J=13.4, 12.9, 4.3 Hz, 1H).

Example 85

Preparation of tert-butyl 4-{[(4aR,5R,11bR)-14-methyl-2,3,4,4a,5,6-hexahydro-1H-5,11b-(epiminoethano)phenanthro[3,2-d][1,3]thiazol-9-yl]carbamoyl}piperidine-1-carboxylate (85)

(85)

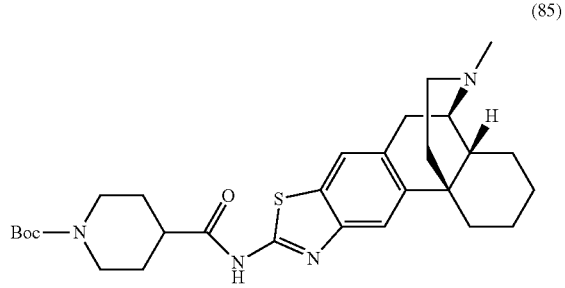 [SMILES: CN1CC[C@]23CCCC[C@H]2[C@H]1Cc1cc2sc(NC(=O)C4CCN(C(=O)OC(C)(C)C)CC4)nc2cc13]

To a dichloromethane solution of (4aR,5R,11bR)-14-methyl-2,3,4,4a,5,6-hexahydro-1H-5,11b-(epiminoethano)phenanthro[3,2-d][1,3]thiazol-9-amine (0.064 g, 0.20 mmol) was added Boc-isonipecotic acid (0.056 g, 0.25 mmol), O-(benzotriazol-1-yl)-N,N,N',N'-tetramethyluronium tetrafluoroborate (0.079 g, 0.25 mmol) and triethylamine (0.062 g, 0.61 mmol), the reaction mixture was stirred at room temperature overnight. Dichloromethane (30 mL) was added to the reaction mixture and the dichloromethane phase was washed with 0.1 N hydrochloric acid solution twice. After removing all solvents, the yellow residue was loaded on a 10 g of silica gel column and purified by Biotage using dichloromethane/methanol as eluent. tert-Butyl 4-{[(4aR,5R,11bR)-14-methyl-2,3,4,4a,5,6-hexahydro-1H-5,11b-(epiminoethano)phenanthro[3,2-d][1,3]thiazol-9-yl]carbamoyl}piperidine-1-carboxylate was obtained as a colorless solid (0.043 g, 45% yield). $^1$H NMR (500 MHz, Chloroform-d) δ 7.51 (s, 2H), 3.51-3.44 (m, 1H), 3.29 (s, 2H), 3.07 (m, 1H), 2.84 (s, 2H), 2.78 (m, 1H), 2.52-2.42 (m, 1H), 2.34 (m, 1H), 2.26-2.16 (m, 2H), 1.97 (d, 3H), 1.78-1.67 (m, 4H), 1.60-1.40 (m, 5H), 1.45 (s, 9H), 1.29-1.17 (m, 2H), 1.09 (m, 1H). MS (EI) for $C_{29}H_{40}N_4O_3S$: 525.2 (MH$^+$).

Example 86

Preparation of 17-(2-methoxyethyl)-N-(pyridin-3-yl)morphinan-3-amine (86), hydrochloride salt

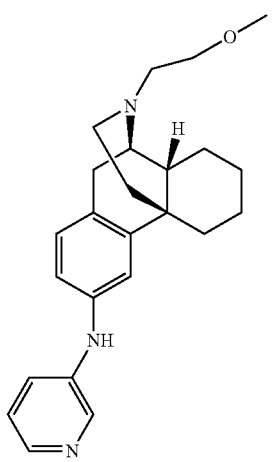

(86)

Step 1: Preparation of 17-methylmorphinan-3-yl trifluoromethanesulfonate

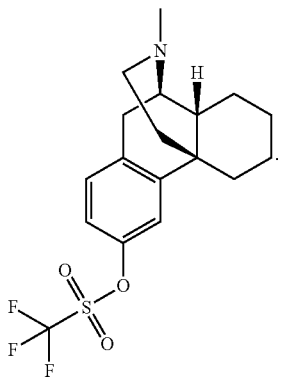 [SMILES: CN1CC[C@]23CCCC[C@H]2[C@H]1Cc1ccc(OS(=O)(=O)C(F)(F)F)cc13]

To a tetrahydrofuran (100 mL) solution of levorphanol tartrate (6.71 g, 15.1 mmol) was added cesium carbonate (16.0 g, 45.4 mmol) and 1,1,1-trifluoro-N-phenyl-N-((trifluoromethyl)sulfonyl)methanesulfonamide (8.1 g, 22.7 mmol). The reaction mixture was heated at 70° C. under nitrogen for twenty hours. Once all organic solvent was removed, dichloromethane (200 mL) and water (100 mL) were added. The dichloromethane phase was washed three times with a saturated potassium carbonate/sodium chloride aqueous solution. The dichloromethane phase was then dried over anhydrous sodium sulfate. After filtration and concentration, a light-yellow liquid was obtained. The crude product was purified by chromatography on silica gel using Biotage with dichloromethane/methanol as eluents and pure 17-methylmorphinan-3-yl trifluoromethanesulfonate was obtained as a light-yellow oil (5.3 g, 89% yield).

Step 2: Preparation of morphinan-3-yl trifluoromethanesulfonate

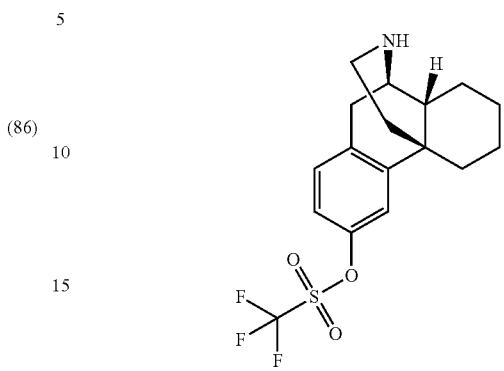

A 1-chloroethyl chloroformate (8.7 mL, 79 mmol) solution of 17-methylmorphinan-3-yl trifluoromethanesulfonate (3.1 g, 7.9 mmol) was heated at 110° C. under nitrogen for 18 hours. After the reaction was cooled to room temperature, all solvent was removed and 50 mL of methanol was added. The reaction mixture was then heated at 50° C. for one hour. Once all solvent was removed, a light-yellow liquid was obtained. The residue was purified by Biotage with dichloromethane/methanol eluents and morphinan-3-yl trifluoromethanesulfonate was obtained as a white solid (2.9 g, 96% yield), MS (EI) for $C_{17}H_{20}F_3NO_3S$: 376.0 (MH$^+$).

Step 3: Preparation of 17-(2-methoxyethyl)morphinan-3-yl trifluoromethanesulfonate

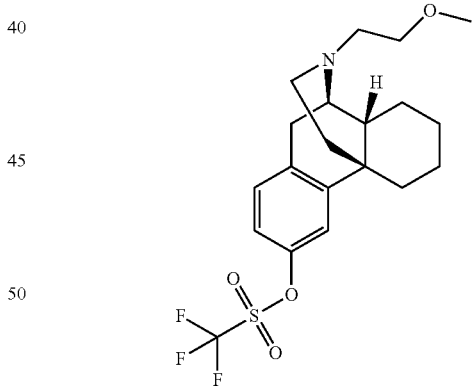

An acetonitrile solution of morphinan-3-yl trifluoromethanesulfonate (0.63 g, 1.68 mmol), 1-bromo-2-methoxyethane (0.37 g, 2.01 mmol) and cesium carbonate (1.09 g, 3.36 mmol) was heated at 65° C. for fifteen hours. After cooling to room temperature, all solvent was removed and the product was extracted with dichloromethane three times. The solvent was evaporated and the residue was purified by chromatography on silica gel using a Biotage instrument using dichloromethane/methanol as eluent. Pure 17-(2-methoxyethyl)morphinan-3-yl trifluoromethanesulfonate was obtained as a light-yellow liquid (0.59 g, 815 yield), MS (EI) for $C_{20}H_{26}F_3NO_4S$: 434.0 (MH$^+$).

Step 4: Preparation of 17-(2-methoxyethyl)-N-(pyridin-3-yl)morphinan-3-amine A dioxane solution of 17-(2-methoxyethyl)morphinan-3-yl trifluoromethanesulfonate (0.083 g, 0.19 mmol), tris(dibenzylideneacetone)dipalladium(0) (0.017 g, 0.019 mmol), dicyclohexyl(2',4',6-triisopropyl-[1,1'-biphenyl]-2-yl)phosphine (0.022 g, 0.046 mmol), pyridin-3-amine (0.027 g, 0.29 mmol) and cesium carbonate (0.25 g, 0.77 mmol) was heated at 80° C. for 3.5 hours. HPLC indicated that the reaction was complete. After all solvent was removed, a brown solid was obtained. The crude product was dissolved in dichloromethane and loaded on a 10 g silica gel column and purified by chromatography on a Biotage instrument with dichloromethane/methanol. Pure 17-(2-methoxyethyl)-N-(pyridin-3-yl)morphinan-3-amine (86) was obtained as a colorless liquid (0.043 g, 60% yield). $^1$H NMR (500 MHz, Chloroform-d) δ 8.32 (d, 1H), 8.11 (dt, 1H), 7.35-7.24 (m, 1H), 7.14 (dd, 1H), 7.08-6.98 (m, 2H), 6.90 (dd, 1H), 5.70 (s, 1H), 3.61-3.51 (m, 2H), 3.36 (s, 3H), 2.98 (d, 1H), 2.85-2.71 (m, 4H), 2.32-2.18 (m, 2H), 2.00-1.80 (m, 2H), 1.70-1.58 (m, 1H), 1.57-1.51 (m, 1H), 1.47-1.22 (m, 5H), 1.14 (m, 1H). MS (EI) for $C_{24}H_{31}N_3O$: 378.2 (MH$^+$).

The free base (0.043 g, 0.11 mmol) was dissolved in methanol and a 2 N hydrochloric acid ether solution (0.57 mL, 1.14 mmol) was added. Thereafter, the mixture was lyophilized to give 17-(2-methoxyethyl)-N-(pyridin-3-yl)morphinan-3-amine hydrochloride salt as a light-yellow solid (0.054 g, 0.11 mmol, 98% yield).

Example 87

Preparation of 17-(oxetan-3-yl)morphinan-3-ol (87)

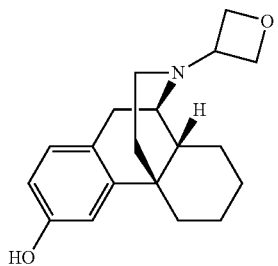

(87)

Step 1: Preparation of morphinan-3-yl trifluoromethanesulfonate

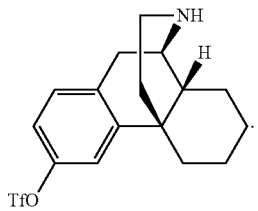 [SMILES: O=S(=O)(Oc1ccc2c(c1)[C@@]13CCCC[C@H]1[C@@H](C2)NCC3)C(F)(F)F]

A version of this same synthesis is described above in Step 3 of Example 86.

Under nitrogen, a 100 mL flask charged with 17-methylmorphinan-3-yl trifluoromethanesulfonate (4.29 g, 11.0 mmol), and N,N-diisopropylethylamine (2.3 mL, 13.2 mmol) in dry 1,2-dichloroethane (10 mL) was cooled to 0° C., whereupon neat 2-chloroethyl chloroformate (6.00 mL, 55.0 mmol) was added dropwise over fifteen minutes. The pale orange solution was stirred at 0° C. for a further five minutes, then warmed to room temperature. The flask was fitted with a reflux condenser, and the mixture was heated to reflux for fifty minutes. The re-cooled mixture was treated with additional N,N-diisopropylethylamine (0.6 mL, 3.4 mmol), and 2-chloroethyl chloroformate (0.6 mL, 5.5 mmol) over two minutes. The solution was warmed to room temperature, and stirred overnight. After an additional twenty hours, the mixture was concentrated to a pale brown oily suspension. The residue was taken up in methanol (40 mL) and water (4 mL), and aged at room temperature (CAUTION—mild exotherm & effervescence within five minutes). After one hour, the mixture was concentrated in vacuo, and the residue was taken up in ethyl acetate (150 mL), was washed with saturated brine/0.6 M pH 7 phosphate buffer (1:1, 2×100 mL), was dried (sodium sulfate), was filtered through celite, and was concentrated to afford a pale brown solid foam. The residue was digested in refluxing ether (100 mL), affording a crystalline solid. The cooled mixture was filtered, and the filter cake was dried under high vacuum to afford morphinan-3-yl trifluoromethanesulfonate as a pale tan solid (3.98 g, 96% over 2 steps). $^1$H NMR (500 MHz, CDCl$_3$) δ 9.83 (s, 1H), 7.31 (d, J=8.5 Hz, 1H), 7.20 (d, J=2.5 Hz, 1H), 7.16 (dd, J=8.5, 2.5 Hz, 1H), 3.79 (ddd, J=5.3, 2.9, 1.0 Hz, 1H), 3.37 (d, J=19.4 Hz, 1H), 3.27 (dd, J=19.4, 6.3 Hz, 1H), 3.22 (ddd, J=12.6, 4.5, 1.6 Hz, 1H), 2.69 (td, J=13.5, 3.6 Hz, 1H), 2.36 (dt, J=13.8, 2.5 Hz, 1H), 2.25 (dt, J=12.8, 3.2 Hz, 1H), 2.10 (td, J=13.8, 4.7 Hz, 1H), 1.68-1.51 (m, 2H), 1.46 (qt, J=13.0, 3.6 Hz, 1H), 1.21 (qt, J=12.9, 3.3 Hz, 1H), 1.02 (qd. J=12.8, 3.8 Hz, 1H); MS (EI) for $C_{17}H_{20}F_3NO_4S$: 376.2 (MH$^+$).

Step 2: Preparation of 17-(oxetan-3-yl)morphinan-3-yl trifluoromethanesulfonate

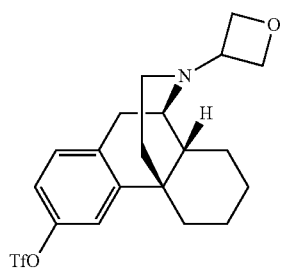 [SMILES: O=S(=O)(Oc1ccc2c(c1)[C@@]13CCCC[C@H]1[C@@H](C2)N(C1COC1)CC3)C(F)(F)F]

A 0.5-2 mL microwave vial was charged with powdered anhydrous potassium carbonate (0.50 mg, 3.6 mmol) and a solution of morphinan-3-yl trifluoromethanesulfonate (135 mg, 0.36 mmol) in dry acetonitrile (1 mL), whereupon neat 3-iodooxetane (0.093 mL, 1.08 mmol) was added in one portion, and the mixture stirred at 125° C. for 34 hours. The mixture was diluted with ether (10 mL), was filtered through celite and was concentrated. Automated flash chromatography on silica (dichloromethane to 1:10:180 ammonium hydroxide:methanol:dichloromethane) afforded 17-(oxetan-3-yl)morphinan-3-yl trifluoromethanesulfonate as a yellow oil (34 mg, 22%). $^1$H NMR (500 MHz, CDCl$_3$) δ 7.17 (d, J=8.5 Hz, 1H), 7.14 (d, J=2.6 Hz, 1H), 7.04 (dd, J=8.5, 2.6

Hz, 1H), 4.66 (d, J=6.7 Hz, 2H), 4.63 (d, J=6.6 Hz, 2H), 3.99 (p, J=6.8 Hz, 1H), 2.82 (d, J=18.5 Hz, 1H), 2.78 (dd, J=5.8, 3.1 Hz, 1H), 2.67 (dd, J=18.4, 5.6 Hz, 1H), 2.39 (ddd, J=11.7, 4.9, 2.0 Hz, 1H), 2.32 (dq, J=14.7, 2.8, 2.0 Hz, 1H), 1.96 (dd, J=12.3, 3.1 Hz, 1H), 1.91 (dt, J=13.5, 3.3 Hz, 1H), 1.79 (td, J=12.6, 4.7 Hz, 1H), 1.72-1.65 (m, 1H), 1.62-1.55 (m, 1H), 1.50-1.30 (m, 4H), 1.21 (qt, J=13.4, 3.5 Hz, 1H), 1.04 (qd, J=12.5, 3.6 Hz, 1H); MS (EI) for $C_{20}H_{24}F_3NO_4S$: 432.0 (M+H).

Step 3

Preparation of 17-(oxetan-3-yl)morphinan-3-ol. A 4 mL vial was charged with a solution of 17-(oxetan-3-yl)morphinan-3-yl trifluoromethanesulfonate (34 mg, 0.08 mmol) in ethanol (1.5 mL), aqueous 1 M potassium hydroxide(1 mL, 1.0 mmol) was added, and the stirred mixture was heated to 50° C. After two hours, the mixture was diluted with saturated ammonium chloride (0.25 mL), and partitioned between dichloromethane (10 mL) and water (10 mL). The aqueous layer was extracted with dichloromethane (2×10 mL), and the combined organic layer was dried (sodium sulfate), was filtered and was concentrated. Automated flash chromatography on silica (1:10:450 to 1:10:90 ammonium hydroxide:methanol:dichloromethane) afforded 17-(oxetan-3-yl)morphinan-3-ol (87) as a solid foam (20 mg; 85%). $^1$H NMR (500 MHz, CDCl$_3$) δ 6.95 (d, J=8.2 Hz, 1H), 6.75 (d, J=2.7 Hz, 1H), 6.63 (dd, J=8.2, 2.6 Hz, 1H), 4.73-4.67 (m, 3H), 4.65 (t, J=6.4 Hz, 1H), 4.04 (p, J=6.9 Hz, 1H), 2.76 (dd, J=5.5, 3.1 Hz, 1H), 2.71 (d, J=18.1 Hz, 1H), 2.63 (dd, J=18.1, 5.6 Hz, 1H), 2.40 (ddd, J=11.6, 4.8, 1.9 Hz, 1H), 2.36-2.28 (m, 1H), 2.06 (td, J=12.2, 3.2 Hz, 1H), 1.86 (dt, J=12.9, 3.2 Hz, 1H), 1.74 (td, J=12.7, 4.7 Hz, 1H), 1.70-1.62 (m, 1H), 1.53 (dt, J=11.0, 3.0 Hz, 1H), 1.46-1.24 (m, 6H), 1.13 (qd, J=12.6, 3.8 Hz, 1H); MS (EI) for $C_{19}H_{25}NO_2$: 300.2 (M+H).

Example 88

Preparation of 17-(oxetan-3-ylmethyl)morphinan-3-ol (88)

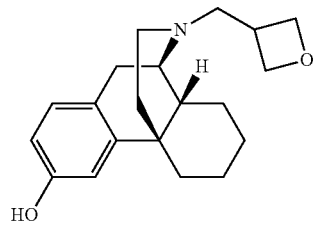

(88)

Step 1: Preparation of 17-(oxetan-3-ylmethyl)morphinan-3-yl trifluoromethanesulfonate

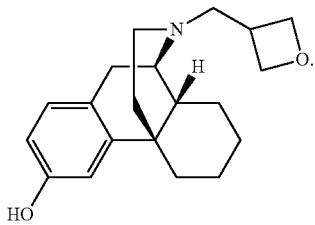 [SMILES: Oc1ccc2c(c1)[C@@]13CCCC[C@H]1[C@@H](C2)N(CC1COC1)CC3]

A 4 mL screw cap vial was charged with powdered anhydrous potassium carbonate (368 mg, 2.66 mmol) and a solution of morphinan-3-yl trifluoromethanesulfonate (100 mg, 0.27 mmol) in dry acetonitrile (1.3 mL), whereupon neat 3-(iodomethyl)oxetane (0.046 mL, 0.45 mmol) was added in one portion, and the stirred mixture was heated to 80° C. in a heat block. After 17 hours, the mixture was diluted with ether (10 mL), was filtered through celite and was concentrated. Automated flash chromatography on silica (dichloromethane to 1:10:90 ammonium hydroxide: methanol:dichloromethane) afforded 17-(oxetan-3-ylmethyl)morphinan-3-yl trifluoromethanesulfonate as a yellow oil (85 mg; 72%). $^1$H NMR (500 MHz, CDCl$_3$) δ 7.20 (d, J=8.5 Hz, 1H), 7.14 (d, J=2.6 Hz, 1H), 7.04 (dd, J=8.5, 2.6 Hz, 1H), 4.82 (ddd, J=12.8, 7.8, 6.0 Hz, 2H), 4.42 (dt, J=20.2, 6.1 Hz, 2H), 3.19 (p, J=7.1 Hz, 1H), 3.03 (d, J=18.4 Hz, 1H), 2.89 (dd, J=12.5, 7.5 Hz, 1H), 2.81 (dd, J=12.6, 7.1 Hz, 1H), 2.78 (t, J=5.9, 3.2 Hz, 1H), 2.69 (dd, J=18.5, 5.8 Hz, 1H), 2.38 (ddd, J=12.1, 4.9, 2.0 Hz, 1H), 2.30 (dq, J=14.4, 2.9, 2.1, 1.1 Hz, 1H), 2.01 (td, J=12.3, 3.2 Hz, 1H), 1.85 (dt, J=13.2, 3.2 Hz, 1H), 1.74 (td, J=12.7, 4.8 Hz, 1H), 1.70-1.64 (m, 1H), 1.58 (dp, J=14.5, 2.9 Hz, 1H), 1.47-1.32 (m, 3H), 1.29 (ddd, J=12.7, 3.2, 1.9 Hz, 1H), 1.21 (qt, J=13.3, 3.5 Hz, 1H), 1.04 (qd, J=12.5, 3.5 Hz, 1H); MS (EI) for $C_2H_{26}F_3NO_4S$: 446.0 (MH+).

Step 2

Preparation of 17-(oxetan-3-ylmethyl)morphinan-3-ol. A 4 mL screw cap vial was charged with a solution 17-(oxetan-3-ylmethyl)morphinan-3-yl trifluoromethanesulfonate (85 mg, 0.19 mmol) in ethanol (1.5 mL), aqueous 1 M potassium hydroxide(1 mL, 1.0 mmol) was added, and the stirred mixture was heated to 50° C. After two hours, the mixture was diluted with saturated ammonium chloride (0.25 mL), and partitioned between dichloromethane (10 mL) and water (10 mL). The aqueous layer was extracted with dichloromethane (2×10 mL), and the combined organic layer was dried (sodium sulfate), was filtered and was concentrated. Automated flash chromatography on silica (1:10:450 to 1:10:90 ammonium hydroxide:methanol:dichloromethane) afforded 17-(oxetan-3-ylmethyl)morphinan-3-ol (88) as a colorless oil (52 mg; 87%). $^1$H NMR (500 MHz, CDCl$_3$) δ 6.97 (d, J=8.1 Hz, 1H), 6.69 (d, J=2.5 Hz, 1H), 6.60 (dd, J=8.2, 2.5 Hz, 1H), 4.86-4.77 (m, 2H), 4.47 (dd, J=7.0, 5.2 Hz, 1H), 4.43 (dd, J=6.9, 5.1 Hz, 1H), 3.26 (hept, J=7.2 Hz, 1H), 2.97 (d, J=17.5 Hz, 1H), 2.94 (dd, J=12.8, 6.3 Hz, 1H), 2.87 (dd, J=12.7, 7.0 Hz, 1H), 2.78 (dd, J=5.7, 3.0 Hz, 1H), 2.65 (dd, J=18.0, 5.7 Hz, 1H), 2.39 (dd, J=12.0, 4.6 Hz, 1H), 2.30-2.24 (m, 1H), 2.15 (td, J=12.2, 3.1 Hz, 1H), 1.82 (dt, J=12.8, 2.9 Hz, 1H), 1.71 (td, J=12.7, 4.6 Hz, 1H), 1.67-1.61 (m, 1H), 1.53-1.46 (m, 1H), 1.43-1.23 (m, 6H), 1.14 (qd, J=12.6, 3.7 Hz, 1H); MS (EI) for $C_2H_{27}NO_2$: 314.2 (MH+).

Example 89

Preparation of (4aR,5R,12bR)-15-methyl-2,3,4,4a,5, 6-hexahydro-1H-5,12b-(epiminoethano)naphtho[2,1-g]quinoline (89), hydrochloride salt

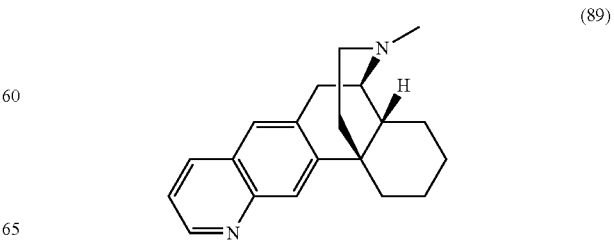

(89)

A 20 mL microwave vial was charged with 17-methylmorphinan-3-amine (160 mg, 0.62 mmol), and methanesulfonic acid (2 mL, 31 mmol), and the mixture was stirred to dissolution, while warming to 70° C. Solid iron (II) sulfate heptahydrate (35 mg, 0.13 mmol), boric acid (38.6 mg, 0.62 mmol) and nitrobenzene (0.038 mL, 0.37 mmol) were added, and the mixture was heated to 120° C., whereupon neat glycerol (0.18 mL, 2.50 mmol) was added dropwise under nitrogen over one hour. Additional glycerol (0.18 mL, 2.50 mmol) was added in four portions over forty minutes. Additional nitrobenzene (0.038 mL, 0.37 mmol) was added after five hours. After 22 hours, the mixture was diluted with 1 M sulfuric acid (30 mL) and ether (100 mL) and was filtered through celite. The resulting cake was washed with an additional 1 M sulfuric acid (30 mL). The aqueous filtrates were washed with additional ether (50 mL), and basified to pH>12 with 4 M sodium hydroxide (40 mL), followed by extraction of the aqueous layer with dichloromethane (100 mL, 25 mL). The combined dichloromethane layers were concentrated, and the residue was taken up in ethyl acetate (75 mL), and extracted with 1 M sodium dihydrogen phosphate (3×25 mL). The combined phosphate extracts were basified to pH>12 with 4 M sodium hydroxide (40 mL), extracted with dichloromethane (2×30 mL), and the organic layer was dried (sodium sulfate), was filtered and was concentrated. Automated flash chromatography on silica (dichloromethane to 1:10:90 NH₄OH:methanol:dichloromethane) afforded (4aR,5R,12bR)-15-methyl-2,3,4,4a,5,6-hexahydro-1H-5,12b-(epiminoethano)naphtho[2,1-g]quinoline (89) as a pale brown oil (86 mg, 47%). $^1$H NMR (500 MHz, CDCl₃) δ 8.83 (dd, J=4.2, 1.7 Hz, 1H), 8.07 (dt, J=8.2, 1.6, 0.8 Hz, 1H), 8.06 (d, J=1.2 Hz, 1H), 7.59 (t, J=1.3 Hz, 1H), 7.34 (dd, J=8.2, 4.2 Hz, 1H), 3.33 (d, J=18.1 Hz, 1H), 2.96 (dd, J=6.0, 3.1 Hz, 1H), 2.91 (ddt, J=18.5, 6.0, 1.1 Hz, 1H), 2.66 (dq, J=12.9, 3.3, 2.8, 1.2 Hz, 1H), 2.49 (ddd, J=12.2, 5.2, 2.4 Hz, 1H), 2.47 (s, 3H), 2.10 (td, J=12.5, 3.2 Hz, 1H), 1.98 (dtd, J=12.7, 2.8, 0.9 Hz, 1H), 1.90 (td, J=12.8, 4.8 Hz, 1H), 1.71-1.61 (m, 1H), 1.63-1.55 (m, 1H), 1.55-1.32 (m, 5H), 1.14 (qd, J=12.6, 3.9 Hz, 1H); $^{13}$C NMR (126 MHz, CDCl₃) δ 149.42, 147.45, 144.24, 137.02, 134.75, 126.30, 125.63, 125.04, 120.51, 57.73, 47.10, 45.09, 42.91, 42.69, 37.72, 36.68, 29.57, 26.98, 26.47, 23.97, 21.96; LCMS for C₂₀H₂₄N₂: 293.2 (M⁺H⁺). A portion (10 mg) was converted to the hydrochloride salt by dissolution in 10% acetonitrile/water (1 mL) and addition of 2 M hydrochloric acid (0.05 mL), followed by lyophilization to afford a light brown solid.

Example 90

Preparation of (6R,6aR,11aS)-9-amino-14-methyl-6,6a,7,11-tetrahydro-5H-6,11a-(epiminoethano)phenanthro[3,2-d]thiazol-2-ol (90), hydrochloride salt

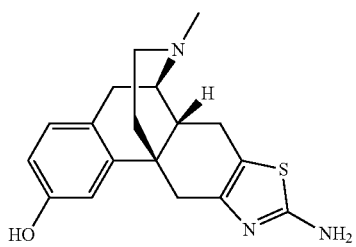

(90)

This compound was synthesized following the procedure described in Zhang et al. (2007) *J. Med. Chem.* 50(11):2747-2751.

Example 91

Preparation of 17-(oxetan-2-ylmethyl)morphinan-3-ol (91)

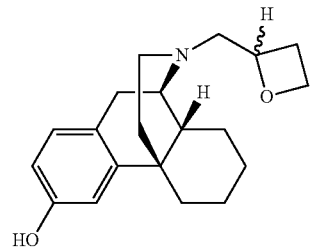

(91)

Step 1: Preparation of 17-(oxetan-2-ylmethyl)morphinan-3-yl trifluoromethanesulfonate

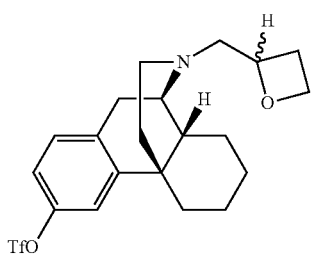

A 4 mL screw cap vial was charged with powdered anhydrous potassium carbonate (0.50 g, 3.6 mmol) and a solution of morphinan-3-yl trifluoromethanesulfonate (135 mg, 0.36 mmol) in dry acetonitrile (1 mL), whereupon neat 2-(bromomethyl)oxetane (0.069 mL, 0.72 mmol) was added in one portion, and the stirred mixture was heated to 80° C. in a heat block. After 21 hours, the mixture was diluted with ether (10 mL), was filtered through celite and was concentrated. Automated flash chromatography on silica (dichloromethane to 1:10:90 ammonium hydroxide:methanol:dichloromethane) afforded 17-(oxetan-2-ylmethyl)morphinan-3-yl trifluoromethanesulfonate as a pale yellow oil (91 mg; 57%), in a 4:1 mixture of diastereomers by $^1$H NMR. The sample was carried forward to the next step without further purification. Data for major isomer: $^1$H NMR (500 MHz, CDCl₃) δ 7.20 (d, J=8.4 Hz, 1H), 7.13 (d, J=2.6 Hz, 1H), 7.03 (dd, J=8.5, 2.6 Hz, 1H), 5.03 (qd, J=7.5, 3.4 Hz, 1H), 4.68 (td, J=8.0, 5.8 Hz, 1H), 4.54 (dt, J=9.2, 5.7 Hz, 1H), 3.08 (d, J=18.7 Hz, 1H), 3.01 (dd, J=13.5, 7.6 Hz, 1H), 2.93 (dd, J=5.8, 3.1 Hz, 1H), 2.72-2.65 (m, 2H), 2.62 (dd, J=13.6, 3.3 Hz, 1H), 2.52 (ddd, J=12.1, 4.9, 1.9 Hz, 1H), 148-234 (m, 1H), 2.29 (dq, J=14.3, 2.3, 1.9 Hz, 1H), 2.16-2.11 (m, 0H), 2.08 (td, J=12.4, 3.3 Hz, 1H), 1.91 (dt, J=13.0, 3.2 Hz, 1H), 1.80 (td, J=12.7, 4.7 Hz, 1H), 1.70-1.61 (m, 1H), 1.61-1.51 (m, 1H), 1.48-1.31 (m, 3H), 1.28 (ddd, J=12.7, 3.2, 2.0 Hz, 1H), 1.20 (qt, J=13.3, 3.4 Hz, 1H), 1.02 (qd, J=12.6, 3.8 Hz, 1H); MS (EI) for $C_{21}H_{26}F_3NO_4S$: 446.0 (MH+).

Step 2: Preparation of 17-(oxetan-2-ylmethyl)morphinan-3-ol

A 4 mL screw cap vial was charged with a solution of 17-(oxetan-2-ylmethyl)morphinan-3-yl trifluoromethanesulfonate (91 mg, 0.20 mmol) in ethanol (1.5 mL), aqueous 1 M potassium hydroxide (1 mL, 1.0 mmol) was added, and the stirred mixture was heated to 50° C. After 1.7 hours, the mixture was diluted with saturated ammonium chloride (0.25 mL), and was partitioned between dichloromethane (10 mL) and water (10 mL). The aqueous layer was extracted with dichloromethane (2×10 mL), and the combined organic layer was dried (sodium sulfate), was filtered and was concentrated. Automated flash chromatography on silica (1:10:450 to 1:10:90 ammonium hydroxide:methanol:dichloromethane) afforded 17-(oxetan-2-ylmethyl)morphinan-3-ol as a colorless glass (63 mg; 98%) as a 4.8:1 ratio of epimers by $^1$H NMR (CDCl$_3$). Automated flash chromatography on silica (1-10% methanol/dichloromethane) afforded first fractions enriched in the minor epimer (ratio 1:3 [minor:major]; 7.9 mg), a middle fraction (ratio 1:6.7 [minor:major]; 36.1 mg) and a fraction enriched in the major epimer (ratio 10:1 [major:minor]; 16.1 mg), by $^1$H NMR (CDCl$_3$). Data for major epimer: $^1$H NMR (500 MHz, CDCl$_3$) δ 6.99 (d, J=8.3 Hz, 1H), 6.73 (d, J=2.5 Hz, 1H), 6.63 (dd, J=8.2, 2.5 Hz, 1H), 5.09 (qd, J=7.5, 3.1 Hz, 1H), 4.73-4.63 (m, 1H), 4.55 (dt, J=8.5, 5.7 Hz, 1H), 3.07 (dd, J=13.5, 7.5 Hz, 1H), 3.02 (d, J=18.2 Hz, 1H), 2.94 (dd, J=5.6, 3.0 Hz, 1H), 2.73-2.61 (m, 3H), 2.52 (dt, J=11.9, 4.6, 2.0 Hz, 1H), 2.42 (tt, J=10.7, 8.0 Hz, 1H), 2.32-2.26 (m, 1H), 2.20 (td, J=12.3, 3.1 Hz, 1H), 1.87 (dt, J=12.7, 3.1 Hz, 1H), 1.75 (td, J=12.7, 4.7 Hz, 1H), 1.68-1.57 (m, 1H), 1.53-1.44 (m, 1H), 1.44-1.37 (m, 1H), 1.37-1.23 (m, 5H), 1.11 (qd, J=12.4, 11.8, 3.9 Hz, 1H); MS (EI) for $C_{20}H_{27}NO_2$: 314.2 (MH+).

Example 92

1-(2-methoxyethyl)-3-((4aR,5R,11bR)-14-methyl-2,3,4,4a,5,6-hexahydro-1H-5,11b-(epiminoethano)phenanthro[3,2-d]thiazol-9-yl)guanidine (92)

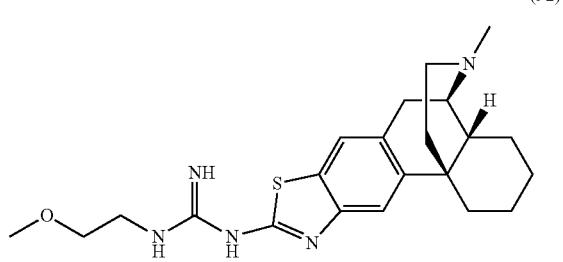

(92)

A solution of (4aR,5R,11bR)-14-methyl-2,3,4,4a,5,6-hexahydro-1H-5,11b-(epiminoethano)phenanthro[3,2-d]thiazol-9-amine (525.4 mg, 1.425 mmol) and di(1H-imidazol-1-yl)methanimine (459 mg, 2.85 mmol) in tetrahydrofuran (5 ml) was irradiated in a microwave at 110° C. for one hour. LCMS showed formation of desired product. The solvent was removed via rotovap. The residue was dissolved in dichloromethane (50 mL) and washed with brine (50 mL). The organic layer was dried over sodium sulfate, was filtered, was concentrated and purified by chromatography on silica gel using a Biotage instrument to give N-((4aR,5R,11bR)-14-methyl-2,3,4,4a,5,6-hexahydro-1H-5,11b-(epiminoethano)phenanthro[3,2-d]thiazol-9-yl)-1H-imidazole-1-carboximidamide (132 mg, 0.325 mmol, 22.79% yield) as a colorless solid. MS (EI) for $C_{22}H_{26}N_6S$: 407.2 (MH+).

To a solution of N-((4aR,5R,11bR)-14-methyl-2,3,4,4a,5,6-hexahydro-1H-5,11b-(epiminoethano)phenanthro[3,2-d]thiazol-9-yl)-1H-imidazole-1-carboximidamide (132 mg, 0.325 mmol) in tetrahydrofuran (2 ml) was added 2-methoxyethanamine (0.042 ml, 0.487 mmol). The mixture was irradiated in a microwave at 110° C. for two hours. The solvent was removed and the residue was purified by chromatography using a Biotage instrument using a KP-NH column to obtain 1-(2-methoxyethyl)-3-((4aR,5R,11bR)-14-methyl-2,3,4,4a,5,6-hexahydro-1H-5,11b-(epiminoethano)phenanthro[3,2-d]thiazol-9-yl)guanidine (92) (44.5 mg, 0.108 mmol, 33.1% yield) as a colorless solid. MS (EI) for $C_{22}H_{31}N_5OS$: 414.2 (MH+). 1H NMR (500 MHz, Methanol-d4) δ 7.46 (s, 1H), 7.40-7.26 (m, 1H), 3.58 (t, J=5.2 Hz, 2H), 3.52-3.40 (m, 6H), 3.38 (s, 2H), 3.15 (d, J=18.4 Hz, 1H), 2.90-2.75 (m, 3H), 2.54-2.35 (m, 5H), 2.18-2.09 (m, 1H), 1.86 (dt, J=13.0, 3.3 Hz, 1H), 1.76 (td, J=12.8, 4.7 Hz, 1H), 1.68 (d, J=12.0 Hz, 1H), 1.59-1.52 (m, 1H), 1.49-1.28 (m, 5H), 1.25-1.13 (m, 1H).

Example 93

Preparation of 17-(2-methoxyethyl)-N-(pyridin-4-yl)morphinan-3-amine (93), hydrochloride salt

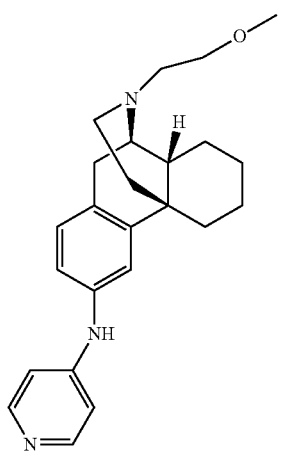

(93)

A dioxane solution of 17-(2-methoxyethyl)morphinan-3-yl trifluoromethanesulfonate (0.10 g, 0.19 mmol), tris(dibenzylideneacetone)dipalladium(0) (0.032 g, 0.035 mmol), dicyclohexyl(2',4',6'-triisopropyl-[1,1'-biphenyl]-2-yl)phosphine (0,040 g, 0.083 mmol), pyridin-4-amine (0.043 g, 0.46 mmol) and cesium carbonate (0.38 g, 1.15 mmol) was heated at 90° C. for sixteen hours. After all solvent was removed, a brown solid was obtained. The crude product was dissolved in ethyl acetate and was washed with water three times. All solvent was removed and the residue was loaded on a 10 g silica gel column and purified by chromatography on a Biotage instrument with dichloromethane/ methanol. Pure 17-(2-methoxyethyl)-N-(pyridin-4-yl)morphinan-3-amine (93) was obtained as a colorless liquid (0.043 g, 49% yield). $^1$H NMR (500 MHz, Chloroform-d) δ 8.28-8.23 (m, 2H), 7.13-7.05 (m, 2H), 6.96 (dd, 1H), 6.76-6.71 (m, 2H), 5.96 (s, 1H), 3.53 (dtd, 2H), 3.36 (s, 3H), 3.03-2.93 (d, 1H), 2.81 (dt, 1H), 2.69 (dt, 2H), 2.61 (d, 1H), 2.34-2.25 (m, 1H), 2.13 (t, 1H), 1.92 (d, 1H), 1.81 (dd, 1H), 1.70-1.61 (m, 1H), 1.58-1.51 (m, 1H), 1.47-1.20 (m, 5H), 1.13 (qd, 1H). MS (EI) for $C_{24}H_{31}N_3O$: 378.2 (MH$^+$).

The free base (0.041 g, Oil mmol) was dissolved in methanol and a 2 N hydrochloric acid ether solution (0.54 mL, 1.09 mmol) was added. The mixture was then lyophilized to give 17-(2-methoxyethyl)-N-(pyridin-4-yl)morphinan-3-amine hydrochloride salt as a colorless solid (0.045 g, 0.11 mmol, 85% yield).

Example 94

Preparation of (4aR,5R,12bR)-15-methyl-2,3,4,4a,5,6-hexahydro-1H-5,12b-(epiminoethano)naphtho[1,2-g]quinoxalin-10-amine (94), hydrochloride salt

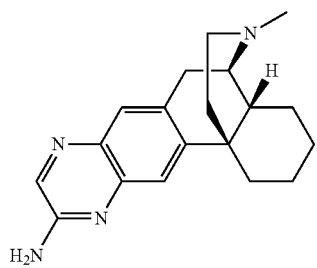

(94)

Step 1: Preparation of 2-chloro-N-(17-methyl-2-nitromorphinan-3-yl)acetamide

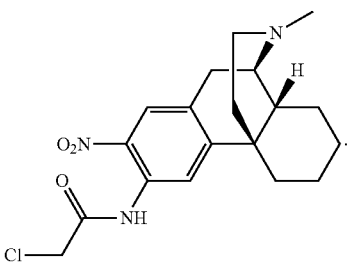 [SMILES: CN1CC[C@]23CCCC[C@H]2[C@H]1Cc1cc([N+](=O)[O-])c(NC(=O)CCl)cc13]

Under nitrogen, a solution of 17-methyl-2-nitromorphinan-3-amine (120 mg, 0.04 mmol) and pyridine (0.097 mL, 1.2 mmol) in dry dichloromethane (4 mL) was cooled to 0° C., whereupon a solution of chloroacetyl chloride (0.038 mL, 0.48 mmol) in dry dichloromethane (1 mL) was added dropwise over ten minutes. Additional chloroacetyl chloride (0.04 mL, 0.48 mmol) in dry dichloromethane (1 mL) was added dropwise. The reaction was quenched after two hours with 1 M sodium dihydrogen phosphate (5 mL), and the organic layer was washed sequentially with 1 M sodium dihydrogen phosphate (2×7 mL) and 1 M sodium bicarbonate (7 mL), was dried (sodium sulfate), was filtered and was concentrated to afford crude 2-chloro-N-(17-methyl-2-nitromorphinan-3-yl)acetamide as a brown oil (129 mg), which was carried forward to the next step without further purification. $^1$H NMR (500 MHz, CDCl$_3$) δ 8.74 (s, 1H), 8.05 (s, 1H), 4.25 (s, 2H), 3.13 (d, J=18.7 Hz, 1H), 2.97 (d, J=5.4 Hz, 1H), 2.80-2.71 (m, 1H), 2.61-2.55 (m, 1H), 2.47 (s, 3H), 2.52-2.43 (m, 1H), 2.07 (td, J=11.7, 3.0 Hz, 1H), 2.01 (d, J=12.7 Hz, 1H), 1.92 (td, J=12.9, 4.6 Hz, 1H), 1.72-1.59 (m, 1H), 1.55-1.35 (m, 4H), 1.24 (ddt, J=16.8, 13.4, 6.6 Hz, 1H), 1.03 (qd, J=12.9, 3.8 Hz, 1H); LCMS for $C_{19}H_{24}ClN_3O_3$: 378.0 (MH$^+$).

Step 2: Preparation of N-(2-amino-17-methylmorphinan-3-yl)-2-chloroacetamide

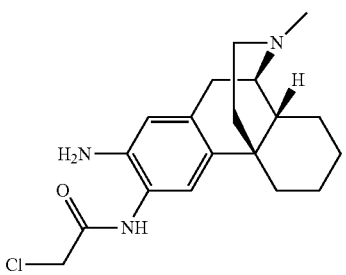

A clear solution of 2-chloro-N-(17-methyl-2-nitromorphinan-3-yl)acetamide (87 mg, 0.23 mmol) and ammonium chloride (184 mg, 3.44 mmol) in ethanol (10 mL) and water (2 mL), was treated with iron powder (0.26 g, 4.6 mmol, 325 mesh) in one portion, and the mixture was stirred at room temperature. After 19 hours, the mixture was diluted with 1 M sodium hydroxide (12 mL), water (25 mL) and chloroform (75 mL), and then was filtered through celite. The aqueous layer was extracted with chloroform (2×25 mL), and the combined chloroform extract was washed with brine (50 mL, basified to pH>12 with 4 M sodium hydroxide), was dried (sodium sulfate), was filtered and was concentrated to afford crude N-(2-amino-17-methylmorphinan-3-yl)-2-chloroacetamide as a yellow glass (51 mg). The product was carried forward to the next step without further purification. MS (EI) for $C_{19}H_{26}ClN_3O$: 348.2 (MI$^+$).

Step 3: Preparation of (4aR,5R,12bR)-15-methyl-2,3,4,4a,5,6-hexahydro-1H-5,12b-(epiminoethano)naphtho[1,2-g]quinoxalin-10-ol

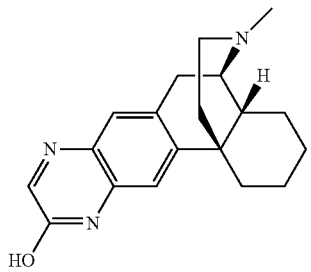

A 2-5 mL microwave vial was charged with sodium bicarbonate (171 mg, 2.04 mmol) to which was added a solution of N-(2-amino-17-methylmorphinan-3-yl)-2-chloroacetamide (47 mg, 0.14 mmol) in dry DMSO (2.5 mL). The mixture was heated to 180° C. for fifteen minutes in a microwave. The reaction mixture was diluted with 10 mM ammonium hydroxide in water (8 mL). Purification by RPLC (Biotage C18 SNAP 12 g cartridge, 0-25% acetonitrile in 10 mM ammonium hydroxide/water) afforded (4aR,5R,12bR)-15-methyl-2,3,4,4a,5,6-hexahydro-1H-5,12b-(epiminoethano)naphtho[1,2-g]quinoxalin-10-ol as a light yellow film (8 mg, 12% over 2 steps). $^1$H NMR (500 MHz, CDCl$_3$) δ 8.32 (s, 1H), 7.64 (s, 1H), 7.22 (s, 1H), 5.60 (br s, 1H), 3.21 (d, J=18.3 Hz, 1H), 2.92 (t, J=4.4 Hz, 1H), 2.80 (dd, J=18.8, 5.9 Hz, 1H), 2.55-2.42 (m, 2H), 2.44 (s, 3H), 2.11-2.01 (m, 1H), 1.92 (d, J=12.6 Hz, 1H), 1.85 (td, J=12.6, 4.5 Hz, 1H), 1.71-1.64 (m, 1H), 1.63-1.56 (m, 1H), 1.54-1.35 (m, 4H), 1.31-1.19 (m, 1H), 1.12 (tt, J=14.4, 7.3 Hz, 1H); MS (EI) for C$_{19}$H$_{23}$N$_3$O: 310.2 (M$^+$H$^+$).

Step 4: Preparation of (4aR,5R,12bR)-10-chloro-15-methyl-2,3,4,4a,5,6-hexahydro-1H-5,12b-(epiminoethano)naphtho[1,2-g]quinoxaline

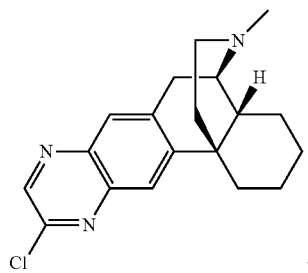

A 10 mL flask was charged with (4aR,5R,12bR)-15-methyl-2,3,4,4a,5,6-hexahydro-1H-5,12b-(epiminoethano)naphtho[1,2-g]quinoxalin-10-ol (11 mg, 0.036 mmol) and phosphoryl trichloride (2 mL), and the yellow mixture placed in an oil bath heated at 105° C. The mixture was removed from the heat after 2.7 hours, and concentrated to afford a brown film. The residue was taken up in dichloromethane (5 mL), and was stirred with 1 M sodium bicarbonate (5 mL) for one hour, followed by the aqueous layer being extracted with additional dichloromethane (5 mL). The combined organic layer was dried (sodium sulfate), was filtered and was concentrated to afford (4aR,5R,12bR)-10-chloro-15-methyl-2,3,4,4a,5,6-hexahydro-1H-5,12b-(epiminoethano)naphtho[1,2-g]quinoxaline as a light brown film (10.6 mg, 91%), which was carried forward to the next step without further purification. $^1$H NMR (500 MHz, CDCl$_3$) δ 8.72 (s, 1H), 7.97 (s, 1H), 7.89 (s, 1H), 3.39 (d, J=18.0 Hz, 1H), 3.03-2.93 (m, 2H), 2.59 (dt, J=14.1, 3.0 Hz, 1H), 2.54 (ddd, J=12.3, 4.1, 1.2 Hz, 1H), 2.49 (s, 3H), 2.08 (td, J=12.9, 3.4 Hz, 1H), 2.03 (dt, J=13.2, 3.0 Hz, 1H), 1.95 (td, J=12.8, 4.7 Hz, 1H), 1.68 (dt, J=13.2, 3.7 Hz, 1H), 1.61 (ddd, J=14.0, 4.1, 3.4 Hz, 1H), 1.57-1.37 (m, 4H), 1.31 (tt, J=13.3, 3.5 Hz, 1H), 1.09 (qd, J=12.8; 3.8 Hz, 1H); MS (EI) for C$_{19}$H$_{22}$N$_3$Cl: 328.0 (M$^+$H$^+$).

Step 5: Preparation of (4aR,5R,12bR)-15-methyl-2,3,4,4a,5,6-hexahydro-1H-5,12b-(epiminoethano)naphtho[1,2-g]quinoxalin-10-amine A 2-5 mL microwave vial was charged with copper (I) iodide (15 mg, 0.08 mmol), a solution of (4aR,5R,12bR)-10-chloro-15-methyl-2,3,4,4a,5,6-hexahydro-1H-5,12b-(epiminoethano)naphtho[1,2-g]quinoxaline (10.6 mg, 0.032 mmol) in ethanol (0.45 mL), and 33% ammonium hydroxide (3 mL, 77 mmol). The resultant mixture was heated at 140° C. for fifteen minutes. Dioxane (0.45 mL) and additional copper (I) iodide (15 mg, 0.08 mmol) were added, and the mixture again heated at 140° C. for one hour. The mixture was partitioned between dichloromethane (10 mL) and water (5 mL), and the aqueous phase was extracted with dichloromethane (2×5 mL). The combined dichloromethane layer was dried (sodium sulfate), was filtered and was concentrated. Automated flash chromatography on silica (1:10:450 to 1:10:50 ammonium hydroxide:methanol:dichloromethane) afforded the partially purified aniline as a pale yellow solid (1.6 mg). The residue was taken up in ethyl acetate (5 mL) and was sequentially extracted with 0.5 M disodium hydrogen phosphate (2 mL), and 0.6 M pH 6 phosphate buffer (2×2 mL). The combined pH 6 aqueous extract was basified to pH>12 with 4 M sodium hydroxide, and then was extracted with dichloromethane (2×5 mL). The combined dichloromethane layer was dried (sodium sulfate), was filtered and was concentrated to afford (4aR,5R,12bR)-15-methyl-2,3,4,4a,5,6-hexahydro-1H-5,12b-(epiminoethano)naphtho[1,2-g]quinoxalin-10-amine (94) as a colorless solid (0.8 mg; 8%). $^1$H NMR (500 MHz, CDCl$_3$) δ 8.29 (s, 1H), 7.68 (s, 1H); 7.60 (s, 1H), 3.30 (d, J=18.0 Hz, 1H), 2.92 (dd, J=6.1, 3.1 Hz, 1H), 2.86 (ddd, J=18.3, 7.0, 1.8 Hz, 1H), 2.58 (dt, J=13.9, 3.4 Hz, 1H), 2.48 (ddd, J=12.0, 5.0, 1.7 Hz, 1H), 2.49 (s, 3H), 2.11 (td, J=12.4, 3.2 Hz, 1H), 1.99-1.91 (m, 1H), 1.87 (td, J=12.7, 4.9 Hz, 1H), 1.75-1.27 (m, 8H), 1.16 (qd, J=12.5, 3.6 Hz, 1H); MS (EI) for C$_{19}$H$_{24}$N$_4$: 309.2 (M$^+$H$^+$). The sample was dissolved in 0.5 M hydrochloric acid (0.5 mL), and was concentrated to afford the HCl salt.

Example 95

Preparation of (4aR,5R,12bR)-15-methyl-2,3,4,4a,5,6-hexahydro-1H-5,12b-(epiminoethano)phenanthro[3,2-e][1,2,4]triazin-10-amine (95), hydrochloride salt

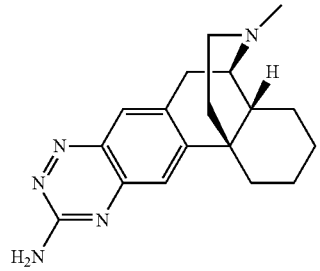

Step 1: Preparation of (4aR,5R,12bR)-15-methyl-2,3,4,4a,5,6-hexahydro-1H-5,12b-(epiminoethano)phenanthro[3,2-e][1,2,4]triazin-10-amine-8-oxide

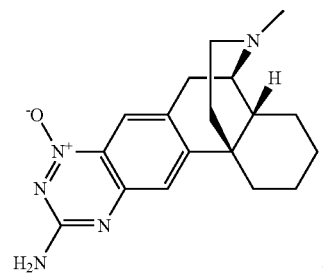

A 0.5-2 mL microwave vial was charged with 17-methyl-2-nitromorphinan-3-amine (120 mg, 0.40 mmol), cyanamide (125 mg, 3.0 mmol) and concentrated hydrochloric acid (1.2 mL, 15 mmol), and the resultant yellow solution was heated at 110° C. in a microwave for 1.5 hours. Additional cyanamide (250 mg, 6.0 mmol) was added, and the resultant orange-red solution was heated in a microwave at 150° C. for thirty minutes. The orange suspension was brought to pH>12 with 50% aqueous sodium hydroxide (0.85 mL, 16 mmol), and was transferred to a 2-5 mL microwave vial. Water (2.5 mL) was added and the orange suspension was heated at 110° C. in a microwave for one hour. The mixture was diluted with water (5 mL), and was extracted with dichloromethane (3×15 mL). The combined dichloromethane layers were dried (sodium sulfate), filtered and concentrated to afford crude (4aR,5R,12bR)-15-methyl-2,3,4,4a,5,6-hexahydro-1H-5,12b-(epiminoethano)phenanthro[3,2-e][1,2,4]triazin-10-amine 8-oxide as an orange oil (119 mg). The material was carried forward to the next step without further purification. MS (EI) for $C_{18}H_{23}N_5O$: 326.2 (MH$^+$).

Step 2: Preparation of (4aR,5R,12bR)-15-methyl-2,3,4,4a,5,6-hexahydro-1H-5,12b-(epiminoethano)phenanthro[3,2-e][1,2,4]triazin-10-amine A 25 mL flask was charged with impure (4aR,5R,12bR)-15-methyl-2,3,4,4a,5,6-hexahydro-1H-5,12b-(epiminoethano)phenanthro[3,2-e][1,2,4]triazin-10-amine 8-oxide (130 mg, assumed 0.40 mmol) and methanol (10 mL). Isopropanol (3 mL) and Raney nickel (0.15 mL, 0.4 mmol; ca. 50 wt % slurry in water) were added, and the mixture was hydrogenated at room temperature for one hour. The mixture was filtered through celite, and was concentrated. Automated flash chromatography on silica (1:10:450 to 1:10:90 ammonium hydroxide:methanol:dichloromethane) afforded 4aR,5R,12bR)-15-methyl-2,3,4,4a,5,6-hexahydro-1H-5,12b-(epiminoethano)phenanthro[3,2-e][1,2,4]triazin-10-amine (95) as a yellow-orange solid (28 mg, 23% over 3 steps). $^1$H NMR (500 MHz, CDCl$_3$) δ 8.02 (d, J=1.4 Hz, 1H), 7.54 (s, 1H), 5.85 (s. 2H), 3.33 (d, J=18.5 Hz, 1H), 2.93 (dd, J=6.0, 3.1 Hz, 1H), 2.91-2.83 (m, 1H), 2.52 (dt, J=16.6, 2.4 Hz, 1H), 2.48 (ddd, J=12.4, 4.5, 1.7 Hz, 1H), 2.45 (s, 3H), 2.08 (td, J=12.6, 3.1 Hz, 1H), 1.95 (dt, J=12.6, 3.2 Hz, 1H), 1.89 (td, J=12.8, 4.9 Hz, 1H), 1.71-1.63 (m, 1H), 1.57 (dt, J=13.1, 3.5 Hz, 1H), 1.54-1.49 (m, 1H), 1.49-1.33 (m, 3H), 1.27 (dtt, J=16.7, 10.4, 3.4 Hz, 1H), 1.08 (qd. J=12.8, 3.8 Hz, 1H); $^{13}$C NMR (126 MHz, CDCl$_3$) δ 159.47, 152.87, 142.20, 140.87, 137.03, 126.57, 122.21, 57.44, 47.06, 45.07, 43.02, 42.81, 38.71, 36.90, 27.25, 26.43, 23.93, 22.11; MS (EI) for $C_{18}H_{23}N_5$: 310.2 (MH$^+$). The sample was converted to the HCl salt by dissolution in methanol (2 mL) followed by the addition of 2 M hydrochloric acid (0.1 mL), which was concentrated and lyophilized from water (1.5 mL) to afford an orange solid.

Example 96

(4bR,8aR,9R)-11-(2-(2-methoxyethoxy)ethyl)-6,7,8,8a,9,10-hexahydro-5H-9,4b-(epiminoethano)phenanthren-3-amine (96)

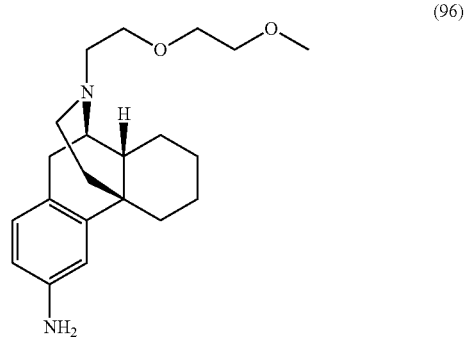 [SMILES: COCCOCCN1CC[C@]23CCCC[C@H]2[C@H]1Cc1ccc(N)cc13]

(96)

To a flask were added diacetoxypalladium (0.018 g, 0.080 mmol), 2,2'-bis(diphenylphosphino)-1,1'-binaphthalene (0.050 g, 0.080 mmol), cesium carbonate (0.674 g, 2.069 mmol), and tetrahydrofuran (30 ml). (4bR,8aR,9R)-11-(2-(2-Methoxyethoxy)ethyl)-6,7,8,8a,9,10-hexahydro-5H-9,4b-(epiminoethano)phenanthren-3-yl trifluoromethanesulfonate (0.76 g, 1.591 mmol) was dissolved in 1 mL of THF and added to the above mixture, followed by the addition of diphenylmethanimine (0.375 g, 2.069 mmol). The reaction was stirred at 70° C. for 17 hours. The solvent was removed via rotovap. The residue was dissolved in dichloromethane (100 mL) and was washed with brine. The organic layer was dried over sodium sulfate, was filtered and was concentrated. The crude (4bR,8aR,9R)—N-(diphenylmethylene)-11-(2-(2-methoxyethoxy)ethyl)-6,7,8,8a,9,10-hexahydro-5H-9,4b-(epiminoethano)phenanthren-3-amine was used directly in the next step.

(4bR,8aR,9R)—N-(Diphenylmethylene)-11-(2-(2-methoxyethoxy)ethyl)-6,7,8,8a,9,10-hexahydro-5H-9,4b-(epiminoethano)phenanthren-3-amine (809 mg, 1.590 mmol) was dissolved in methanol (15 mL). To the solution were added sodium acetate (261 mg, 3.18 mmol) and hydroxylamine hydrochloride (166 mg, 2.386 mmol) followed by water (0.5 mL). The mixture was stirred at room temperature for two hours. The solvent was removed via rotovap. The residue was dissolved in dichloromethane (100 mL), and then was washed with brine. The organic layer was dried over sodium sulfate, was filtered and was concentrated. The crude product was purified by chromatography using a Biotage KP-NH column. (4bR,8aR,9R)-11-(2-(2-methoxyethoxy)ethyl)-6,7,8,8a,9,10-hexahydro-5H-9,4b-(epiminoethano)phenanthren-3-amine (96) (229.1 mg, 0.665 mmol, 41.8% yield) was obtained as a yellow oil (41.8% in two steps). MS (EI) for $C_{21}H_{32}N_2O_2$: 345.2 (MH$^+$). 1H NMR (500 MHz, Methanol-d4) δ 6.90 (d, J=8.1 Hz, 1H), 6.74 (d, J=2.3 Hz, 1H), 6.59 (dd, J=8.1, 2.2 Hz, 1H), 3.68-3.53 (m, 6H), 3.38 (s, 3H), 3.00-2.92 (m, 2H), 2.83 (dt, J=12.4, 6.0 Hz, 1H), 2.76-2.54 (m, 3H), 2.41 (dd, J=10.8, 3.4 Hz, 1H), 2.19 (td, J=12.4, 3.3 Hz, 1H), 1.83 (dt, J=12.8, 3.2 Hz, 1H), 1.78-1.64 (m, 2H), 1.53 (q, J=3.7, 3.2 Hz, 1H), 1.48-1.27 (m, 5H), 1.19 (qd, J=13.3, 4.3 Hz, 1H).

Example 97

Preparation of (4aR,5R,11bR)-14-(2-(2-methoxyethoxy)ethyl)-2,3,4,4a,5,6-hexahydro-1H-5,10-(epiminoethano)phenanthro[3,2-d]thiazol-9-amine (97)

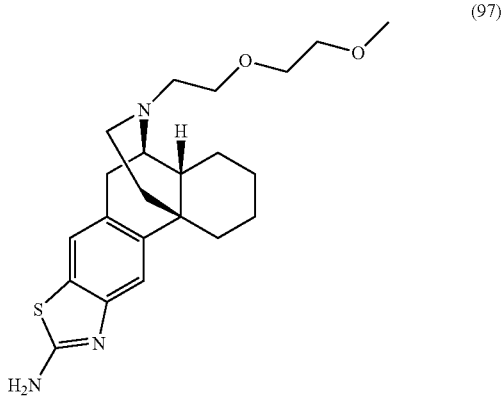 [SMILES: COCCOCCN1CC[C@]23CCCC[C@H]2[C@H]1Cc1cc2sc(N)nc2cc13]

(4bR,8aR,9R)-11-(2-(2-Methoxyethoxy)ethyl)-6,7,8,8a,9,10-hexahydro-5H-9,4b-(epiminoethano)phenanthren-3-amine (88 mg, 0.255 mmol) and potassium thiocyanate (99 mg, 1.022 mmol) were dissolved in acetic acid (3 ml). To the solution was added dibromine (0.013 ml, 0.255 mmol) in acetic acid (0.5 mL) dropwise. The reaction was stirred at room temperature overnight. LCMS showed completion of reaction. The reaction was basified using 2N NaOH to pH 9 and extracted with dichloromethane (3×20 mL). The combined organic layer was dried over sodium sulfate, was filtered and was concentrated. The crude product was purified by chromatography on silica gel using a Biotage instrument. The pure product, (4aR,5R,11bR)-14-(2-(2-methoxyethoxy)ethyl)-2,3,4,4a,5,6-hexahydro-1H-5,11b-(epiminoethano)phenanthro[3,2-d]thiazol-9-amine (82.7 mg, 0.206 mmol, 81% yield), was obtained as an off-white solid. MS (EI) for $C_{22}H_{31}N_3O_2S$: 402.2 (MH+). 1H NMR (500 MHz, Methanol-d4) δ 7.36 (d, J=17.4 Hz, 2H), 3.71-3.59 (m, 4H), 3.61-3.53 (m, 2H), 3.38 (s, 3H), 3.15 (d, J=18.5 Hz, 1H), 3.08 (s, 1H), 2.88 (s, 2H), 2.82 (s, 1H), 2.65 (s, 1H), 2.50 (d, J=13.4 Hz, 1H), 2.23 (s, 1H), 1.91 (d, J=12.5 Hz, 1H), 1.81 (td, J=13.0, 4.7 Hz, 1H), 1.70 (d, J=12.3 Hz, 1H), 1.57 (d, J=12.3 Hz, 1H), 1.51-1.28 (m, 5H), 1.19 (qd, J=13.6, 13.1, 3.6 Hz, 1H).

Example 98

Preparation of 17-[2-(2-methoxyethoxy)ethyl]-N-(pyridin-4-yl)morphinan-3-amine (98), hydrochloride salt

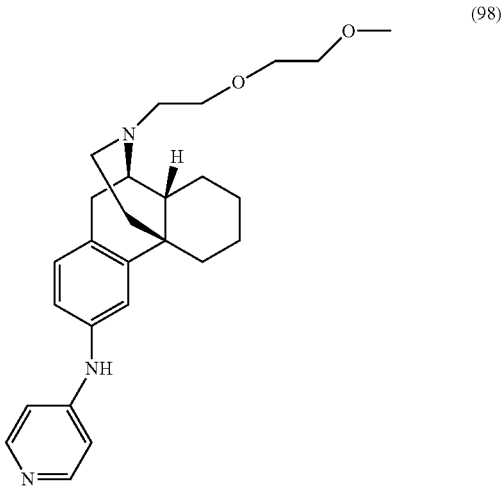 [SMILES: COCCOCCN1CC[C@]23CCCC[C@H]2[C@H]1Cc1ccc(Nc2ccncc2)cc13]

A dioxane solution of 17-[2-(2-methoxyethoxy)ethyl]morphinan-3-yl trifluoromethanesulfonate (0.090 g, 0.19 mmol), tris(dibenzylideneacetone)dipalladium(0) (0.017 g, 0.019 mmol), dicyclohexyl(2',4',6'-triisopropyl-[1,1'-biphenyl]-2-yl)phosphine (0.022 g, 0.047 mmol), pyridin-4-amine (0.027 g, 0.28 mmol) and cesium carbonate (0.18 g, 0.57 mmol) was heated at 80° C. for eighteen hours. After all solvent was removed, a brown solid was obtained. The crude product was dissolved in ethyl acetate and washed with water three times. The organic layer was concentrated and the residue was loaded on a 10 g silica gel column and purified by chromatography using Biotage with dichloromethane/methanol as eluent. Pure 17-[2-(2-methoxyethoxy)ethyl]-N-(pyridin-4-yl)morphinan-3-amine (98) was obtained as a colorless solid (0.063 g, 79% yield). 1H NMR (500 MHz, Chloroform-d) δ 8.28-8.23 (m, 2H), 7.13-7.06 (m, 2H), 6.98 (dd, 1H), 6.79-6.74 (m, 2H), 6.35 (s, 1H), 3.71-3.58 (m, 4H), 3.60-3.53 (m, 2H), 3.40 (s, 3H), 3.04-2.94 (m, 2H), 2.85 (dt, 1H), 2.79-2.59 (m, 3H), 2.29 (dt, 1H), 2.17 (td, 1H), 1.91 (dt, 1H), 1.80 (td, 1H), 1.71-1.62 (m, 1H), 1.55 (ddt, 1H), 1.48-1.21 (m, 5H), 1.13 (qd, 1H). MS (EI) for $C_{26}H_{35}N_3O_2$: 422.2 (MH+).

The free base (0.063 g, 0.15 mmol) was dissolved in methanol and a 2 N hydrochloric acid ether solution (0.75 mL, 1.49 mmol) was added. The mixture was lyophilized to give 17-[2-(2-methoxyethoxy)ethyl]-N-(pyridin-4-yl)morphinan-3-amine hydrochloride salt as a colorless solid (0.073 g, 0.14 mmol, 92% yield).

Example 99

Preparation of (4bR,8aR,9R)-11-(2-(2-methoxyethoxy)ethyl)-N-(pyridazin-4-yl)-6,7,8,8a,9,10-hexahydro-5H-9,4b-(epiminoethano)phenanthren-3-amine (99)

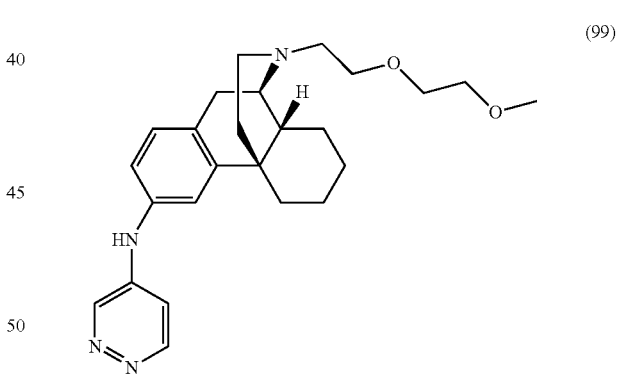

A suspension of (4bR,8aR,9R)-11-(2-(2-methoxyethoxy)ethyl)-6,7,8,8a,9,10-hexahydro-5H-9,4b-(epiminoethano)phenanthren-3-yl trifluoromethanesulfonate (97.5 mg, 0.204 mmol), pyridazin-4-amine (29.1 mg, 0.306 mmol), XPhos (19.47 mg, 0.041 mmol), and $Cs_2CO_3$ (100 mg, 0.306 mmol) in dioxane (2 ml) was degassed under nitrogen for ten minutes before tris(dibenzylideneacetone)dipalladium(0) (18.70 mg, 0.020 mmol) was added. The mixture was irradiated in a microwave at 100° C. for two hours. LCMS showed the desired product formation with a small amount of starting material remaining. Upon removal of the solvent, the residue was taken up in dichloromethane (30 mL) and washed with brine (30 mL). The organic layer was dried over sodium sulfate; was filtered and was concentrated. The crude product was purified by chromatography using a Biotage instrument using a KP-NH column and dichloromethane/methanol as the mobile phase. Pure fractions were combined and concentrated. After drying under high vacuum, (4bR,5aR,9R)-11-(2-(2-methoxyethoxy)ethyl)-N-(pyridazin-4-yl)-6,7,8,8a,9,10-hexahydro-5H-9,4b-(epiminoethano)phenanthren-3-amine (99) (46.1 mg, 0.109 mmol, 53.4% yield) was obtained as an oil. MS (EI) for $C_{25}H_{34}N_4O_2$: 423.2 (MH+). 1H NMR (500 MHz, Methanol-d4) δ 8.72 (d, J=3.0 Hz, 1H), 8.57 (dd, J=6.3, 1.0 Hz, 1H), 7.25-7.14 (m, 2H), 7.07 (ddd, J=19.3, 7.2, 2.6 Hz, 2H), 3.69-3.53 (m, 6H), 3.38 (s, 3H), 3.13-3.00 (m, 2H), 2.85 (dt, J=13.1, 5.9 Hz, 1H), 2.80-2.69 (m, 2H), 2.63 (dq, J=12.4, 2.0 Hz, 1H), 2.44-2.36 (m, 1H), 2.17 (td, J=12.5, 3.2 Hz, 1H), 1.94-1.68 (m, 3H), 1.59 (dd, J=12.8, 4.4 Hz, 1H), 1.52-1.24 (m, 6H), 1.16 (qd, J=13.5, 13.1, 4.2 Hz, 1H).

Example 100

Preparation of (4bR,8aR,9R)-11-(2-(2-methoxyethoxy)ethyl)-3-(1H-pyrazol-4-yl)-6,7,8,8a,9,10-hexahydro-5H-9,4b-(epiminoethano)phenanthrene (100)

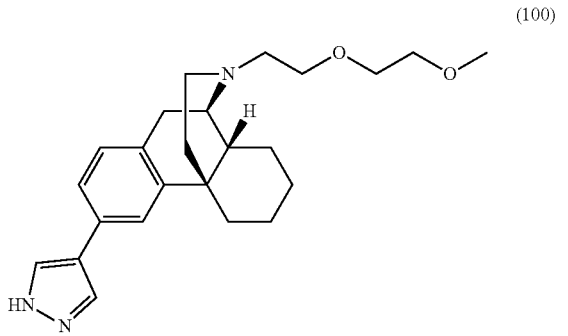 [SMILES: COCCOCCN1CC[C@]23CCCC[C@H]2[C@H]1Cc1ccc(-c2cn[nH]c2)cc13]

(4bR,8aR,9R)-11-(2-(2-Methoxyethoxy)ethyl)-6,7,8,8a,9,10-hexahydro-5H-9,4b-(epiminoethano)phenanthren-3-yl trifluoromethanesulfonate (95 mg, 0.199 mmol), (1H-pyrazol-4-yl)boronic acid (33.4 mg, 0.298 mmol), and sodium carbonate (63.3 mg, 0.597 mmol) were placed in a microwave reaction tube. Dioxane (2 mL) and water (0.5 mL) were added to the tube. The mixture was degassed for five minutes under nitrogen. Tetrakis(triphenylphosphine)palladium(0) (46.0 mg, 0.040 mmol) was added to the mixture and the reaction was irradiated in a microwave for two hours at 100° C. The solvent was removed via lyophilization. The residue was dissolved in dichloromethane and washed with brine. The organic layer was dried over sodium sulfate, was filtered and was concentrated. After purification by chromatography on silica gel using a Biotage instrument, (4bR,8aR,9R)-11-(2-(2-methoxyethoxy)ethyl)-3-(1H-pyrazol-4-yl)-6,7,8,8a,9,10-hexahydro-5H-9,4b-(epiminoethano)phenanthrene (23.6 mg, 0.060 mmol, 30.0% yield) (100) was obtained as a colorless solid. MS (EI) for $C_{24}H_{33}N_3O_2$: 396.2 (MH+). 1H NMR (500 MHz, Methanol-d4) δ 7.91 (s, 2H), 7.49-7.44 (m, 1H), 7.33 (dd, J=7.9, 1.7 Hz, 1H), 7.13 (d, J=8.0 Hz, 1H), 3.67-3.52 (m, 6H), 3.37 (s, 3H), 3.08-2.96 (m, 2H), 2.82 (dt, J=12.4, 6.0 Hz, 1H), 2.79-2.64 (m, 2H), 2.63-2.52 (m, 2H), 2.16 (td, J=12.5, 3.2 Hz, 1H), 1.87 (dt, J=12.9, 3.1 Hz, 1H), 1.77 (td, J=12.8, 4.7 Hz, 1H), 1.72-1.64 (m, 1H), 1.60-1.52 (m, 1H), 1.52-1.24 (m, 5H), 1.16 (qd, J=13.0, 3.8 Hz, 1H).

Example 101

Preparation of (4aR,5R,12bR)-15-methyl-2,3,4,4a,5,6-hexahydro-1H-5,12b-(epiminoethano)naphtho[2,1-g]quinolin-10-amine (101), hydrochloride salt

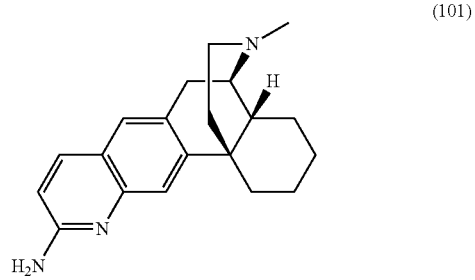 [SMILES: CN1CC[C@]23CCCC[C@H]2[C@H]1Cc1cc2ccc(N)nc2cc13]

Step 1: Preparation of (4aR,5R,12bR)-10-chloro-15-methyl-2,3,4,4a,5,6-hexahydro-1H-5,12b-(epiminoethano)naphtho[2,1-g]quinolone

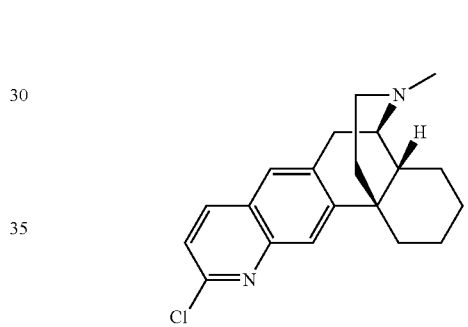

A 50 mL flask was charged with (4aR,5R,12bR)-15-methyl-1,2,3,4,4a,5,6,11-octahydro-10H-5,12b-(epiminoethano)naphtho[2,1-g]quinolin-10-one (preparation described in Example 102) (259 mg, 0.84 mmol) and phosphoryl trichloride (4 mL), and the yellow mixture was placed in an oil bath heated at 115° C. The mixture was removed from the heat after one hour and was concentrated. The residue was taken up in dichloromethane (25 mL) and stirred with 1 M sodium bicarbonate (15 mL) for thirty minutes, and the aqueous layer was then extracted with dichloromethane (15 mL). The combined organic layer was dried (sodium sulfate), was filtered and was concentrated to afford (4aR,5R,12bR)-10-chloro-15-methyl-2,3,4,4a,5,6-hexahydro-1H-5,12b-(epiminoethano)naphtho[2,1-g]quinoline as a yellow solid foam (244 mg 89%). $^1$H NMR (500 MHz, CDCl$_3$) δ 8.00 (d, J=8.5 Hz, 1H), 7.96 (s, 1H), 7.57 (s, 1H), 7.30 (dd, J=8.6, 1.5 Hz, 1H), 3.30 (d, J=18.4 Hz, 1H), 2.93 (dd, J=6.2, 3.2 Hz, 1H), 2.86 (dd, J=18.4, 5.9 Hz, 1H), 2.59 (d, J=13.6 Hz, 1H), 2.47 (dd, J=12.7, 4.8 Hz, 1H), 2.45 (s, 3H), 2.04 (td, J=12.7, 11.6, 2.7 Hz, 1H), 1.96 (dd, J=12.8, 3.2 Hz, 1H), 1.88 (td, J=12.6, 4.6 Hz, 1H), 1.65 (dd, J=12.3, 2.7 Hz, 1H), 1.56 (d with fine str., J=13.2 Hz, 1H), 1.53-1.26 (m, 5H), 1.09 (qd, J=13.8, 4.1 Hz, 1H); MS (EI) for $C_{19}H_{22}N_2Cl$: 327.0 (M$^{-1}$H$^+$).

Step 2: Preparation of (4aR,5R,12bR)—N-(4-methoxybenzyl)-15-methyl-2,3,4,4a,5,6-hexahydro-1H-5,12b-(epiminoethano)naphtho[2,1-g]quinolin-10-amine

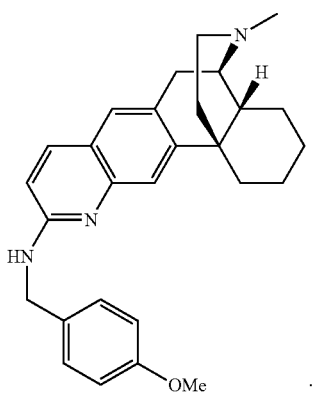 [SMILES: COc1ccc(CNc2ccc3cc4c(cc3n2)[C@@]23CCCC[C@H]2[C@@H](C4)N(C)CC3)cc1]

A 0.5-2 mL microwave vial charged with a solution of (4aR,5R,12bR)-10-chloro-15-methyl-2,3,4,4a,5,6-hexahydro-1H-5,12b-(epiminoethano)naphtho[2,1-g]quinoline (107 mg, 0.33 mmol), and (4-methoxy)benzylamine (0.58 mL, 4.4 mmol) in dry acetonitrile (1 mL) was heated at 225° C. in a microwave for 2.5 hours. The mixture was diluted with ethyl acetate (50 mL), washed with 0.6 M pH 6 phosphate buffer (20 mL, 2×10 mL; 8:3 0.5M disodium hydrogen phosphate:1M sodium dihydrogen phosphate), dried (sodium sulfate), filtered and concentrated to afford an orange viscous oil (389 mg). MS (EI) for $C_{28}H_{33}NO_3$: 428.2 ($M^+H^+$). The reaction was carried forward to the next step without further purification.

Step 3: Preparation of (4aR,5R,12bR)-15-methyl-2,3,4,4a,5,6-hexahydro-1H-5,12b-(epiminoethano)naphtho[2,1-g]quinolin-10-amine A 2-5 mL microwave vial was charged with a solution of (4aR,5R,12bR)—N-(4-methoxybenzyl)-15-methyl-2,3,4,4a,5,6-hexahydro-1H-5,12b-(epiminoethano)naphtho[2,1-g]quinolin-10-amine (389 mg, assumed 0.33 mmol) and triethylsilane (0.52 mL, 3.3 mmol) in trifluoroacetic acid (3 mL), and the mixture was heated in a microwave at 70° C. for 1.3 hours. The mixture was concentrated, and the residue was taken up in ethyl acetate (50 mL), washed with 2 M sodium carbonate (30 mL), and extracted with 0.5 M pH 6 phosphate buffer (3×15 mL). The combined acidic extract was basified to pH>12, then extracted with dichloromethane (2×30 mL), and the combined dichloromethane layer was dried (sodium sulfate), was filtered and was concentrated to afford a yellow oil. Automated flash chromatography on silica (1:10:450 to 1:10:90 ammonium hydroxide:methanol:dichloromethane) afforded (4aR,5R,12bR)-15-methyl-2,3,4,4a,5,6-hexahydro-1H-5,12b-(epiminoethano)naphtho[2,1-g]quinolin-10-amine (101) as a colorless solid foam (79 mg, 71% over 2 steps). $^1$H NMR (500 MHz, CDCl$_3$) 7.80 (d, J=8.8 Hz, 1H), 7.60 (s, 1H), 7.37 (s, 1H), 6.67 (d, J=8.8 Hz, 1H), 4.65 (s, 2H), 3.21 (d, J=18.1 Hz, 1H), 2.88 (dd, J=5.9, 3.1 Hz, 1H), 2.79 (ddq, J=18.1, 5.6, 1.0 Hz, 1H), 2.58 (dd, J=12.3, 2.2 Hz, 1H), 2.44 (ddd, J=11.7, 4.8, 1.8 Hz, 1H), 2.43 (s, 3H), 2.09 (td, J=12.4, 3.2 Hz, 1H), 1.90 (dt, J=12.9, 2.9 Hz, 1H), 1.82 (td, J=12.7, 4.9 Hz, 1H), 1.68-1.60 (m, 1H), 1.57-1.32 (m, 6H), 1.15 (qd, J=12.5, 4.0 Hz, 1H); MS (EI) for $C_{20}H_{25}N_3$: 308.2 ($M^+H^+$). A 12 mg portion was converted to the HCl salt by dissolution in methanol (0.5 mL), followed by the addition of 2 M hydrochloric acid (0.08 mL). The mixture was concentrated in vacuo to afford a pale yellow glass.

Example 102

Preparation of (4aR,5R,12bR)-15-methyl-1,2,3,4,4a,5,6,11-octahydro-10H-5,12b-(epiminoethano)naphtho[2,1-g]quinolin-10-one (102), hydrochloride salt

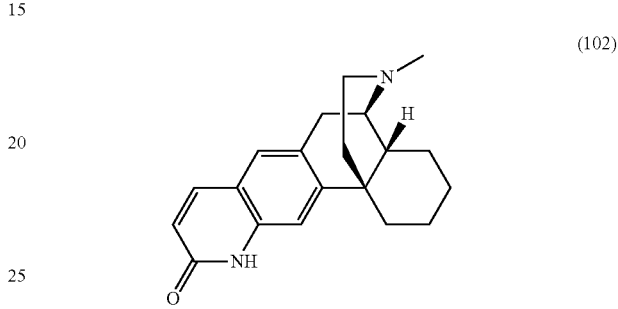

(102)

Step 1: Preparation of 2-iodo-17-methylmorphinan-3-amine

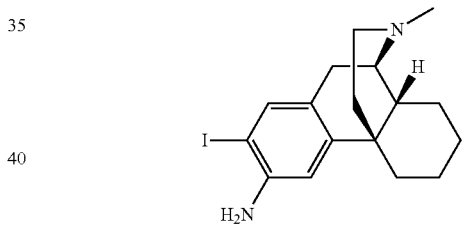

A 250 mL flask was charged with a solution of 17-methylmorphinan-3-amine (1.425 g, 5.56 mmol) in dichloromethane (20 mL) and acetic acid (10 mL), whereupon solid N-iodosuccinimide (1.25 g, 5.56 mmol) was added in one portion, and the mixture was stirred at room temperature in the dark. After 23 hours, the mixture was concentrated to afford a brown oil, and the residue was taken up in ethyl acetate (50 mL) and was extracted with 2 M sulfuric acid (40 mL, 2×15 mL). The combined acid extract was decolorized with 0.5 M sodium bisulfite (2 mL), basified to pH>12 with 4 M sodium hydroxide (60 mL), and extracted with isopropyl acetate (2×30 mL). The combined organic layer was dried (sodium sulfate), was filtered and was concentrated to afford 2-iodo-17-methylmorphinan-3-amine as a pale red-brown foam (1.831 g, 86%). $^1$H NMR (500 MHz, CDCl$_3$) δ 7.39 (s, 1H), 6.66 (s, 1H), 3.91 (s, 2H), 2.90 (d, J=17.9 Hz, 1H), 2.76 (dd, J=5.8, 3.1 Hz, 1H), 2.51 (ddd, J=18.1, 5.9, 1.2 Hz, 1H), 2.42 (ddd, J=12.0, 4.9, 1.8 Hz, 1H), 2.38 (s, 3H), 2.26 (dd, J=10.3, 3.4 Hz, 1H), 2.09 (td, J=12.3, 3.3 Hz, 2H), 1.77 (dt, J=12.9, 3.2 Hz, 1H), 1.71 (td, J=12.6, 4.9 Hz, 1H), 1.67-1.59 (m, 1H), 1.56-1.45 (m, 1H), 1.44-1.25 (m, 4H), 1.12 (qd, J=12.5, 3.8 Hz, 1H); MS (EI) for $C_{17}H_{23}IN_2$: 383.0 ($M^+H^+$).

Step 2: Preparation of methyl (2E)-3-(3-amino-17-methylmorphinan-2-yl)acrylate

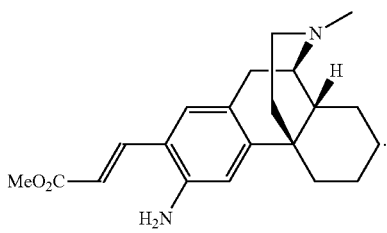 [SMILES: COC(=O)/C=C/c1cc2c(cc1N)[C@@]13CCCC[C@H]1[C@@H](C2)N(C)CC3]

A 25 mL flask was charged with (4bR,8aR,9R)-2-iodo-11-methyl-6,7,8,8a,9,10-hexahydro-5H-9,4b-(epiminoethano)phenanthren-3-amine (441 mg, 1.15 mmol), palladium (II) acetate (25.9 mg, 0.12 mmol) and tri-o-tolylphosphine (105 mg, 0.35 mmol), purged with nitrogen, whereupon a nitrogen sparged (10 minutes) solution of methyl acrylate (0.314 mL, 3.46 mmol) and triethylamine (0.37 mL, 2.7 mmol) in dry acetonitrile (6 mL) was added, and the stirred mixture was placed in an oil bath heated at 90° C. After four hours, the mixture was concentrated in vacuo, and the brown residue was carried forward to the next step without further purification. MS (EI) for $C_{21}H_{28}H_2O_2$: 341.2 ($M^+H^+$).

Step 3: Preparation of (4aR,5R,12bR)-15-methyl-1,2,3,4,4a,5,6,11-octahydro-10H-5,12b-(epiminoethano)naphtho[2,1-g]quinolin-10-one A solution of methyl (2E)-3-(3-amino-17-methylmorphinan-2-yl)acrylate (393 mg, assumed 1.15 mmol) in THF (4 mL) and water (4 mL) was treated with concentrated hydrochloric acid (0.76 mL, 9.2 mmol), and the mixture was heated to reflux. After twenty hours, the mixture was transferred to a 20 mL microwave vial, diluted with THF:water (1:1, 3 mL), and heated at 130° C. for thirty minutes. The mixture was diluted with ethyl acetate (30 mL), and was extracted with 0.5 M sulfuric acid (2×20 mL). The combined acid extract was washed with ether (30 mL), then basified to pH~10 with ammonium hydroxide (10 mL), and extracted with dichloromethane (2×30 mL). The combined dichloromethane layer was dried (sodium sulfate), was filtered and was concentrated to afford a brown oil. Automated flash chromatography on silica (dichloromethane to 1:10:90 ammonium hydroxide:methanol:dichloromethane) afforded of (4aR,5R,12bR)-15-methyl-1,2,3,4,4a,5,6,11-octahydro-1 OH-5,12b-(epiminoethano)naphtho[2,1-g]quinolin-10-one (102) as a yellow glass (302 mg, 85% over 2 steps). $^1$H NMR (500 MHz, CDCl$_3$) δ 7.74 (d, J=9.4 Hz, 1H), 7.32 (s, 1H), 7.25 (s, 1H), 6.68 (d, J=9.4 Hz, 1H), 3.15 (d, J=18.1 Hz, 1H), 2.88 (dd, J=5.2, 2.7 Hz, 1H), 2.74 (dd, J=18.2, 5.8 Hz, 1H), 2.52 (dd, J=13.8, 3.4 Hz, 1H), 2.46 (ddd, J=12.0, 4.7, 1.7 Hz, 1H), 2.43 (s, 3H), 2.04 (td, J=12.4, 3.1 Hz, 2H), 1.90 (dt, J=12.8, 3.3 Hz, 1H), 1.82 (td, J=12.7, 4.8 Hz, 1H), 1.70-1.63 (m, 1H), 1.58 (dt, J=13.1, 3.5 Hz, 1H), 1.52-1.35 (m, 4H), 1.27 (qt, J=13.1, 3.1 Hz, 1H), 1.11 (qd, J=12.7, 3.8 Hz, 1H); $^{13}$C NMR (126 MHz, CDCl$_3$) δ 164.40, 145.16, 140.26, 137.39, 132.53, 126.02, 120.90, 118.17, 112.49, 77.32, 77.27, 77.06, 76.81, 57.66, 47.16, 45.26, 42.79, 42.43, 37.80, 36.69, 27.01, 26.50, 23.60, 22.27; MS (EI) for $C_{20}H_{24}N_2O$: 309.2 ($M^+H^+$). A 43 mg portion was converted to the HCl salt by dissolution in methanol (2 mL) followed by the addition of 2 M hydrochloric acid (0.1 mL). The dried residue was lyophilized from water/acetonitrile (8:1, 2.2 mL) affording a pale tan solid.

Example 103

Preparation of 3-amino-17-methylmorphinan-2-carbonitrile (103), hydrochloride salt

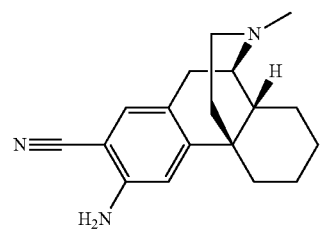

(103)

A 50 mL flask was charged with 2-iodo-17-methylmorphinan-3-amine (302 mg, 0.79 mmol), zinc cyanide (232 mg, 2.0 mmol) and tetrakis(triphenylphosphine)palladium (0) (183 mg, 0.16 mmol), and purged with nitrogen. Thereafter, dry N,N-dimethylformamide (5 mL) was added, whereupon the orange suspension was placed in an oil bath heated at 80° C. The mixture was removed from the heat after three hours, was diluted with ethyl acetate (50 mL), and was washed with brine (50 mL). The brine layer was diluted to 75 mL, and was back extracted with ethyl acetate (25 mL). The combined organic layer was washed with brine (4×15 mL) buffered with ammonium hydroxide (0.3 mL), dried (sodium sulfate), filtered and concentrated. Automated flash chromatography on silica (dichloromethane to 1:10:90 ammonium hydroxide:methanol:dichloromethane) afforded 3-amino-17-methylmorphinan-2-carbonitrile (103) as a light brown viscous oil (167 mg, 73%). $^1$H NMR (500 MHz, CDCl$_3$) δ 7.17 (s, 1H), 6.69 (s, 1H), 4.23 (s, 2H), 2.95 (d, J=18.1 Hz, 1H), 2.82 (dd, J=5.7, 3.4 Hz, 1H), 2.54 (dd, J=18.1, 5.8 Hz, 1H), 2.46 (ddd, J=12.1, 4.7, 1.9 Hz, 1H), 2.40 (s, 3H), 2.29 (dq, J=14.1, 2.4 Hz, 1H), 2.07 (td, J=12.4, 3.2 Hz, 1H), 1.84 (dt, J=12.9, 3.3 Hz, 1H), 1.78 (td, J=12.7, 4.8 Hz, 1H), 1.72-1.64 (m, 1H), 1.55 (dt, J=13.3, 3.6 Hz, 1H), 1.50-1.29 (m, 5H), 1.24 (qt, J=13.1, 3.2 Hz, 1H), 1.08 (qd, J=12.7, 3.8 Hz, 1H); LCMS for $C_{18}H_{23}N_3$: 282.2 ($M^+H^+$). An 11 mg portion was converted to the HCl salt by dissolution in methanol (2 mL), addition of 2 M hydrochloric acid (0.1 mL), concentration to dryness, redissolution in water/acetonitrile (8:1, 0.6 mL), and lyophilization to afford a pale brown solid.

Example 104

Preparation of 17-[2-(2-methoxyethoxy)ethyl]-N-(5-fluoro-pyridin-3-yl)morphinan-3-amine (104), hydrochloride salt

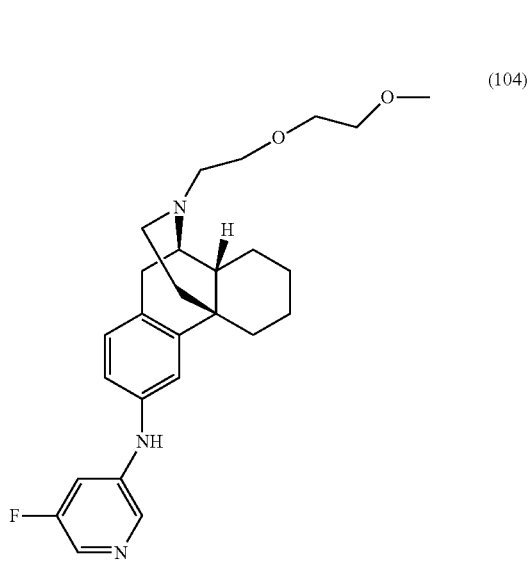 [SMILES: COCCOCCN1CC[C@]23CCCC[C@H]2[C@H]1Cc1ccc(Nc2cncc(F)c2)cc13]

(104)

A dioxane solution of 17-[2-(2-methoxyethoxy)ethyl] morphinan-3-yl trifluoromethanesulfonate (0.10 g, 0.21 mmol), tris(dibenzylideneacetone)dipalladium(0) (0.010 g, 0.010 mmol), dicyclohexyl(2',4',6'-triisopropyl-[1,1'-biphenyl]-2-yl)phosphine (0.012 g, 0.025 mmol), 5-fluoro-pyridin-3-amine (0.035 g, 0.31 mmol) and cesium carbonate (0.14 g, 0.42 mmol) was heated at 80° C. under nitrogen for five hours. HPLC indicated that the reaction was complete. After all solvent was removed, a brown solid was obtained. The crude product was dissolved in ethyl acetate and was washed with water three times. All solvent was removed again and the residue was loaded on a 10 g silica gel column and purified by Biotage with dichloromethane/methanol. Pure 17-[2-(2-methoxyethoxy)ethyl]-N-(5-fluoro-pyridin-3-yl)morphinan-3-amine (104) was obtained as a light-yellow solid (0.071 g, 77% yield). $^1$H NMR (500 MHz, Chloroform-d) δ 8.11-8.06 (m, 1H), 7.94-7.90 (m, 1H), 7.08 (d, 1H), 7.01 (dp, 2H), 6.93 (dd, 1H), 5.92 (s, 1H), 3.71-3.58 (m, 4H), 3.54 (dd, 2H), 3.38 (d, 3H), 3.03-2.95 (m, 1H), 2.86 (dt, 1H), 2.81-2.61 (m, 3H), 2.32-2.24 (m, 1H), 2.23-2.14 (m, 1H), 1.91 (d, 1H), 1.87-1.71 (m, 1H), 1.70-1.59 (m, 2H), 1.47-1.20 (m, 5H), 1.12 (qd, 1H). MS (EI) for $C_{26}H_{34}FN_3O_2$: 440.2 (MH+).

The free base (0.050 g, 0.11 mmol) was dissolved in methanol followed by addition of a 2 N hydrochloric acid ether solution (0.57 mL, 1.1 mmol). The mixture was then lyophilized to give 17-[2-(2-methoxyethoxy)ethyl]-N-(5-fluoro-pyridin-3-yl)morphinan-3-amine hydrochloride salt as a light-yellow solid (0.053 g, 86% yield).

Example 105

Preparation of N-((4bR,8aR,9R)-11-(2-(2-methoxyethoxy)ethyl)-6,7,8,8a,9,10-hexahydro-5H-9,4b-(epiminoethano)phenanthren-3-yl)thiazol-2-amine (105)

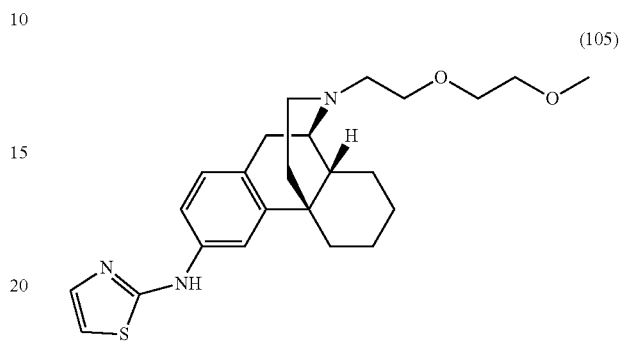

(105)

(4bR,8aR,9R)-11-(2-(2-Methoxyethoxy)ethyl)-6,7,8,8a,9,10-hexahydro-5H-9,4b-(epiminoethano)phenanthren-3-amine (99 mg, 0.287 mmol) was dissolved in 2-propanol (2 ml). To the solution were added 2-bromothiazole (0.052 ml, 0.575 mmol) followed by HCl (0.024 ml, 0.287 mmol). The reaction was irradiated in a microwave at 100° C. for two hours. The solvent was removed via rotovap. The residue was purified by chromatography on silica gel using a Biotage instrument to give the desired product N-((4bR,8aR,9R)-11-(2-(2-methoxyethoxy)ethyl)-6,7,8,8a,9,10-hexahydro-5H-9,4b-(epiminoethano)phenanthren-3-yl)thiazol-2-amine (105) (21.9 mg, 0.051 mmol, 17.82% yield) as a colorless solid. MS (EI) for $C_{24}H_{33}N_3O_2S$: 428.2 (MH+). 1H NMR (500 MHz, Methanol-d4) δ 7.62 (d, J=2.3 Hz, 1H), 7.47-7.34 (m, 1H), 7.25-7.18 (m, 2H), 6.78 (d, J=3.7 Hz, 1H), 3.93-3.67 (m, 5H), 3.68-3.58 (m, 2H), 3.39 (d, J=24.6 Hz, 6H), 3.32-3.27 (m, 1H), 3.21 (d, J=3.9 Hz, 2H), 2.82 (d, J=14.4 Hz, 1H), 2.54 (d, J=13.9 Hz, 1H), 2.17-2.10 (m, 1H), 2.01 (td, J=13.9, 4.6 Hz, 1H), 1.80-1.72 (m, 1H), 1.71-1.56 (m, 3H), 1.55-1.29 (m, 3H), 1.20 (qd, J=12.7, 3.8 Hz, 1H).

Example 106

Preparation of (4bR,8aR,9R)-3-(furan-3-yl)-11-(2-(2-methoxyethoxy)ethyl)-6,7,8,8a,9,10-hexahydro-5H-9,4b-(epiminoethano)phenanthrene (106)

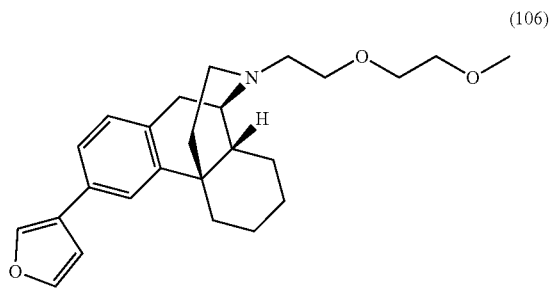 [SMILES: COCCOCCN1CC[C@]23CCCC[C@H]2[C@H]1Cc1ccc(-c2ccoc2)cc13]

(106)

(4bR,8aR,9R)-11-(2-(2-Methoxyethoxy)ethyl)-6,7,8,8a,9,10-hexahydro-5H-9,4b-(epiminoethano)phenanthren-3-yl trifluoromethanesulfonate (92.6 mg, 0.194 mmol), 2-(furan-3-yl)-4,4,5,5-tetramethyl-1,3,2-dioxaborolane (56.4 mg, 0.291 mmol) and sodium carbonate (61.7 mg, 0.582 mmol) were placed in a microwave reaction tube. Dioxane (2 mL) and water (0.5 mL) were added to the tube. The mixture was degassed for five minutes under nitrogen. Tetrakis(triphenylphosphine)palladium(0) (44.8 mg, 0.039 mmol) was added to the mixture and the reaction was irradiated in a microwave for two hours at 100° C. The solvent was removed via lyophilization. The residue was dissolved in dichloromethane and washed with brine. The organic layer was dried over sodium sulfate, was filtered and was concentrated. After purification by chromatography on silica gel using a Biotage instrument, (4bR,8aR,9R)-3-(furan-3-yl)-11-(2-(2-methoxyethoxy)ethyl)-6,7,8,8a,9,10-hexahydro-5H-9,4b-(epiminoethano)phenanthrene (106) (32.6 mg, 0.082 mmol, 42.5% yield) was obtained as an off-white semi solid. MS (EI) for $C_{25}H_{33}NO_3$: 396.2 (MH+). 1H NMR (500 MHz, Methanol-d4) δ 7.85 (d, J=1.5 Hz, 1H), 7.54 (t, J=1.7 Hz, 1H), 7.46-7.42 (m, 1H), 7.32 (dd, J=7.9, 1.8 Hz, 1H), 7.15 (d, J=7.9 Hz, 1H), 6.79-6.75 (m, 1H), 3.70-3.53 (m, 6H), 3.36 (d, J=23.2 Hz, 4H), 3.11-3.00 (m, 2H), 2.85 (dt, J=12.3, 5.9 Hz, 1H), 2.81-2.69 (m, 2H), 2.66-2.51 (m, 2H), 2.19 (td, J=12.6, 3.3 Hz, 1H), 1.90 (dt, J=13.1, 3.0 Hz, 1H), 1.79 (td, J=12.9, 4.7 Hz, 1H), 1.74-1.65 (m, 1H), 1.58 (dt, J=10.9, 2.9 Hz, 1H), 1.51-1.25 (m, 6H), 1.17 (qd, J=13.6, 12.9, 3.6 Hz, 1H).

Example 107

Preparation of 2-[3-(pyridin-4-ylamino)morphinan-17-yl]ethanol (107), hydrochloride salt

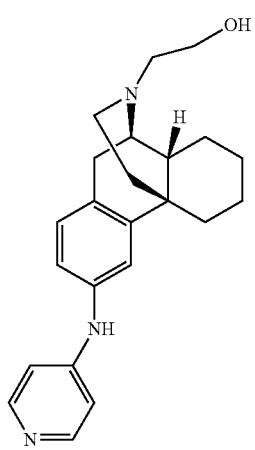

(107)

Step 1: Preparation of 17-(2-hydroxyethyl)morphinan-3-yl trifluoromethanesulfonate

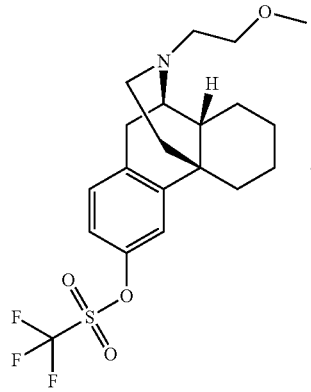

The 2-chloroethanol (5 mL, 6.0 g, 75 mmol) solution of morphinan-3-yl trifluoromethanesulfonate (0.21 g, 0.56 mmol) and cesium carbonate (0.98 g, 2.78 mmol) was heated at 100° C. for four hours. After cooling to room temperature, all solvent was removed and the products were extracted with dichloromethane three times. The solvent was removed and the residue was purified by chromatography on silica gel using a Biotage instrument with dichloromethane/methanol eluent. Pure 17-(2-hoxyethyl)morphinan-3-yl trifluoromethanesulfonate was obtained as a colorless solid (0.090 g, 39% yield), MS (EI) for $C_{19}H_{24}F_3NO_4S$: 420.0 ($MH^F$).

Step 2

Preparation of 2-[3-(pyridin-4-ylamino)morphinan-17-yl] ethanol. A dioxane solution of 17-(2-hydroxyethyl)morphinan-3-yl trifluoromethanesulfonate (0.090 g, 0.22 mmol), tris(dibenzylideneacetone)dipalladium(0) (0.098 g, 0.011 mmol), dicyclohexyl (2',4',6'-triisopropyl-[1,1'-biphenyl]-2-yl)phosphine (0.012 g, 0.026 mmol), pyridin-4-amine (0.040 g, 0.43 mmol) and cesium carbonate (0.14 g, 0.43 mmol) was heated at 90° C. under nitrogen for 18 hours. After all solvent was removed, a brown solid was obtained. The crude product was dissolved in ethyl acetate and washed with water three times. All solvent was removed and the residue was loaded on a 10 g silica gel column and purified by chromatography using a Biotage instrument with dichloromethane/methanol as eluent. Pure 2-[3-(pyridin-4-ylamino)morphinan-17-yl]ethanol (107) was obtained as a colorless solid (0.023 g, 29% yield). $^1$H NMR (500 MHz, Chloroform-d) δ 8.31-8.24 (m, 2H), 7.14-7.06 (m, 2H), 6.98 (dd, 1H), 6.77-6.72 (m, 2H), 6.02 (s, 1H), 3.67-3.54 (m, 2H), 2.98-2.89 (m, 1H), 2.87-2.76 (m, 2H), 2.72-2.58 (m. 2H), 2.35-2.15 (m, 2H), 1.91 (dt, 1H), 1.81-1.60 (m, 2H), 1.56 (dd, 1H), 1.49-1.21 (m, 5H), 1.13 (qd, 1H). MS (EI) for $C_{23}H_{29}N_3O$: 364.2 (MH+).

The free base (0.023 g, 0.063 mmol) was dissolved in methanol and a 2 N hydrochloric acid ether solution (0.32 mL, 0.63 mmol) was thereafter added. The mixture was then lyophilized to give 2-[3-(pyridin-4-ylamino)morphinan-17-yl]ethanol hydrochloride salt as a light-yellow solid (0.020 g, 67% yield).

Example 108

Preparation of N-(17-methylmorphinan-3-yl)acetamide (108), hydrochloride salt

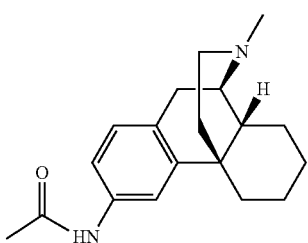 [SMILES: CC(=O)Nc1ccc2c(c1)[C@@]13CCCC[C@H]1[C@@H](C2)N(C)CC3]

A solution of 17-methylmorphinan-3-amine (72 mg, 0.281 mmol) and triethylamine (0.059 mL, 0.421 mmol) in dichloromethane (2 mL) was cooled to 0° C. Acetyl chloride (0.024 mL, 0.337 mmol) was added to the above solution. The reaction was then stirred at room temperature for two hours. The reaction was taken up in 10 mL of dichloromethane, washed with brine (10 mL) and dried over magnesium sulfate. After filtration, the solvent was removed and the residue was purified with flash column chromatography on silica gel to afford 35.2 mg of product (108) as free base in 42% yield. MS (EI) for $C_{19}H_{26}N_2O$: 299.2 (MH+). 1H NMR (500 MHz, DMSO-d6) δ 9.79 (s, 1H), 7.40 (d, J=8.0 Hz, 2H), 7.02 (d, J=8.0 Hz, 1H), 2.92 (d, J=18.3 Hz, 1H), 2.69 (dd, J=5.6, 3.1 Hz, 1H), 2.36-2.21 (m, 5H), 2.00 (s, 3H), 1.91 (td, J=12.1, 12 Hz, 1H), 1.71 (dt, J=13.2, 3.3 Hz, 1H), 1.66-1.56 (m, 2H), 1.48 (d, J=12.8 Hz, 1H), 1.42-1.11 (m, 5H), 1.00 (qd, J=13.5, 13.1, 4.1 Hz, 1H).

The free base (27.6 mg) was dissolved in 1 mL of acetonitrile. To the solution was added 0.5 mL of 1N hydrochloride. The mixture was lyophilized to afford 28.8 mg of product as the hydrochloride salt.

Example 109

Preparation of 1-(2-methoxyethyl)-3-((4aR,5R,11bR)-14-methyl-2,3,4,4a,5,6-hexahydro-1H-5,11b-(epiminoethano)phenanthro[3,2-d]thiazol-9-yl)urea (109), hydrochloride salt

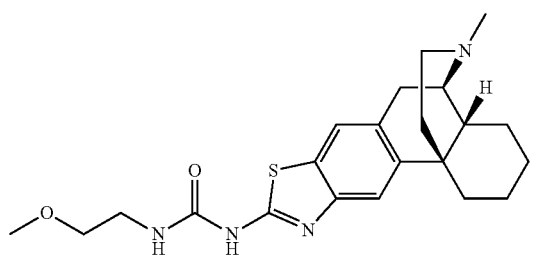 [SMILES: COCCNC(=O)Nc1nc2cc3c(cc2s1)C[C@@H]1[C@@H]2CCCC[C@]32CCN1C]

To a suspension of 2'-amino-thiazolo[5,4-b]-N-methyl-morphinan (80.8 mg, 0.258 mmol) in dichloromethane (3 ml) were added triethylamine (0.108 ml, 0.773 mmol), followed by 1-isocyanato-2-methoxyethane (52.1 mg, 0.516 mmol). The reaction was stirred at room temperature overnight. Dichloromethane (30 mL) was added to the reaction and the mixture was washed sequentially with saturated sodium bicarbonate solution (50 mL) and brine (50 mL). Organic layer was dried over sodium sulfate, was filtered and was concentrated. The crude product was purified by chromatography on silica gel using a Biotage instrument to give 1-(2-methoxyethyl)-3-((4aR,5R,11bR)-14-methyl-2,3,4,4a,5,6-hexahydro-1H-5,11b-(epiminoethano)phenanthro[3,2-d]thiazol-9-yl)urea (46.3 mg, 0.112 mmol, 43.3% yield) as a colorless solid. MS (EI) for C22H30N4O2S: 415.2 (MH+). 1H NMR (500 MHz, Methanol-d4) δ 7.57 (dd, J=12.9, 2.6 Hz, 2H), 3.54 (d, J=4.3 Hz, 2H), 3.41 (d, J=2.5 Hz, 3H), 3.35-3.31 (m, 4H), 3.22 (d, J=18.2 Hz, 1H), 2.94-2.82 (m, 2H), 2.57-2.48 (m, 1H), 2.43 (d, J=2.7 Hz, 3H), 2.14 (t, J=12.5 Hz, 1H), 1.93-1.86 (m, 1H), 1.86-1.75 (m, 1H), 1.69 (d, J=12.6 Hz, 1H), 1.58 (d, J=13.2 Hz, 1H), 1.52-1.34 (m, 4H), 1.36-1.26 (m, 1H), 1.17 (q, J=12.8, 12.4 Hz, 1H).

The free base (31.9 mg, 0.077 mmol) was dissolved in methanol (5 mL). To the solution was added HCl (4N in dioxane) (38.5 µl, 0.154 mmol). The solution was stirred at room temperature for 5 min and concentrated. After drying under vacuum, 1-(2-methoxyethyl)-3-44aR,5R,11bR)-14-methyl-2,3,4,4a,5,6-hexahydro-1H-5,11b-(epiminoethano) phenanthro[3,2-d]thiazol-9-yl)urea HCl was obtained as a colorless solid in quantitative yield.

Example 110

Preparation of 3-(2-trifluoromethyl-pyridin-4-yl)-amino-17-methyl-morphinan (110), hydrochloride salt

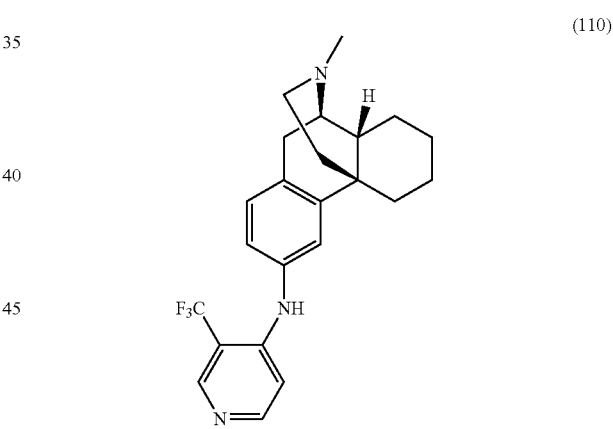

A toluene solution of 17-methylmorphinan-3-yl trifluoromethanesulfonate (0.100 g, 0.26 mmol), tris(dibenzylideneacetone)dipalladium(0) (0.012 g, 0.013 mmol), dicyclohexyl(2',4',6-triisopropyl-[1,1'-biphenyl]-2-yl)phosphine (0.015 g, 0.031 mmol), 3-(trifluoromethyl)pyridin-4-amine (0.062 g, 0.39 mmol) and cesium carbonate (0.17 g, 0.51 mmol) was heated at 110° C. for 18 hours. HPLC indicated that the reaction was complete. After all solvent was removed, a brown solid was obtained. The crude product was dissolved in dichloromethane and loaded on a 10 g of silica gel column and purified by Biotage with dichloromethane/methanol. Pure 3-(2-trifluoromethyl-pyridin-4-yl)-amino-17-methyl-morphinan (NKT-11914) was obtained as a white solid (0.050 g, 49% yield). 1H NMR (500 MHz, Chloroform-d) δ 8.55 (s, 1H), 8.28 (d, J=5.9 Hz, 1H), 7.17 (d, J=8.1 Hz, 1H), 7.09 (d, J=2.2 Hz, 1H), 6.99 (dd, J=8.1, 2.2 Hz, 1H), 6.83 (d, J=6.0 Hz, 1H), 6.44 (s, 1H), 3.49 (t, J=0.9 Hz, 1H), 3.06 (d, J=18.5 Hz, 1H), 2.87 (dd, J=5.8, 3.1 Hz, 1H), 2.67 (dd, J=18.5, 5.8 Hz, 1H), 2.50 (ddd, J=12.1, 4.9, 1.8 Hz, 1H), 2.42 (s, 2H), 2.32 (d, J=14.0 Hz, 1H), 2.08 (td, J=12.4, 3.2 Hz, 1H), 1.88 (dt, J=12.9, 3.3 Hz, 1H), 1.79 (td, J=12.7, 4.8 Hz, 1H), 1.72-1.62 (m, 1H), 1.56 (d, J=13.2 Hz, 1H), 1.51-1.20 (m, 5H), 1.15 (pd, J=13.9, 12.5, 3.4 Hz, 1H). MS (EI) for $C_{24}H_{31}N_3O$: 402.2 (MH+).

The free base (0.050 g, 0.12 mmol) was dissolved in methanol and added 2N hydrochloric acid ether solution (0.62 mL, 1.24 mmol), the mixture was lyophilized to give 3-(2-trifluoromethyl-pyridin-4-yl)-amino-17-methyl-morphinan (110) hydrochloride salt as a light-yellow solid (0.056 g, 0.11 mmol, 88% yield).

Example 111

Preparation of (4aR,5R,11bR)-14-methyl-N-(pyrimidin-2-yl)-2,3,4,4a,5,6-hexahydro-1H-5,11b-(epiminoethano)phenanthro[3,2-d]thiazol-9-amine (111)

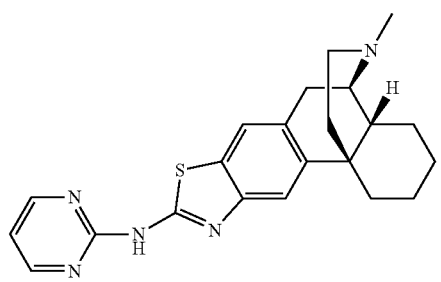

(111)

(4aR,5R,11bR)-14-methyl-2,3,4,4a,5,6-hexahydro-1H-5,11b-(epiminoethano)phenanthro[3,2-d]thiazol-9-amine (138 mg, 0.440 mmol), Cs₂CO3 (287 mg, 0.880 mmol), 2-bromopyrimidine (105 mg, 0.660 mmol) were mixed in 1,4-dioxane (3 mL). The mixture was degassed under nitrogen for ten minutes before 4,5-bis(diphenylphosphino)-9,9-dimethylxanthene (38.2 mg, 0.066 mmol) and Pd2(dba)3 (40.3 mg, 0.044 mmol) were added. The reaction was irradiated under microwave at 120° C. for two hours. LCMS showed completion of the reaction. The solvent was then removed. The residue was purified on chromatography on silica gel using a Biotage instrument to give (4aR,5R,11bR)-14-methyl-N-(pyrimidin-2-yl)-2,3,4,4a,5,6-hexahydro-1H-5,11b-(epiminoethano)phenanthro[3,2-d]thiazol-9-amine (111) (20.2 mg, 0.052 mmol, 11.72% yield) as an off-white solid. MS (EI) for $C_{22}H_{25}N_5S$: 392.2 (MH+). 1H NMR (500 MHz, Methanol-d4) δ 8.66 (d, J=4.8 Hz, 2H), 7.67 (s, 1H), 7.61 (s, 1H), 7.06 (t, J=4.8 Hz, 1H), 3.26 (d, J=17.6 Hz, 1H), 2.92 (s, 1H), 2.96-2.85 (m, 1H), 2.57 (d, J=13.5 Hz, 1H), 2.54-2.46 (m, 1H), 2.45 (s, 3H), 2.43 (d, J=4.1 Hz, 1H), 2.17 (td, J=12.5, 3.3 Hz, 1H), 1.92 (dt, J=12.9, 3.1 Hz, 1H), 1.83 (td, J=12.8, 4.7 Hz, 1H), 1.74-1.67 (m, 1H), 1.59 (d, J=12.8 Hz, 1H), 1.54-1.31 (m, 4H), 1.22 (tt, J=13.9, 6.6 Hz, 1H).

Example 112

Preparation of 2-(2-(3-(1-pyrazol-4-yl)morphinan-17-yl)ethoxy)ethanol (112), hydrochloride salt

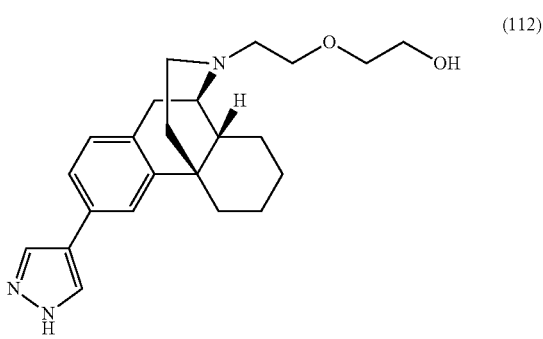 [SMILES: OCCOCCN1CC[C@]23CCCC[C@H]2[C@H]1Cc1ccc(-c2cn[nH]c2)cc13]

(112)

Step 1: Preparation of 17-[2-(2-Hydroxyethoxy)ethyl]morphinan-3-yl trifluoromethanesulfonate A 4 mL screw cap vial was charged with powdered anhydrous potassium carbonate (0.50 g, 3.60 mmol) and a solution of morphinan-3-yl trifluoromethanesulfonate (135 mg, 0.36 mmol) in dry acetonitrile (1 mL) was added, whereupon neat 2-(2-chloroethoxy)ethanol (0.114 mL, 1.08 mmol) was added in one portion, and the stirred mixture was heated to 80° C. in a heat block for three hours. The mixture was diluted with ether (15 mL), filtered through celite and the filter cake was washed with dichloromethane (30 mL), and the filtrate was concentrated. Chromatography on silica (dichloromethane to 1:10:90 ammonium hydroxide:methanol:dichloromethane) afforded 17-(2-(2-hydroxyethoxy)ethyl)morphinan-3-yl trifluoromethanesulfonate as a pale yellow oil (36 mg, 22%). NMR (500 MHz, CDCl₃) δ 7.19 (d, J=8.5 Hz, 1H), 7.14 (d, J=2.6 Hz, 1H), 7.04 (dd, J=8.5, 2.6 Hz, 1H), 4.50 (br s, 1H), 3.83-3.55 (m, 6H), 3.00 (d, J=7.9 Hz, 1H), 2.99 (d, J=17.9 Hz, 1H), 2.80 (ddd, J=13.2, 7.5, 4.2 Hz, 1H), 2.76 (dd, J=18.3, 5.9 Hz, 1H), 2.70-2.62 (m, 2H), 2.30 (dt, J=14.1, 3.2 Hz, 1H), 2.06 (td, J=12.4, 3.2 Hz, 1H), 1.95 (dt, J=13.0, 3.3 Hz, 1H), 1.84 (td, J=12.8, 4.7 Hz, 1H), 1.71-1.62 (m, 1H), 1.58 (dt, J=13.4, 3.7 Hz, 1H), 1.51-1.36 (m, 3H), 1.32 (dt, J=13.0, 2.7 Hz, 1H), 1.20 (qt, J=13.3, 3.5 Hz, 1H), 1.03 (qd, J=12.6, 3.6 Hz, 1H); MS (EI) for $C_{21}H_{28}F_3NO_5S$: 464.2 (MH+).

Step 2: Preparation of 2-(2-(3-(1-pyrazol-4-yl)morphinan-17-yl)ethoxy)ethanol, dihydrochloride salt A 2-5 mL microwave vial was charged with (1H-pyrazol-4-yl)boronic acid (44 mg, 0.39 mmol), tetrakistriphenylphosphinepalladium (54 mg, 0.047 mmol), sodium carbonate (99 mg, 0.93 mmol), purged with nitrogen, then water (1 mL) was added and the mixture degassed by sparging nitrogen for >15 minutes. A solution of 17-[2-(2-hydroxyethoxy)ethyl]morphinan-3-yl trifluoromethanesulfonate (36 mg, 0.078 mmol) in degassed dioxane (2 mL) was added, and the mixture was heated at 100° C. in a microwave for two hours. The mixture was partitioned between ethyl acetate (15 mL) and 1 M aqueous sodium carbonate (2×10 mL), and then was extracted with 2 M sulfuric acid (3×5 mL). The combined acid extract was basified to pH>12 with 4 M sodium hydroxide, and extracted with chloroform (30 mL, and then 15 mL). The combined chloroform layer was dried (sodium sulfate), filtered and concentrated. Purification by reverse phase prep HPLC (eluting with 30-45% acetonitrile in 10 mM aqueous ammonium hydroxide on a 150×21.2 mm i.d., 10 um Gemini C18 column) afforded 2-(2-(3-(1-pyrazol-4-yl)morphinan-17-yl)ethoxy)ethanol (112) as a colorless film (7 mg, 24%). $^1$H NMR (500 MHz, CDCl$_3$) δ 7.85 (s, 2H), 7.41 (d, J=1.8 Hz, 1H), 7.29 (dd, J=7.8, 1.8 Hz, 1H), 7.13 (d, J=7.8 Hz, 1H), 3.80-3.70 (m, 4H), 3.70-3.58 (m, 2H), 3.00 (d, J=8.3 Hz, 1H), 2.98 (d, J=18.1 Hz, 1H), 2.87-2.72 (m, 2H), 2.72-2.61 (m, 2H), 2.46 (d, J=13.5 Hz, 1H), 2.17 (td, J=12.4, 3.2 Hz, 1H), 1.93 (dt, J=12.9, 3.3 Hz, 1H), 1.83 (td, J=12.8, 4.7 Hz, 1H), 1.66 (d, J=12.5 Hz, 1H), 1.56 (d, J=12.8 Hz, 1H), 1.51-1.22 (m, 7H), 1.16 (qd, J=12.4, 3.8 Hz, 1H); MS (EI) for C$_{23}$H$_{31}$N$_3$O$_2$: 382.2 (MH+).

The free base was dissolved in acetonitrile:water (1:10, 1 mL), treated with 2 M hydrochloric acid (100 uL), frozen and lyophilized to afford the hydrochloride salt as a cream solid.

Example 113

Preparation of 3-hydroxy-17-(2-methoxyethyl)morphinan (113)

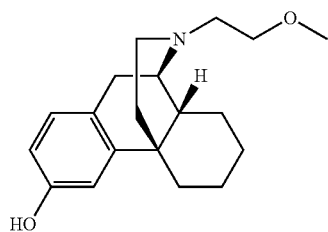

(113)

3-Hydroxy-17-(2-methoxyethyl)morphinan (113) was prepared. An approach described in Zhang et al. (2004) *J Med. Chem.* 47(1):165-174 can be used to prepare this compound.

Example 114

Preparation of 3-amino-17-morphinan (114)

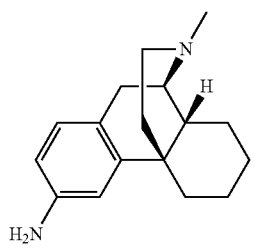

(114)

3-Amino-17-morphinan (114) was prepared. An approach described in Neumeyer et al. (2001) *Bioorganic & Medicinal Chemistry Letters* 11(20):2735-2740 can be used to prepare this compound.

Example 115

Preparation of (4aR,5R,11bR)-14-methyl-2,3,4,4a,5,6-hexahydro-1H-5,11b-(epiminoethano)phenanthro[3,2-d]thiazol-9-amine (115)

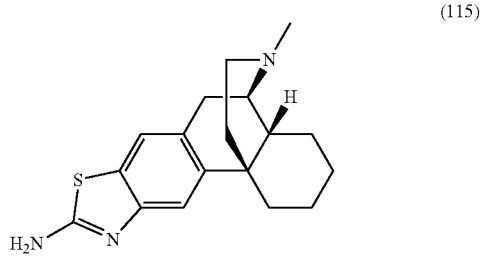 [SMILES: CN1CC[C@]23CCCC[C@H]2[C@H]1Cc1cc2sc(N)nc2cc13]

(115)

(4aR,5R,11bR)-14-Methyl-2,3,4,4a,5,6-hexahydro-1H-5,11b-(epiminoethano)phenanthro[3,2-d]thiazol-9-amine3-amino-17-morphinan (115) was prepared. An approached described in WO2004/045562 can be used to prepare this compound.

Example 116

In Vitro Analysis

Certain compounds of the present invention were analyzed.

The in vitro affinities and activity of certain compounds were obtained.

Receptor Binding at MOR and NMDA.

Affinities of various compounds were measured in vitro using competitive radioligand binding assays. Serial dilutions of test compounds were incubated with membranes prepared from CHO-K1 cells expressing the mu opioid receptor (MOR; for opioid receptor binding) or rat forebrain membranes (for NMDA receptor binding). 2 nM [$^3$H] Naloxone (MOR) or 0.2 nM [$^3$H] MK801 (NMDA) were used as the specific, competitive radioligands. 10 uM Naloxone (MOR), or 10 uM MK801 (NMDA) was used to determine non-specific binding. Bound radioactivity was measured using a scintillation counter & IC50 values for test compounds were determined by non-linear regression analysis using a one-site competition model (Graph Pad Prizm). Due to each test compound being solubilized in a buffered system for the assay, the results presented herein reflect the free base activity.

cAMP Accumulation Assay.

Mu opioid agonist activity for selected compounds was determined by the inhibition of forskolin-stimulated cAMP accumulation following MOR activation in CHO-K1 cells stably expressing the hMOR. Serial dilutions of test compounds were prepared in assay buffer containing 0.5 mM IBMX and were added to hMOR-expressing CHO cells, followed by addition of 10 μM forskolin. cAMP accumulation was measured following a 60 minute incubation using a commercial cAMP HTRF kit (Cisbio).DAMGO, a full mu opioid agonist, was used as positive control in these assays (IC50=2.5 nM). IC50 values were calculated from non-regression analysis of the concentration-response curves using Graph Pad Prizm.

The in vivo efficacy of certain compounds was obtained.

Automated Formalin Paw.

The in vivo efficacy of selected compounds following oral administration was measured using the rat formalin model of persistent pain. Test compounds were administered 30-60 minutes prior to injection of 5% formalin to the hind-paw of rats and paw movements were measured using the automated Nociception Analyzer (ANA Instrument; University of California, San Diego) for 60 minutes post-formalin. In some experiments, rats were pre-treated 16-22 hours priors to the experiment with the cytochrome-P450 inhibitor, 1-aminobenzotriazole (ABT), to assess the activity of compounds in the absence of significant quantities of metabolites. $ED_{50}$ values (mg/kg) were calculated from non-linear regression analyses of the cumulative number of flinches in Phase II (10-60 mins) versus dose of test compounds.

In Table 1, the relative affinities of various compounds at the mu opioid receptor (MOR) and NMDA receptor in vitro are provided. In the table, symbols are used to denote relative affinities/activities, as follows:

at the MOR (for binding and cAMP agonist activity)
+++: IC50 values range from 0.1-10 nM
++: IC50 values range from 10-100 nM
+: IC50 values range from 100-1000 nM
−: IC50 values are greater than 1000 nM; and at the NMDA receptor
+++: IC50 values range from 0.1-100 nM
++: IC50 values range from 100-1000 nM
+: IC50 values range from 1000-10,000 nM
−: IC50 values are greater than 10,000 nM.

TABLE 1

Relative Affinities of Various Compounds at the Mu Opioid Receptor (MOR) and NMDA Receptor in vitro

| Example/Compound | MOR $IC_{50}$ (nM) | NMDA $IC_{50}$ (nM) | MOR cAMP $IC_{50}$ (nM) |
|---|---|---|---|
| 1 | − | − | |
| 2 | − | − | |
| 3 | +++ | | +++ |
| 4 | − | − | |
| 5 | + | − | |
| 6 | + | − | |
| 7 | + | − | + |
| 8 | − | − | |
| 9 | ++ | − | |
| 10 | + | − | |
| 11 | + | + | |
| 12 | − | − | − |
| 13 | − | − | |
| 14 | − | − | |
| 15 | ++ | − | ++ |
| 16 | − | | − |
| 17 | − | − | |
| 18 | + | + | + |
| 21 | + | | |
| 22 | ++ | | ++ |
| 23 | + | − | |
| 24 | + | − | |
| 25 | − | − | |
| 26 | − | − | |
| 27 | ++ | + | |
| 28 | +++ | + | |
| 29 | +++ | + | |
| 30 | ++ | + | ++ |
| 31 | +++ | + | |
| 32 | − | ++ | |
| 33 | + | − | + |
| 34 | +++ | − | |
| 35 | + | − | |
| 36 | ++ | + | ++ |
| 37 | + | + | |
| 38 | + | − | |
| 39 | + | − | |
| 40 | + | + | |

TABLE 1-continued

Relative Affinities of Various Compounds at the Mu Opioid Receptor (MOR) and NMDA Receptor in vitro

| Example/Compound | MOR $IC_{50}$ (nM) | NMDA $IC_{50}$ (nM) | MOR cAMP $IC_{50}$ (nM) |
|---|---|---|---|
| 41 | − | − | |
| 42 | + | − | |
| 43 | +++ | +++ | +++ |
| 44 | ++ | ++ | ++ |
| 45 | − | + | |
| 46 | ++ | ++ | ++ |
| 47 | +++ | | +++ |
| 48 | ++ | − | |
| 49 | + | +++ | |
| 50 | + | +++ | |
| 51 | ++ | + | |
| 52 | − | + | |
| 53 | ++ | − | |
| 54 | ++ | − | |
| 55 | +++ | − | |
| 56 | + | +++ | |
| 57 | − | + | |
| 58 | ++ | − | |
| 59 | + | + | |
| 60 | + | − | |
| 61 | + | + | |
| 62 | ++ | ++ | |
| 63 | + | ++ | |
| 64 | ++ | − | |
| 65 | − | − | |
| 66 | + | + | |
| 67 | + | − | |
| 68 | − | + | |
| 69 | + | + | + |
| 70 | − | − | |
| 71 | + | + | |
| 72 | − | − | |
| 73 | + | + | |
| 74 | − | − | |
| 75 | ++ | − | |
| 76 | − | − | |
| 77 | − | − | |
| 78 | − | − | |
| 79 | − | − | |
| 80 | − | + | |
| 81 | ++ | − | |
| 82 | + | − | |
| 83 | + | + | |
| 84 | + | + | |
| 85 | − | − | |
| 86 | +++ | + | |
| 87 | − | − | |
| 88 | ++ | + | |
| 89 | + | + | |
| 90 | ++ | − | |
| 91 | +++ | + | |
| 92 | + | − | |
| 93 | ++ | +++ | |
| 94 | − | ++ | |
| 95 | − | + | |
| 96 | − | − | |
| 97 | − | + | |
| 98 | + | ++ | |
| 99 | − | + | |
| 100 | − | + | |
| 101 | ++ | + | |
| 102 | − | − | |
| 103 | − | − | |
| 104 | ++ | − | |
| 105 | + | − | |
| 106 | + | − | |
| 113 | +++ | ++ | +++ |
| 114 | + | ++ | + |
| 115 | ++ | +++ | ++ |

In the rat formalin paw model of persistent pain, compounds 83, 113, 114 and 115 (described in Examples 83, 113, 114 and 115, respectively) were tested. In each case, the oral efficacy of the compounds was measured in the presence and absence of the cytochrome CYP-450 inhibitor, 1-aminobenzotriazole. At at least one dosage between 10 mg/kg and 300 mg/kg (inclusive), each of Compounds 83, 113, 114 and 115 demonstrated statistically significant efficacy in Phase I and Phase II of this model in the presence of 1-aminobenzotriazole.

What is claimed is:

1. A compound of Formula I:

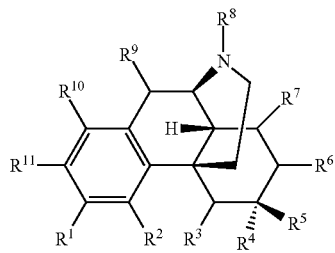

Formula I wherein:
$R^1$ is —N($R^{17}$)($R^{18}$);
$R^2$, $R^3$, $R^4$, $R^5$, $R^6$, $R^7$ $R^9$, $R^{19}$, and $R^{11}$ are hydrogen;
$R^8$ is —$CH_3$;
$R^{17}$ is a heteroaryl substituted with —X-POLY;
$R^{18}$ is hydrogen;
X is a linker;
POLY is a poly(alkylene oxide); and
pharmaceutically acceptable salts thereof.

2. The compound of claim 1, having a structure of Formula II,

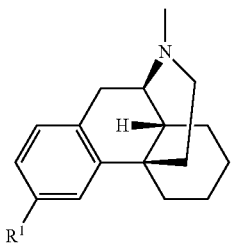

Formula II wherein:
—X-POLY is —X—($CH_2CH_2O$)$_n$—R, where n is 1 to 30 and R is selected from hydrogen, lower alkyl, haloalkyl and carboxyl.

3. A method for treating an individual in need of treatment for neuropathic pain, the method comprising the step of administering to the individual a compound having the following formula:

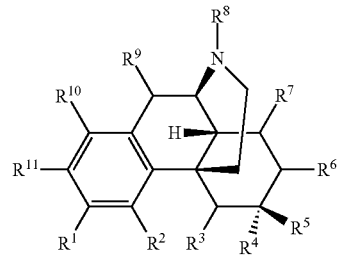

wherein:
$R^1$ is —N($R^{17}$)($R^{18}$);
$R^2$, $R^3$, $R^4$, $R^5$, $R^6$, $R^7$, $R^9$, $R^{10}$, and $R^{11}$ are hydrogen
$R^8$ is —$CH_3$;
$R^{17}$ is a heteroaryl substituted with X-POLY;
$R^{18}$ is hydrogen;
X is a linker;
POLY is a poly(alkylene oxide); and
pharmaceutically acceptable salts thereof.

4. A pharmaceutical composition comprising a compound of claim 1, and at least one pharmaceutically acceptable excipient.

5. A composition of matter comprising a compound of 1, wherein the compound is present in a dosage form.

6. The compound of claim 1, wherein a heteroatom of the heterocycle is selected from O, N, and S.

7. The compound of claim 1, wherein the heterocycle is selected from an imidazole, a pyrimidine, a thiazole, and a pyridine.

8. The compound of claim 1, wherein $R^{17}$ is selected from

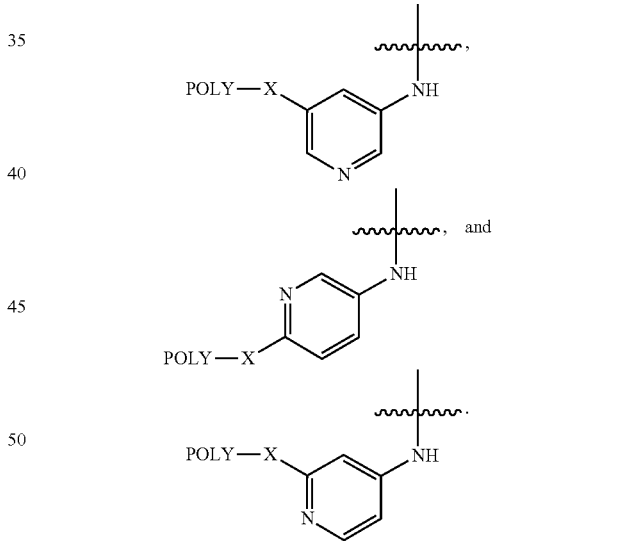

* * * * *